United States Patent

Baumann et al.

[11] Patent Number: 6,143,696
[45] Date of Patent: Nov. 7, 2000

[54] SUBSTITUTED 4-(3-ALKENYLBENZOYL) PYRAZOLES

[75] Inventors: Ernst Baumann, Dudenhofen; Wolfgang von Deyn, Neustadt; Stefan Engel, Idstein; Regina Luise Hill, Speyer; Uwe Kardorff, Mannheim; Guido Mayer, Neustadt; Martina Otten, Ludwigshafen; Michael Rack, Heidelberg; Joachim Rheinheimer; Matthias Witschel, both of Ludwigshafen; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 09/423,077

[22] PCT Filed: May 5, 1998

[86] PCT No.: PCT/EP98/02433

§ 371 Date: Nov. 2, 1999

§ 102(e) Date: Nov. 2, 1999

[87] PCT Pub. No.: WO98/50366

PCT Pub. Date: Nov. 12, 1998

[30] Foreign Application Priority Data

May 7, 1997 [DE] Germany .................... 197 26 710

[51] Int. Cl.$^7$ .................... C07D 231/22; A01N 43/56
[52] U.S. Cl. .................... 504/282; 544/238; 544/333; 544/405; 546/276.1; 548/204; 548/236; 548/314.4; 548/364.1; 548/364.4; 548/365.1; 548/365.7; 548/369.4
[58] Field of Search ................ 548/369.4, 365.7; 546/276.1; 504/282

[56] References Cited

U.S. PATENT DOCUMENTS 4,643,757  2/1987  Baba et al. .

FOREIGN PATENT DOCUMENTS 240 001  10/1987  European Pat. Off. .
282 944   9/1988  European Pat. Off. .

*Primary Examiner*—Robert W. Ramsuer
*Attorney, Agent, or Firm*—Keil & Weinkauf

[57] ABSTRACT

4-(3-Alkenylbenzoyl)pyrazoles of the formula I

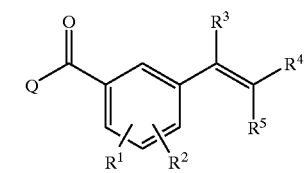

and agriculturally useful salts thereof; processes for preparing the compounds of the formula I; compositions comprising them; and the use of these derivatives or of compositions comprising them for controlling undesirable plants.

9 Claims, No Drawings

SUBSTITUTED 4-(3-ALKENYLBENZOYL) PYRAZOLES

This application is a 371 of PCT/EP98/02433 filed May 5, 1998.

The present invention relates to 4-(3-alkenylbenzoyl) pyrazoles of the formula I

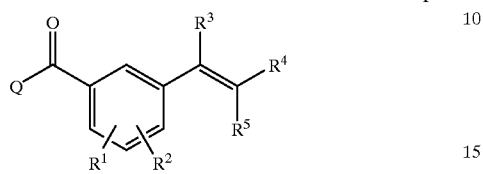

where:
- $R^1$ and $R^2$ are each hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$, —$OCOR^7$, —$OSO_2R^7$, —SH, —$S(O)_nR^8$, —$SO_2OR^6$, —$SO_2NR^6R^9$, —$NR^9SO_2R^7$ or —$NR^9COR^7$;
- $R^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl;
- $R^4$ and $R^5$ are each hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which carries a radical from the following group: hydroxyl, —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, it being possible for the last six radicals to be substituted;

or
- $R^4$ and $R^5$ together form a $C_2$–$C_6$-alkanediyl chain which may be mono- to tetrasubstituted by $C_1$–$C_4$-alkyl and/or interrupted by oxygen or sulfur or by nitrogen with or without substitution by $C_1$–$C_4$-alkyl;
- n is 0, 1 or 2;
- $R^6$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
- $R^7$ is $C_1$–$C_6$-alkyl or $C_1$–$C_6$-haloalkyl;
- $R^8$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
- $R^9$ is hydrogen or $C_1$–$C_6$-alkyl;
- $R^{10}$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, phenyl or benzyl, it being possible for the last two radicals to be partially or fully halogenated and/or to carry one to three radicals from the following group:
  - nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;
- $R^{11}$ is hydrogen, $C_1$–$C_6$-alkyl, $C_3$–$C_6$-alkenyl or $C_3$–$C_6$-alkynyl;

or
- $R^{10}$ and $R^{11}$ together form a $C_2$–$C_6$-alkanediyl chain which may be mono- to tetrasubstituted by $C_1$–$C_4$-alkyl and/or interrupted by oxygen or sulfur or by nitrogen with or without substitution by $C_1$–$C_4$-alkyl;
- $R^{12}$ is hydrogen, $C_1$–$C_6$-alkyl, $C_1$–$C_6$-haloalkyl, $C_1$–$C_6$-alkoxy, $C_1$–$C_6$-alkoxycarbonyl, $C_3$–$C_6$-cycloalkyl, $C_2$–$C_6$-alkenyl, $C_2$–$C_6$-alkynyl, phenyl or benzyl, it being possible for the last two radicals to be partially or fully halogenated and/or to carry one to three radicals of the following group:
  - nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;
- $R^{13}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy, $C_1$–$C_6$-haloalkoxy, $C_3$–$C_6$-cycloalkoxy, $C_3$–$C_6$-alkenyloxy, $C_3$–$C_6$-alkynyloxy, phenyl, benzyl or phenyl-$C_1$–$C_4$-alkoxy, it being possible for the last three radicals to be partially or fully halogenated and/or to carry one to three radicals from the following group:
  - nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;
- Q is a pyrazole of the formula II

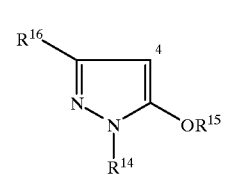

which is linked in position 4 and where
- $R^{14}$ is $C_1$–$C_6$-alkyl, $C_1$–$C_6$-haloalkyl, phenyl or phenyl which is partially or fully halogenated and/or carries one to three of the following radicals:
  - nitro, cyano, $C_1$–$C_4$-alkyl, $C_1$–$C_4$-haloalkyl, $C_1$–$C_4$-alkoxy, $C_1$–$C_4$-haloalkoxy;
- $R^{15}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenyl-$C_1$–$C_4$-alkyl, phenylcarbonyl, phenylcarbonylmethyl, phenoxycarbonyl or phenylsulfonyl, the last five substituents being unsubstituted or the phenyl ring in question being partially or fully halogenated and/or carrying one to three of the following radicals:
  - nitro, cyano, $C_1$–$C_4$-alkyl, $C_1$–$C_4$-haloalkyl, $C_1$–$C_4$-alkoxy, $C_1$–$C_4$-haloalkoxy;
- $R^{16}$ is hydrogen, $C_1$–$C_6$-alkyl or $C_1$–$C_6$-haloalkyl;

and agriculturally useful salts thereof.

Moreover, the invention relates to processes for preparing compounds of the formula I, to compositions comprising them and to the use of the compounds of the formula I and to compositions comprising them for controlling harmful plants.

4-[3-(2-Alkoxy-1-ethenyl)benzoyl]pyrazoles are disclosed in EP-A 282 944. However, the herbicidal properties of these compounds and their crop safety are only partly satisfactory.

It is an object of the present invention to provide in particular herbicidally active compounds having improved properties.

We have found that this object is achieved by the 4-(3-alkenylbenzoyl)pyrazoles of the formula I and by their herbicidal activity.

Furthermore, we have found highly effective herbicidal compositions which comprise the compounds I. In addition, we have found processes for preparing these compositions and methods for controlling undesirable vegetation using the compounds I.

The present invention also relates to stereoisomers of the compounds of the formula I. These include pure stereoisomers and mixtures of these.

The compounds of the formula I contain a carbon—carbon double bond and therefore exist in the form of E isomers or Z isomers or E/Z isomer mixtures. Furthermore, the compounds of the formula I may contain further carbon or carbon-nitrogen double bonds. The invention relates both to the pure geometric isomers and to mixtures of these.

Depending on the substitution pattern, the compounds of the formula I may contain one or more chiral centers, in which case they exist in the form of enantiomers or diastereomer mixtures. The invention relates both to pure enantiomers or diastereomers and to mixtures of these.

The compounds of the formula I may also be present in the form of their agriculturally useful salts, the type of salt generally being of no importance. In general, suitable salts are salts of those cations, or the acid addition salts of those acids, whose cations, or anions, do not adversely affect the herbicidal activity of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di-(2-hydroxyeth-1-yl)ammonium, trimethylbenzylammonium, and furthermore phosphonium ions, sulfonium ions, preferably tri($C_1$–$C_4$-alkyl)sulfonium, and sulfoxonium ions, preferably tri ($C_1$–$C_4$-alkyl)sulfoxonium.

Anions of useful acid addition salts are primarily chloride, bromide, fluoride, hydrogen sulfate, sulfate, dihydrogen phoshate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

The organic moieties mentioned for the substituents $R^1$–$R^{16}$ or as radicals on phenyl, hetaryl and heterocyclyl rings are collective terms for individual enumerations of the individual group members. All hydrocarbon chains, ie. all alkyl, haloalkyl, cycloalkyl, alkoxyalkyl, alkoxy, haloalkoxy, cycloalkoxy, alkylthio, alkylsulfonyl, haloalkylsulfonyl, alkylcarbonyl, haloalkylcarbonyl, alkoxycarbonyl, alkenyl, cycloalkenyl, alkynyl, alkenyloxy and alkynyloxy moieties may be straight-chain or branched. Unless otherwise specified, halogenated substituents preferably carry one to five identical or different halogen atoms, halogen being in each case fluorine, chlorine, bromine or iodine.

Examples of other meanings are:

$C_2$–$C_4$-alkyl: ethyl, n-propyl, 1-methylethyl, butyl, 1-methylpropyl, 2-methylpropyl or 1,1-dimethylethyl;

$C_1$–$C_4$-alkyl and the alkyl moieties of $C_1$–$C_4$-alkoxy-$C_1$–$C_4$-alkyl, hydroxy-$C_1$–$C_4$-alkoxy-$C_1$–$C_4$-alkyl, $C_1$–$C_4$-alkylcarbonyl, heterocyclyl-$C_1$–$C_4$-alkyl, phenyl-$C_1$–$C_4$-alkyl and hetaryl-$C_1$–$C_4$-alkyl: $C_2$–$C_4$-alkyl as mentioned above and also methyl;

$C_2$–$C_6$-alkyl and the alkyl moieties of $C_1$–$C_6$-alkoxy-$C_2$–$C_6$-alkyl: $C_2$–$C_4$-alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_6$-alkyl and the alkyl moieties of $C_1$–$C_6$-alkoxy-$C_1$–$C_6$-alkyl and $C_1$–$C_6$-alkylcarbonyl: $C_2$–$C_6$-alkyl as mentioned above, and also methyl;

$C_1$–$C_4$-haloalkyl: a $C_1$–$C_4$-alkyl radical as mentioned above which is partially or fully substituted by fluorine, chlorine, bromine and/or iodine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy and the alkoxy moieties of $C_1$–$C_4$-alkoxy-$C_1$–$C_4$-alkyl, hydroxy-$C_1$–$C_4$-alkoxy-$C_1$–$C_4$-alkyl, $C_1$–$C_4$-alkoxycarbonyl: methoxy, ethoxy, propoxy, 1-methylethoxy, butoxy, 1-methylpropoxy, 2-methylpropoxy or 1,1-dimethylethoxy;

$C_1$–$C_6$-alkoxy and the alkoxy moieties of $C_1$–$C_6$-alkoxy-$C_1$–$C_6$-alkyl, $C_1$–$C_6$-alkoxy-$C_2$–$C_6$-alkyl and $C_1$–$C_6$-alkoxycarbonyl: $C_1$–$C_4$-alkoxy as mentioned above, and also pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxyrest as mentioned above which is partially or fully substituted by fluorine, chlorine, bromine and/or iodine, ie. for example fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3- dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above, and also eg. 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_6$-alkylthio: eg. methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_6$-alkylsulfonyl ($C_1$–$C_6$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl or 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, ie. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkenyloxy: eg. prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-Methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1- dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethyl-but-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_2$–$C_6$-alkynyl: $C_3$–$C_6$-alkynyl as mentioned above, and also ethynyl:

$C_3$–$C_6$-alkynyloxy: eg. prop-1-yn-1-yloxy, prop-2-yn-1-yloxy, but-1-yn-1-yloxy, but-1-yn-3-yloxy, but-1-yn-4-yloxy, but-2-yn-1-yloxy, pent-1-yn-1-yloxy, pent-1-yn-3-yloxy, pent-1-yn-4-yloxy, pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, hex-1-yn-1-yloxy, hex-1-yn-3-yloxy, hex-1-yn-4-yloxy, hex-1-yn-5-yloxy, hex-1-yn-6-yloxy, hex-2-yn-1-yloxy, hex-2-yn-4-yloxy, hex-2-yn-5-yloxy, hex-2-yn-6-yloxy, hex-3-yn-1-yloxy, hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy;

$C_3$–$C_6$-cycloalkyl: cyclopropyl, cyclobutyl, cyclopentyl or cyclohexyl;

$C_3$–$C_6$-cycloalkoxy: cyclopropoxy, cyclobutoxy, cyclopentoxy or cyclohexoxy;

$C_4$–$C_6$-cycloalkenyl: cyclobuten-1-yl, cyclobuten-3-yl, cyclopenten-1-yl, cyclopenten-3-yl, cyclohexen-1-yl, cyclohexen-3-yl or cyclohexen-4-yl;

heterocyclyl, and also the heterocyclyl radicals in heterocyclyloxy and heterocyclyl-$C_1$–$C_4$-alkyl: three- to seven-membered saturated or partially unsaturated mono- or polycyclic heterocycles which contain one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 1,3-dioxolan-4-yl, 1,3-dithiolan-2-yl, 1,3-dithiolan-4-yl, 1,3-dioxan-2-yl, 1,3-dioxan-4-yl, 1,3-dioxan-5-yl, 1,3-dithian-2-yl, 1,3-dithian-4-yl, 1,3-dithian-5-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl or 1,3-dihydrooxazin-2-yl;

hetaryl, and also hetaryl radicals in hetaryloxy and hetaryl-$C_1$–$C_4$-alkyl: aromatic mono- or polycyclic radicals which, besides carbon ring members, may additionally contain one to four nitrogen atoms or one to three nitrogen atoms and one oxygen or one sulfur atom or one oxygen or one sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4- triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and also the corresponding benzo-fused derivatives;

$C_2$–$C_6$-alkanediyl: eg. ethane-1,2-diyl, propane-1,3-diyl, butane-1,4-diyl, pentane-1,5-diyl or hexane-1,6-diyl.

All phenyl, hetaryl and heterocyclyl rings are preferably unsubstituted or carry one to three halogen atoms and/or one or two radicals selected from the following group: nitro, cyano, methyl, trifluoromethyl, methoxy, trifluoromethoxy or methoxycarbonyl.

With a view to the use of the compounds of the formula I according to the invention as herbicides, the variables preferably have the following meanings, viz. in each case alone or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$ or —$S(O)_nR^8$; particularly preferably nitro, halogen, eg. fluorine, chlorine or bromine, $C_1$–$C_6$-haloalkyl, —$OR^6$ or —$SO_2R^8$;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$ or —$S(O)_nR^8$; particularly preferably hydrogen, nitro, halogen, eg. fluorine, chlorine or bromine, $C_1$–$C_6$-alkyl, $C_1$–$C_6$-haloalkyl, —$OR^6$ or —$SO_2R^8$; especially preferably nitro, halogen, eg. fluorine, chlorine or bromine, $C_1$–$C_6$-alkyl, eg. methyl or ethyl, $C_1$–$C_6$-haloalkyl, eg. difluoromethyl or trifluoromethyl, —$OR^6$ or $SO_2R^8$;

$R^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl; particularly preferably hydrogen, halogen, eg. fluorine, chlorine or bromine, $C_1$–$C_4$-alkyl, eg. methyl or ethyl, $C_1$–$C_4$-haloalkyl, eg. trifluoromethyl, $C_1$–$C_4$-alkoxy, eg. methoxy or ethoxy, allyl or propargyl; especially preferably hydrogen or methyl;

$R^4$ is hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which carries a radical from the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, it being possible for the last six radicals to be substituted in turn by one to three halogen atoms and/or to carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl;

$R^5$ is hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which carries a radical from the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, it being possible for the last six radicals to be substituted in turn by one to three halogen atoms and/or to carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl or $C_1$–$C_4$-alkoxycarbonyl; particularly preferably hydrogen, halogen, cyano, thiocyanato, $C_1$–$C_6$-alkyl, $C_1$–$C_6$-haloalkyl, —$COR^{10}$, —$CO_2R^{10}$, —$COSR^{10}$, —$CONR^{10}R^{11}$ or —$PO(OR^{10})(OR^{11})$;

$R^4$ and $R^5$ together form a $C_2$–$C_6$-alkanediyl chain which may be mono- to tetrasubstituted by $C_1$–$C_4$-alkyl and/or interrupted by oxygen or sulfur or by nitrogen with or without substitution by $C_1$–$C_4$-alkyl, for example butane-1,4-diyl, pentane-1,5-diyl, hexane-1,6-diyl, 3-oxapentane-1,5-diyl or 3-methyl-3-azapentane-1,5-diyl;

n is 0 or 2;

$R^6$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl; particularly preferably $C_1$–$C_4$-alkyl, eg. methyl or ethyl, $C_1$–$C_4$-haloalkyl, eg. trifluoromethyl or difluoromethyl, $C_1$–$C_4$-alkoxy-$C_2$–$C_4$-alkyl, eg. methoxyethyl, allyl or propargyl;

$R^8$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl; particularly preferably $C_1$–$C_4$-alkyl, eg. methyl or ethyl, $C_1$–$C_4$-haloalkyl, eg. trifluoromethyl or difluoromethyl, $C_1$–$C_4$-alkoxy-$C_2$–$C_4$-alkyl, eq. methoxyethyl, allyl or propargyl;

$R^{10}$ is hydrogen, $C_1$–$C_6$-alkyl, $C_3$–$C_6$-cycloalkyl, $C_1$–$C_6$-haloalkyl, $C_3$–$C_6$-alkenyl, $C_3$–$C_6$-alkynyl, phenyl or benzyl; particularly preferably hydrogen, $C_1$–$C_4$-alkyl, eg. methyl or ethyl, $C_1$–$C_4$-haloalkyl, eg. trifluoromethyl, allyl, propargyl and benzyl;

$R^{11}$ is hydrogen, $C_1$–$C_6$-alkyl, $C_3$–$C_6$-alkenyl or $C_3$–$C_6$-alkynyl or $R^{10}$ and $R^{11}$ together form a $C_2$–$C_6$-alkanediyl chain which may be mono- to tetrasubstituted by $C_1$–$C_4$-alkyl;

$R^{12}$ is hydrogen, $C_1$–$C_6$-alkyl, $C_1$–$C_6$-haloalkyl, $C_1$–$C_6$-alkoxy, $C_1$–$C_6$-alkoxycarbonyl, $C_3$–$C_6$-cycloalkyl, $C_2$–$C_6$-alkenyl, $C_2$–$C_6$-alkynyl, phenyl or benzyl; particularly preferably hydrogen, $C_1$–$C_4$-alkyl, eg. methyl or ethyl, $C_1$–$C_4$-alkoxycarbonyl, eg. methoxycarbonyl or ethoxycarbonyl, $C_1$–$C_4$-haloalkyl, eg. trifluoromethyl, $C_1$–$C_4$-alkoxy, eg. methoxy or ethoxy;

$R^{13}$ is $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, $C_1$–$C_6$-alkoxy, $C_1$–$C_6$-haloalkoxy, $C_3$–$C_6$-cycloalkoxy, $C_3$–$C_6$-alkenyloxy, $C_3$–$C_6$-alkynyloxy, phenyl, benzyl or benzyloxy; particularly preferably $C_1$–$C_4$-alkyl, eg. methyl or ethyl, $C_1$–$C_4$-alkoxy, eg. methoxy or ethoxy, allyloxy, propargyloxy, benzyl or benzyloxy;

$R^{14}$ is $C_1$–$C_6$-alkyl or $C_1$–$C_6$-haloalkyl; particularly preferably $C_1$–$C_4$-alkyl, eg. methyl, ethyl, propyl, isopropyl, butyl or isobutyl;

$R^{15}$ is hydrogen, $C_1$–$C_6$-alkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonylmethyl or phenylsulfonyl, it being possible for the phenyl ring of the last two substituents to be partially or fully halogenated and/or to carry one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy;

$R^{16}$ is hydrogen, $C_1$–$C_6$-alkyl or $C_1$–$C_6$-haloalkyl;

particularly preferably hydrogen, $C_1$–$C_4$-alkyl, eg. methyl or ethyl, or $C_1$–$C_4$-haloalkyl, eg. trifluoromethyl;

especially preferably hydrogen or methyl.

Very particular preference is given to the compounds of the formula I, where $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$ or —$S(O)_nR^8$;

$R^2$ is hydrogen or a radical as mentioned above under $R^1$.

Most particular preference is given to the compounds of the formula I, where $R^1$ is nitro, halogen, eg. fluorine, chlorine or bromine, $C_1$–$C_6$-haloalkyl, —$OR^6$ or —$SO_2R^8$;

$R^2$ is nitro, halogen, eg. fluorine, chlorine or bromine, $C_1$–$C_6$-alkyl, eg. methyl or ethyl, $C_1$–$C_6$-haloalkyl, —$OR^6$ or —$SO_2R^8$, eg. methylsulfonyl or ethylsulfonyl.

Likewise, very particular preference is given to the compounds of the formula I, where $R^4$ is hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which carries a radical from the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, it being possible for the last six radicals to be substituted;

$R^5$ is hydrogen, halogen, cyano, thiocyanato, $C_1$–$C_6$-alkyl, $C_1$–$C_6$-haloalkyl, —$COR^{10}$, —$CO_2R^{10}$, —$COSR^{10}$, —$CONR^{10}R^{11}$ or —$PO(OR^{10})(OR^{11})$;

or $R^4$ and $R^5$ together form a $C_2$–$C_6$-alkanediyl chain which may be mono- to tetrasubstituted by $C_1$–$C_4$-alkyl and/or interrupted by oxygen or sulfur or by nitrogen with or without substitution by $C_1$–$C_4$-alkyl.

Most particular preference is given to the compounds of the formula I, where $R^4$ is hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which carries a radical from the following group: —$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, it being possible for the last six radicals to be substituted;

$R^5$ is hydrogen, halogen, cyano, thiocyanato, $C_1$–$C_6$-alkyl, $C_1$–$C_6$-haloalkyl, —$COR^{10}$, —$CO_2R^{10}$, —$COSR^{10}$, —$CONR^{10}R^{11}$ or —$PO(OR^{10})(OR^{11})$.

Very especially preferred are compounds of the formula I where $R^4$ is hydrogen, cyano, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, —$COR^{10}$, —$CO_2R^{10}$, —$COSR^{10}$, —$CONR^{10}R^{11}$, —$C(R^{12})$=$NR^{13}$, $C_1$–$C_4$-alkyl which carries a radical from the following group: —$COR^{10}$, $CO_2R^{10}$, —$COSR^{10}$, —$CONR^{10}R^{11}$, —$C(R^{12})$=$NR^{13}$; heterocyclyl, heterocyclyl-$C_1$–$C_4$-alkyl, phenyl, phenyl-$C_1$–$C_4$-alkyl, hetaryl or hetaryl-$C_1$–$C_4$-alkyl, it being possible for the last six radicals to be substituted;

$R^5$ is hydrogen, cyano, $C_1$–$C_6$-alkyl, $C_1$–$C_6$-haloalkyl, —$COR^{10}$, —$CO_2R^{10}$, —$COSR^{10}$, —$CONR^{10}R^{11}$ or —$PO(OR^{10})(OR^{11})$.

Likewise, very particular preference is given to compounds of the formula I, where $R^1$ is nitro, halogen, $C_1$–$C_6$-haloalkyl or $C_1$–$C_6$-alkylsulfonyl;

in particular nitro, chlorine, trifluoromethyl, methylsulfonyl or ethylsulfonyl;

$R^2$ is nitro, halogen, $C_1$–$C_6$-alkyl, $C_1$–$C_6$-haloalkyl, $C_1$–$C_6$-alkoxy or $C_1$–$C_6$-alkylsulfonyl;

in particular nitro, chlorine, methyl, trifluoromethyl, methoxy or methylsulfonyl;

$R^3$ is hydrogen or $C_1$–$C_6$-alkyl; in particular hydrogen or methyl, preferably hydrogen;

$R^4$ is hydrogen, halogen, cyano, $C_1$–$C_6$-alkyl, $C_1$–$C_4$-hydroxyalkyl, $C_1$–$C_4$-alkylcarbonyl, $C_1$–$C_4$-alkoxycarbonyl, formyl, hydroxycarbonyl or —$C(R^{12})$=$NR^{13}$;

in particular hydrogen, chlorine, bromine, cyano, methyl, ethyl, isopropyl, methylcarbonyl, ethylcarbonyl, methoxycarbonyl, ethoxycarbonyl or —$C(R^{12})$=$NR^{13}$;

$R^5$ is hydrogen, halogen or $C_1$–$C_4$-alkyl;

in particular hydrogen, chlorine, methyl or ethyl;

$R^{12}$ is hydrogen, $C_1$–$C_4$-alkyl or $C_1$–$C_4$-alkoxy;

in particular hydrogen or methyl;

$R^{13}$ is $C_1$–$C_6$-alkyl or $C_1$–$C_6$-alkoxy;

in particular methoxy or ethoxy;

$R^{14}$ is $C_1$–$C_6$-alkyl;

in particular methyl or ethyl;

$R^{15}$ is hydrogen, $C_1$–$C_6$-alkylsulfonyl or phenyl-$C_1$–$C_4$-alkyl, it being possible for the phenyl ring of the last radical to be partially or fully halogenated and/or to carry one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy;

in particular hydrogen, methylsulfonyl, ethylsulfonyl or benzyl;

$R^{16}$ is hydrogen or $C_1$–$C_4$-alkyl;

in particular hydrogen or methyl, the radical definitions $R^1$ to $R^{16}$ not only in combination with one another but also in each case on their own being especially important for the compounds of the formula I according to the invention.

Particularly especially preferred are compounds of the formula Ia (= I where $R^1$ is attached in position 4 of the phenyl ring and $R^2$ is attached in position 2 of the phenyl ring).

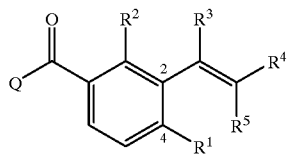

Extraordinary preference is given to the compounds Ia1 (= I where $R^1$=Cl, $R^{14}$=$CH_3$ and $R^{15}$ and $R^{16}$=H, and where $R^1$ is attached in position 4 of the phenyl ring and $R^2$ is attached in position 2 of the phenyl ring), in particular the compounds of Table 1, the radical definitions $R^2$ to $R^5$ not only in combination with one another but also in each case on their own being specially important for the compounds according to the invention.

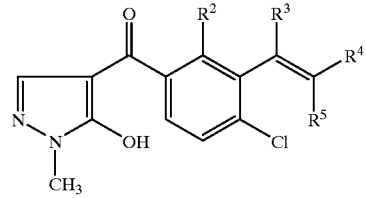

TABLE 1

| No. | $R^2$ | $R^3$ | $R^4$ | $R^5$ |
|---|---|---|---|---|
| Ia1.001 | Cl | H | H | H |
| Ia1.002 | Cl | H | $CH_3$ | H |
| Ia1.003 | Cl | H | $CH_3$ | $CH_3$ |
| Ia1.004 | Cl | H | $C_2H_5$ | H |
| Ia1.005 | Cl | H | n-$C_3H_7$ | H |
| Ia1.006 | Cl | H | n-$C_4H_9$ | H |
| Ia1.007 | Cl | H | $CH(CH_3)_2$ | H |
| Ia1.008 | Cl | H | cyclo-$C_3H_5$ | H |
| Ia1.009 | Cl | H | cyclo-$C_4H_7$ | H |
| Ia1.010 | Cl | H | cyclo-$C_5H_9$ | H |
| Ia1.011 | Cl | H | cyclo-$C_6H_{11}$ | H |
| Ia1.012 | Cl | H | $C_6H_5$ | H |
| Ia1.013 | Cl | H | $CH_2$—$C_6H_5$ | H |
| Ia1.014 | Cl | H | 2-furyl | H |
| Ia1.015 | Cl | H | 3-furyl | H |
| Ia1.016 | Cl | H | 2-thienyl | H |
| Ia1.017 | Cl | H | 3-thienyl | H |
| Ia1.018 | Cl | H | 1,3-dioxan-2-yl | H |
| Ia1.019 | Cl | H | CHO | H |
| Ia1.020 | Cl | H | $COCH_3$ | H |
| Ia1.021 | Cl | H | $COOCH_3$ | H |
| Ia1.022 | Cl | H | $COOC_2H_5$ | H |
| Ia1.023 | Cl | H | COO-n-$C_3H_7$ | H |
| Ia1.024 | Cl | H | CN | H |
| Ia1.025 | Cl | H | $SCH_3$ | H |
| Ia1.026 | Cl | H | $COCF_3$ | H |
| Ia1.027 | Cl | H | $COC_6H_5$ | H |
| Ia1.028 | Cl | H | CH=$NOCH_3$ | H |
| Ia1.029 | Cl | H | CH=$NOC_2H_5$ | H |
| Ia1.030 | Cl | H | $C(CH_3)$=$NOCH_3$ | H |
| Ia1.031 | $CH_3$ | H | H | H |
| Ia1.032 | $CH_3$ | H | $CH_3$ | H |
| Ia1.033 | $CH_3$ | H | $CH_3$ | $CH_3$ |
| Ia1.034 | $CH_3$ | H | $C_2H_5$ | H |
| Ia1.035 | $CH_3$ | H | n-$C_3H_7$ | H |
| Ia1.036 | $CH_3$ | H | n-$C_4H_9$ | H |
| Ia1.037 | $CH_3$ | H | CHO | H |
| Ia1.038 | $CH_3$ | H | $COCH_3$ | H |
| Ia1.039 | $CH_3$ | H | $COOCH_3$ | H |
| Ia1.040 | $CH_3$ | H | $COOC_2H_5$ | H |
| Ia1.041 | $CH_3$ | H | $C_6H_5$ | H |
| Ia1.042 | $CH_3$ | H | $C_6H_5$ | $CH_3$ |
| Ia1.043 | $CH_3$ | H | $C_6H_5$ | $C_2H_5$ |
| Ia1.044 | $CH_3$ | H | $CH_2$—CHO | H |
| Ia1.045 | $CH_3$ | H | $COOCH_2C_6H_5$ | H |
| Ia1.046 | $CH_3$ | Cl | $CH_3$ | H |
| Ia1.047 | $CH_3$ | $CH_3$ | $CH_3$ | H |
| Ia1.048 | $CH_3$ | $C_2H_5$ | $CH_3$ | H |
| Ia1.049 | $CH_3$ | $CF_3$ | $CH_3$ | H |
| Ia1.050 | $CH_3$ | $OCH_3$ | $CH_3$ | H |
| Ia1.051 | $CH_3$ | $OC_2H_5$ | $CH_3$ | H |
| Ia1.052 | $CH_3$ | $CH_2$—C≡CH | $CH_3$ | H |
| Ia1.053 | $CH_3$ | $CH_2$—CH=$CH_2$ | $CH_3$ | H |
| Ia1.054 | $CH_3$ | Cl | $C_2H_5$ | H |
| Ia1.055 | $CH_3$ | $CH_3$ | $C_2H_5$ | H |
| Ia1.056 | $CH_3$ | $CF_3$ | $C_2H_5$ | H |
| Ia1.057 | $CH_3$ | $OCH_3$ | $C_2H_5$ | H |

TABLE 1-continued

| No. | $R^2$ | $R^3$ | $R^4$ | $R^5$ |
|---|---|---|---|---|
| Ia1.058 | $CH_3$ | $OC_2H_5$ | $C_2H_5$ | H |
| Ia1.059 | $CH_3$ | $CH_2-C\equiv CH$ | $C_2H_5$ | H |
| Ia1.060 | $CH_3$ | $CH_2-CH=CH_2$ | $C_2H_5$ | H |
| Ia1.061 | $OCH_3$ | H | H | H |
| Ia1.062 | $OCH_3$ | H | $CH_3$ | H |
| Ia1.063 | $OCH_3$ | H | $C_2H_5$ | H |
| Ia1.064 | $OCH_3$ | H | $n-C_3H_7$ | H |
| Ia1.065 | $OCH_3$ | H | $n-C_4H_9$ | H |
| Ia1.066 | $OCH_3$ | H | CHO | H |
| Ia1.067 | $OCH_3$ | H | $COCH_3$ | H |
| Ia1.068 | $OCH_3$ | H | $COOCH_3$ | H |
| Ia1.069 | $OCH_3$ | H | $COOC_2H_5$ | H |
| Ia1.070 | $OCH_3$ | H | $C_6H_5$ | H |
| Ia1.071 | $OCH_3$ | H | $CH=NOCH_3$ | H |
| Ia1.072 | $OCH_3$ | H | $C(CH_3)=NOCH_3$ | H |
| Ia1.073 | $OCH_3$ | $CH_3$ | $2-Cl-C_6H_4$ | H |
| Ia1.074 | $OCH_3$ | $CH_3$ | $3-Br-C_6H_4$ | H |
| Ia1.075 | $OCH_3$ | $CH_3$ | $4-F-C_6H_4$ | H |
| Ia1.076 | $OCH_3$ | $CH_3$ | $2,4-Cl_2-C_6H_3$ | H |
| Ia1.077 | $OCH_3$ | $CH_3$ | $2-NO_2-C_6H_4$ | H |
| Ia1.078 | $OCH_3$ | $CH_3$ | $3-CN-C_6H_4$ | H |
| Ia1.079 | $OCH_3$ | $CH_3$ | $4-CH_3-C_6H_4$ | H |
| Ia1.080 | $OCH_3$ | $CH_3$ | $2-OCH_3-C_6H_4$ | H |
| Ia1.081 | $OCH_3$ | $CH_3$ | $3-CF_3-C_6H_4$ | H |
| Ia1.082 | $OCH_3$ | $CH_3$ | $4-OCF_3-C_6H_4$ | H |
| Ia1.083 | $OCH_3$ | $CH_3$ | $2-CH_3-C_6H_4$ | H |
| Ia1.084 | $OCH_3$ | $CH_3$ | $3-CH_3-C_6H_4$ | H |
| Ia1.085 | $OCH_3$ | $CH_3$ | $2-COCH_3-C_6H_4$ | H |
| Ia1.086 | $OCH_3$ | $CH_3$ | $3-COOMe-C_6H_4$ | H |
| Ia1.087 | $OCH_3$ | $CH_3$ | $4-CF_3-C_6H_4$ | H |
| Ia1.088 | $OCH_3$ | $CH_3$ | $2-CF_3-C_6H_4$ | H |
| Ia1.089 | $OCH_3$ | $CH_3$ | $3-OCH_3-C_6H_4$ | H |
| Ia1.090 | $OCH_3$ | $CH_3$ | $4-OCH_3-C_6H_4$ | H |
| Ia1.091 | $CF_3$ | H | H | H |
| Ia1.092 | $CF_3$ | H | $CH_3$ | H |
| Ia1.093 | $CF_3$ | H | $C_2H_5$ | H |
| Ia1.094 | $CF_3$ | H | $n-C_3H_7$ | H |
| Ia1.095 | $CF_3$ | H | $n-C_4H_9$ | H |
| Ia1.096 | $CF_3$ | H | CHO | H |
| Ia1.097 | $CF_3$ | H | $COCH_3$ | H |
| Ia1.098 | $CF_3$ | H | $COOCH_3$ | H |
| Ia1.099 | $CF_3$ | H | $COOC_2H_5$ | H |
| Ia1.100 | $CF_3$ | H | $C_6H_5$ | H |
| Ia1.101 | $CF_3$ | H | $CH=NOCH_3$ | H |
| Ia1.102 | $CF_3$ | H | $C(CH_3)=NOCH_3$ | H |
| Ia1.103 | $CF_3$ | H | 2-furyl | $CH_3$ |
| Ia1.104 | $CF_3$ | H | 3-furyl | $CH_3$ |
| Ia1.105 | $CF_3$ | H | 2-thienyl | $CH_3$ |
| Ia1.106 | $CF_3$ | H | 3-thienyl | $CH_3$ |
| Ia1.107 | $CF_3$ | H | 2-pyridyl | $CH_3$ |
| Ia1.108 | $CF_3$ | H | 3-pyridyl | $CH_3$ |
| Ia1.109 | $CF_3$ | H | 4-pyridyl | $CH_3$ |
| Ia1.110 | $CF_3$ | H | 2-thiazolyl | $CH_3$ |
| Ia1.111 | $CF_3$ | H | 4-thiazolyl | $CH_3$ |
| Ia1.112 | $CF_3$ | H | 5-thiazolyl | $CH_3$ |
| Ia1.113 | $CF_3$ | H | 2-pyrrolyl | $CH_3$ |
| Ia1.114 | $CF_3$ | H | 3-pyrrolyl | $CH_3$ |
| Ia1.115 | $CF_3$ | H | 4-pyrrolyl | $CH_3$ |
| Ia1.116 | $CF_3$ | H | 3-isoxazolyl | $CH_3$ |
| Ia1.117 | $CF_3$ | H | 4-isoxazolyl | $CH_3$ |
| Ia1.118 | $CF_3$ | H | 5-isoxazolyl | $CH_3$ |
| Ia1.119 | $CF_3$ | H | 2-oxazolyl | $CH_3$ |
| Ia1.120 | $CF_3$ | H | 4-oxazolyl | $CH_3$ |
| Ia1.121 | $SO_2CH_3$ | H | H | H |
| Ia1.122 | $SO_2CH_3$ | H | $CH_3$ | H |
| Ia1.123 | $SO_2CH_3$ | H | $C_2H_5$ | H |
| Ia1.124 | $SO_2CH_3$ | H | $n-C_3H_7$ | H |
| Ia1.125 | $SO_2CH_3$ | H | $n-C_4H_9$ | H |
| Ia1.126 | $SO_2CH_3$ | H | CHO | H |
| Ia1.127 | $SO_2CH_3$ | H | $COCH_3$ | H |
| Ia1.128 | $SO_2CH_3$ | H | $COOCH_3$ | H |
| Ia1.129 | $SO_2CH_3$ | H | $CO_2C_2H_5$ | H |
| Ia1.130 | $SO_2CH_3$ | H | $C_6H_5$ | H |
| Ia1.131 | $SO_2CH_3$ | H | $CH=NOCH_3$ | H |
| Ia1.132 | $SO_2CH_3$ | H | $C(CH_3)=NOCH_3$ | H |
| Ia1.133 | $SO_2CH_3$ | $C_2H_5$ | 5-oxazolyl | H |
| Ia1.134 | $SO_2CH_3$ | $C_2H_5$ | 3-pyrazolyl | H |

TABLE 1-continued

| No. | $R^2$ | $R^3$ | $R^4$ | $R^5$ |
|---|---|---|---|---|
| Ia1.135 | $SO_2CH_3$ | $C_2H_5$ | 4-pyrazolyl | H |
| Ia1.136 | $SO_2CH_3$ | $C_2H_5$ | 5-pyrazolyl | H |
| Ia1.137 | $SO_2CH_3$ | $C_2H_5$ | 2-imidazolyl | H |
| Ia1.138 | $SO_2CH_3$ | $C_2H_5$ | 4-imidazolyl | H |
| Ia1.139 | $SO_2CH_3$ | $C_2H_5$ | 5-imidazolyl | H |
| Ia1.140 | $SO_2CH_3$ | $C_2H_5$ | 2-pyrimidinyl | H |
| Ia1.141 | $SO_2CH_3$ | $C_2H_5$ | 4-pyrimidinyl | H |
| Ia1.142 | $SO_2CH_3$ | $C_2H_5$ | 5-pyrimidinyl | H |
| Ia1.143 | $SO_2CH_3$ | $C_2H_5$ | 1,3-dioxolan-2-yl | H |
| Ia1.144 | $SO_2CH_3$ | $C_2H_5$ | 1,3-dioxolan-4-yl | H |
| Ia1.145 | $SO_2CH_3$ | $C_2H_5$ | 1,3-dioxan-2-yl | H |
| Ia1.146 | $SO_2CH_3$ | $C_2H_5$ | 3-pyridazinyl | H |
| Ia1.147 | $SO_2CH_3$ | $C_2H_5$ | 4-pyridazinyl | H |
| Ia1.148 | $SO_2CH_3$ | $C_2H_5$ | 2-pyrazinyl | H |
| Ia1.149 | $SO_2CH_3$ | $C_2H_5$ | 2-pyridyl | H |
| Ia1.150 | $SO_2CH_3$ | $C_2H_5$ | 2-N-methylpyrrolyl | H |
| Ia1.151 | $NO_2$ | H | H | H |
| Ia1.152 | $NO_2$ | H | $CH_3$ | H |
| Ia1.153 | $NO_2$ | H | $C_2H_5$ | H |
| Ia1.154 | $NO_2$ | H | $n-C_3H_7$ | H |
| Ia1.155 | $NO_2$ | H | $n-C_4H_9$ | H |
| Ia1.156 | $NO_2$ | H | CHO | H |
| Ia1.157 | $NO_2$ | H | $COCH_3$ | H |
| Ia1.158 | $NO_2$ | H | $COOCH_3$ | H |
| Ia1.159 | $NO_2$ | H | $CO_2C_2H_5$ | H |
| Ia1.160 | $NO_2$ | H | $C_6H_5$ | H |
| Ia1.161 | $NO_2$ | H | $CH=NOCH_3$ | H |
| Ia1.162 | $NO_2$ | H | $C(CH_3)=NOCH_3$ | H |
| Ia1.163 | $NO_2$ | H | COOH | $C_2H_5$ |
| Ia1.164 | $NO_2$ | H | COOMe | $C_2H_5$ |
| Ia1.165 | $NO_2$ | H | $COOC_2H_5$ | $C_2H_5$ |
| Ia1.166 | $NO_2$ | H | $COOCH_2C_6H_5$ | $C_2H_5$ |
| Ia1.167 | $NO_2$ | H | $COOC(CH_3)_3$ | $C_2H_5$ |
| Ia1.168 | $NO_2$ | H | $CH=NOCH_3$ | $C_2H_5$ |
| Ia1.169 | $NO_2$ | H | $CH=NOC_2H_5$ | $C_2H_5$ |
| Ia1.170 | $NO_2$ | H | $CH=NOCH_2C_6H_5$ | $C_2H_5$ |
| Ia1.171 | $NO_2$ | H | $CH=NOCH(CH_3)_2$ | $C_2H_5$ |
| Ia1.172 | $NO_2$ | H | $C(CH_3)=NOCH_3$ | $C_2H_5$ |
| Ia1.173 | $NO_2$ | H | $C(CH_3)=NOC_2H_5$ | $C_2H_5$ |
| Ia1.174 | $NO_2$ | H | $C(CH_3)=NOCH(CH_3)_2$ | $C_2H_5$ |
| Ia1.175 | $NO_2$ | H | $C(CH_3)=NOCH_2C_6H_5$ | $C_2H_5$ |
| Ia1.176 | $NO_2$ | H | $CH=NOCH_2-CH=CH_2$ | $C_2H_5$ |
| Ia1.177 | $NO_2$ | H | $CH=NOCH_2-C\equiv CH$ | $C_2H_5$ |
| Ia1.178 | $NO_2$ | H | $CH_2-CHO$ | $C_2H_5$ |
| Ia1.179 | $NO_2$ | H | $CH_2-CH=NOCH_3$ | $C_2H_5$ |
| Ia1.180 | $NO_2$ | H | $CH_2-CH=NOC_2H_5$ | $C_2H_5$ |

Likewise, extraordinary preference is given to the compounds Ia2, in particular to the compounds Ia2.001–Ia2.180, which differ from the corresponding compounds Ia1.001–Ia1.180 in that $R^{14}$ is ethyl:

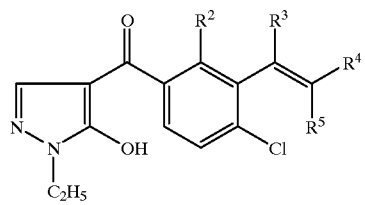

Ia2

Likewise, extraordinary preference is given to the compounds Ia3, in particular to the compounds Ia3.001–Ia3.180, which differ from the corresponding compounds Ia1.001–Ia1.180 in that $R^{14}$ is n-propyl:

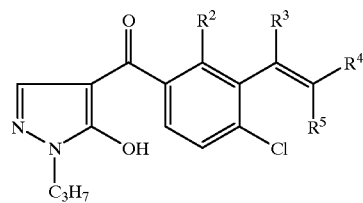

Ia3

Likewise, extraordinary preference is given to the compounds Ia4, in particular to the compounds Ia4.001–Ia4.180, which differ from the corresponding compounds Ia1.001–Ia1.180 in that $R^{14}$ is n-butyl:

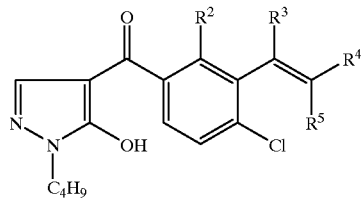

Ia4

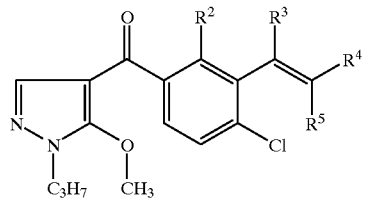

Ia8

Likewise, extraordinary preference is given to the compounds Ia5, in particular to the compounds Ia5.001–Ia5.180, which differ from the corresponding compounds Ia1.001–Ia1.180 in that $R^{14}$ is isobutyl steht:

Likewise, extraordinary preference is given to the compounds Ia9, in particular to the compounds Ia9.001–Ia9.180, which differ from the corresponding compounds Ia1.001–Ia1.180 in that $R^{14}$ is n-butyl and $R^{15}$ is methyl:

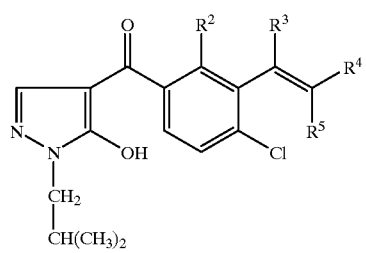

Ia5

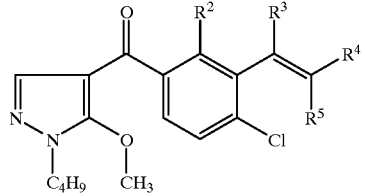

Ia9

Likewise, extraordinary preference is given to the compounds Ia6, in particular to the compounds Ia6.001–Ia6.180, which differ from the corresponding compounds Ia1.001–Ia1.180 in that $R^{15}$ is methyl:

Likewise, extraordinary preference is given to the compounds Ia10, in particular to the compounds Ia10.001–Ia10.180, which differ from the corresponding compounds Ia1.001–Ia1.180 in that $R^{14}$ is isobutyl and $R^{15}$ is methyl:

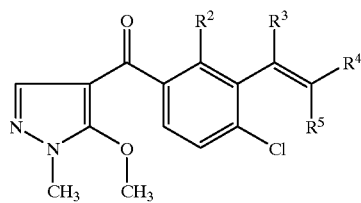

Ia6

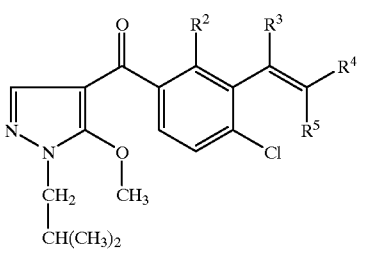

Ia10

Likewise, extraordinary preference is given to the compounds Ia7, in particular to the compounds Ia7.001–Ia7.180, which differ from the corresponding compounds Ia1.001–Ia1.180 in that $R^{14}$ is ethyl and $R^{15}$ is methyl:

Likewise, extraordinary preference is given to the compounds Ia11, in particular to the compounds Ia11.001–Ia11.180, which differ from the corresponding compounds Ia1.001–Ia1.180 in that $R^{15}$ is ethyl:

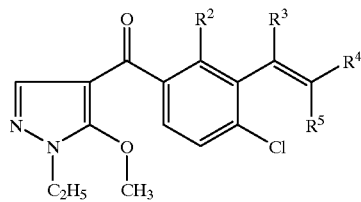

Ia7

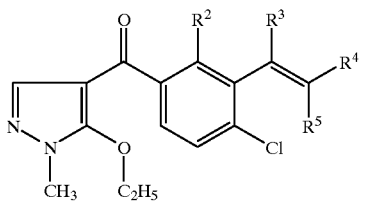

Ia11

Likewise, extraordinary preference is given to the compounds Ia8, in particular to the compounds Ia8.001–Ia8.180, which differ from the corresponding compounds Ia1.001–Ia1.180 in that $R^{14}$ is n-propyl and $R^{15}$ is methyl:

Likewise, extraordinary preference is given to the compounds Ia12, in particular to the compounds Ia12.001–Ia12.180, which differ from the corresponding compounds Ia1.001–Ia1.180 in that $R^{14}$ and $R^{15}$ are each ethyl:

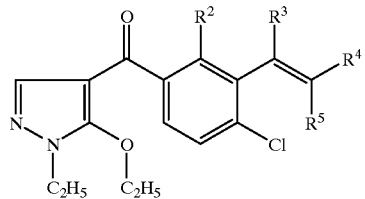

Ia12

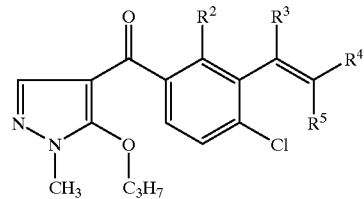

Ia16

Likewise, extraordinary preference is given to the compounds Ia13, in particular to the compounds Ia13.001–Ia13.180, which differ from the corresponding compounds Ia1.001–Ia1.180 in that $R^{14}$ is propyl and $R^{15}$ is ethyl:

Likewise, extraordinary preference is given to the compounds Ia15, in particular to the compounds Ia15.001–Ia15.180, which differ from the corresponding compounds Ia1.001–Ia1.180 in that $R^{15}$ is n-propyl:

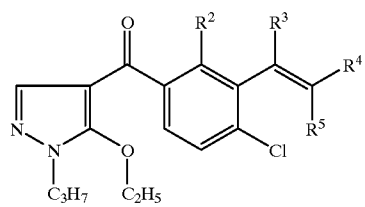

Ia13

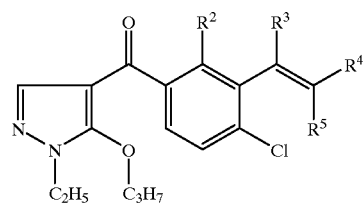

Ia17

Likewise, extraordinary preference is given to the compounds Ia14, in particular to the compounds Ia14.001–Ia14.180, which differ from the corresponding compounds Ia1.001–Ia1.180 in that $R^{14}$ is n-butyl and $R^{15}$ is ethyl:

Likewise, extraordinary preference is given to the compounds Ia18, in particular to the compounds Ia18.001–Ia18.180, which differ from the corresponding compounds Ia1.001–Ia1.180 in that $R^{14}$ and $R^{15}$ are each n-propyl:

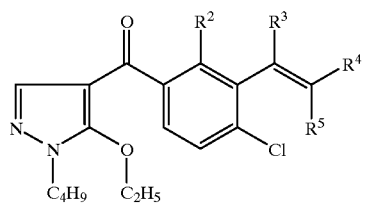

Ia14

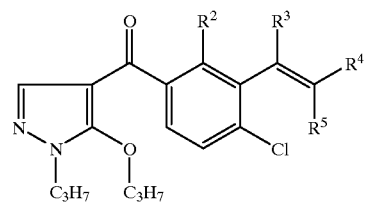

Ia18

Likewise, extraordinary preference is given to the compounds Ia15, in particular to the compounds Ia15.001–Ia15.180, which is differ from the corresponding compounds Ia1.001–Ia1.180 in that $R^{14}$ is isobutyl and $R^{15}$ is ethyl:

Likewise, extraordinary preference is given to the compounds Ia19, in particular to the compounds Ia19.001–Ia19.180, which differ from the corresponding compounds Ia1.001–Ia1.180 in that $R^{14}$ is n-butyl and $R^{15}$ is n-propyl:

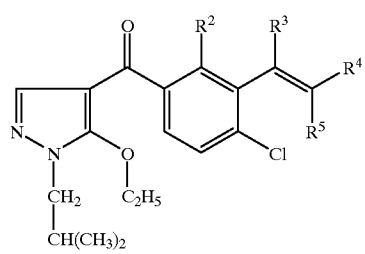

Ia15

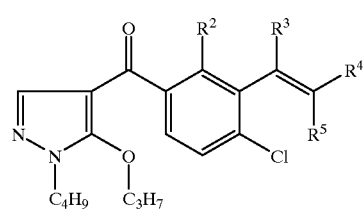

Ia19

Likewise, extraordinary preference is given to the compounds Ia16, in particular to the compounds Ia16.001–Ia16.180, which differ from the corresponding compounds Ia1.001–Ia1.180 in Likewise, extraordinary preference is given to the compounds Ia20, in particular to the compounds Ia20.001–Ia20.180, which differ from the corresponding compounds Ia1.001–Ia1.180 in that $R^{14}$ is isobutyl and $R^{15}$ is n-propyl:

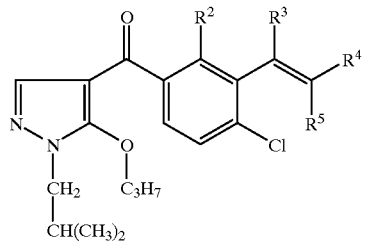
Ia20

Likewise, extraordinary preference is given to the compounds Ia21, in particular to the compounds Ia21.001–Ia21.180, which differ from the corresponding compounds Ia1.001–Ia1.180 in that $R^{15}$ is isopropyl:

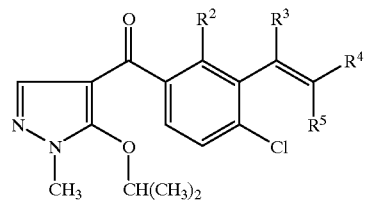
Ia21

Likewise, extraordinary preference is given to the compounds Ia22, in particular to the compounds Ia22.001–Ia22.180, which differ from the corresponding compounds Ia1.001–Ia1.180 in that $R^{14}$ is ethyl and $R^{15}$ is isopropyl:

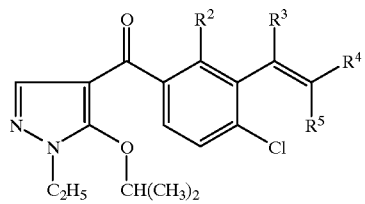
Ia22

Likewise, extraordinary preference is given to the compounds Ia23, in particular to the compounds Ia23.001–Ia23.180, which differ from the corresponding compounds Ia1.001–Ia1.180 in that $R^{14}$ is n-propyl and $R^{15}$ is isopropyl:

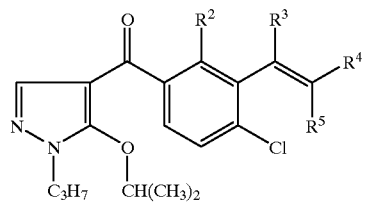
Ia23

Likewise, extraordinary preference is given to the compounds Ia24, in particular to the compounds Ia24.001–Ia24.180, which differ from the corresponding compounds Ia1.001–Ia1.180 in that $R^{14}$ is n-butyl and $R^{15}$ is isopropyl:

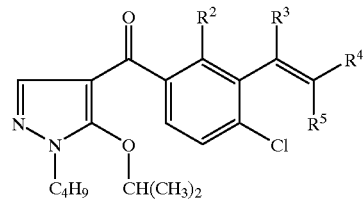
Ia24

Likewise, extraordinary preference is given to the compounds Ia25, in particular to the compounds Ia25.001–Ia25.180, which differ from the corresponding compounds Ia1.001–Ia1.180 in that $R^{14}$ is isobutyl and $R^{15}$ is isopropyl:

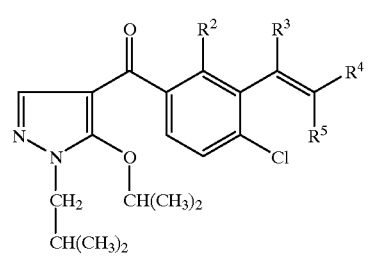
Ia25

Likewise, extraordinary preference is given to the compounds Ia26, in particular to the compounds Ia26.001–Ia26.180, which differ from the corresponding compounds Ia1.001–Ia1.180 in that $R^{15}$ is n-butyl:

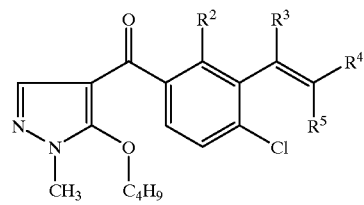
Ia26

Likewise, extraordinary preference is given to the compounds Ia27, in particular to the compounds Ia27.001–Ia27.180, which differ from the corresponding compounds Ia1.001–Ia1.180 in that $R^{14}$ is ethyl and $R^{15}$ is n-butyl:

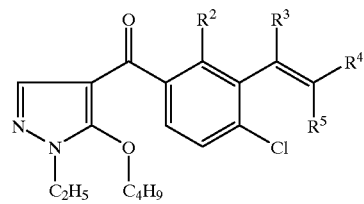
Ia27

Likewise, extraordinary preference is given to the compounds Ia28, in particular to the compounds Ia28.001–Ia28.180, which differ from the corresponding compounds Ia1.001–Ia1.180 in that $R^{14}$ is n-propyl and $R^{15}$ is n-butyl:

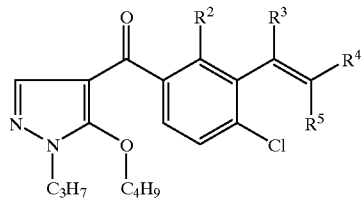

Ia28

Likewise, extraordinary preference is given to the compounds Ia29, in particular to the compounds Ia29.001–Ia29.180, which differ from the corresponding compounds Ia1.001–Ia1.180 in that $R^{14}$ and $R^{15}$ are each n-butyl:

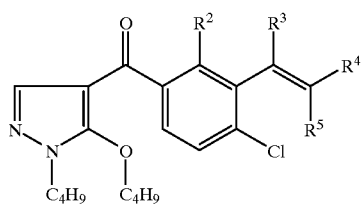

Ia29

Likewise, extraordinary preference is given to the compounds Ia32, in particular to the compounds Ia32.001–Ia32.180, which differ from the corresponding compounds Ia1.001–Ia1.180 in that $R^{14}$ is isobutyl and $R^{15}$ is n-butyl:

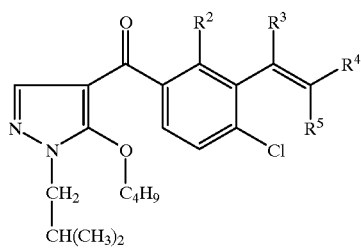

Ia30

Likewise, extraordinary preference is given to the compounds Ia31, in particular to the compounds Ia31.001–Ia31.180, which differ from the corresponding compounds Ia1.001–Ia1.180 in that $R^{15}$ is sec-butyl:

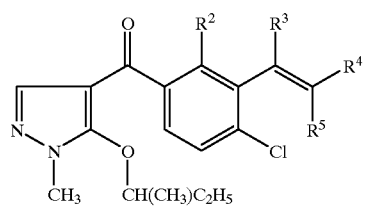

Ia31

Likewise, extraordinary preference is given to the compounds Ia32, in particular to the compounds Ia32.001–Ia32.180, which differ from the corresponding compounds Ia1.001–Ia1.180 in that $R^{14}$ is ethyl and $R^{15}$ is sec-butyl:

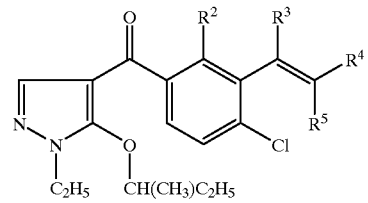

Ia32

Likewise, extraordinary preference is given to the compounds Ia33, in particular to the compounds Ia33.001–Ia33.180, which differ from the corresponding compounds Ia1.001–Ia1.180 in that $R^{14}$ is n-propyl and $R^{15}$ is sec-butyl:

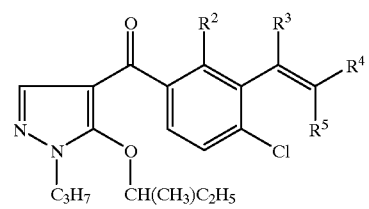

Ia33

Likewise, extraordinary preference is given to the compounds Ia34, in particular to the compounds Ia34.001–Ia34.180, which differ from the corresponding compounds Ia1.001–Ia1.180 in that $R^{14}$ is n-butyl and $R^{15}$ is sec-butyl:

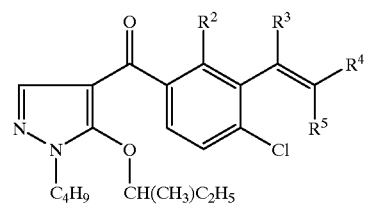

Ia34

Likewise, extraordinary preference is given to the compounds Ia35, in particular to the compounds Ia35.001–Ia35.180, which differ from the corresponding compounds Ia1.001–Ia1.180 in that $R^{14}$ is isobutyl and $R^{15}$ is sec-butyl:

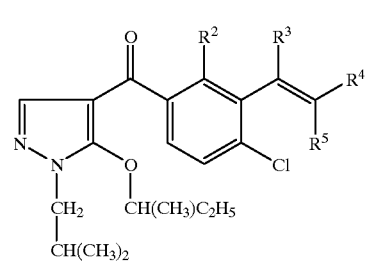

Ia35

Likewise, extraordinary preference is given to the compounds Ia36, in particular to the compounds Ia36.001–Ia36.180, which differ from the corresponding compounds Ia1.001–Ia1.180 in that $R^{15}$ is isobutyl:

Ia36
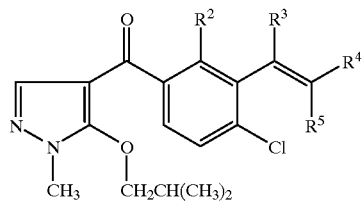

Likewise, extraordinary preference is given to the compounds Ia37, in particular to the compounds Ia37.001–Ia37.180, which differ from the corresponding compounds Ia1.001–Ia1.180 in that $R^{15}$ is ethyl and $R^{16}$ is isobutyl:

Ia37

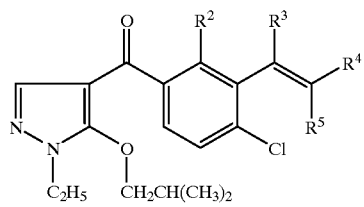

Likewise, extraordinary preference is given to the compounds Ia38, in particular to the compounds Ia38.001–Ia38.180, which differ from the corresponding compounds Ia1.001–Ia1.180 in that $R^{14}$ is n-propyl and $R^{15}$ is isobutyl:

Ia38

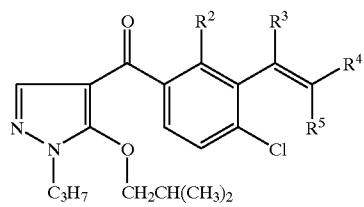

Likewise, extraordinary preference is given to the compounds Ia39, in particular to the compounds Ia39.001–Ia39.180, which differ from the corresponding compounds Ia1.001–Ia1.180 in that $R^{14}$ is n-butyl and $R^{15}$ is isobutyl:

Ia39

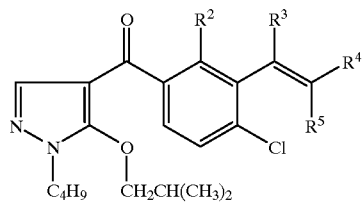

Likewise, extraordinary preference is given to the compounds Ia40, in particular to the compounds Ia40.001–Ia40.180, which differ from the corresponding compounds Ia1.001–Ia1.180 in that $R^{14}$ and $R^{15}$ are each isobutyl:

Ia40

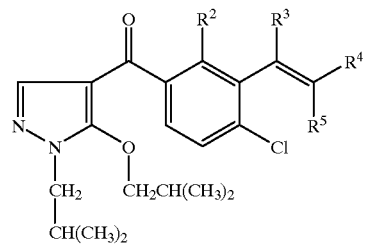

Likewise, extraordinary preference is given to the compounds Ia41, in particular to the compounds Ia41.001–Ia41.180, which differ from the corresponding compounds Ia1.001–Ia1.180 in that $R^{15}$ is methylcarbonyl:

Ia41

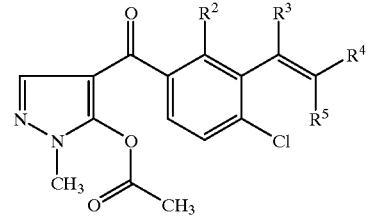

Likewise, extraordinary preference is given to the compounds Ia42, in particular to the compounds Ia42.001–Ia42.180, which differ from the corresponding compounds Ia1.001–Ia1.180 in that $R^{14}$ is ethyl and $R^{15}$ is methylcarbonyl:

Ia42

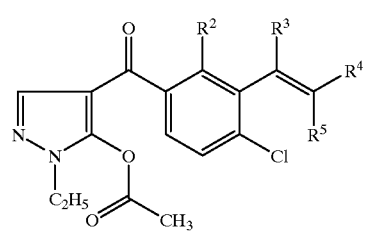

Likewise, extraordinary preference is given to the compounds Ia43, in particular to the compounds Ia43.001–Ia43.180, which differ from the corresponding compounds Ia1.001–Ia1.180 in that $R^{14}$ is propyl and $R^{15}$ is methylcarbonyl:

Ia43

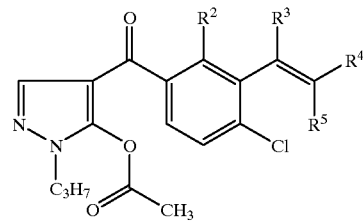

Likewise, extraordinary preference is given to the compounds Ia44, in particular to the compounds Ia44.001–Ia44.180, which differ from the corresponding compounds Ia1.001–Ia1.180 in that $R^{14}$ is n-butyl and $R^{15}$ is methylcarbonyl:

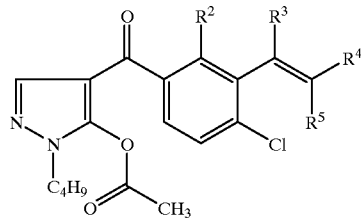

Ia44

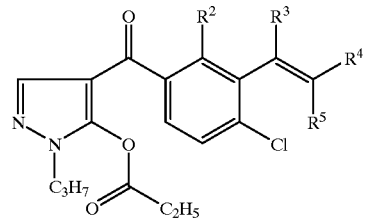

Ia48

Likewise, extraordinary preference is given to the compounds Ia45, in particular to the compounds Ia45.001–Ia45.180, which differ from the corresponding compounds Ia1.001–Ia1.180 in that $R^{14}$ is isobutyl and $R^{15}$ is methylcarbonyl:

Likewise, extraordinary preference is given to the compounds Ia49, in particular to the compounds Ia49.001–Ia49.180, which differ from the corresponding compounds Ia1.001–Ia1.180 in that $R^{14}$ is n-butyl and $R^{15}$ is ethylcarbonyl:

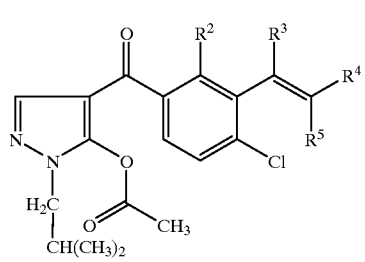

Ia45

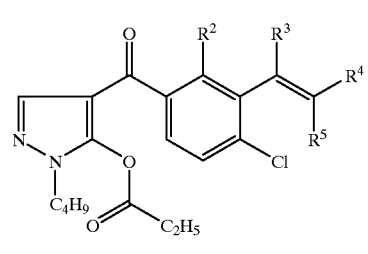

Ia49

Likewise, extraordinary preference is given to the compounds Ia46, in particular to the compounds Ia46.001–Ia46.180, which differ from the corresponding compounds Ia1.001–Ia1.180 in that $R^{15}$ is ethylcarbonyl:

Likewise, extraordinary preference is given to the compounds Ia50, in particular to the compounds Ia50.001–Ia50.180, which differ from the corresponding compounds Ia1.001–Ia1.180 in that $R^{14}$ is isobutyl and $R^{15}$ is ethylcarbonyl:

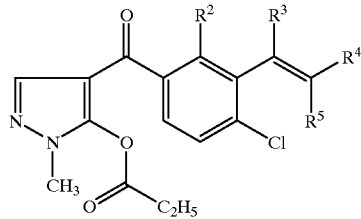

Ia46

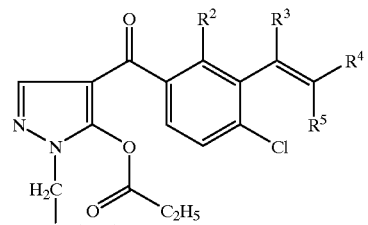

Ia50

Likewise, extraordinary preference is given to the compounds Ia47, in particular to the compounds Ia47.001–Ia47.180, which differ from the corresponding compounds Ia1.001–Ia1.180 in that $R^{14}$ is ethyl and $R^{15}$ is ethylcarbonyl:

Likewise, extraordinary preference is given to the compounds Ia51, in particular to the compounds Ia51.001–Ia51.180, which differ from the corresponding compounds Ia1.001–Ia1.180 in that $R^{15}$ is n-propylcarbonyl:

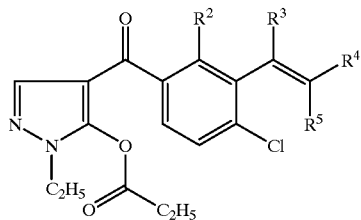

Ia47

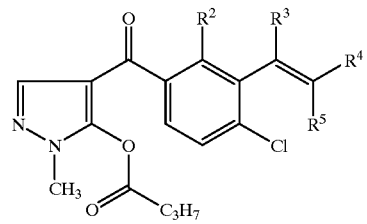

Ia51

Likewise, extraordinary preference is given to the compounds Ia48, in particular to the compounds Ia48.001–Ia48.180, which differ from the corresponding compounds Ia1.001–Ia1.180 in that $R^{14}$ is propyl and $R^{15}$ is ethylcarbonyl:

Likewise, extraordinary preference is given to the compounds Ia52, in particular to the compounds Ia52.001–Ia52.180, which differ from the corresponding compounds Ia1.001–Ia1.180 in that $R^{14}$ is ethyl and $R^{15}$ is n-propylcarbonyl:

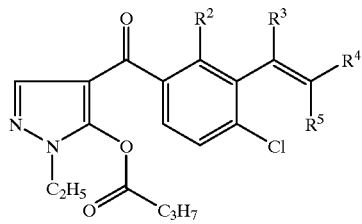
Ia52

Likewise, extraordinary preference is given to the compounds Ia53, in particular to the compounds Ia53.001–Ia53.180, which differ from the corresponding compounds Ia1.001–Ia1.180 in that $R^{14}$ is propyl and $R^{15}$ is n-propylcarbonyl:

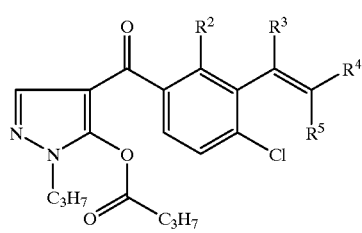
Ia53

Likewise, extraordinary preference is given to the compounds Ia54, in particular to the compounds Ia54.001–Ia54.180, which differ from the corresponding compounds Ia1.001–Ia1.180 in that $R^{14}$ is n-butyl and $R^{15}$ is n-propylcarbonyl:

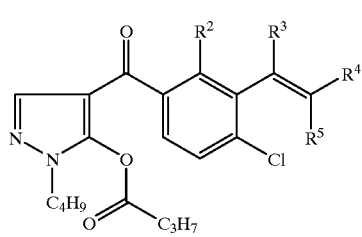
Ia54

Likewise, extraordinary preference is given to the compounds Ia55, in particular to the compounds Ia55.001–Ia55.180, which differ from the corresponding compounds Ia1.001–Ia1.180 in that $R^{14}$ is isobutyl and $R^{15}$ is n-propylcarbonyl:

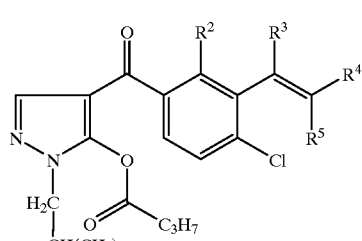
Ia55

Likewise, extraordinary preference is given to the compounds Ia56, in particular to the compounds Ia56.001–Ia56.180, which differ from the corresponding compounds Ia1.001–Ia1.180 in that $R^{15}$ is trifluoromethylcarbonyl:

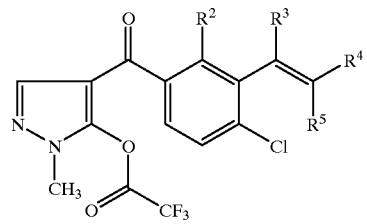
Ia56

Likewise, extraordinary preference is given to the compounds Ia57, in particular to the compounds Ia57.001–Ia57.180, which differ from the corresponding compounds Ia1.001–Ia1.180 in that $R^{14}$ is ethyl and is $R^{15}$ trifluoromethylcarbonyl:

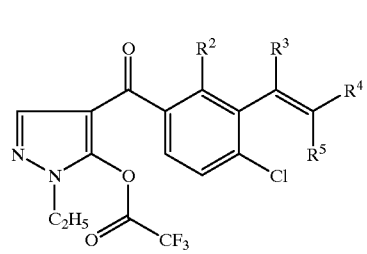
Ia57

Likewise, extraordinary preference is given to the compounds Ia58, in particular to the compounds Ia58.001–Ia58.180, which differ from the corresponding compounds Ia1.001–Ia1.180 in that $R^{14}$ is n-propyl and $R^{15}$ is trifluoromethylcarbonyl:

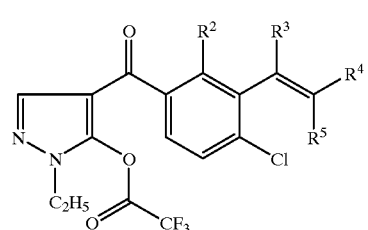
Ia58

Likewise, extraordinary preference is given to the compounds Ia59, in particular to the compounds Ia59.001–Ia59.180, which differ from the corresponding compounds Ia1.001–Ia1.180 in that $R^{14}$ is n-butyl and $R^{15}$ is trifluoromethylcarbonyl:

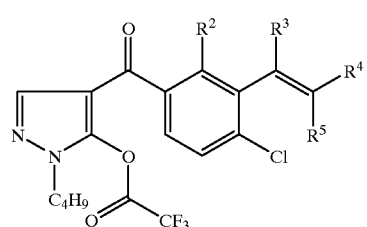
Ia59

Likewise, extraordinary preference is given to the compounds Ia60, in particular to the compounds Ia60.001–Ia60.180, which differ from the corresponding compounds Ia1.001–Ia1.180 in that $R^{14}$ is isobutyl and $R^{15}$ is trifluoromethylcarbonyl:

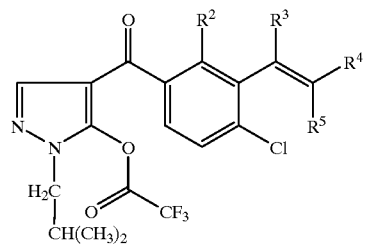

Ia60

Likewise, extraordinary preference is given to the compounds Ia61, in particular to the compounds Ia61.001–Ia61.180, which differ from the corresponding compounds Ia1.001–Ia1.180 in that $R^{15}$ is methylsulfonyl:

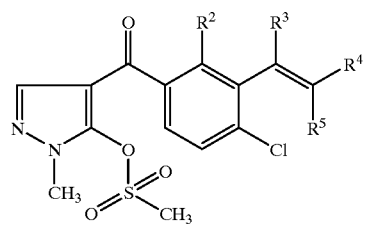

Ia61

Likewise, extraordinary preference is given to the compounds Ia62, in particular to the compounds Ia62.001–Ia62.180, which differ from the corresponding compounds Ia1.001–Ia1.180 in that $R^{14}$ is ethyl and $R^{15}$ is methylsulfonyl:

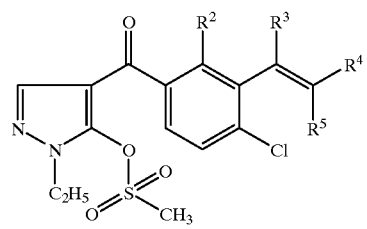

Ia62

Likewise, extraordinary preference is given to the compounds Ia63, in particular to the compounds Ia63.001–Ia63.180, which differ from the corresponding compounds Ia1.001–Ia1.180 in that $R^{14}$ is n-propyl and $R^{15}$ is methylsulfonyl:

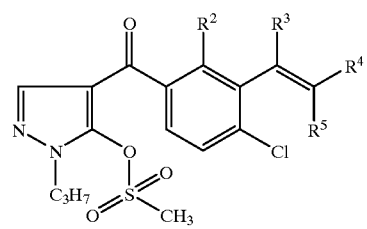

Ia63

Likewise, extraordinary preference is given to the compounds Ia64, in particular to the compounds Ia64.001–Ia64.180, which differ from the corresponding compounds Ia1.001–Ia1.180 in that $R^{14}$ is n-butyl and $R^{15}$ is methylsulfonyl:

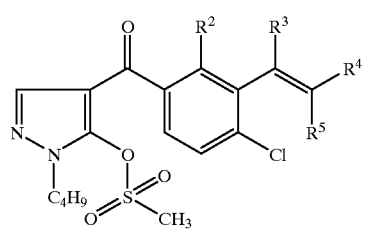

Ia64

Likewise, extraordinary preference is given to the compounds Ia65, in particular to the compounds Ia65.001–Ia65.180, which differ from the corresponding compounds Ia1.001–Ia1.180 in that $R^{14}$ is isobutyl and $R^{15}$ is methylsulfonyl:

Ia65

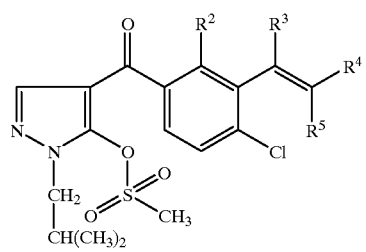

Likewise, extraordinary preference is given to the compounds Ia66, in particular to the compounds Ia66.001–Ia66.180, which differ from the corresponding compounds Ia1.001–Ia1.180 in that $R^{14}$ is n-butyl and $R^{15}$ is methylsulfonyl:

Ia66

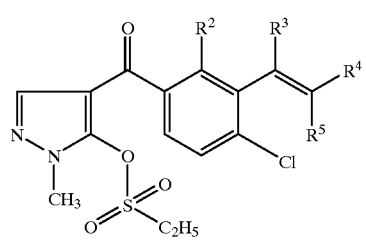

Likewise, extraordinary preference is given to the compounds Ia67, in particular to the compounds Ia67.001–Ia67.180, which differ from the corresponding compounds Ia1.001–Ia1.180 in that $R^{14}$ is ethyl and $R^{15}$ is ethylsulfonyl:

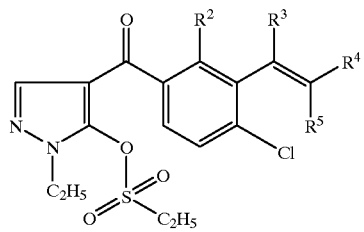

Ia67

Likewise, extraordinary preference is given to the compounds Ia68, in particular to the compounds Ia68.001–Ia68.180, which differ from the corresponding compounds Ia1.001–Ia1.180 in that $R^{14}$ is propyl and $R^{15}$ is ethylsulfonyl:

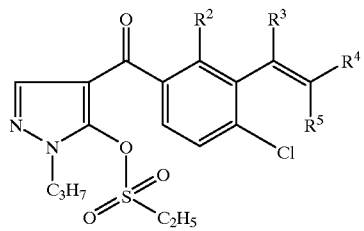

Ia68

Likewise, extraordinary preference is given to the compounds Ia69, in particular to the compounds Ia69.001–Ia69.180, which differ from the corresponding compounds Ia1.001–Ia1.180 in that $R^{14}$ is n-butyl and $R^{15}$ is ethylsulfonyl:

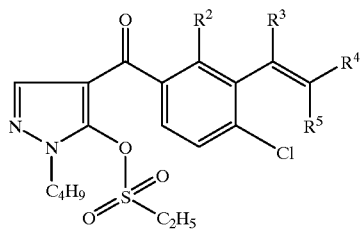

Ia69

Likewise, extraordinary preference is given to the compounds Ia70, in particular to the compounds Ia70.001–Ia70.180, which differ from the corresponding compounds Ia1.001–Ia1.180 in that $R^{14}$ is isobutyl and $R^{15}$ is ethylsulfonyl:

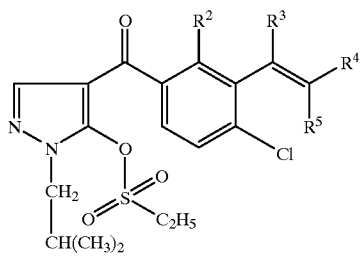

Ia70

Likewise, extraordinary preference is given to the compounds Ia71, in particular to the compounds Ia71.001–Ia71.180, which differ from the corresponding compounds Ia1.001–Ia1.180 in that $R^{15}$ is n-propylsulfonyl:

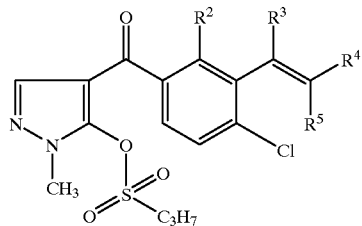

Ia71

Likewise, extraordinary preference is given to the compounds Ia72, in particular to the compounds Ia72.001–Ia72.180, which differ from the corresponding compounds Ia1.001–Ia1.180 in that $R^{14}$ is ethyl and for [sic] $R^{15}$ is n-propylsulfonyl:

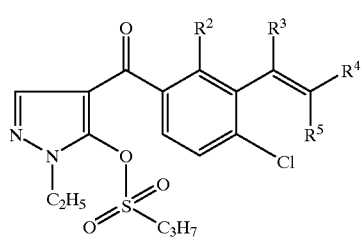

Ia72

Likewise, extraordinary preference is given to the compounds Ia73, in particular to the compounds Ia73.001–Ia73.180, which differ from the corresponding compounds Ia1.001–Ia1.180 in that $R^{14}$ is n-propyl and $R^{15}$ is n-propylsulfonyl:

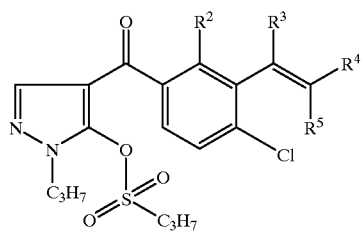

Ia73

Likewise, extraordinary preference is given to the compounds Ia74, in particular to the compounds Ia74.001–Ia74.180, which differ from the corresponding compounds Ia1.001–Ia1.180 in that $R^{14}$ is n-butyl and $R^{15}$ is n-propylsulfonyl:

Ia74

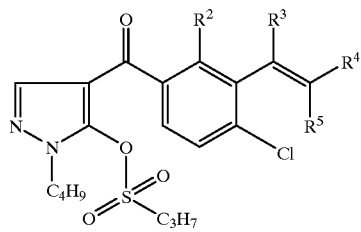

Likewise, extraordinary preference is given to the compounds Ia75, in particular to the compounds Ia75.001–Ia75.180, which differ from the corresponding compounds Ia1.001–Ia1.180 in that $R^{14}$ is isobutyl and $R^{15}$ is n-propylsulfonyl:

Ia75

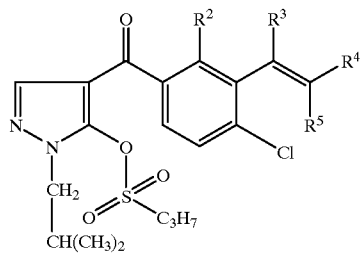

Likewise, extraordinary preference is given to the compounds Ia76, in particular to the compounds Ia76.001–Ia76.180, which differ from the corresponding compounds Ia1.001–Ia1.180 in that $R^{15}$ is isopropylsulfonyl:

Ia76

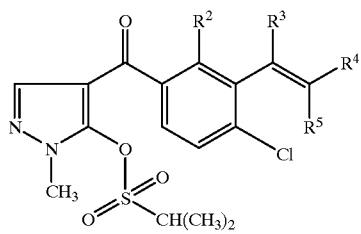

Likewise, extraordinary preference is given to the compounds Ia77, in particular to the compounds Ia77.001–Ia77.180, which differ from the corresponding compounds Ia1.001–Ia1.180 in that $R^{14}$ is ethyl and $Ri^5$ is isopropylsulfonyl:

Ia77

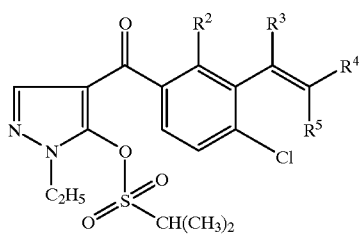

Likewise, extraordinary preference is given to the compounds Ia78, in particular to the compounds Ia78.001–Ia78.180, which differ from the corresponding compounds Ia1.001–Ia1.180 in that $R^{14}$ is propyl and $R^{15}$ is isopropylsulfonyl:

Ia78

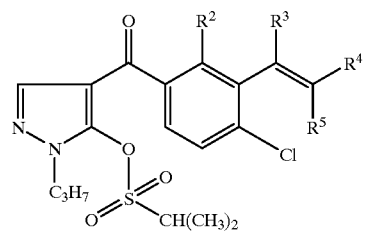

Likewise, extraordinary preference is given to the compounds Ia79, in particular to the compounds Ia79.001–Ia79.180, which differ from the corresponding compounds Ia1.001–Ia1.180 in that $R^{14}$ is n-butyl and $R^{15}$ is isopropylsulfonyl:

Ia79

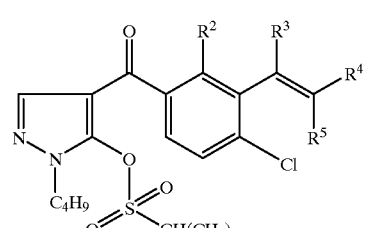

Likewise, extraordinary preference is given to the compounds Ia80, in particular to the compounds Ia80.001–Ia80.180, which differ from the corresponding compounds Ia1.001–Ia1.180 in that $R^{14}$ is isobutyl and $R^{15}$ is isopropylsulfonyl:

Ia80

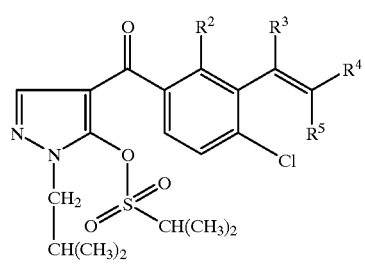

Likewise, extraordinary preference is given to the compounds Ia81, in particular to the compounds Ia81.001–Ia81.180, which differ from the corresponding compounds Ia1.001–Ia1.180 in that $R^{15}$ is n-butylsulfonyl:

Ia81

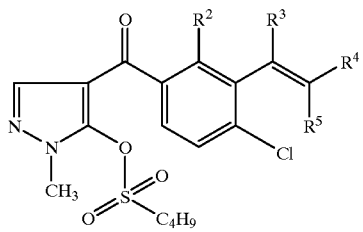

Likewise, extraordinary preference is given to the compounds Ia82, in particular to the compounds Ia82.001–Ia82.180, which differ from the corresponding compounds Ia1.001–Ia1.180 in that $R^{14}$ is ethyl and $R^{15}$ is n-butylsulfonyl:

Ia82

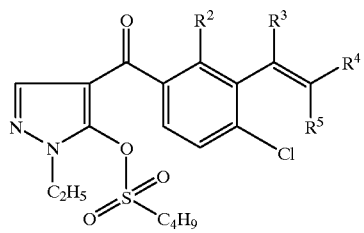

Likewise, extraordinary preference is given to the compounds Ia83, in particular to the compounds Ia83.001–Ia83.180, which differ from the corresponding compounds Ia1.001–Ia1.180 in that $R^{14}$ is n-propyl and $R^{15}$ is n-butylsulfonyl:

Ia83

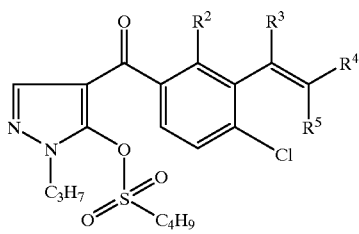

Likewise, extraordinary preference is given to the compounds Ia84, in particular to the compounds Ia84.001–Ia84.180, which differ from the corresponding Ia1.001–Ia1.180 in that $R^{14}$ is n-butyl and $R^{15}$ is n-butylsulfonyl:

Ia84

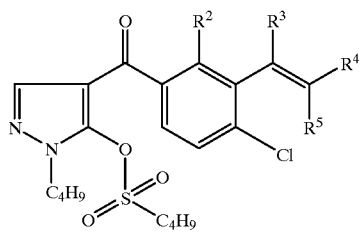

Likewise, extraordinary preference is given to the compounds Ia85, in particular to the compounds Ia85.001–Ia85.180, which differ from the corresponding compounds Ia1.001–Ia1.180 in that $R^{14}$ is isobutyl and $R^{15}$ is n-butylsulfonyl:

Ia85

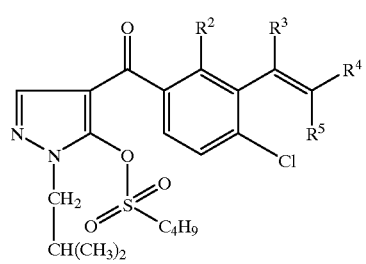

Likewise, extraordinary preference is given to the compounds Ia86, in particular to the compounds Ia86.001–Ia86.180, which differ from the corresponding compounds Ia1.001–Ia1.180 in that $R^{15}$ is isobutylsulfonyl:

Ia86

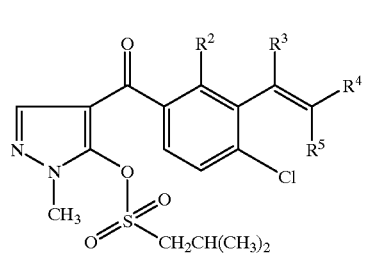

Likewise, extraordinary preference is given to the compounds Ia87, in particular to the compounds Ia87.001–Ia87.180, which differ from the corresponding compounds Ia1.001–Ia1.180 in that $R^{14}$ is ethyl and $R^{15}$ is isobutylsulfonyl:

Ia87

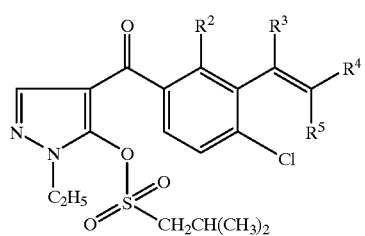

Likewise, extraordinary preference is given to the compounds Ia88, in particular to the compounds Ia88.001–Ia88.180, which differ from the corresponding compounds Ia1.001–Ia1.180 in that $R^{14}$ is n-propyl and $R^{15}$ is isobutylsulfonyl:

Ia88

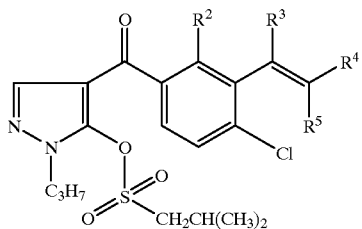

Likewise, extraordinary preference is given to the compounds Ia89, in particular to the compounds Ia89.001–Ia89.180, which differ from the corresponding compounds Ia1.001–Ia1.180 in that $R^{14}$ is n-butyl and $R^{15}$ is isobutylsulfonyl:

Ia89

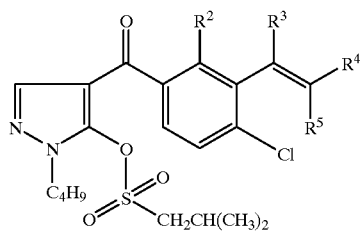

Likewise, extraordinary preference is given to the compounds Ia90, in particular to the compounds Ia90.001–Ia90.180, which differ from the corresponding compounds Ia1.001–Ia1.180 in that $R^{14}$ is isobutyl and $R^{15}$ is isobutylsulfonyl:

Ia90

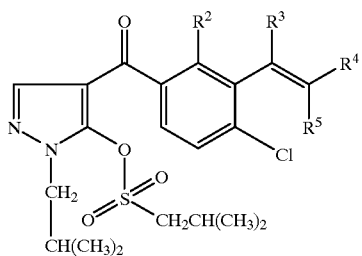

Likewise, extraordinary preference is given to the compounds Ia91, in particular to the compounds Ia91.001–Ia91.180, which differ from the corresponding compounds Ia1.001–Ia1.180 in that $R^{15}$ is sec-butylsulfonyl:

Ia91

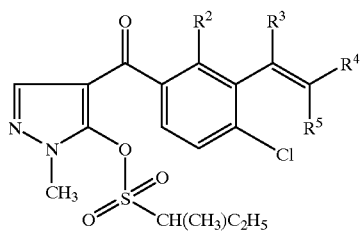

Likewise, extraordinary preference is given to the compounds Ia92, in particular to the compounds Ia92.001–Ia92.180, which differ from the corresponding compounds Ia1.001–Ia1.180 in that $R^{14}$ is ethyl and $R^{15}$ is sec-butylsulfonyl:

Ia92

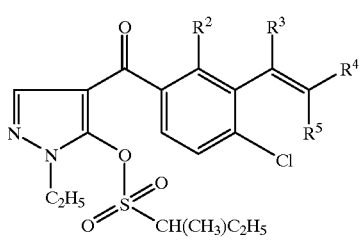

Likewise, extraordinary preference is given to the compounds Ia93, in particular to the compounds Ia93.001–Ia93.180, which differ from the corresponding compounds Ia1.001–Ia1.180 in that $R^{14}$ is n-propyl and $R^{15}$ is sec-butylsulfonyl:

Ia93

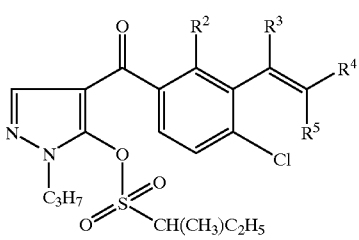

Likewise, extraordinary preference is given to the compounds Ia94, in particular to the compounds Ia94.001–Ia94.180, which differ from the corresponding compounds Ia1.001–Ia1.180 in that $R^{14}$ is n-butyl and $R^{15}$ is sec-butylsulfonyl:

Ia94

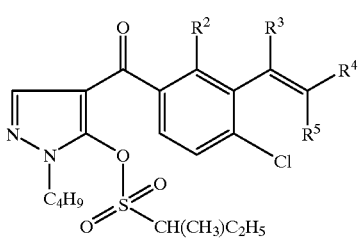

Likewise, extraordinary preference is given to the compounds Ia95, in particular to the compounds Ia95.001–Ia95.180, which differ from the corresponding compounds Ia1.001–Ia1.180 in that $R^{14}$ is isobutyl and $R^{15}$ is sec-butylsulfonyl:

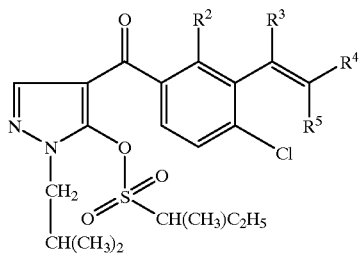

Ia95

Likewise, extraordinary preference is given to the compounds Ia96, in particular to the compounds Ia96.001–Ia96.180, which differ from the corresponding compounds Ia1.001–Ia1.180 in that $R^{15}$ is trifluoromethylsulfonyl:

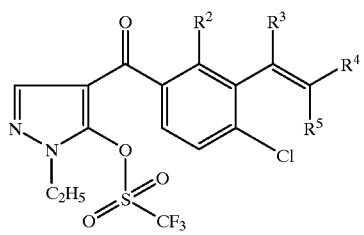

Ia96

Likewise, extraordinary preference is given to the compounds Ia97, in particular to the compounds Ia97.001–Ia97.180, which differ from the corresponding compounds Ia1.001–Ia1.180 in that $R^{14}$ is ethyl and $R^{15}$ is trifluoromethylsulfonyl:

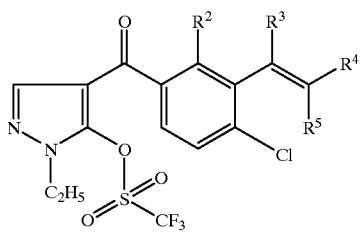

Ia97

Likewise, extraordinary preference is given to the compounds Ia98, in particular to the compounds Ia98.001–Ia98.180, which differ from the corresponding compounds Ia1.001–Ia1.180 in that $R^{14}$ is n-propyl and $R^{15}$ is trifluoromethylsulfonyl:

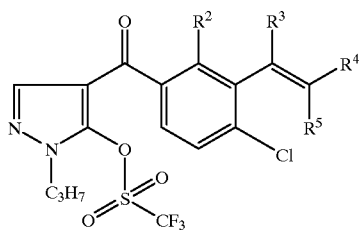

Ia98

Likewise, extraordinary preference is given to the compounds Ia99, in particular to the compounds Ia99.001–Ia99.180, which differ from the corresponding compounds Ia1.001–Ia1.180 in that $R^{14}$ is n-butyl and $R^{15}$ is trifluoromethylsulfonyl:

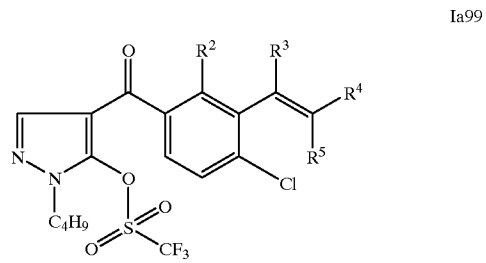

Ia99

Likewise, extraordinary preference is given to the compounds Ia100, in particular to the compounds Ia100.001–Ia100.180, which differ from the corresponding compounds Ia1.001–Ia1.180 in that $R^{14}$ is isobutyl and $R^{15}$ is trifluoromethylsulfonyl:

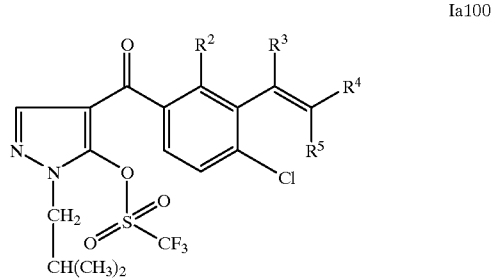

Ia100

Likewise, extraordinary preference is given to the compounds Ia101, in particular to the compounds Ia101.001–Ia101.180, which differ from the corresponding compounds Ia1.001–Ia1.180 in that $R^{15}$ is phenylcarbonylmethyl:

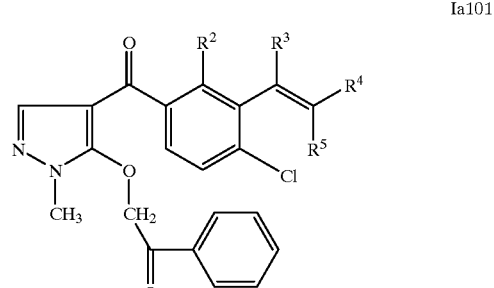

Ia101

Likewise, extraordinary preference is given to the compounds Ia102, in particular to the compounds Ia102.001–Ia102.180, which differ from the corresponding compounds Ia1.001–Ia1.180 in that $R^{14}$ is ethyl and $R^{15}$ is phenylcarbonylmethyl:

Ia102

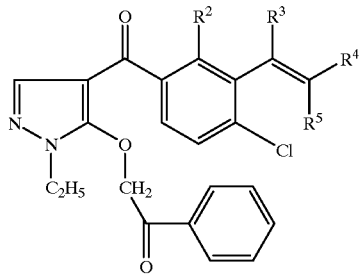

Likewise, extraordinary preference is given to the compounds Ia103, in particular to the compounds Ia103.001–Ia103.180, which differ from the corresponding compounds Ia1.001–Ia1.180 in that $R^{14}$ is n-propyl and $R^{15}$ is phenylcarbonylmethyl:

Ia103

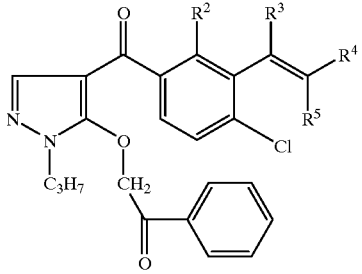

Likewise, extraordinary preference is given to the compounds Ia104, in particular to the compounds Ia104.001–Ia104.180, which differ from the corresponding compounds Ia1.001–Ia1.180 in that $R^{14}$ is n-butyl and $R^{15}$ is phenylcarbonylmethyl:

Ia104

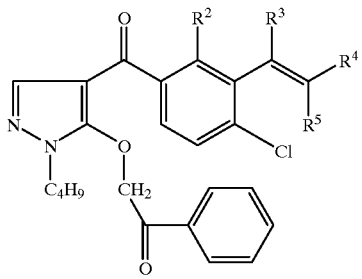

Likewise, extraordinary preference is given to the compounds Ia105, in particular to the compounds Ia105.001–Ia105.180, which differ from the corresponding compounds Ia1.001–Ia1.180 in that $R^{14}$ is isobutyl and $R^{15}$ is phenylcarbonylmethyl:

Ia105

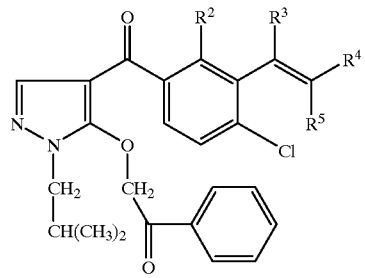

Likewise, extraordinary preference is given to the compounds Ia106, in particular to the compounds Ia106.001–Ia106.180, which differ from the corresponding compounds Ia1.001–Ia1.180 in that $R^{15}$ is phenylsulfonyl:

Ia106

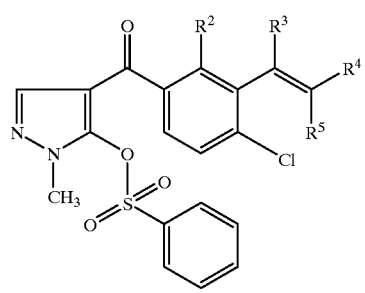

Likewise, extraordinary preference is given to the compounds Ia107, in particular to the compounds Ia107.001–Ia107.180, which differ from the corresponding compounds Ia1.001–Ia1.180 in that $R^{14}$ is ethyl and $R^{15}$ is phenylsulfonyl:

Ia107

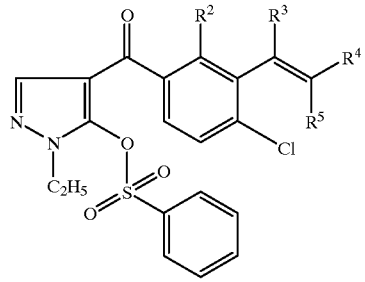

Likewise, extraordinary preference is given to the compounds Ia108, in particular to the compounds Ia108.001–Ia108.180, which differ from the corresponding compounds Ia1.001–Ia1.180 in that $R^{14}$ is n-propyl and $R^{15}$ is phenylsulfonyl:

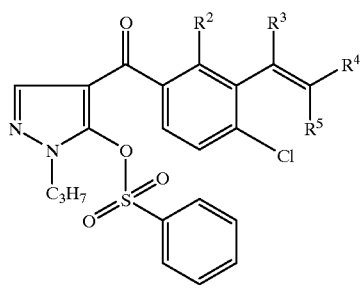

Ia108

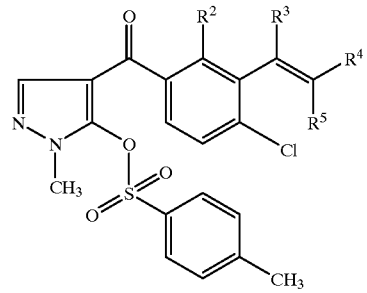

Ia111

Likewise, extraordinary preference is given to the compounds Ia109, in particular to the compounds Ia109.001–Ia109.180, which differ from the corresponding compounds Ia1.001–Ia1.180 in that $R^{14}$ is n-butyl and $R^{15}$ is phenylsulfonyl:

Likewise, extraordinary preference is given to the compounds Ia112, in particular to the compounds Ia112.001–Ia112.180, which differ from the corresponding compounds Ia1.001–Ia1.180 in that $R^{14}$ is ethyl and $R^{15}$ is 4-methylphenylsulfonyl:

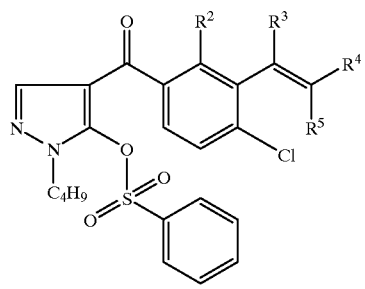

Ia109

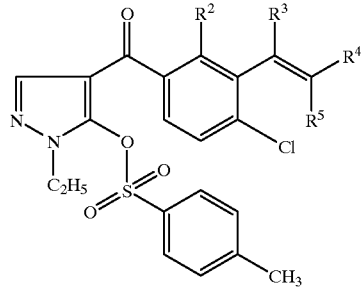

Ia112

Likewise, extraordinary preference is given to the compounds Ia110, in particular to the compounds Ia110.001–Ia110.180, which differ from the corresponding compounds Ia1.001–Ia1.180 in that $R^{14}$ is isobutyl and $R^{15}$ is phenylsulfonyl:

Likewise, extraordinary preference is given to the compounds Ia113, in particular to the compounds Ia113.001–Ia113.180, which differ from the corresponding compounds Ia1.001–Ia1.180 in that $R^{14}$ is n-propyl and $R^{15}$ is 4-methylphenylsulfonyl:

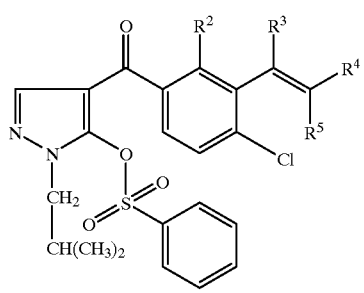

Ia110

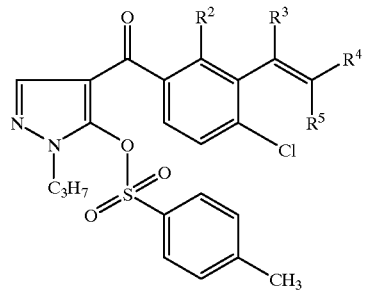

Ia113

Likewise, extraordinary preference is given to the compounds Ia111, in particular to the compounds Ia111.001–Ia111.180, which differ from the corresponding compounds Ia1.001–Ia1.180 in that $R^{15}$ is 4-methylphenylsulfonyl:

Likewise, extraordinary preference is given to the compounds Ia114, in particular to the compounds Ia114.001–Ia114.180, which differ from the corresponding compounds Ia1.001–Ia1.180 in that $R^{14}$ is n-butyl and $R^{15}$ is 4-methylphenylsulfonyl:

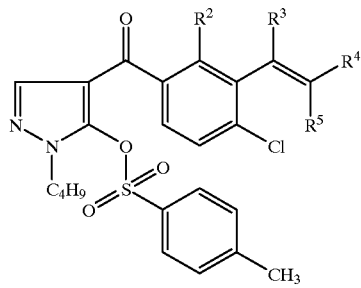

Ia114

Likewise, extraordinary preference is given to the compounds Ia115, in particular to the compounds Ia115.001–Ia115.180, which differ from the corresponding compounds Ia1.001–Ia1.180 in that $R^{14}$ is isobutyl and $R^{15}$ is 4-methylphenylsulfonyl:

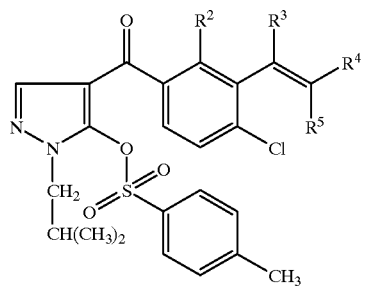

Ia115

Likewise, extraordinary preference is given to the compounds Ia116, in particular to the compounds Ia116.001–Ia116.180, which differ from the corresponding compounds Ia1.001–Ia1.180 in that $R^1$ is nitro:

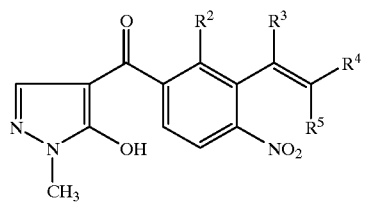

Ia116

Likewise, extraordinary preference is given to the compounds Ia117, in particular to the compounds Ia117.001–Ia117.180, which differ from the corresponding compounds Ia1.001–Ia1.180 in that $R^1$ is nitro and $R^{14}$ is ethyl:

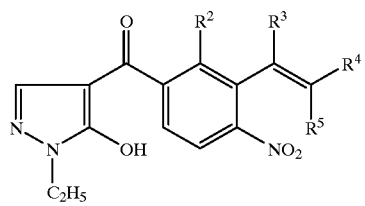

Ia117

Likewise, extraordinary preference is given to the compounds Ia118, in particular to the compounds Ia118.001–Ia118.180, which differ from the corresponding compounds Ia1.001–Ia1.180 in that $R^1$ is nitro and $R^{14}$ is propyl:

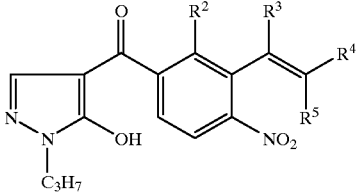

Ia118

Likewise, extraordinary preference is given to the compounds Ia119, in particular to the compounds IaII9.001–Ia119.180, which differ from the corresponding compounds Ia1.001–Ia1.180 in that $R^1$ is nitro and $R^{14}$ is n-butyl:

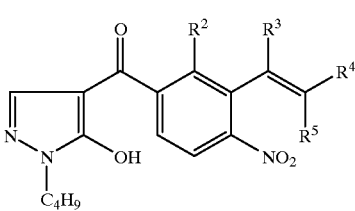

Ia119

Likewise, extraordinary preference is given to the compounds Ia120, in particular to the compounds Ia120.001–Ia120.180, which differ from the corresponding compounds Ia1.001–Ia1.180 in that $R^1$ is nitro and $R^{14}$ is isobutyl:

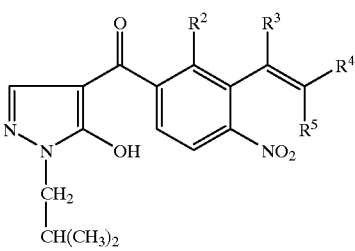

Ia120

Likewise, extraordinary preference is given to the compounds Ia121, in particular to the compounds Ia121.001–Ia121.180, which differ from the corresponding compounds Ia1.001–Ia1.180 in that $R^{15}$ is methyl:

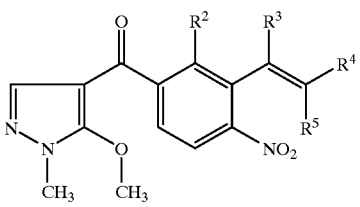

Ia121

Likewise, extraordinary preference is given to the compounds Ia122, in particular to the compounds Ia122.001–Ia122.180, which differ from the corresponding compounds Ia1.001–Ia1.180 in that $R^1$ is nitro, $R^{14}$ is ethyl and $R^{15}$ is methyl:

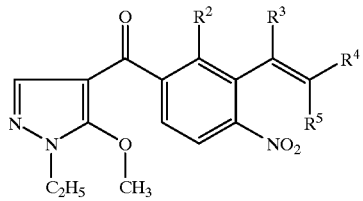

Ia122

Likewise, extraordinary preference is given to the compounds Ia123, in particular to the compounds Ia123.001–Ia123.180, which differ from the corresponding compounds Ia1.001–Ia1.180 in that $R^1$ is nitro, $R^{14}$ is n-propyl and $R^{15}$ is methyl:

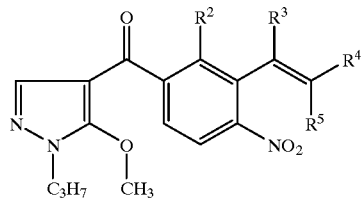

Ia123

Likewise, extraordinary preference is given to the compounds Ia124, in particular to the compounds Ia124.001–Ia124.180, which differ from the corresponding compounds Ia1.001–Ia1.180 in that $R^1$ is nitro, $R^{14}$ is n-butyl and $R^{15}$ is methyl:

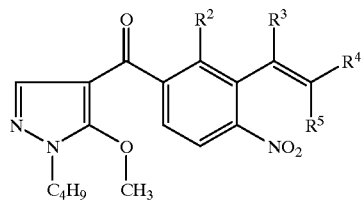

Ia124

Likewise, extraordinary preference is given to the compounds Ia125, in particular to the compounds Ia125.001–Ia125.180, which differ from the corresponding compounds Ia1.001–Ia1.180 in that $R^1$ is nitro, $R^{14}$ is isobutyl and $R^{15}$ is methyl:

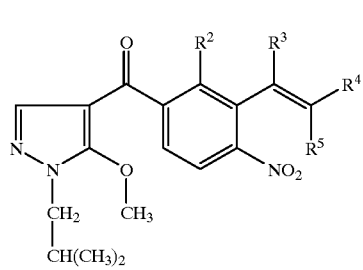

Ia125

Likewise, extraordinary preference is given to the compounds Ia126, in particular to the compounds Ia126.001–Ia126.180, which differ from the corresponding compounds Ia1.001–Ia1.180 in that $R^1$ is nitro and $R^{15}$ is ethyl:

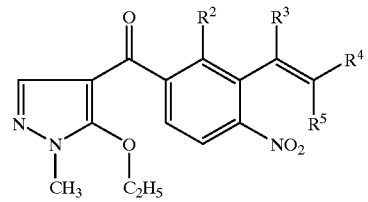

Ia126

Likewise, extraordinary preference is given to the compounds Ia127, in particular to the compounds Ia127.001–Ia127.180, which differ from the corresponding compounds Ia1.001–Ia1.180 in that $R^1$ is nitro and $R^{14}$ and $R^{15}$ are each ethyl:

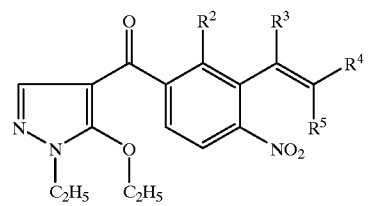

Ia127

Likewise, extraordinary preference is given to the compounds Ia128, in particular to the compounds Ia128.001–Ia128.180, which differ from the corresponding compounds Ia1.001–Ia1.180 in that $R^1$ is nitro, $R^{14}$ is n-propyl and $R^{15}$ is ethyl:

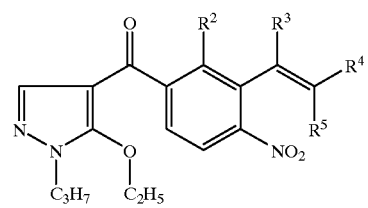

Ia128

Likewise, extraordinary preference is given to the compounds Ia129, in particular to the compounds Ia129.001–Ia129.180, which differ from the corresponding compounds Ia1.001–Ia1.180 in that $R^1$ is nitro, $R^{14}$ is n-butyl and $R^{15}$ is ethyl:

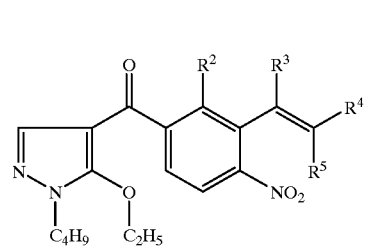

Ia129

Likewise, extraordinary preference is given to the compounds Ia130, in particular to the compounds Ia130.001–Ia130.180, which differ from the corresponding compounds Ia1.001–Ia1.180 in that $R^1$ is nitro, $R^{14}$ is isobutyl and $R^{15}$ is ethyl:

Ia130

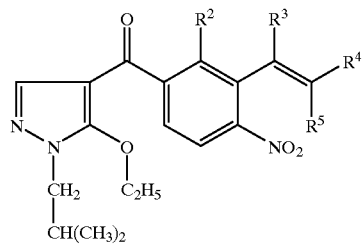

Likewise, extraordinary preference is given to the compounds Ia13, in particular to the compounds Ia131.001–Ia131.180, which differ from the corresponding compounds Ia1.001–Ia1.180 in that $R^1$ is nitro and $R^{15}$ is n-propyl:

Ia131

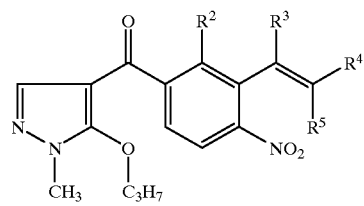

Likewise, extraordinary preference is given to the compounds Ia132, in particular to the compounds Ia132.001–Ia132.180, which differ from the corresponding compounds Ia1.001–Ia1.180 in that $R^1$ is nitro, $R^{14}$ is ethyl and $R^{15}$ is n-propyl:

Ia132

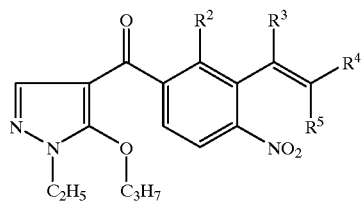

Likewise, extraordinary preference is given to the compounds Ia133, in particular to the compounds Ia133.001–Ia133.180, which differ from the corresponding compounds Ia1.001–Ia1.180 in that $R^1$ is nitro, $R^{14}$ and $R^{15}$ are each n-propyl:

Ia133

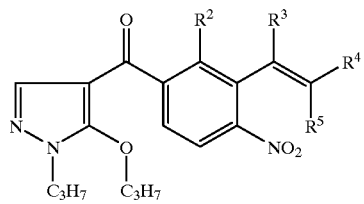

Likewise, extraordinary preference is given to the compounds Ia134, in particular to the compounds Ia134.001–Ia134.180, which differ from the corresponding compounds Ia1.001–Ia1.180 in that $R^1$ is nitro, $R^{14}$ is n-butyl and $R^{15}$ is n-propyl:

Ia134

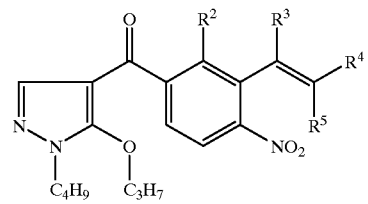

Likewise, extraordinary preference is given to the compounds Ia135, in particular to the compounds Ia135.001–Ia135.180, which differ from the corresponding compounds Ia1.001–Ia1.180 in that $R^1$ is nitro, $R^{14}$ is isobutyl and $R^{15}$ is n-propyl:

Ia135

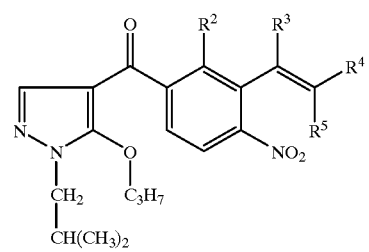
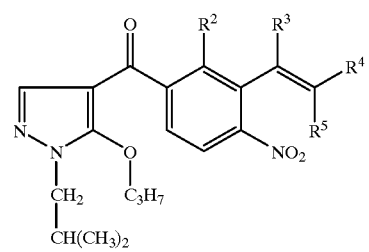

Likewise, extraordinary preference is given to the compounds Ia136, in particular to the compounds Ia136.001–Ia136.180, which differ from the corresponding compounds Ia1.001–Ia1.180 in that $R^1$ is nitro and $R^{15}$ is isopropyl:

Ia136

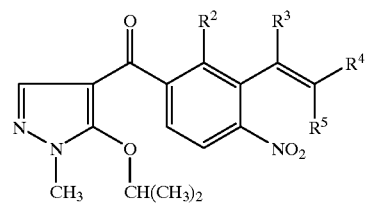
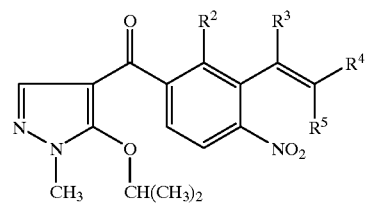

Likewise, extraordinary preference is given to the compounds Ia137, in particular to the compounds Ia137.001–Ia137.180, which differ from the corresponding compounds Ia1.001–Ia1.180 in that $R^1$ is nitro, $R^{14}$ is ethyl and $R^{15}$ is isopropyl:

Ia137

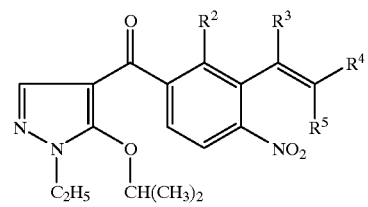
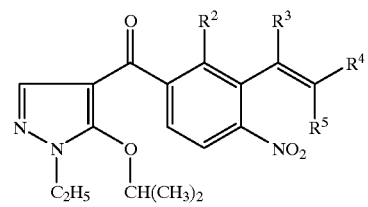

Likewise, extraordinary preference is given to the compounds Ia138, in particular to the compounds Ia138.001–Ia138.180, which differ from the corresponding compounds Ia1.001–Ia1.180 in that $R^1$ is nitro, $R^{14}$ is n-propyl and $R^{15}$ is isopropyl:

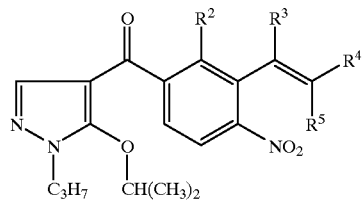

Ia138

Likewise, extraordinary preference is given to the compounds Ia139, in particular to the compounds Ia139.001–Ia139.180, which differ from the corresponding compounds Ia1.001–Ia1.180 in that $R^1$ is nitro, $R^{14}$ is n-butyl and $R^{15}$ is isopropyl:

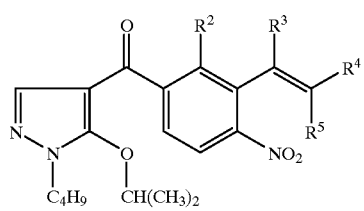

Ia139

Likewise, extraordinary preference is given to the compounds Ia140, in particular to the compounds Ia140.001–Ia140.180, which differ from the corresponding compounds Ia1.001–Ia1.180 in that $R^1$ is nitro, $R^{14}$ is isobutyl and $R^{15}$ is isopropyl:

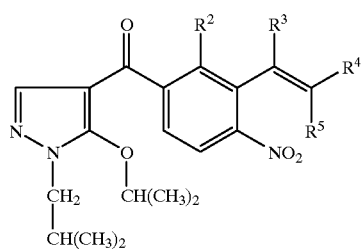

Ia140

Likewise, extraordinary preference is given to the compounds Ia141, in particular to the compounds Ia141.001–Ia141.180, which differ from the corresponding compounds Ia1.001–Ia1.180 in that $R^1$ is nitro and $R^{15}$ is n-butyl:

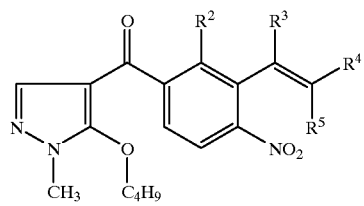

Ia141

Likewise, extraordinary preference is given to the compounds Ia142, in particular to the compounds Ia142.001–Ia142.180, which differ from the corresponding compounds Ia1.001–Ia1.180 in that $R^1$ is nitro, $R^{14}$ is ethyl and $R^{15}$ is n-butyl:

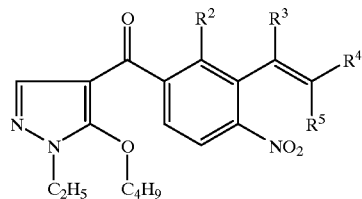

Ia142

Likewise, extraordinary preference is given to the compounds Ia143, in particular to the compounds Ia143.001–Ia143.180, which differ from the corresponding compounds Ia1.001–Ia1.180 in that $R^1$ is nitro, $R^{14}$ is n-propyl and $R^{15}$ is n-butyl:

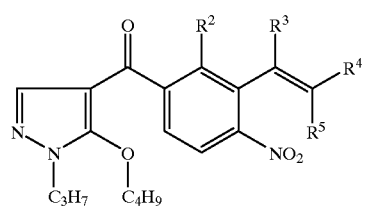

Ia143

Likewise, extraordinary preference is given to the compounds Ia144, in particular to the compounds Ia144.001–Ia144.180, which differ from the corresponding compounds Ia1.001–Ia1.180 in that $R^1$ is nitro, $R^{14}$ and $R^{15}$ are each n-butyl:

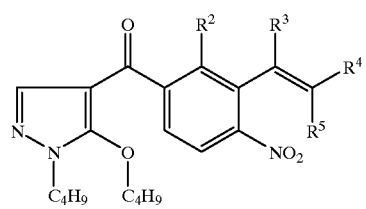

Ia144

Likewise, extraordinary preference is given to the compounds Ia145, in particular to the compounds Ia145.001–Ia145.180, which differ from the corresponding compounds Ia1.001–Ia1.180 in that $R^1$ is nitro, $R^{14}$ is isobutyl and $R^{15}$ is n-butyl:

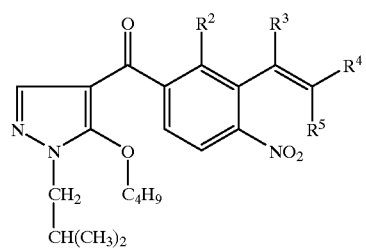

Ia145

Likewise, extraordinary preference is given to the compounds Ia146, in particular to the compounds Ia146.001–Ia146.180, which differ from the corresponding compounds Ia1.001–Ia1.180 in that $R^1$ is nitro and $R^{15}$ is sec-butyl:

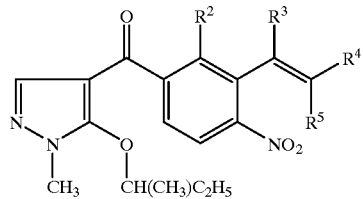

Ia146

Likewise, extraordinary preference is given to the compounds Ia147, in particular to the compounds Ia147.001–Ia147.180, which differ from the corresponding compounds Ia1.001–Ia1.180 in that $R^1$ is nitro, $R^{14}$ is ethyl and $R^{15}$ is sec-butyl:

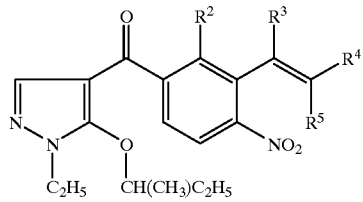

Ia147

Likewise, extraordinary preference is given to the compounds Ia148, in particular to the compounds Ia148.001–Ia148.180, which differ from the corresponding compounds Ia1.001–Ia1.180 in that $R^1$ is nitro, $R^{14}$ is n-propyl and $R^{15}$ is sec-butyl:

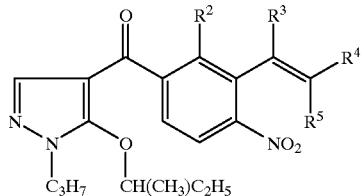

Ia148

Likewise, extraordinary preference is given to the compounds Ia149, in particular to the compounds Ia149.001–Ia149.180, which differ from the corresponding compounds Ia1.001–Ia1.180 in that $R^1$ is nitro, $R^{14}$ is n-butyl and $R^{15}$ is sec-butyl:

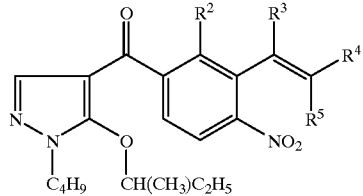

Ia149

Likewise, extraordinary preference is given to the compounds Ia150, in particular to the compounds Ia150.001–Ia150.180, which differ from the corresponding compounds Ia1.001–Ia1.180 in that $R^1$ is nitro, $R^{14}$ is isobutyl and $R^{15}$ is sec-butyl:

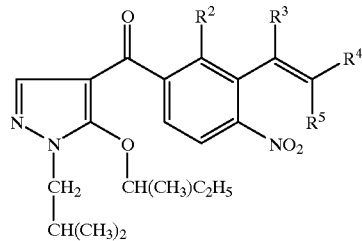

Ia150

Likewise, extraordinary preference is given to the compounds Ia151, in particular to the compounds Ia151.001–Ia151.180, which differ from the corresponding compounds Ia1.001–Ia1.180 in that $R^1$ is nitro and $R^{15}$ is isobutyl:

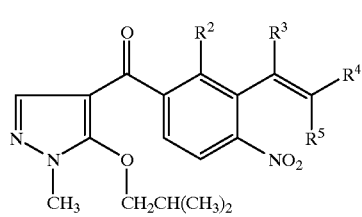

Ia151

Likewise, extraordinary preference is given to the compounds Ia152, in particular to the compounds Ia152.001–Ia152.180, which differ from the corresponding compounds Ia1.001–Ia1.180 in that $R^1$ is nitro, $R^{14}$ is ethyl and $R^{15}$ is isobutyl:

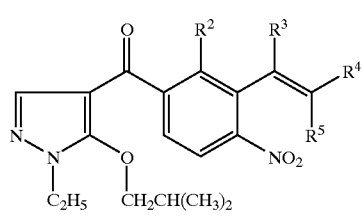

Ia152

Likewise, extraordinary preference is given to the compounds Ia153, in particular to the compounds Ia153.001–Ia153.180, which differ from the corresponding compounds Ia1.001–Ia1.180 in that $R^1$ is nitro, $R^{14}$ is n-propyl and $R^{15}$ is isobutyl:

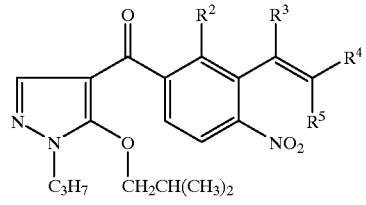

Ia153

Likewise, extraordinary preference is given to the compounds Ia154, in particular to the compounds Ia154.001–Ia154.180, which differ from the corresponding compounds Ia1.001–Ia1.180 in that $R^1$ is nitro, $R^{14}$ is n-butyl and $R^{15}$ is isobutyl:

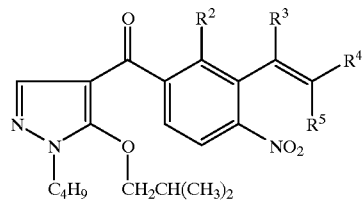
Ia154

Likewise, extraordinary preference is given to the compounds Ia155, in particular to the compounds Ia155.001–Ia154.180, which differ from the corresponding compounds Ia1.001–Ia1.180 in that $R^1$ is nitro, $R^{14}$ and $R^{15}$ are each isobutyl:

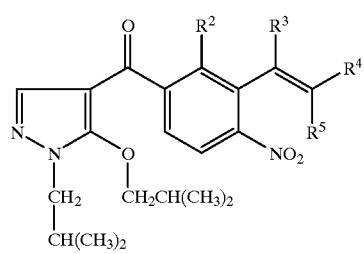
Ia155

Likewise, extraordinary preference is given to the compounds Ia156, in particular to the compounds Ia156.001–Ia156.180, which differ from the corresponding compounds Ia1.001–Ia1.180 in that $R^1$ is nitro and $R^{15}$ is methylcarbonyl:

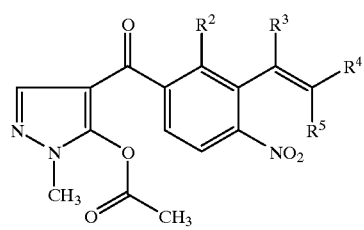
Ia156

Likewise, extraordinary preference is given to the compounds Ia157, in particular to the compounds Ia157.001–Ia157.180, which differ from the corresponding compounds Ia1.001–Ia1.180 in that $R^1$ is nitro, $R^{14}$ is ethyl and $R^{15}$ is methylcarbonyl:

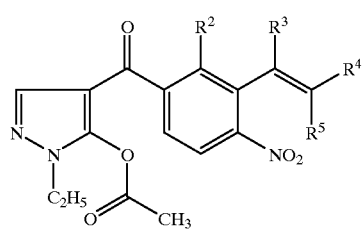
Ia157

Likewise, extraordinary preference is given to the compounds Ia158, in particular to the compounds Ia158.001–Ia158.180, which differ from the corresponding compounds Ia1.001–Ia1.180 in that $R^1$ is nitro, $R^{14}$ is n-propyl and $R^{15}$ is methylcarbonyl:

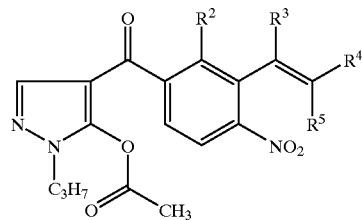
Ia158

Likewise, extraordinary preference is given to the compounds Ia159, in particular to the compounds Ia159.001–Ia159.180, which differ from the corresponding compounds Ia1.001–Ia1.180 in that $R^1$ is nitro, $R^{14}$ is n-butyl and $R^{15}$ is methylcarbonyl:

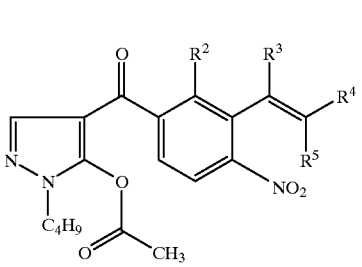
Ia159

Likewise, extraordinary preference is given to the compounds Ia160, in particular to the compounds Ia160.001–Ia160.180, which differ from the corresponding compounds Ia1.001–Ia1.180 in that $R^1$ is nitro, $R^{14}$ is isobutyl and $R^{15}$ is methylcarbonyl:

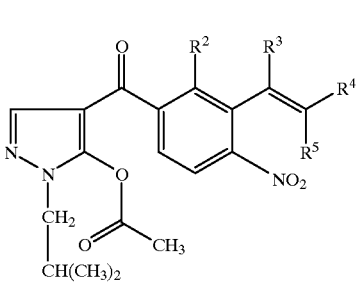
Ia160

Likewise, extraordinary preference is given to the compounds Ia161, in particular to the compounds Ia161.001–Ia161.180, which differ from the corresponding compounds Ia1.001–Ia1.180 in that $R^1$ is nitro and $R^{15}$ is ethylcarbonyl:

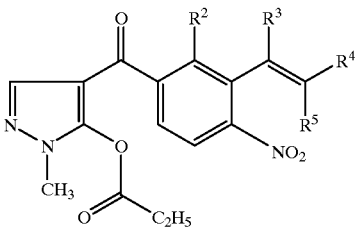
Ia161

Likewise, extraordinary preference is given to the compounds Ia162, in particular to the compounds Ia162.001–Ia162.180, which differ from the corresponding compounds Ia1.001–Ia1.180 in that $R^1$ is nitro, $R^{14}$ is ethyl and $R^{15}$ is ethylcarbonyl:

Ia162

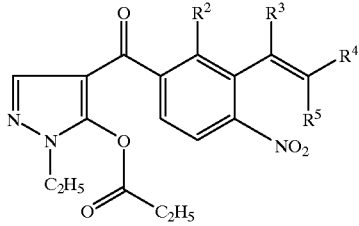

Likewise, extraordinary preference is given to the compounds Ia163, in particular to the compounds Ia163.001–Ia163.180, which differ from the corresponding compounds Ia1.001–Ia1.180 in that $R^1$ is nitro, $R^{14}$ is n-propyl and $R^{15}$ is ethylcarbonyl:

Ia163

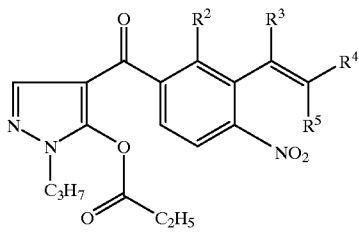

Likewise, extraordinary preference is given to the compounds Ia164, in particular to the compounds Ia164.001–Ia164.180, which differ from the corresponding compounds Ia1.001–Ia1.180 in that $R^1$ is nitro, $R^{14}$ is n-butyl and $R^{15}$ is ethylcarbonyl:

Ia164

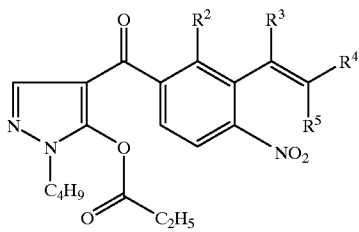

Likewise, extraordinary preference is given to the compounds Ia165, in particular to the compounds Ia165.001–Ia165.180, which differ from the corresponding compounds Ia1.001–Ia1.180 in that $R^1$ is nitro, $R^{14}$ is isobutyl and $R^{15}$ is ethylcarbonyl:

Ia165

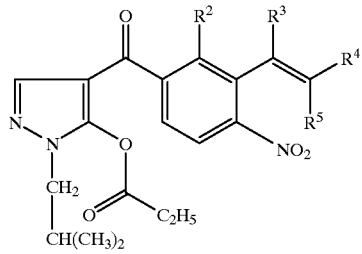

Likewise, extraordinary preference is given to the compounds Ia166, in particular to the compounds Ia166.001–Ia166.180, which differ from the corresponding compounds Ia1.001–Ia1.180 in that $R^1$ is nitro and $R^{15}$ is n-propylcarbonyl:

Ia166

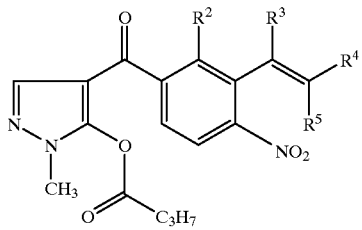

Likewise, extraordinary preference is given to the compounds Ia167, in particular to the compounds Ia167.001–Ia167.180, which differ from the corresponding compounds Ia1.001–Ia1.180 in that $R^1$ is nitro, $R^{14}$ is ethyl and $R^{15}$ is n-propylcarbonyl:

Ia167

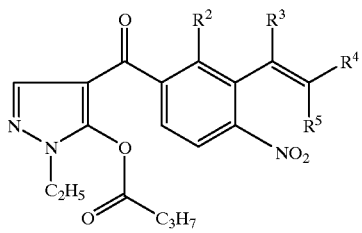

Likewise, extraordinary preference is given to the compounds Ia168, in particular to the compounds Ia168.001–Ia168.180, which differ from the corresponding compounds Ia1.001–Ia1.180 in that $R^1$ is nitro, $R^{14}$ is n-propyl and $R^{15}$ is n-propylcarbonyl:

Ia168

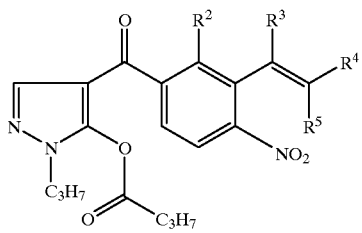

Likewise, extraordinary preference is given to the compounds Ia169, in particular to the compounds Ia169.001–Ia169.180, which differ from the corresponding compounds Ia1.001–Ia1.180 in that $R^1$ is nitro, $R^{14}$ is n-butyl and $R^{15}$ is n-propylcarbonyl:

Ia169

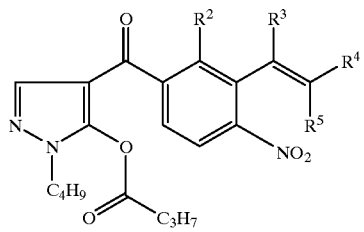

Likewise, extraordinary preference is given to the compounds Ia170, in particular to the compounds Ia170.001–Ia170.180, which differ from the corresponding compounds Ia1.001–Ia1.180 in that $R^1$ is nitro, $R^{14}$ is isobutyl and $R^{15}$ is n-propylcarbonyl:

Ia170

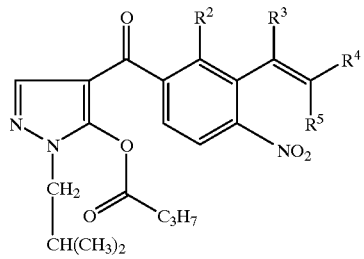

Likewise, extraordinary preference is given to the compounds Ia171, in particular to the compounds Ia171.001–Ia171.180, which differ from the corresponding compounds Ia1.001–Ia1.180 in that $R^1$ is nitro and $R^{15}$ is trifluoromethylcarbonyl:

Ia171

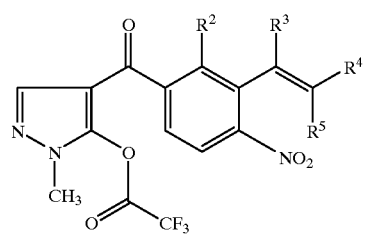

Likewise, extraordinary preference is given to the compounds Ia172, in particular to the compounds Ia172.001–Ia172.180, which differ from the corresponding compounds Ia1.001–Ia1.180 in that $R^1$ is nitro, $R^{14}$ is ethyl and $R^{15}$ is trifluoromethylcarbonyl:

Ia172

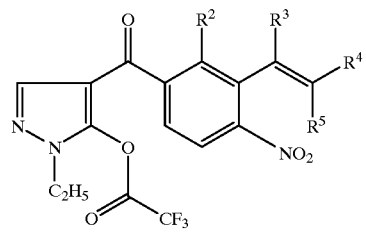

Likewise, extraordinary preference is given to the compounds Ia173, in particular to the compounds Ia173.001–Ia173.180, which differ from the corresponding compounds Ia1.001–Ia1.180 in that $R^1$ is nitro, $R^{14}$ is n-propyl and $R^{15}$ is trifluoromethylcarbonyl:

Ia173

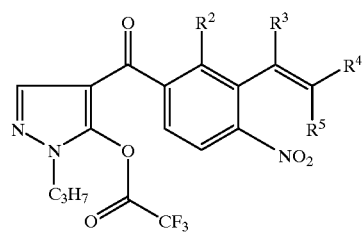

Likewise, extraordinary preference is given to the compounds Ia174, in particular to the compounds Ia174.001–Ia174.180, which differ from the corresponding compounds Ia1.001–Ia1.180 in that $R^1$ is nitro, $R^{14}$ is n-butyl and $R^{15}$ is trifluoromethylcarbonyl:

Ia174

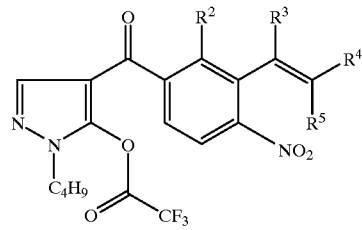

Likewise, extraordinary preference is given to the compounds Ia175, in particular to the compounds Ia175.001–Ia175.180, which differ from the corresponding compounds Ia1.001–Ia1.180 in that $R^1$ is nitro, $R^{14}$ is isobutyl and $R^{15}$ is trifluoromethylcarbonyl:

Ia175

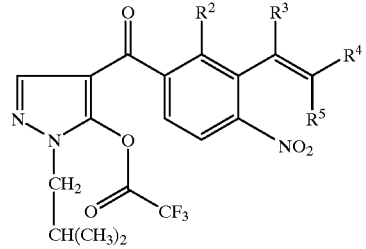

Likewise, extraordinary preference is given to the compounds Ia176, in particular to the compounds Ia176.001–Ia176.180, which differ from the corresponding compounds Ia1.001–Ia1.180 in that $R^1$ is nitro and $R^{15}$ is methylsulfonyl:

Ia176

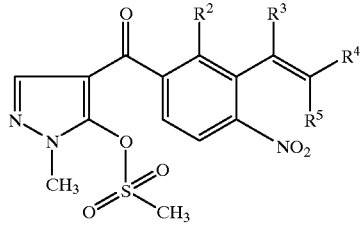

Likewise, extraordinary preference is given to the compounds Ia177, in particular to the compounds Ia177.001–Ia177.180, which differ from the corresponding compounds Ia1.001–Ia1.180 in that $R^1$ is nitro, $R^{14}$ is ethyl and $R^{15}$ is methylsulfonyl:

Ia177

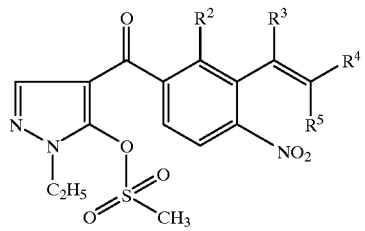

Likewise, extraordinary preference is given to the compounds Ia178, in particular to the compounds Ia178.001–Ia178.180, which differ from the corresponding compounds Ia1.001–Ia1.180 in that $R^1$ is nitro, $R^{14}$ is n-propyl and $R^{15}$ is methylsulfonyl:

Ia178

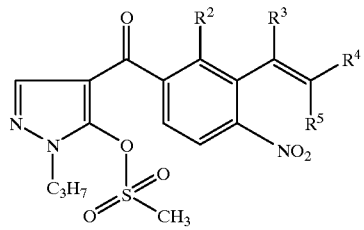

Likewise, extraordinary preference is given to the compounds Ia179, in particular to the compounds Ia179.001–Ia179.180, which differ from the corresponding compounds Ia1.001–Ia1.180 in that $R^1$ is nitro, $R^{14}$ is n-butyl and $R^{15}$ is methylsulfonyl:

Ia179

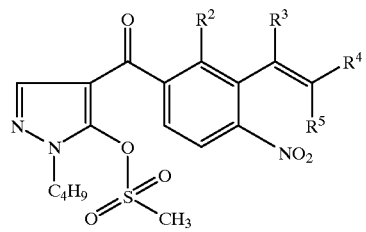

Likewise, extraordinary preference is given to the compounds Ia180, in particular to the compounds Ia180.001–Ia180.180, which differ from the corresponding compounds Ia1.001–Ia1.180 in that $R^1$ is nitro, $R^{14}$ is isobutyl and $R^{15}$ is methylsulfonyl:

Ia180

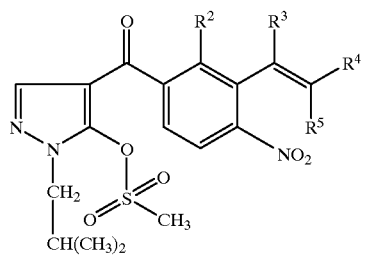

Likewise, extraordinary preference is given to the compounds Ia181, in particular to the compounds Ia181.001–Ia181.180, which differ from the corresponding compounds Ia1.001–Ia1.180 in that $R^1$ is nitro and $R^{15}$ is ethylsulfonyl:

Ia181

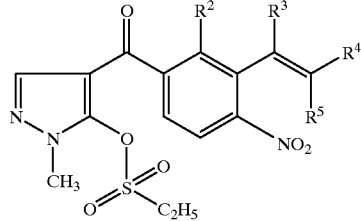

Likewise, extraordinary preference is given to the compounds Ia182, in particular to the compounds Ia182.001–Ia182.180, which differ from the corresponding compounds Ia1.001–Ia1.180 in that $R^1$ is nitro, $R^{14}$ is ethyl and $R^{15}$ is ethylsulfonyl:

Ia182

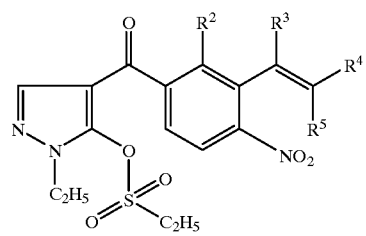

Likewise, extraordinary preference is given to the compounds Ia183, in particular to the compounds Ia183.001–Ia183.180, which differ from the corresponding compounds Ia1.001–Ia1.180 in that $R^1$ is nitro, $R^{14}$ is n-propyl and $R^{15}$ is ethylsulfonyl:

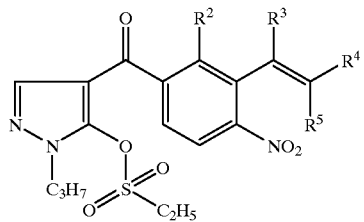

Ia183

Likewise, extraordinary preference is given to the compounds Ia184, in particular to the compounds Ia184.001–Ia184.180, which differ from the corresponding compounds Ia1.001–Ia1.180 in that $R^1$ is nitro, $R^{14}$ is n-butyl and $R^{15}$ is ethylsulfonyl:

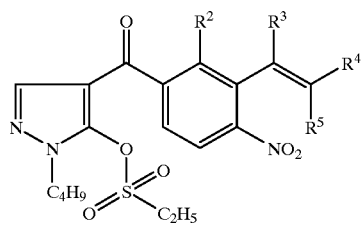

Ia184

Likewise, extraordinary preference is given to the compounds Ia185, in particular to the compounds Ia185.001–Ia185.180, which differ from the corresponding compounds Ia1.001–Ia1.180 in that $R^1$ is nitro, $R^{14}$ is isobutyl and $R^{15}$ is ethylsulfonyl:

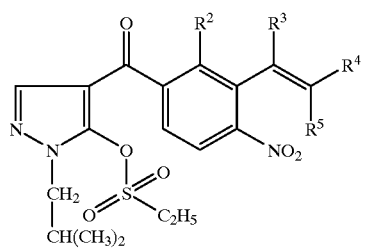

Ia185

Likewise, extraordinary preference is given to the compounds Ia186, in particular to the compounds Ia186.001–Ia186.180, which differ from the corresponding compounds Ia1.001–Ia1.180 in that $R^1$ is nitro and $R^{15}$ is n-propylsulfonyl:

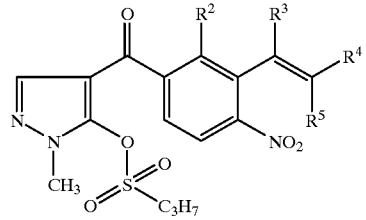

Ia186

Likewise, extraordinary preference is given to the compounds Ia187, in particular to the compounds Ia187.001–Ia187.180, which differ from the corresponding compounds Ia1.001–Ia1.180 in that $R^1$ is nitro, $R^{14}$ is ethyl and $R^{15}$ is n-propylsulfonyl:

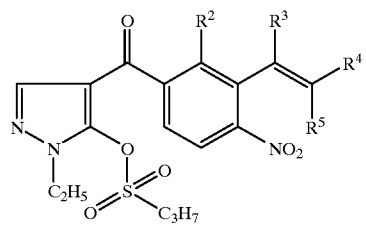

Ia187

Likewise, extraordinary preference is given to the compounds Ia188, in particular to the compounds Ia188.001–Ia188.180, which differ from the corresponding compounds Ia1.001–Ia1.180 in that $R^1$ is nitro, $R^{14}$ is n-propyl and $R^{15}$ is n-propylsulfonyl:

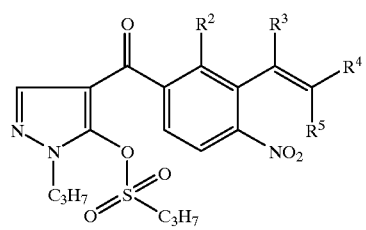

Ia188

Likewise, extraordinary preference is given to the compounds Ia189, in particular to the compounds Ia189.001–Ia189.180, which differ from the corresponding compounds Ia1.001–Ia1.180 in that $R^1$ is nitro, $R^{14}$ is n-butyl and $R^{15}$ is n-propylsulfonyl:

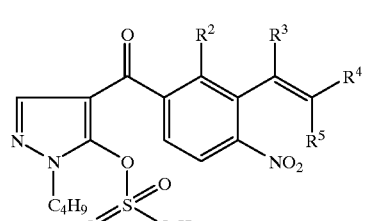

Ia189

Likewise, extraordinary preference is given to the compounds Ia190, in particular to the compounds Ia190.001–Ia190.180, which differ from the corresponding compounds Ia1.001–Ia1.180 in that $R^1$ is nitro, $R^{14}$ is isobutyl and $RI^5$ is n-propylsulfonyl:

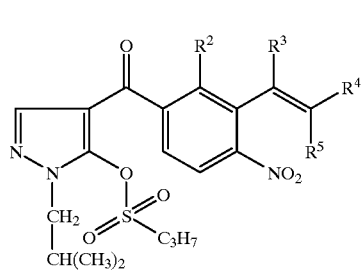

Ia190

Likewise, extraordinary preference is given to the compounds Ia191, in particular to the compounds Ia191.001–Ia191.180, which differ from the corresponding compounds Ia1.001–Ia1.180 in that $R^1$ is nitro and $R^{15}$ is isopropylsulfonyl:

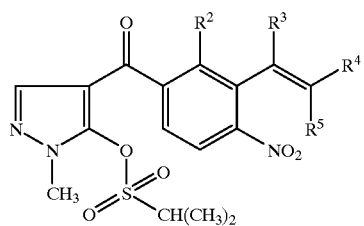

Ia191

Likewise, extraordinary preference is given to the compounds Ia192, in particular to the compounds Ia192.001–Ia192.180, which differ from the corresponding compounds Ia1.001–Ia1.180 in that $R^1$ is nitro, $R^{14}$ is ethyl and $R^{15}$ is isopropylsulfonyl:

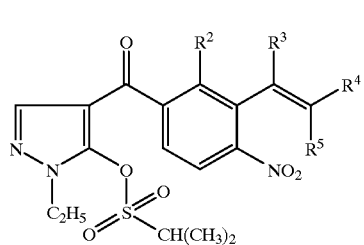

Ia192

Likewise, extraordinary preference is given to the compounds Ia193, in particular to the compounds Ia193.001–Ia193.180, which differ from the corresponding compounds Ia1.001–Ia1.180 in that $R^1$ is nitro, $R^{14}$ is n-propyl and $R^{15}$ is isopropylsulfonyl:

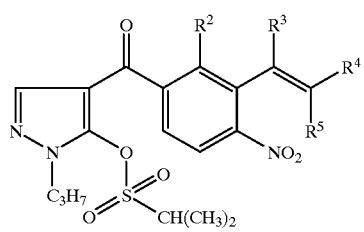

Ia193

Likewise, extraordinary preference is given to the compounds Ia194, in particular to the compounds Ia194.001–Ia194.180, which differ from the corresponding compounds Ia1.001–Ia1.180 in that $R^1$ is nitro, $R^{14}$ is n-butyl and $R^{15}$ is isopropylsulfonyl:

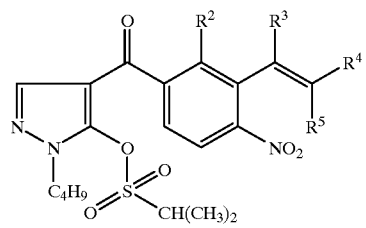

Ia194

Likewise, extraordinary preference is given to the compounds Ia195, in particular to the compounds Ia195.001–Ia195.180, which differ from the corresponding compounds Ia1.001–Ia1.180 in that $R^1$ is nitro, $R^{14}$ is isobutyl and $R^{15}$ is isopropylsulfonyl:

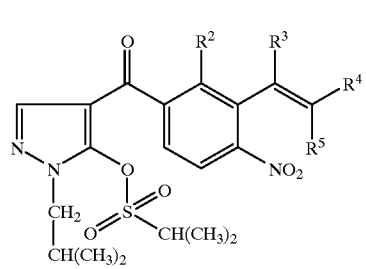

Ia195

Likewise, extraordinary preference is given to the compounds Ia196, in particular to the compounds Ia196.001–Ia196.180, which differ from the corresponding compounds Ia1.001–Ia1.180 in that $R^1$ is nitro and $R^{15}$ is n-butylsulfonyl:

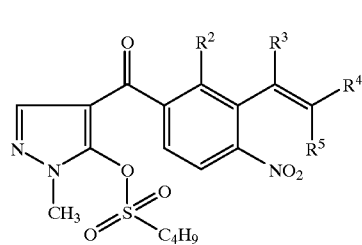

Ia196

Likewise, extraordinary preference is given to the compounds Ia197, in particular to the compounds Ia197.001–Ia197.180, which differ from the corresponding compounds Ia1.001–Ia1.180 in that $R^1$ is nitro, $R^{14}$ is ethyl and $R^{15}$ is n-butylsulfonyl:

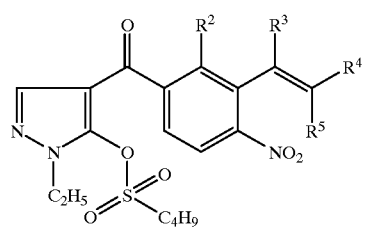

Ia197

Likewise, extraordinary preference is given to the compounds Ia198, in particular to the compounds Ia198.001–Ia198.180, which differ from the corresponding compounds Ia1.001–Ia1.180 in that $R^1$ is nitro, $R^{14}$ is n-propyl and $R^{15}$ is n-butylsulfonyl:

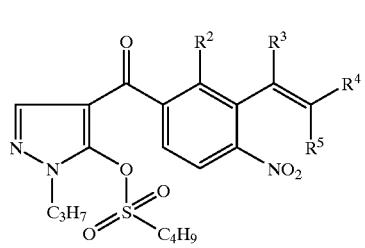
Ia198

Likewise, extraordinary preference is given to the compounds Ia199, in particular to the compounds Ia199.001–Ia199.180, which differ from the corresponding compounds Ia1.001–Ia1.180 in that $R^1$ is nitro, $R^{14}$ is n-butyl and $R^{15}$ is n-butylsulfonyl:

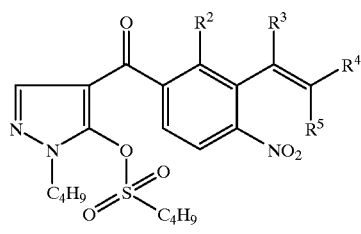
Ia199

Likewise, extraordinary preference is given to the compounds Ia200, in particular to the compounds Ia200.001–Ia200.180, which differ from the corresponding compounds Ia1.001–Ia1.180 in that $R^1$ is nitro, $R^{14}$ is isobutyl and $R^{15}$ is n-butylsulfonyl:

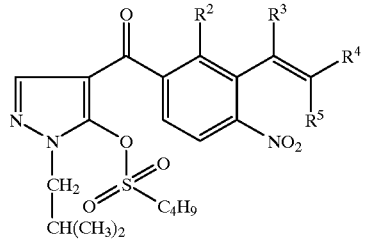
Ia200

Likewise, extraordinary preference is given to the compounds Ia201, in particular to the compounds Ia201.001–Ia201.180, which differ from the corresponding compounds Ia1.001–Ia1.180 in that $R^1$ is nitro and $R^{15}$ is isobutylsulfonyl:

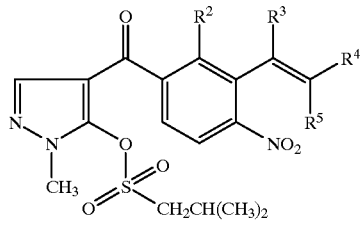
Ia201

Likewise, extraordinary preference is given to the compounds Ia202, in particular to the compounds Ia202.001–Ia202.180, which differ from the corresponding compounds Ia1.001–Ia1.180 in that $R^1$ is nitro, $R^{14}$ is ethyl and $R^{15}$ is isobutylsulfonyl:

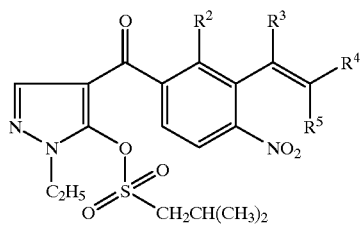
Ia202

Likewise, extraordinary preference is given to the compounds Ia203, in particular to the compounds Ia203.001–Ia203.180, which differ from the corresponding compounds Ia1.001–Ia1.180 in that $R^1$ is nitro, $R^{14}$ is n-propyl and $R^{15}$ is isobutylsulfonyl:

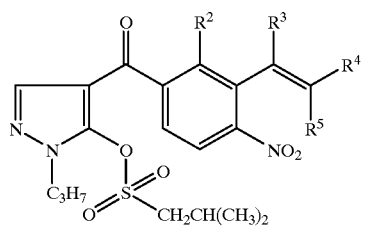
Ia203

Likewise, extraordinary preference is given to the compounds Ia204, in particular to the compounds Ia204.001–Ia204.180, which differ from the corresponding compounds Ia1.001–Ia1.180 in that $R^1$ is nitro, $R^{14}$ is n-butyl and $R^{15}$ is isobutylsulfonyl:

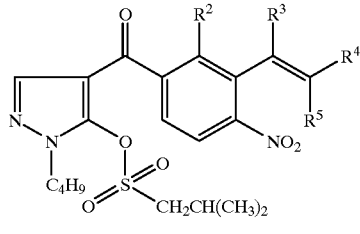
Ia204

Likewise, extraordinary preference is given to the compounds Ia205, in particular to the compounds Ia205.001–Ia205.180, which differ from the corresponding compounds Ia1.001–Ia1.180 in that $R^1$ is nitro, $R^{14}$ is isobutyl and $R^{15}$ is isobutylsulfonyl:

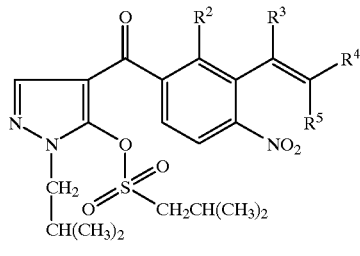
Ia205

Likewise, extraordinary preference is given to the compounds Ia206, in particular to the compounds Ia206.001–Ia206.180, which differ from the corresponding compounds Ia1.001–Ia1.180 in that $R^1$ is nitro and $R^{15}$ is sec-butylsulfonyl:

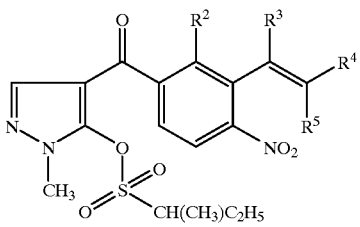

Ia206

Likewise, extraordinary preference is given to the compounds Ia207, in particular to the compounds Ia207.001–Ia207.180, which differ from the corresponding compounds Ia1.001–Ia1.180 in that $R^1$ is nitro, $R^{14}$ is ethyl and $R^{15}$ is sec-butylsulfonyl:

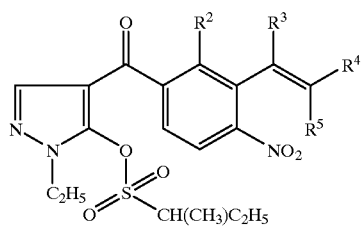

Ia207

Likewise, extraordinary preference is given to the compounds Ia208, in particular to the compounds Ia208.001–Ia208.180, which differ from the corresponding compounds Ia1.001–Ia1.180 in that $R^1$ is nitro, $R^{14}$ is n-propyl and $R^{15}$ is sec-butylsulfonyl:

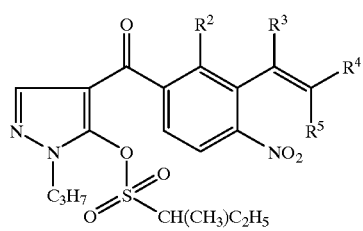

Ia208

Likewise, extraordinary preference is given to the compounds Ia209, in particular to the compounds Ia209.001–Ia209.180, which differ from the corresponding compounds Ia1.001–Ia1.180 in that $R^1$ is nitro, $R^{14}$ is n-butyl and $R^{15}$ is sec-butylsulfonyl:

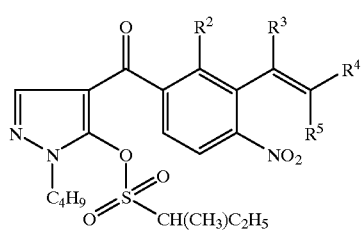

Ia209

Likewise, extraordinary preference is given to the compounds Ia210, in particular to the compounds Ia210.001–Ia210.180, which differ from the corresponding compounds Ia1.001–Ia1.180 in that $R^1$ is nitro, $R^{14}$ is isobutyl and $R^{15}$ is sec-butylsulfonyl:

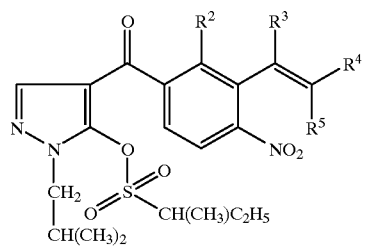

Ia210

Likewise, extraordinary preference is given to the compounds Ia211, in particular to the compounds Ia211.001–Ia211.180, which differ from the corresponding compounds Ia1.001–Ia1.180 in that $R^1$ is nitro and $R^{15}$ is trifluoromethylsulfonyl:

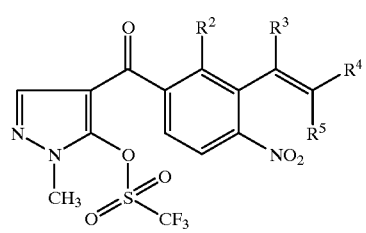

Ia211

Likewise, extraordinary preference is given to the compounds Ia212, in particular to the compounds Ia212.001–Ia212.180, which differ from the corresponding compounds Ia1.001–Ia1.180 in that $R^1$ is nitro, $R^{14}$ is ethyl and $R^{15}$ is trifluoromethylsulfonyl:

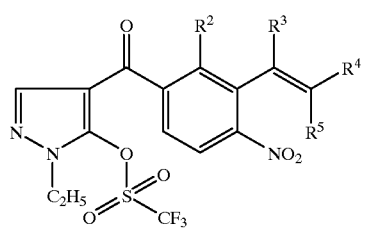

Ia212

Likewise, extraordinary preference is given to the compounds Ia213, in particular to the compounds Ia213.001–Ia213.180, which differ from the corresponding compounds Ia1.001–Ia1.180 in that $R^1$ is nitro, $R^{14}$ is n-propyl and $R^{15}$ is trifluoromethylsulfonyl:

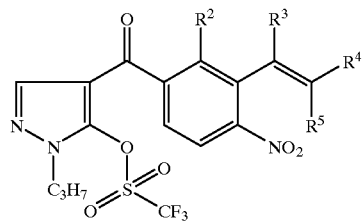

Ia213

Likewise, extraordinary preference is given to the compounds Ia214, in particular to the compounds Ia214.001–Ia214.180, which differ from the corresponding compounds Ia1.001–Ia1.180 in that $R^1$ is nitro, $R^{14}$ is n-butyl and $R^{15}$ is trifluoromethylsulfonyl:

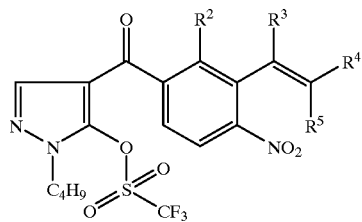

Ia214

Likewise, extraordinary preference is given to the compounds Ia215, in particular to the compounds Ia215.001–Ia125.180, which differ from the corresponding compounds Ia1.001–Ia1.180 in that $R^1$ is nitro, $R^{14}$ is isobutyl and $R^{15}$ is trifluoromethylsulfonyl:

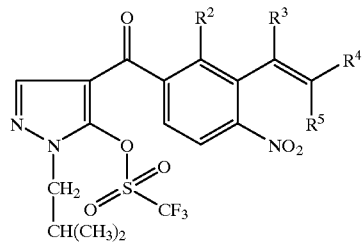

Ia215

Likewise, extraordinary preference is given to the compounds Ia216, in particular to the compounds Ia216.001–Ia216.180, which differ from the corresponding compounds Ia1.001–Ia1.180 in that $R^1$ is nitro and $R^{15}$ is phenylcarbonylmethyl:

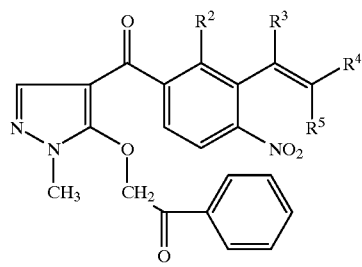

Ia216

Likewise, extraordinary preference is given to the compounds Ia217, in particular to the compounds Ia217.001–Ia217.180, which differ from the corresponding compounds Ia1.001–Ia1.180 in that $R^1$ is nitro, $R^{14}$ is ethyl and $R^{15}$ is phenylcarbonylmethyl:

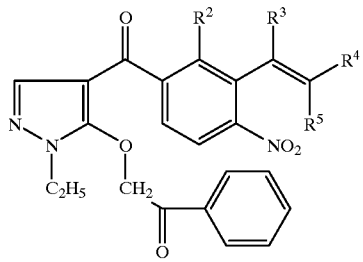

Ia217

Likewise, extraordinary preference is given to the compounds Ia218, in particular to the compounds Ia218.001–Ia218.180, which differ from the corresponding compounds Ia1.001–Ia1.180 in that $R^1$ is nitro, $R^{14}$ is n-propyl and $R^{15}$ is phenylcarbonylmethyl:

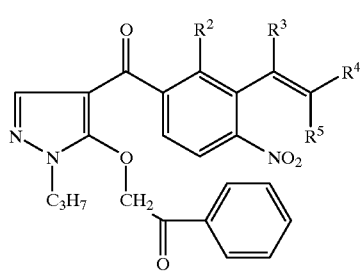

Ia218

Likewise, extraordinary preference is given to the compounds Ia219, in particular to the compounds Ia219.001–Ia219.180, which differ from the corresponding compounds Ia1.001–Ia1.180 in that $R^1$ is nitro, $R^{14}$ is n-butyl and $R^{15}$ is phenylcarbonylmethyl:

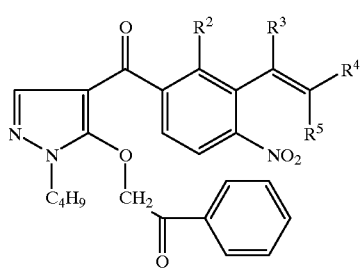

Ia219

Likewise, extraordinary preference is given to the compounds Ia220, in particular to the compounds Ia220.001–Ia220.180, which differ from the corresponding compounds Ia1.001–Ia1.180 in that $R^1$ is nitro, $R^{14}$ is isobutyl and $R^{15}$ is phenylcarbonylmethyl:

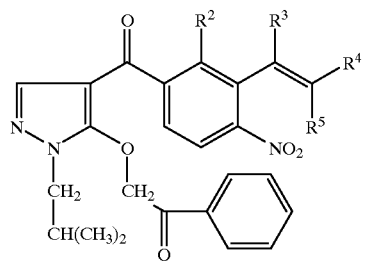

Ia220

Likewise, extraordinary preference is given to the compounds Ia221, in particular to the compounds Ia221.001–Ia221.180, which differ from the corresponding compounds Ia1.001–Ia1.180 in that $R^1$ is nitro and $R^{15}$ is phenylsulfonyl:

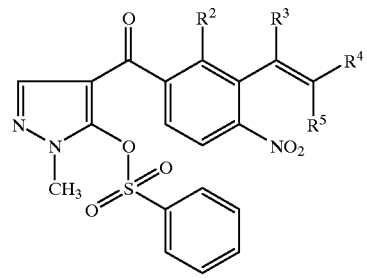

Ia221

Likewise, extraordinary preference is given to the compounds Ia222, in particular to the compounds Ia222.001–Ia222.180, which differ from the corresponding compounds Ia1.001–Ia1.180 in that $R^1$ is nitro, $R^{14}$ is ethyl and $R^{15}$ is phenylsulfonyl:

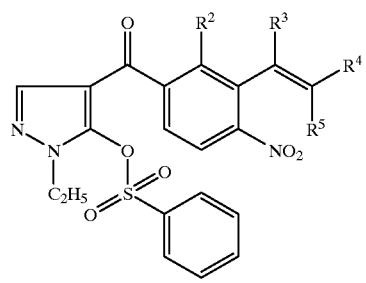

Ia222

Likewise, extraordinary preference is given to the compounds Ia223, in particular to the compounds Ia223.001–Ia223.180, which differ from the corresponding compounds Ia1.001–Ia1.180 in that $R^1$ is nitro, $R^{14}$ is n-propyl and $R^{15}$ is phenylsulfonyl:

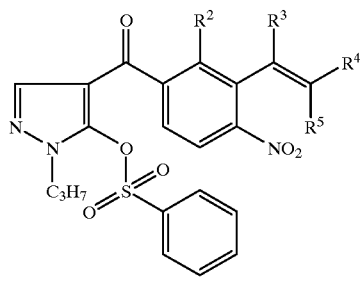

Ia223

Likewise, extraordinary preference is given to the compounds Ia224, in particular to the compounds Ia224.001–Ia224.180, which differ from the corresponding compounds Ia1.001–Ia1.180 in that $R^1$ is nitro, $R^{14}$ is n-butyl and $R^{15}$ is phenylsulfonyl:

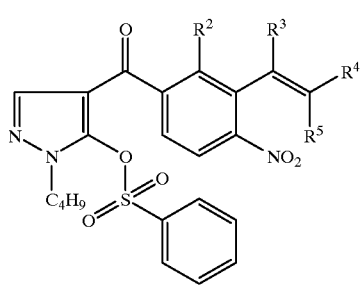

Ia224

Likewise, extraordinary preference is given to the compounds Ia225, in particular to the compounds Ia225.001–Ia225.180, which differ from the corresponding compounds Ia1.001–Ia1.180 in that $R^1$ is nitro, $R^{14}$ is isobutyl and $R^{15}$ is phenylsulfonyl:

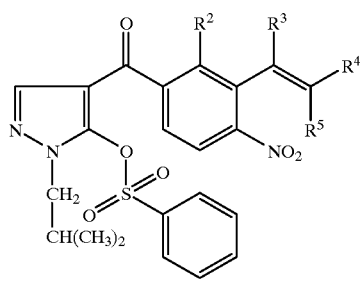

Ia225

Likewise, extraordinary preference is given to the compounds Ia226, in particular to the compounds Ia226.001–Ia226.180, which differ from the corresponding compounds Ia1.001–Ia1.180 in that $R^1$ is nitro and $R^{15}$ is 4-methylphenylsulfonyl:

Likewise, extraordinary preference is given to the compounds Ia227, in particular to the compounds Ia227.001–Ia227.180, which differ from the corresponding compounds Ia1.001–Ia1.180 in that $R^1$ is nitro, $R^{14}$ is ethyl and $R^{15}$ is 4-methylphenylsulfonyl:

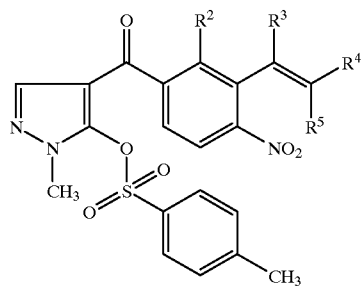

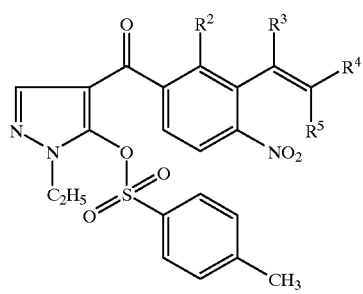

Likewise, extraordinary preference is given to the compounds Ia228, in particular to the compounds Ia228.001–Ia228.180, which differ from the corresponding compounds Ia1.001–Ia1.180 in that $R^1$ is nitro, $R^{14}$ is n-propyl and $R^{15}$ is 4-methylphenylsulfonyl:

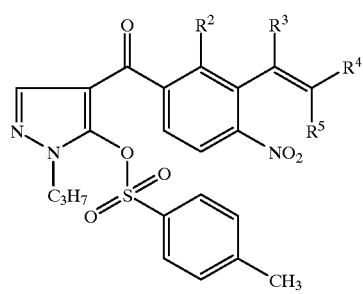

Likewise, extraordinary preference is given to the compounds Ia229, in particular to the compounds Ia229.001–Ia229.180, which differ from the corresponding compounds Ia1.001–Ia1.180 in that $R^1$ is nitro, $R^{14}$ is n-butyl and $R^{15}$ is 4-methylphenylsulfonyl:

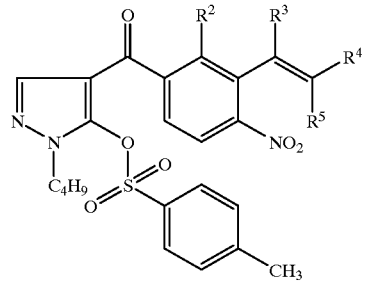

Likewise, extraordinary preference is given to the compounds Ia230, in particular to the compounds Ia230.001–Ia230.180, which differ from the corresponding compounds Ia1.001–Ia1.180 in that $R^1$ is nitro, $R^{14}$ is isobutyl and $R^{15}$ is 4-methylphenylsulfonyl:

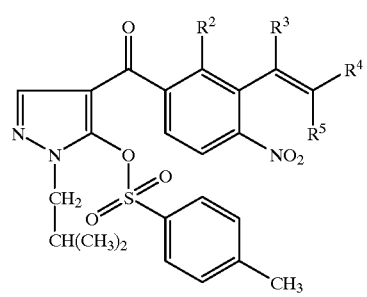

Likewise, extraordinary preference is given to the compounds Ia231, in particular to the compounds Ia231.001–Ia231.180, which differ from the corresponding compounds Ia1.001–Ia1.180 in that $R^1$ is methylsulfonyl:

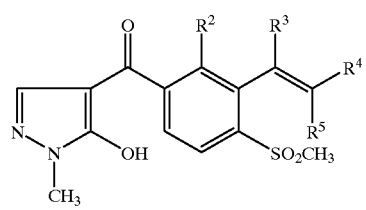

Likewise, extraordinary preference is given to the compounds Ia232, in particular to the compounds Ia232.001–Ia232.180, which differ from the corresponding compounds Ia1.001–Ia1.180 in that $R^1$ is methylsulfonyl and $R^{14}$ is ethyl:

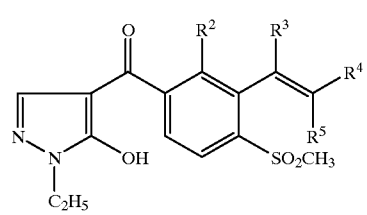

Likewise, extraordinary preference is given to the compounds Ia233, in particular to the compounds Ia233.001–Ia233.180, which differ from the corresponding compounds Ia1.001–Ia1.180 in that $R^1$ is methylsulfonyl and $R^{14}$ is n-propyl:

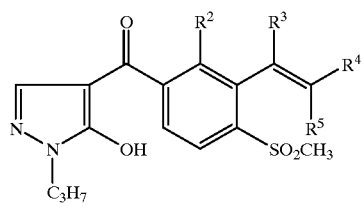

Likewise, extraordinary preference is given to the compounds Ia234, in particular to the compounds Ia234.001–Ia234.180, which differ from the corresponding compounds Ia1.001–Ia1.180 in that $R^1$ is methylsulfonyl and $R^{14}$ is n-butyl:

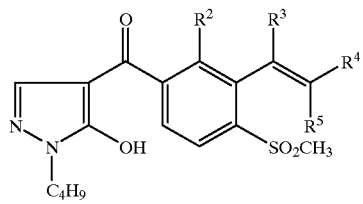

Likewise, extraordinary preference is given to the compounds Ia235, in particular to the compounds Ia235.001–Ia235.180, which differ from the corresponding compounds Ia1.001–Ia1.180 in that $R^1$ is methylsulfonyl and $R^{14}$ is isobutyl:

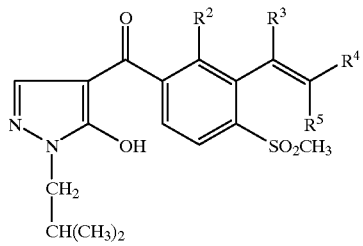

Likewise, extraordinary preference is given to the compounds Ia236, in particular to the compounds Ia236.001–Ia236.180, which differ from the corresponding compounds Ia1.001–Ia1.180 in that $R^1$ is methylsulfonyl and $R^{15}$ is methyl:

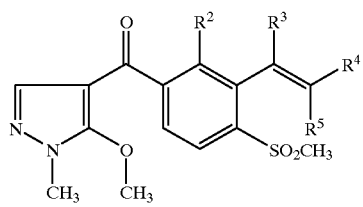

Likewise, extraordinary preference is given to the compounds Ia237, in particular to the compounds Ia237.001–Ia237.180, which differ from the corresponding compounds Ia1.001–Ia1.180 in that $R^1$ is methylsulfonyl, $R^{14}$ is ethyl and $R^{15}$ is methyl:

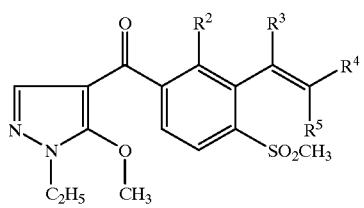

Likewise, extraordinary preference is given to the compounds Ia238, in particular to the compounds Ia238.001–Ia238.180, which differ from the corresponding compounds Ia1.001–Ia1.180 in that $R^1$ is methylsulfonyl, $R^{14}$ is n-propyl and $R^{15}$ is methyl:

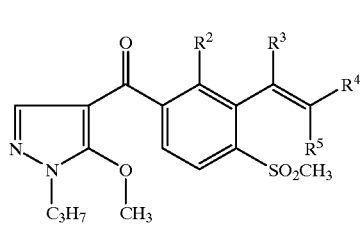

Likewise, extraordinary preference is given to the compounds Ia239, in particular to the compounds Ia239.001–Ia239.180, which differ from the corresponding compounds Ia1.001–Ia1.180 in that $R^1$ is methylsulfonyl, $R^{14}$ is n-butyl and $R^{15}$ is methyl:

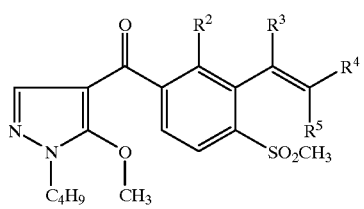

Likewise, extraordinary preference is given to the compounds Ia240, in particular to the compounds Ia240.001–Ia240.180, which differ from the corresponding compounds Ia1.001–Ia1.180 in that $R^1$ is methylsulfonyl, $R^{14}$ is isobutyl and $R^{15}$ is methyl:

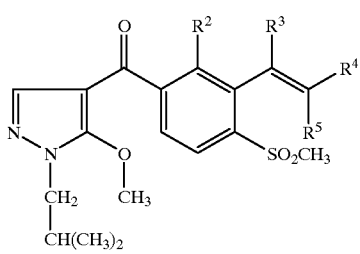

Likewise, extraordinary preference is given to the compounds Ia241, in particular to the compounds Ia241.001–Ia241.180, which differ from the corresponding compounds Ia1.001–Ia1.180 in that $R^1$ is methylsulfonyl and $R^{15}$ is ethyl:

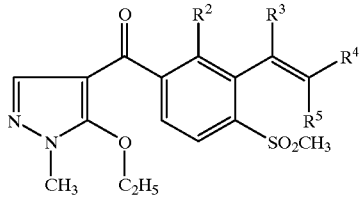

Ia241

Likewise, extraordinary preference is given to the compounds Ia242, in particular to the compounds Ia242.001–Ia242.180, which differ from the corresponding compounds Ia1.001–Ia1.180 in that $R^1$ is methylsulfonyl, $R^{14}$ and $R^{15}$ are each ethyl:

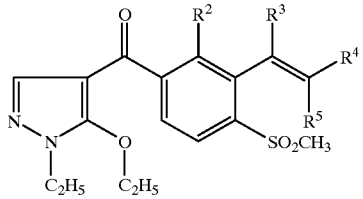

Ia242

Likewise, extraordinary preference is given to the compounds Ia243, in particular to the compounds Ia243.001–Ia243.180, which differ from the corresponding compounds Ia1.001–Ia1.180 in that $R^1$ is methylsulfonyl, $R^{14}$ is n-propyl and $R^{15}$ is ethyl:

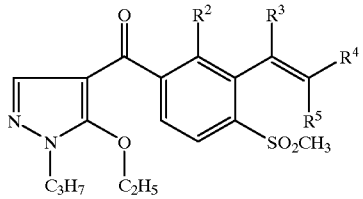

Ia243

Likewise, extraordinary preference is given to the compounds Ia244, in particular to the compounds Ia244.001–Ia244.180, which differ from the corresponding compounds Ia1.001–Ia1.180 in that $R^1$ is methylsulfonyl, $R^{14}$ is n-butyl and $R^{15}$ is ethyl:

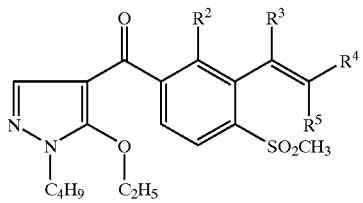

Ia244

Likewise, extraordinary preference is given to the compounds Ia245, in particular to the compounds Ia245.001–Ia245.180, which differ from the corresponding compounds Ia1.001–Ia1.180 in that $R^1$ is methylsulfonyl, $R^{14}$ is isobutyl and $R^{15}$ is ethyl:

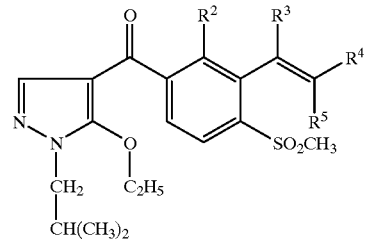

Ia245

Likewise, extraordinary preference is given to the compounds Ia246, in particular to the compounds Ia246.001–Ia246.180, which differ from the corresponding compounds Ia1.001–Ia1.180 in that $R^1$ is methylsulfonyl and $R^{15}$ is n-propyl:

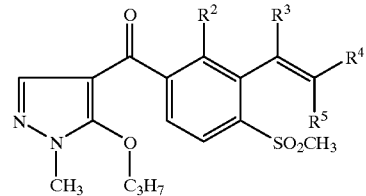

Ia246

Likewise, extraordinary preference is given to the compounds Ia247, in particular to the compounds Ia247.001–Ia247.180, which differ from the corresponding compounds Ia1.001–Ia1.180 in that $R^1$ is methylsulfonyl, $R^{14}$ is ethyl and $R^{15}$ is n-propyl:

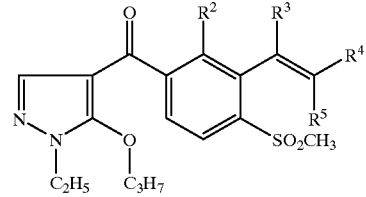

Ia247

Likewise, extraordinary preference is given to the compounds Ia248, in particular to the compounds Ia248.001–Ia248.180, which differ from the corresponding compounds Ia1.001–Ia1.180 in that $R^1$ is methylsulfonyl, $R^{14}$ and $R^{15}$ are each n-propyl:

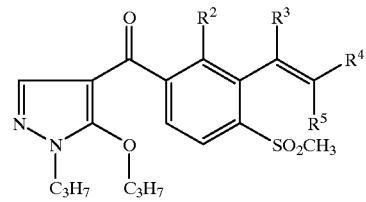

Ia248

Likewise, extraordinary preference is given to the compounds Ia249, in particular to the compounds Ia249.001–Ia249.180, which differ from the corresponding compounds Ia1.001–Ia1.180 in that $R^1$ is methylsulfonyl, $R^{14}$ is n-butyl and $R^{15}$ is n-propyl:

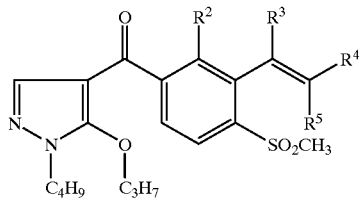
Ia249

Likewise, extraordinary preference is given to the compounds Ia250, in particular to the compounds Ia250.001–Ia250.180, which differ from the corresponding compounds Ia1.001–Ia1.180 in that $R^1$ is methylsulfonyl, $R^{14}$ is isobutyl and $R^{15}$ is n-propyl:

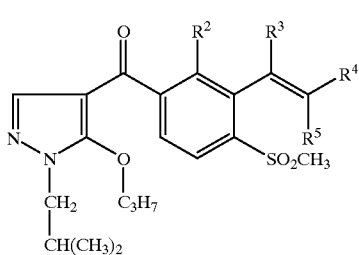
Ia250

Likewise, extraordinary preference is given to the compounds Ia251, in particular to the compounds Ia251.001–Ia251.180, which differ from the corresponding compounds Ia1.001–Ia1.180 in that $R^1$ is methylsulfonyl and $R^{15}$ is isopropyl:

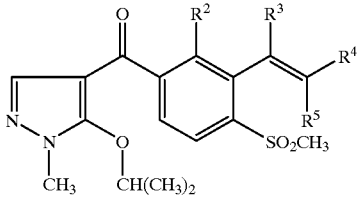
Ia251

Likewise, extraordinary preference is given to the compounds Ia252, in particular to the compounds Ia252.001–Ia252.180, which differ from the corresponding compounds Ia1.001–Ia1.180 in that $R^1$ is methylsulfonyl, $R^{14}$ is ethyl and $R^{15}$ is isopropyl:

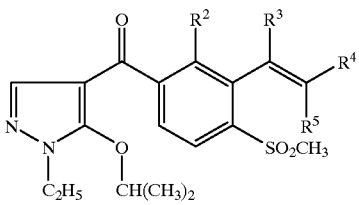
Ia252

Likewise, extraordinary preference is given to the compounds Ia253, in particular to the compounds Ia253.001–Ia253.180, which differ from the corresponding compounds Ia1.001–Ia1.180 in that $R^1$ is methylsulfonyl, $R^{14}$ is n-propyl and $R^{15}$ is isopropyl:

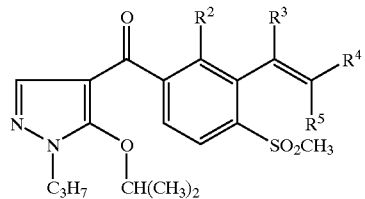
Ia253

Likewise, extraordinary preference is given to the compounds Ia254, in particular to the compounds Ia254.001–Ia254.180, which differ from the corresponding compounds Ia1.001–Ia1.180 in that $R^1$ is methylsulfonyl, $R^{14}$ is n-butyl and $R^{15}$ is isopropyl:

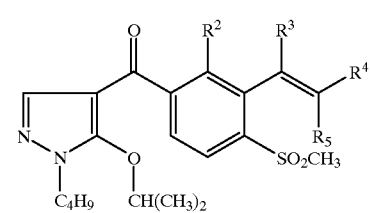
Ia254

Likewise, extraordinary preference is given to the compounds Ia255, in particular to the compounds Ia255.001–Ia255.180, which differ from the corresponding compounds Ia1.001–Ia1.180 in that $R^1$ is methylsulfonyl, $R^{14}$ is isobutyl and $R^{15}$ is isopropyl:

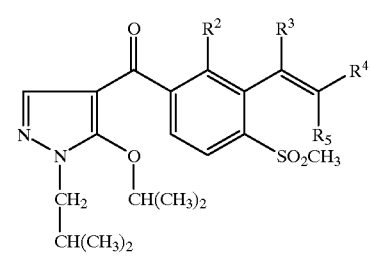
Ia255

Likewise, extraordinary preference is given to the compounds Ia256, in particular to the compounds Ia256.001–Ia256.180, which differ from the corresponding compounds Ia1.001–Ia1.180 in that $R^1$ is methylsulfonyl and $R^{15}$ is n-butyl:

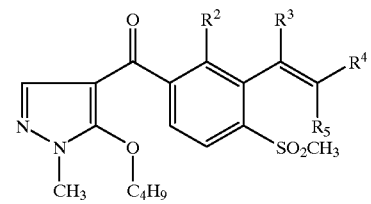
Ia256

Likewise, extraordinary preference is given to the compounds Ia257, in particular to the compounds Ia257.001–Ia257.180, which differ from the corresponding compounds Ia1.001–Ia1.180 in that $R^1$ is methylsulfonyl, $R^{14}$ is ethyl and $R^{15}$ is n-butyl:

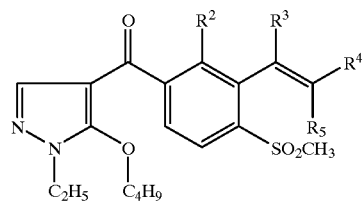

Ia257

Likewise, extraordinary preference is given to the compounds Ia258, in particular to the compounds Ia258.001–Ia258.180, which differ from the corresponding compounds Ia1.001–Ia1.180 in that $R^1$ is methylsulfonyl, $R^{14}$ is n-propyl and $R^{15}$ is n-butyl:

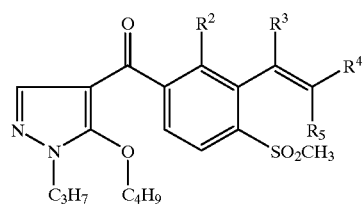

Ia258

Likewise, extraordinary preference is given to the compounds Ia259, in particular to the compounds Ia259.001–Ia259.180, which differ from the corresponding compounds Ia1.001–Ia1.180 in that $R^1$ is methylsulfonyl, $R^{14}$ and $R^{15}$ are each n-butyl:

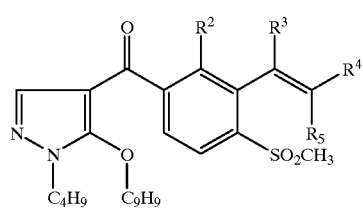

Ia259

Likewise, extraordinary preference is given to the compounds Ia260, in particular to the compounds Ia260.001–Ia260.180, which differ from the corresponding compounds Ia1.001–Ia1.180 in that $R^1$ is methylsulfonyl, $R^{14}$ is isobutyl and $R^{15}$ is n-butyl:

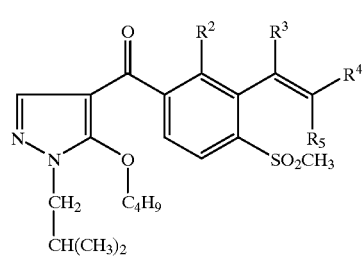

Ia260

Likewise, extraordinary preference is given to the compounds Ia261, in particular to the compounds Ia261.001–Ia261.180, which differ from the corresponding compounds Ia1.001–Ia1.180 in that $R^1$ is methylsulfonyl and $R^{15}$ is sec-butyl:

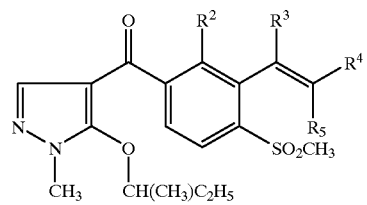

Ia261

Likewise, extraordinary preference is given to the compounds Ia262, in particular to the compounds Ia262.001–Ia262.180, which differ from the corresponding compounds Ia1.001–Ia1.180 in that $R^1$ is methylsulfonyl, $R^{14}$ is ethyl and $R^{15}$ is sec-butyl:

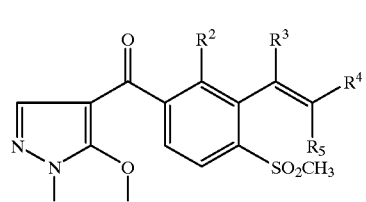

Ia262

Likewise, extraordinary preference is given to the compounds Ia263, in particular to the compounds Ia263.001–Ia263.180, which differ from the corresponding compounds Ia1.001–Ia1.180 in that $R^1$ is methylsulfonyl, $R^{14}$ is n-propyl and $R^{15}$ is sec-butyl:

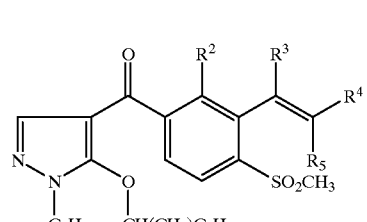

Ia263

Likewise, extraordinary preference is given to the compounds Ia264, in particular to the compounds Ia264.001–Ia264.180, which differ from the corresponding compounds Ia1.001–Ia1.180 in that $R^1$ is methylsulfonyl, $R^{14}$ is n-butyl and $R^{15}$ is sec-butyl:

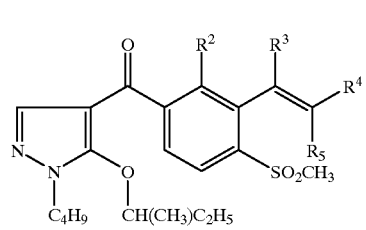

Ia264

Likewise, extraordinary preference is given to the compounds Ia265, in particular to the compounds Ia265.001–Ia265.180, which differ from the corresponding compounds Ia1.001–Ia1.180 in that $R^1$ is methylsulfonyl, $R^{14}$ is isobutyl and $R^{15}$ is sec-butyl:

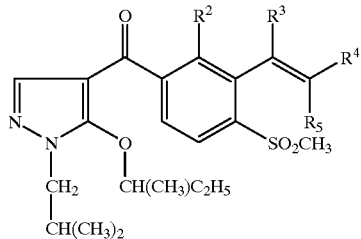

Ia265

Likewise, extraordinary preference is given to the compounds Ia266, in particular to the compounds Ia266.001–Ia266.180, which differ from the corresponding compounds Ia1.001–Ia1.180 in that $R^1$ is methylsulfonyl and $R^{15}$ is isobutyl:

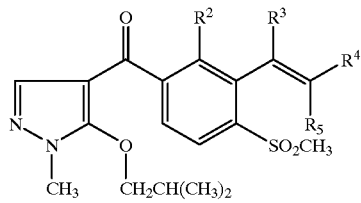

Ia266

Likewise, extraordinary preference is given to the compounds Ia267, in particular to the compounds Ia267.001–Ia267.180, which differ from the corresponding compounds Ia1.001–Ia1.180 in that $R^1$ is methylsulfonyl, $R^{14}$ is ethyl and $R^{15}$ is isobutyl:

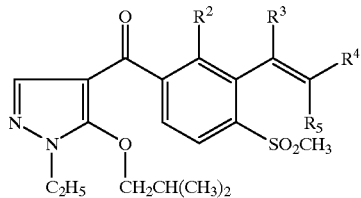

Ia267

Likewise, extraordinary preference is given to the compounds Ia268, in particular to the compounds Ia268.001–Ia268.180, which differ from the corresponding compounds Ia1.001–Ia1.180 in that $R^1$ is methylsulfonyl, $R^{14}$ is n-propyl and $Rl^5$ is isobutyl:

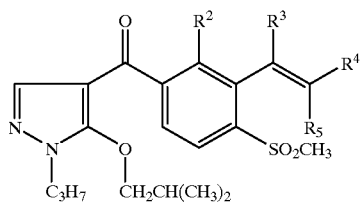

Ia268

Likewise, extraordinary preference is given to the compounds Ia269, in particular to the compounds Ia269.001–Ia269.180, which differ from the corresponding compounds Ia1.001–Ia1.180 in that $R^1$ is methylsulfonyl, $R^{14}$ is n-butyl and $R^{15}$ is isobutyl:

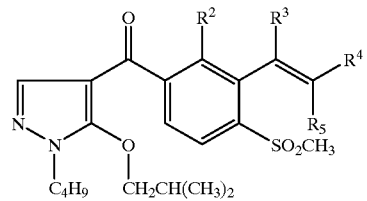

Ia269

Likewise, extraordinary preference is given to the compounds Ia270, in particular to the compounds Ia270.001–Ia270.180, which differ from the corresponding compounds Ia1.001–Ia1.180 in that $R^1$ is methylsulfonyl, $R^{14}$ and $R^{15}$ are each isobutyl:

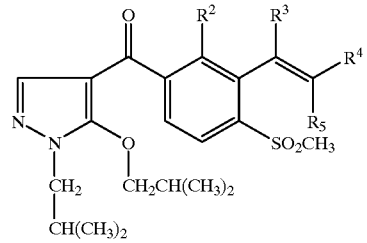

Ia270

Likewise, extraordinary preference is given to the compounds Ia271, in particular to the compounds Ia271.001–Ia271.180, which differ from the corresponding compounds Ia1.001–Ia1.180 in that $R^1$ is methylsulfonyl and $R^{15}$ is methylcarbonyl:

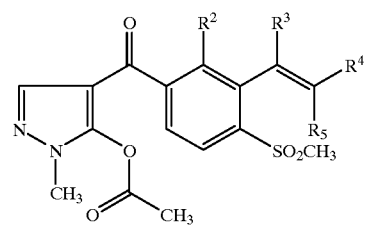

Ia271

Likewise, extraordinary preference is given to the compounds Ia272, in particular to the compounds Ia272.001–Ia272.180, which differ from the corresponding compounds Ia1.001–Ia1.180 in that $R^1$ is methylsulfonyl, $R^{14}$ is ethyl and $R^{15}$ is methylcarbonyl:

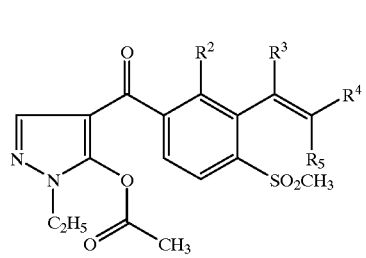

Ia272

Likewise, extraordinary preference is given to the compounds Ia273, in particular to the compounds Ia273.001–Ia273.180, which differ from the corresponding compounds Ia1.001–Ia1.180 in that $R^1$ is methylsulfonyl, $R^{14}$ is n-propyl and $R^{15}$ is methylcarbonyl:

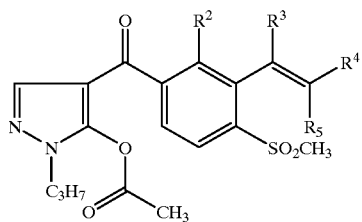

Ia273

Likewise, extraordinary preference is given to the compounds Ia274, in particular to the compounds Ia274.001–Ia274.180, which differ from the corresponding compounds Ia1.001–Ia1.180 in that $R^1$ is methylsulfonyl, $R^{14}$ is n-butyl and $R^{15}$ is methylcarbonyl:

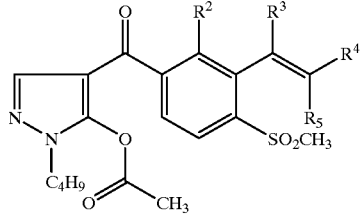

Ia274

Likewise, extraordinary preference is given to the compounds Ia275, in particular to the compounds Ia275.001–Ia275.180, which differ from the corresponding compounds Ia1.001–Ia1.180 in that $R^1$ is methylsulfonyl, $R^{14}$ is isobutyl and $R^{15}$ is methylcarbonyl:

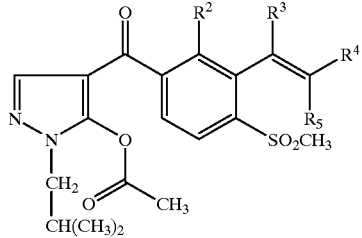

Ia275

Likewise, extraordinary preference is given to the compounds Ia276, in particular to the compounds Ia276.001–Ia276.180, which differ from the corresponding compounds Ia1.001–Ia1.180 in that $R^1$ is methylsulfonyl and $R^{15}$ is ethylcarbonyl:

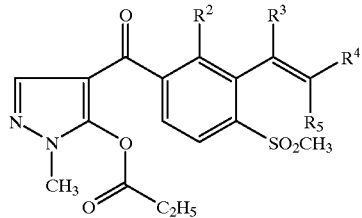

Ia276

Likewise, extraordinary preference is given to the compounds Ia277, in particular to the compounds Ia277.001–Ia277.180, which differ from the corresponding compounds Ia1.001–Ia1.180 in that $R^1$ is methylsulfonyl, $R^{14}$ is ethyl and $R^{15}$ is ethylcarbonyl:

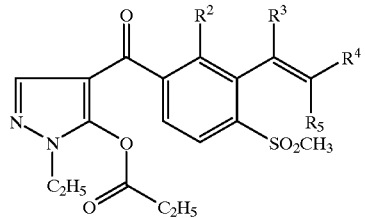

Ia277

Likewise, extraordinary preference is given to the compounds Ia278, in particular to the compounds Ia278.001–Ia278.180, which differ from the corresponding compounds Ia1.001–Ia1.180 in that $R^1$ is methylsulfonyl, $R^{14}$ is n-propyl and $R^{15}$ is ethylcarbonyl:

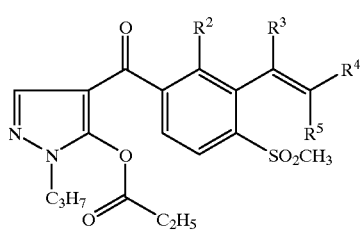

Ia278

Likewise, extraordinary preference is given to the compounds Ia279, in particular to the compounds Ia279.001–Ia279.180, which differ from the corresponding compounds Ia1.001–Ia1.180 in that $R^1$ is methylsulfonyl, $R^{14}$ is n-butyl and $R^{15}$ is ethylcarbonyl:

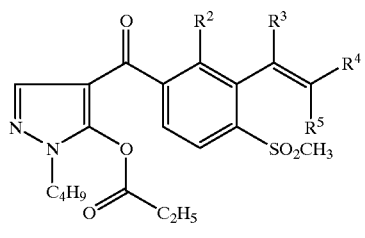

Ia279

Likewise, extraordinary preference is given to the compounds Ia280, in particular to the compounds Ia280.001–Ia280.180, which differ from the corresponding compounds Ia1.001–Ia1.180 in that $R^1$ is methylsulfonyl, $R^{14}$ is isobutyl and $R^{15}$ is ethylcarbonyl:

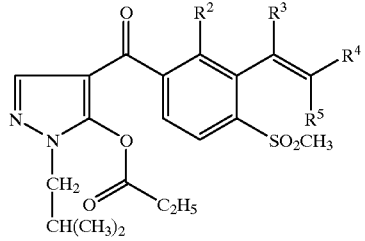

Ia280

Likewise, extraordinary preference is given to the compounds Ia281, in particular to the compounds Ia281.001–Ia281.180, which differ from the corresponding compounds Ia1.001–Ia1.180 in that $R^1$ is methylsulfonyl and $R^{15}$ is n-propylcarbonyl:

Ia281

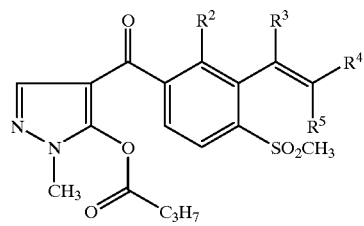

Likewise, extraordinary preference is given to the compounds Ia282, in particular to the compounds Ia282.001–Ia282.180, which differ from the corresponding compounds Ia1.001–Ia1.180 in that $R^1$ is methylsulfonyl, $R^{14}$ is ethyl and $R^{15}$ is n-propylcarbonyl:

Ia282

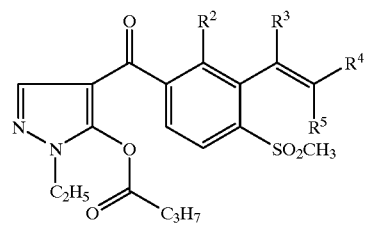

Likewise, extraordinary preference is given to the compounds Ia283, in particular to the compounds Ia283.001–Ia283.180, which differ from the corresponding compounds Ia1.001–Ia1.180 in that $R^1$ is methylsulfonyl, $R^{14}$ is n-propyl and $R^{15}$ is n-propylcarbonyl:

Ia283

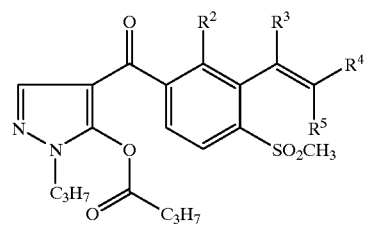

Likewise, extraordinary preference is given to the compounds Ia284, in particular to the compounds Ia284.001–Ia284.180, which differ from the corresponding compounds Ia1.001–Ia1.180 in that $R^1$ is methylsulfonyl, $R^{14}$ is n-butyl and $R^{15}$ is n-propylcarbonyl:

Ia284

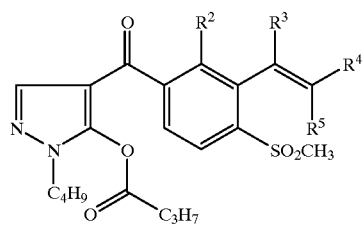

Likewise, extraordinary preference is given to the compounds Ia285, in particular to the compounds Ia285.001–Ia285.180, which differ from the corresponding compounds Ia1.001–Ia1.180 in that $R^1$ is methylsulfonyl, $R^{14}$ is isobutyl and $R^{15}$ is n-propylcarbonyl:

Ia285

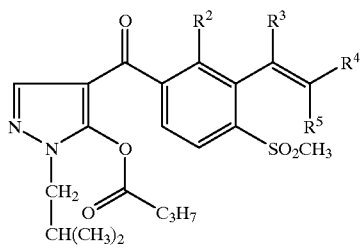

Likewise, extraordinary preference is given to the compounds Ia286, in particular to the compounds Ia286.001–Ia286.180, which differ from the corresponding compounds Ia1.001–Ia1.180 in that $R^1$ is methylsulfonyl and $R^{14}$ is trifluoromethylcarbonyl:

Ia286

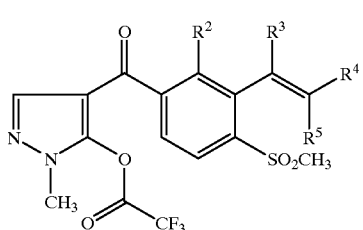

Likewise, extraordinary preference is given to the compounds Ia287, in particular to the compounds Ia287.001–Ia287.180, which differ from the corresponding compounds Ia1.001–Ia1.180 in that $R^1$ is methylsulfonyl, $R^{14}$ is ethyl and $R^{15}$ is trifluoromethylcarbonyl:

Ia287

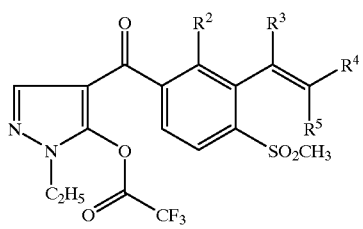

Likewise, extraordinary preference is given to the compounds Ia288, in particular to the compounds Ia288.001–Ia288.180, which differ from the corresponding compounds Ia1.001–Ia1.180 in that $R^1$ is methylsulfonyl, $R^{14}$ is n-propyl and $R^{15}$ is trifluoromethylcarbonyl:

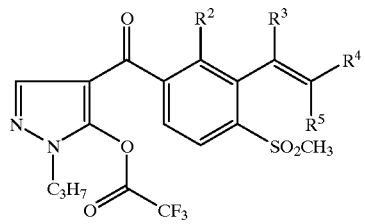

Ia288

Likewise, extraordinary preference is given to the compounds Ia289, in particular to the compounds Ia289.001–Ia289.180, which differ from the corresponding compounds Ia1.001–Ia1.180 in that $R^1$ is methylsulfonyl, $R^{14}$ is n-butyl and $R^{15}$ is trifluoromethylcarbonyl:

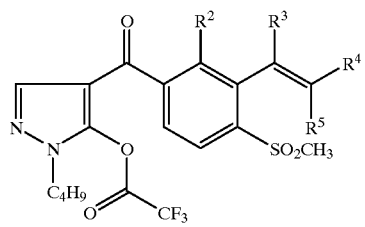

Ia289

Likewise, extraordinary preference is given to the compounds Ia290, in particular to the compounds Ia290.001–Ia290.180, which differ from the corresponding compounds Ia1.001–Ia1.180 in that $R^1$ is methylsulfonyl, $R^{14}$ is isobutyl and $R^{15}$ is trifluoromethylcarbonyl:

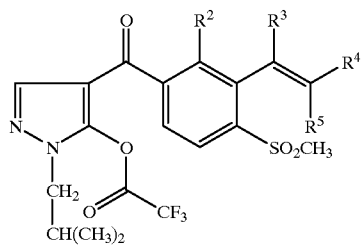

Ia290

Likewise, extraordinary preference is given to the compounds Ia291, in particular to the compounds Ia291.001–Ia291.180, which differ from the corresponding compounds Ia1.001–Ia1.180 in that $R^1$ and $R^{15}$ are each methylsulfonyl:

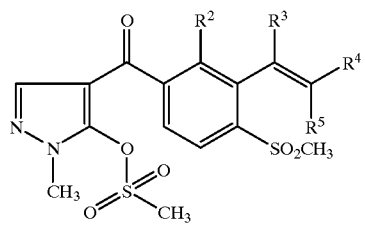

Ia291

Likewise, extraordinary preference is given to the compounds Ia292, in particular to the compounds Ia292.001–Ia292.180, which differ from the corresponding compounds Ia1.001–Ia1.180 in that $R^1$ and $R^{15}$ are each methylsulfonyl and $R^{14}$ is ethyl:

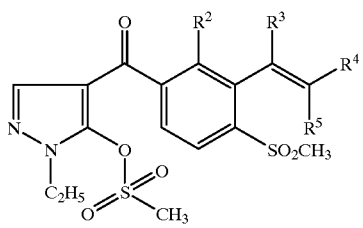

Ia292

Likewise, extraordinary preference is given to the compounds Ia293, in particular to the compounds Ia293.001–Ia293.180, which differ from the corresponding compounds Ia1.001–Ia1.180 in that $R^1$ and $R^{15}$ are each methylsulfonyl and $R^{14}$ is n-propyl:

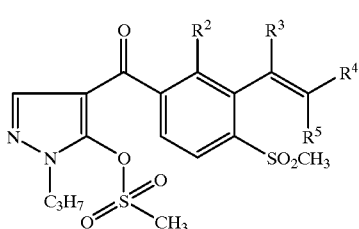

Ia293

Likewise, extraordinary preference is given to the compounds Ia294, in particular to the compounds Ia294.001–Ia294.180, which differ from the corresponding compounds Ia1.001–Ia1.180 in that $R^1$ and $R^{15}$ are each methylsulfonyl and $R^{14}$ is n-butyl:

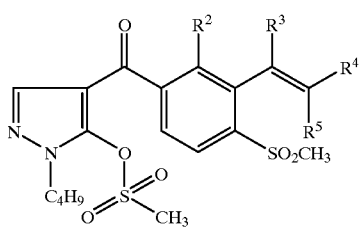

Ia294

Likewise, extraordinary preference is given to the compounds Ia295, in particular to the compounds Ia295.001–Ia295.180, which differ from the corresponding compounds Ia1.001–Ia1.180 in that $R^1$ and $R^{15}$ are each methylsulfonyl and $R^{14}$ is isobutyl:

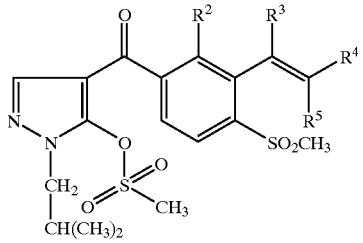

Ia295

Likewise, extraordinary preference is given to the compounds Ia296, in particular to the compounds Ia296.001–Ia296.180, which differ from the corresponding compounds Ia1.001–Ia1.180 in that $R^1$ is methylsulfonyl and $R^{15}$ is ethylsulfonyl:

Ia296

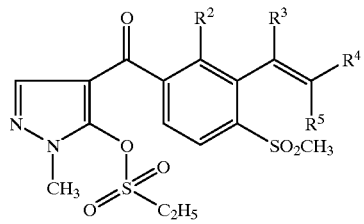

Likewise, extraordinary preference is given to the compounds Ia297, in particular to the compounds Ia297.001–Ia297.180, which differ from the corresponding compounds Ia1.001–Ia1.180 in that $R^1$ is methylsulfonyl, $R^{14}$ is ethyl and $R^{15}$ is ethylsulfonyl:

Ia297

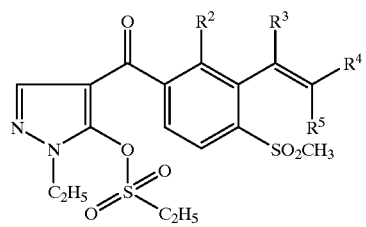

Likewise, extraordinary preference is given to the compounds Ia298, in particular to the compounds Ia298.001–Ia298.180, which differ from the corresponding compounds Ia1.001–Ia1.180 in that $R^1$ is methylsulfonyl, $R^{14}$ is n-propyl and $R^{15}$ is ethylsulfonyl:

Ia298

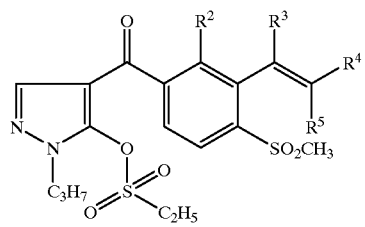

Likewise, extraordinary preference is given to the compounds Ia299, in particular to the compounds Ia299.001–Ia299.180, which differ from the corresponding compounds Ia1.001–Ia1.180 in that $R^1$ is methylsulfonyl, $R^{14}$ is n-butyl and $R^{15}$ is ethylsulfonyl:

Ia299

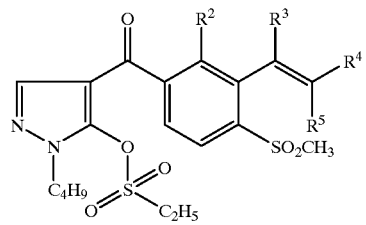

Likewise, extraordinary preference is given to the compounds Ia300, in particular to the compounds Ia300.001–Ia300.180, which differ from the corresponding compounds Ia1.001–Ia1.180 in that $R^1$ is methylsulfonyl, $R^{14}$ is isobutyl and $R^{15}$ is ethylsulfonyl:

Ia300

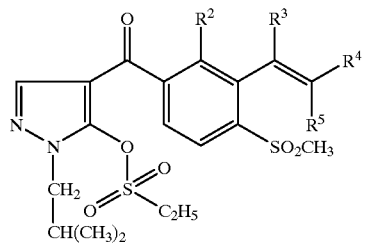

Likewise, extraordinary preference is given to the compounds Ia301, in particular to the compounds Ia301.001–Ia301.180, which differ from the corresponding compounds Ia1.001–Ia1.180 in that $R^1$ is methylsulfonyl and $R^{15}$ is n-propylsulfonyl:

Ia301

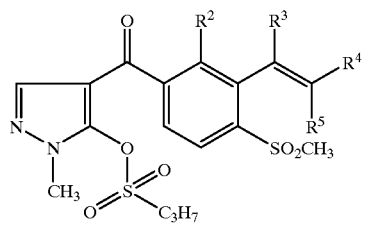

Likewise, extraordinary preference is given to the compounds Ia302, in particular to the compounds Ia302.001–Ia302.180, which differ from the corresponding compounds Ia1.001–Ia1.180 in that $R^1$ is methylsulfonyl, $R^{14}$ is ethyl and $R^{15}$ is n-propylsulfonyl:

Ia302

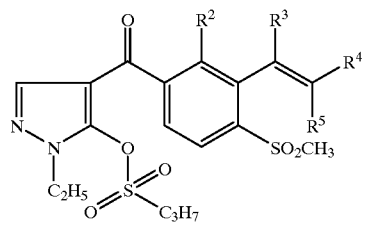

Likewise, extraordinary preference is given to the compounds Ia303, in particular to the compounds Ia303.001–Ia303.180, which differ from the corresponding compounds Ia1.001–Ia1.180 in that $R^1$ is methylsulfonyl, $R^{14}$ is n-propyl and $R^{15}$ is n-propylsulfonyl:

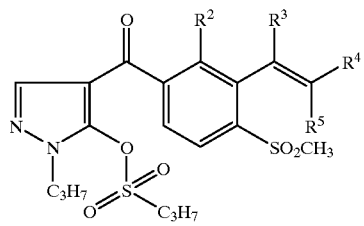

Ia303

Likewise, extraordinary preference is given to the compounds Ia304, in particular to the compounds Ia304.001–Ia304.180, which differ from the corresponding compounds Ia1.001–Ia1.180 in that $R^1$ is methylsulfonyl, $R^{14}$ is n-butyl and $R^{15}$ is n-propylsulfonyl:

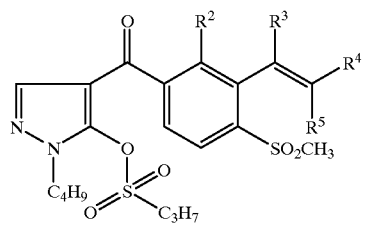

Ia304

Likewise, extraordinary preference is given to the compounds Ia305, in particular to the compounds Ia305.001–Ia305.180, which differ from the corresponding compounds Ia1.001–Ia1.180 in that $R^1$ is methylsulfonyl, $R^{14}$ is isobutyl and $R^{15}$ is n-propylsulfonyl:

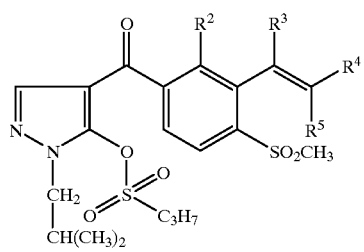

Ia305

Likewise, extraordinary preference is given to the compounds Ia306, in particular to the compounds Ia306.001–Ia306.180, which differ from the corresponding compounds Ia1.001–Ia1.180 in that $R^1$ is methylsulfonyl and $R^{15}$ is isopropylsulfonyl:

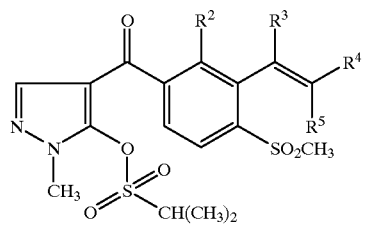

Ia306

Likewise, extraordinary preference is given to the compounds Ia307, in particular to the compounds Ia307.001–Ia307.180, which differ from the corresponding compounds Ia1.001–Ia1.180 in that $R^1$ is methylsulfonyl, $R^{14}$ is ethyl and $R^{15}$ is isopropylsulfonyl:

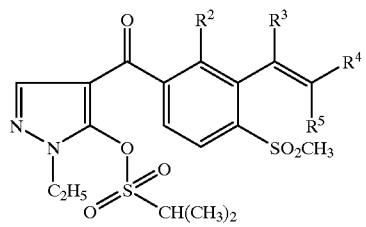

Ia307

Likewise, extraordinary preference is given to the compounds Ia308, in particular to the compounds Ia308.001–Ia308.180, which differ from the corresponding compounds Ia1.001–Ia1.180 in that $R^1$ is methylsulfonyl, $R^{14}$ is n-propyl and $R^{15}$ is isopropylsulfonyl:

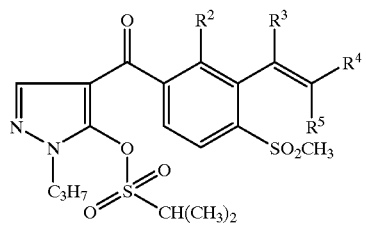

Ia308

Likewise, extraordinary preference is given to the compounds Ia309, in particular to the compounds Ia309.001–Ia309.180, which differ from the corresponding compounds Ia1.001–Ia1.180 in that $R^1$ is methylsulfonyl, $R^{14}$ is n-butyl and $R^{15}$ is isopropylsulfonyl:

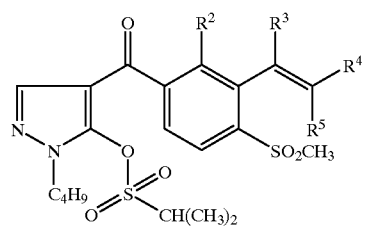

Ia309

Likewise, extraordinary preference is given to the compounds Ia310, in particular to the compounds Ia310.001–Ia310.180, which differ from the corresponding compounds Ia1.001–Ia1.180 in that $R^1$ is methylsulfonyl, $R^{14}$ is isobutyl and $R^{15}$ is isopropylsulfonyl:

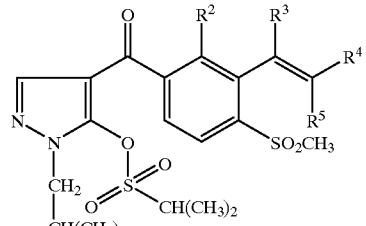

Ia310

Likewise, extraordinary preference is given to the compounds Ia311, in particular to the compounds Ia311.001–Ia311.180, which differ from the corresponding compounds Ia1.001–Ia1.180 in that $R^1$ is methylsulfonyl and $R^{15}$ is n-butylsulfonyl:

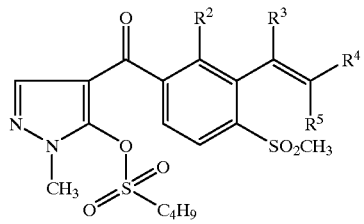

Ia311

Likewise, extraordinary preference is given to the compounds Ia312, in particular to the compounds Ia312.001–Ia312.180, which differ from the corresponding compounds Ia1.001–Ia1.180 in that $R^1$ is methylsulfonyl, $R^{14}$ is ethyl and $R^{15}$ is n-butylsulfonyl:

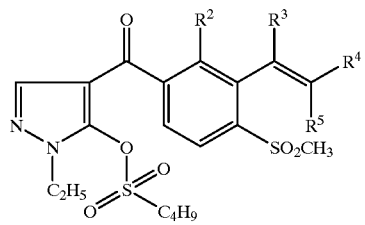

Ia312

Likewise, extraordinary preference is given to the compounds Ia313, in particular to the compounds Ia313.001–Ia313.180, which differ from the corresponding compounds Ia1.001–Ia1.180 in that $R^1$ is methylsulfonyl, $R^{14}$ is n-propyl and $R^{15}$ is n-butylsulfonyl:

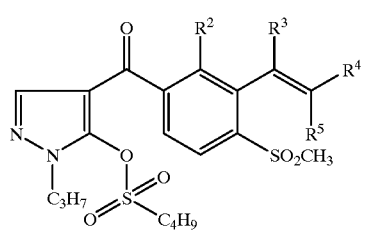

Ia313

Likewise, extraordinary preference is given to the compounds Ia314, in particular to the compounds Ia314.001–Ia314.180, which differ from the corresponding compounds Ia1.001–Ia1.180 in that $R^1$ is methylsulfonyl, $R^{14}$ is n-butyl and $R^{15}$ is n-butylsulfonyl:

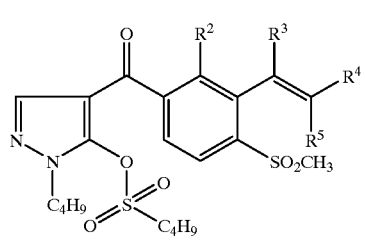

Ia314

Likewise, extraordinary preference is given to the compounds Ia315, in particular to the compounds Ia315.001–Ia315.180, which differ from the corresponding compounds Ia1.001–Ia1.180 in that $R^1$ is methylsulfonyl, $R^{14}$ is isobutyl and $R^{15}$ is n-butylsulfonyl:

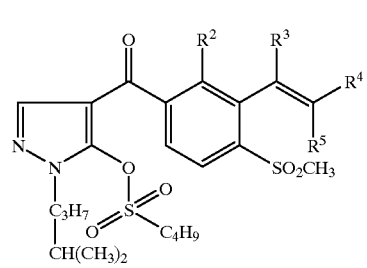

Ia315

Likewise, extraordinary preference is given to the compounds Ia316, in particular to the compounds Ia316.001–Ia316.180, which differ from the corresponding compounds Ia1.001–Ia1.180 in that $R^1$ is methylsulfonyl and $R^{15}$ is isobutylsulfonyl:

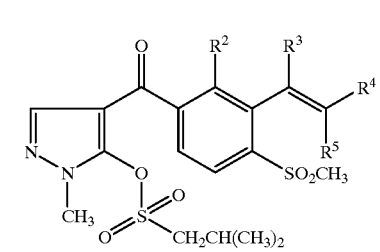

Ia316

Likewise, extraordinary preference is given to the compounds Ia317, in particular to the compounds Ia317.001–Ia317.180, which differ from the corresponding compounds Ia1.001–Ia1.180 in that $R^1$ is methylsulfonyl, $R^{14}$ is ethyl and $R^{15}$ is isobutylsulfonyl:

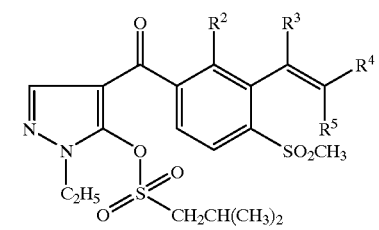

Ia317

Likewise, extraordinary preference is given to the compounds Ia318, in particular to the compounds Ia318.001–Ia318.180, which differ from the corresponding compounds Ia1.001–Ia1.180 in that $R^1$ is methylsulfonyl, $R^{14}$ is n-propyl and $R^{15}$ is isobutylsulfonyl:

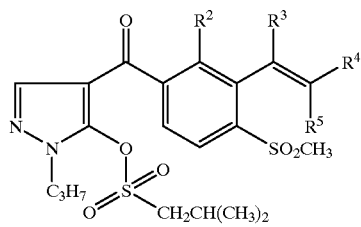

Ia318

Likewise, extraordinary preference is given to the compounds Ia319, in particular to the compounds Ia319.001–Ia319.180, which differ from the corresponding compounds Ia1.001–Ia1.180 in that $R^1$ is methylsulfonyl, $R^{14}$ is n-butyl and $R^{15}$ is isobutylsulfonyl:

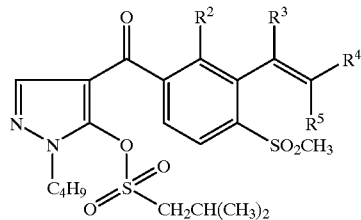

Ia319

Likewise, extraordinary preference is given to the compounds Ia320, in particular to the compounds Ia320.001–Ia320.180, which differ from the corresponding compounds Ia1.001–Ia1.180 in that $R^1$ is methylsulfonyl, $R^{14}$ is isobutyl and $R^{15}$ is isobutylsulfonyl:

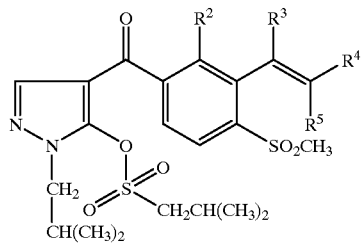

Ia320

Likewise, extraordinary preference is given to the compounds Ia321, in particular to the compounds Ia321.001–Ia321.180, which differ from the corresponding compounds Ia1.001–Ia1.180 in that $R^1$ is methylsulfonyl and $R^{15}$ is sec-butylsulfonyl:

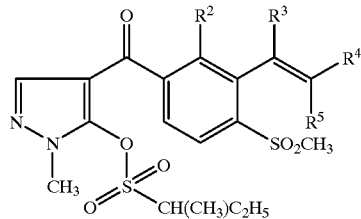

Ia321

Likewise, extraordinary preference is given to the compounds Ia322, in particular to the compounds Ia322.001–Ia322.180, which differ from the corresponding compounds Ia1.001–Ia1.180 in that $R^1$ is methylsulfonyl, $R^{14}$ is ethyl and $R^{15}$ is sec-butylsulfonyl:

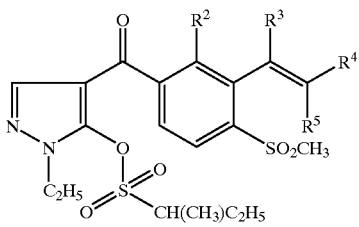

Ia322

Likewise, extraordinary preference is given to the compounds Ia323, in particular to the compounds Ia323.001–Ia323.180, which differ from the corresponding compounds Ia1.001–Ia1.180 in that $R^1$ is methylsulfonyl, $R^{14}$ is for [sic] n-propyl and $R^{15}$ is sec-butylsulfonyl:

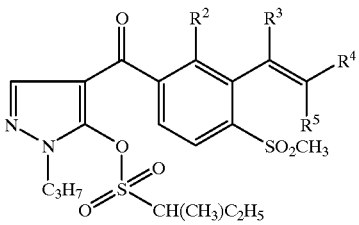

Ia323

Likewise, extraordinary preference is given to the compounds Ia324, in particular to the compounds Ia324.001–Ia324.180, which differ from the corresponding compounds Ia1.001–Ia1.180 in that $R^1$ is methylsulfonyl, $R^{14}$ is n-butyl and $R^{15}$ is sec-butylsulfonyl:

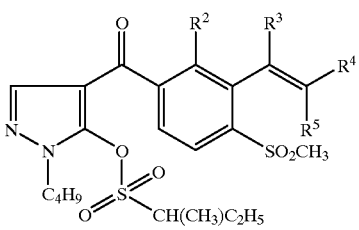

Ia324

Likewise, extraordinary preference is given to the compounds Ia325, in particular to the compounds Ia325.001–Ia325.180, which differ from the corresponding compounds Ia1.001–Ia1.180 in that $R^1$ is methylsulfonyl, $R^{14}$ is isobutyl and $R^{15}$ is sec-butylsulfonyl:

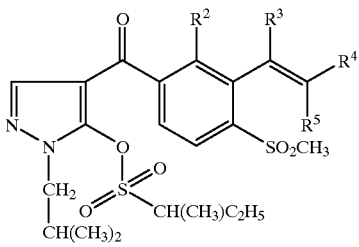

Ia325

Likewise, extraordinary preference is given to the compounds Ia326, in particular to the compounds Ia326.001–Ia326.180, which differ from the corresponding compounds Ia1.001–Ia1.180 in that $R^1$ is methylsulfonyl and $R^{15}$ is trifluoromethylsulfonyl:

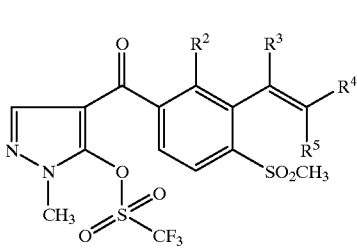

Ia326

Likewise, extraordinary preference is given to the compounds Ia327, in particular to the compounds Ia327.001–Ia327.180, which differ from the corresponding compounds Ia1.001–Ia1.180 in that $R^1$ is methylsulfonyl, $R^{14}$ is ethyl and $R^{15}$ is trifluoromethylsulfonyl:

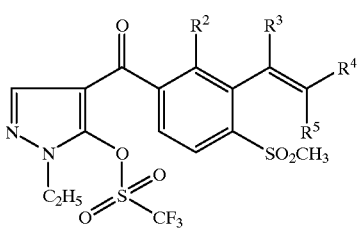

Ia327

Likewise, extraordinary preference is given to the compounds Ia328, in particular to the compounds Ia328.001–Ia328.180, which differ from the corresponding compounds Ia1.001–Ia1.180 in that $R^1$ is methylsulfonyl, $R^{14}$ is n-propyl and $R^{15}$ is trifluoromethylsulfonyl:

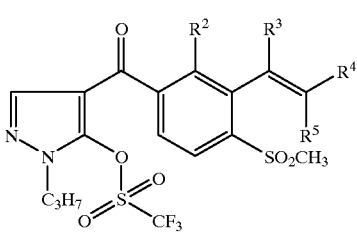

Ia328

Likewise, extraordinary preference is given to the compounds Ia329, in particular to the compounds Ia329.001–Ia329.180, which differ from the corresponding compounds Ia1.001–Ia1.180 in that $R^1$ is methylsulfonyl, $R^{14}$ is n-butyl and $R^{15}$ is trifluoromethylsulfonyl:

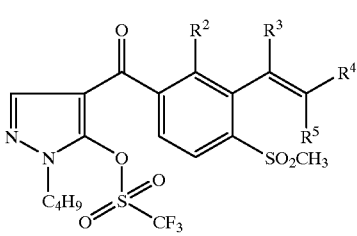

Ia329

Likewise, extraordinary preference is given to the compounds Ia330, in particular to the compounds Ia330.001–Ia330.180, which differ from the corresponding compounds Ia1.001–Ia1.180 in that $R^1$ is methylsulfonyl, $R^{14}$ is isobutyl and $R^{15}$ is trifluoromethylsulfonyl:

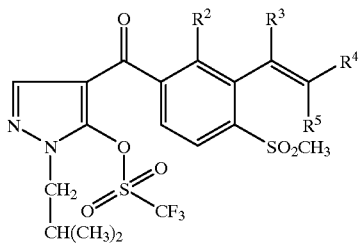

Ia330

Likewise, extraordinary preference is given to the compounds Ia331, in particular to the compounds Ia331.001–Ia331.180, which differ from the corresponding compounds Ia1.001–Ia1.180 in that $R^1$ is methylsulfonyl and $R^{15}$ is phenylcarbonylmethyl:

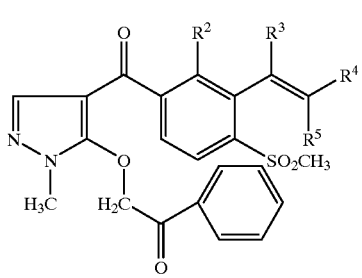

Ia331

Likewise, extraordinary preference is given to the compounds Ia332, in particular to the compounds Ia332.001–Ia332.180, which differ from the corresponding compounds Ia1.001–Ia1.180 in that $R^1$ is methylsulfonyl, $R^{14}$ is ethyl and $R^{15}$ is phenylcarbonylmethyl:

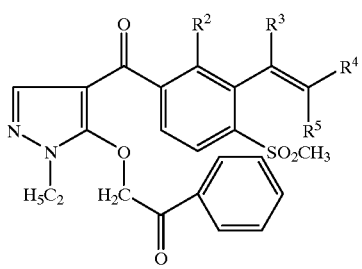

Ia332

Likewise, extraordinary preference is given to the compounds Ia333, in particular to the compounds Ia333.001–Ia333.180, which differ from the corresponding compounds Ia1.001–Ia1.180 in that $R^1$ is methylsulfonyl, $R^{14}$ is n-propyl and $R^{15}$ is phenylcarbonylmethyl:

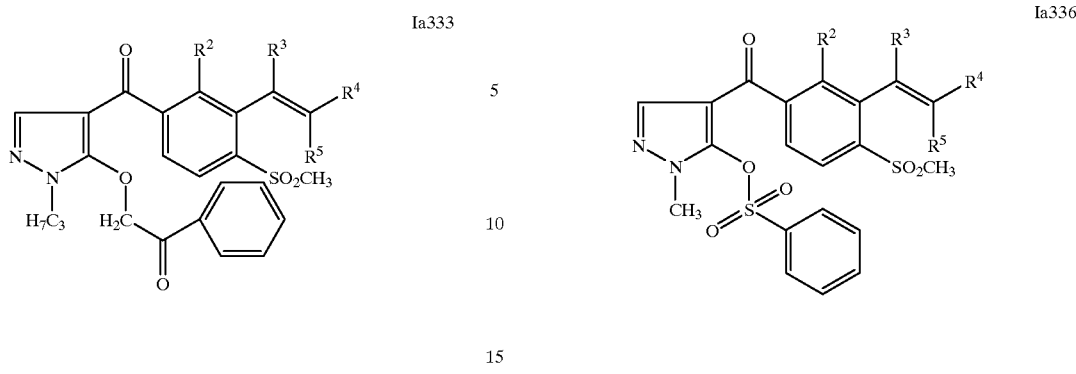

Likewise, extraordinary preference is given to the compounds Ia334, in particular to the compounds Ia334.001–Ia334.180, which differ from the corresponding compounds Ia1.001–Ia1.180 in that $R^1$ is methylsulfonyl, $R^{14}$ is n-butyl and $R^{15}$ is phenylcarbonylmethyl:

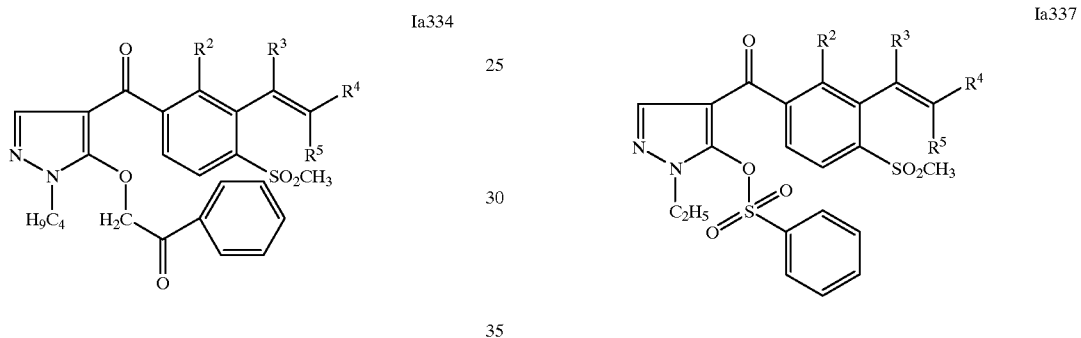

Likewise, extraordinary preference is given to the compounds Ia335, in particular to the compounds Ia335.001–Ia335.180, which differ from the corresponding compounds Ia1.001–Ia1.180 in that $R^1$ is methylsulfonyl, $R^{14}$ is isobutyl and $R^{15}$ is phenylcarbonylmethyl:

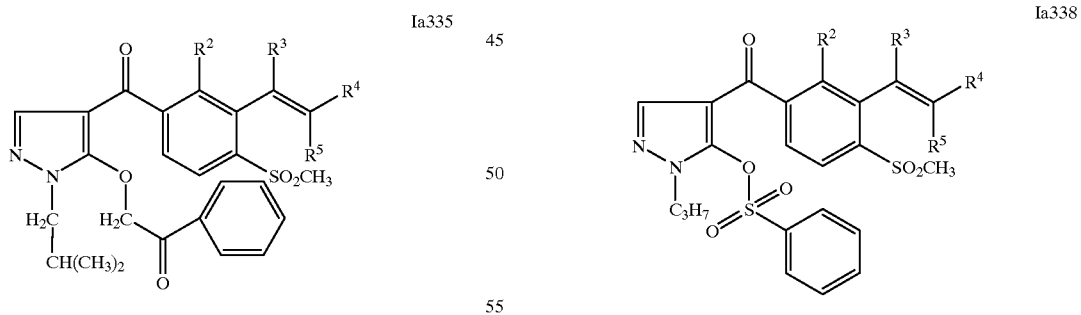

Likewise, extraordinary preference is given to the compounds Ia336, in particular to the compounds Ia336.001–Ia336.180, which differ from the corresponding compounds Ia1.001–Ia1.180 in that $R^1$ is methylsulfonyl and $R^{15}$ is phenylsulfonyl:

Likewise, extraordinary preference is given to the compounds Ia337, in particular to the compounds Ia337.001–Ia337.180, which differ from the corresponding compounds Ia1.001–Ia1.180 in that $R^1$ is methylsulfonyl, $R^{14}$ is ethyl and $R^{15}$ is phenylsulfonyl:

Likewise, extraordinary preference is given to the compounds Ia338, in particular to the compounds Ia338.001–Ia338.180, which differ from the corresponding compounds Ia1.001–Ia1.180 in that $R^1$ is methylsulfonyl, $R^{14}$ is n-propyl and $R^{15}$ is phenylsulfonyl:

Likewise, extraordinary preference is given to the compounds Ia339, in particular to the compounds Ia339.001–Ia339.180, which differ from the corresponding compounds Ia1.001–Ia1.180 in that $R^1$ is methylsulfonyl, $R^{14}$ is n-butyl and $R^{15}$ is phenylsulfonyl:

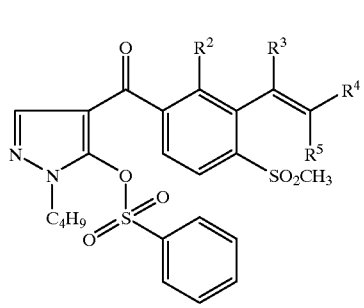

Ia339

Likewise, extraordinary preference is given to the compounds Ia340, in particular to the compounds Ia340.001–Ia340.180, which differ from the corresponding compounds Ia1.001–Ia1.180 in that $R^1$ is methylsulfonyl, $R^{14}$ is isobutyl and $R^{15}$ is phenylsulfonyl:

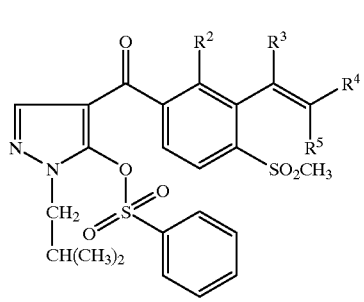

Ia340

Likewise, extraordinary preference is given to the compounds Ia341, in particular to the compounds Ia341.001–Ia341.180, which differ from the corresponding compounds Ia1.001–Ia1.180 in that $R^1$ is methylsulfonyl and $R^{15}$ is 4-methylphenylsulfonyl:

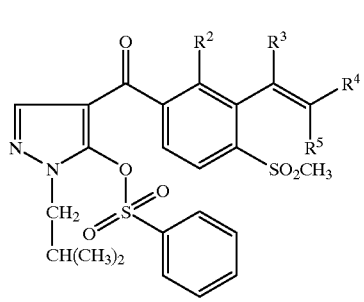

Ia341

Likewise, extraordinary preference is given to the compounds Ia342, in particular to the compounds Ia342.001–Ia342.180, which differ from the corresponding compounds Ia1.001–Ia1.180 in that $R^1$ is methylsulfonyl, $R^{14}$ is ethyl and $R^{15}$ is 4-methylphenylsulfonyl:

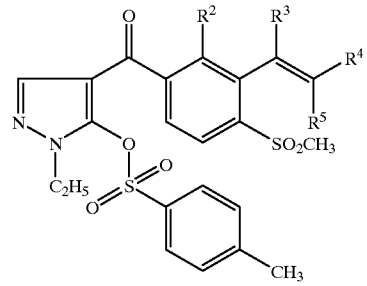

Ia342

Likewise, extraordinary preference is given to the compounds Ia343, in particular to the compounds Ia343.001–Ia343.180, which differ from the corresponding compounds Ia1.001–Ia1.180 in that $R^1$ is methylsulfonyl, $R^{14}$ is n-propyl and $R^{15}$ is 4-methylphenylsulfonyl:

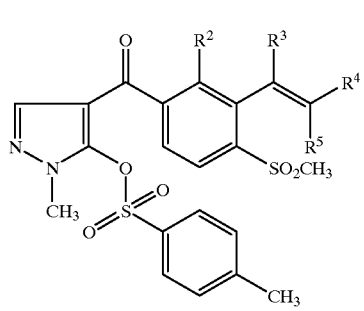

Ia343

Likewise, extraordinary preference is given to the compounds Ia344, in particular to the compounds Ia344.001–Ia344.180, which differ from the corresponding compounds Ia1.001–Ia1.180 in that $R^1$ is methylsulfonyl, $R^{14}$ is n-butyl and $R^{15}$ is 4-methylphenylsulfonyl:

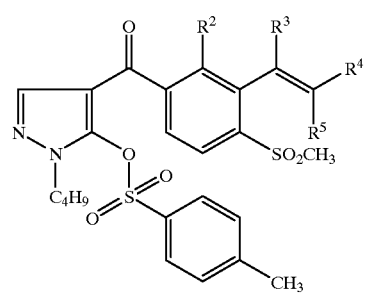

Ia344

Likewise, extraordinary preference is given to the compounds Ia345, in particular to the compounds Ia345.001–Ia345.180, which differ from the corresponding compounds Ia1.001–Ia1.180 in that $R^1$ is methylsulfonyl, $R^{14}$ is isobutyl and $R^{15}$ is 4-methylphenylsulfonyl:

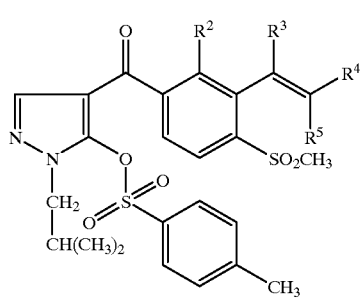

Ia345

Likewise, extraordinary preference is given to the compounds Ia346, in particular to the compounds Ia346.001–Ia346.180, which differ from the corresponding compounds Ia1.001–Ia1.180 in that $R^{16}$ is methyl:

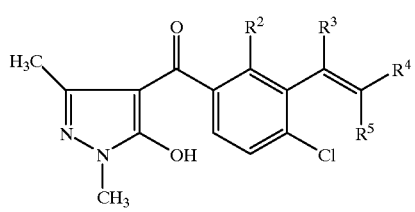

Ia346

Likewise, extraordinary preference is given to the compounds Ia347, in particular to the compounds Ia347.001–Ia347.180, which differ from the corresponding compounds Ia1.001–Ia1.180 in that $R^{14}$ is ethyl and $R^{16}$ is methyl:

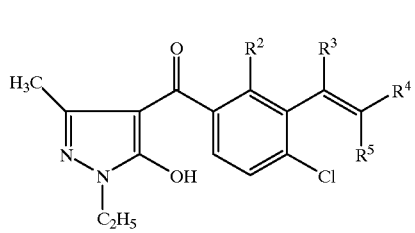

Ia347

Likewise, extraordinary preference is given to the compounds Ia348, in particular to the compounds Ia348.001–Ia348.180, which differ from the corresponding compounds Ia1.001–Ia1.180 in that $R^{14}$ is n-propyl and $R^{16}$ is methyl:

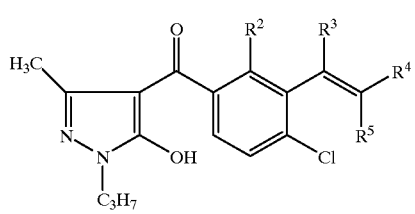

Ia348

Likewise, extraordinary preference is given to the compounds Ia349, in particular to the compounds Ia349.001–Ia349.180, which differ from the corresponding compounds Ia1.001–Ia1.180 in that $R^{14}$ is n-butyl and $R^{16}$ is methyl:

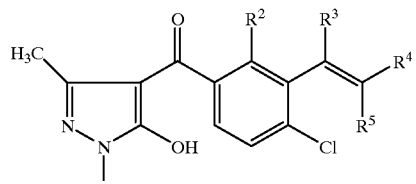

Ia349

Likewise, extraordinary preference is given to the compounds Ia350, in particular to the compounds Ia350.001–Ia350.180, which differ from the corresponding compounds Ia1.001–Ia1.180 in that $R^{14}$ is isobutyl and $R^{16}$ is methyl:

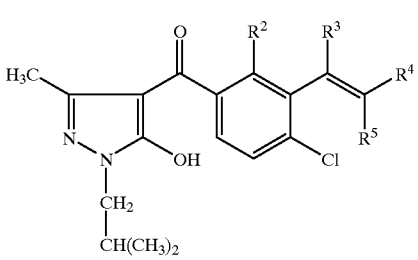

Ia350

Likewise, extraordinary preference is given to the compounds Ia351, in particular to the compounds Ia351.001–Ia351.180, which differ from the corresponding compounds Ia1.001–Ia1.180 in that $R^{15}$ and $R^{16}$ are each methyl:

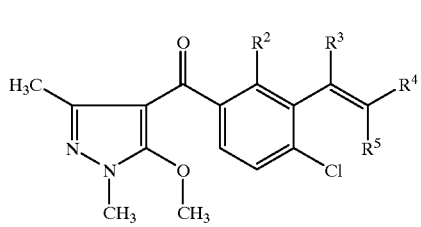

Ia351

Likewise, extraordinary preference is given to the compounds Ia352, in particular to the compounds Ia352.001–Ia352.180, which differ from the corresponding compounds Ia1.001–Ia1.180 in that $R^{14}$ is ethyl, $R^{15}$ and $R^{16}$ are each methyl:

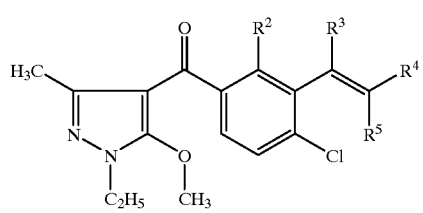

Ia352

Likewise, extraordinary preference is given to the compounds Ia353, in particular to the compounds Ia353.001–Ia353.180, which differ from the corresponding compounds Ia1.001–Ia1.180 in that $R^{14}$ is n-propyl, $R^{15}$ and $R^{16}$ are each methyl:

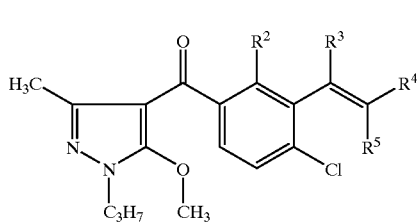

Ia353

Likewise, extraordinary preference is given to the compounds Ia354, in particular to the compounds Ia354.001–Ia354.180, which differ from the corresponding compounds Ia1.001–Ia1.180 in that $R^{14}$ is n-butyl, $R^{15}$ and $R^{16}$ are each methyl:

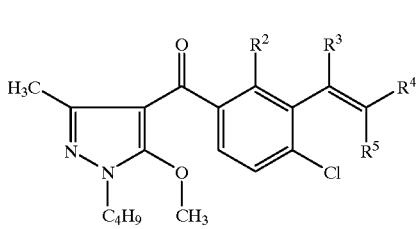

Ia354

Likewise, extraordinary preference is given to the compounds Ia355, in particular to the compounds Ia355.001–Ia355.180, which differ from the corresponding compounds Ia1.001–Ia1.180 in that $R^{14}$ is isobutyl, $R^{15}$ and $R^{16}$ are each methyl:

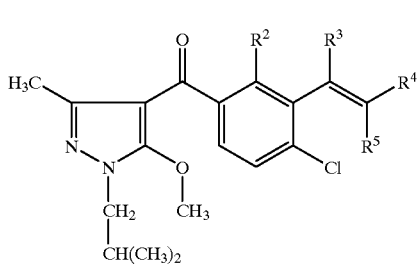

Ia355

Likewise, extraordinary preference is given to the compounds Ia356, in particular to the compounds Ia356.001–Ia356.180, which differ from the corresponding compounds Ia1.001–Ia1.180 in that $R^{15}$ is ethyl and $R^{16}$ is methyl:

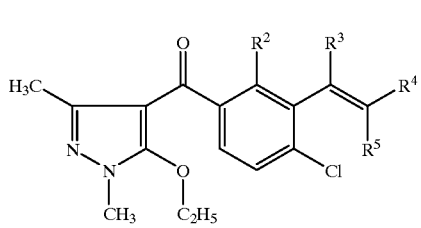

Ia356

Likewise, extraordinary preference is given to the compounds Ia357, in particular to the compounds Ia357.001–Ia357.180, which differ from the corresponding compounds Ia1.001–Ia1.180 in that $R^{14}$ and $R^{15}$ are each ethyl and $R^{16}$ is methyl:

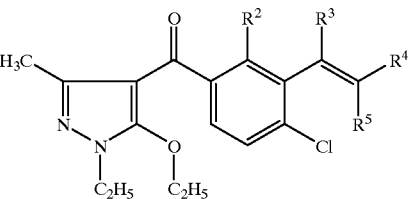

Ia357

Likewise, extraordinary preference is given to the compounds Ia358, in particular to the compounds Ia358.001–Ia358.180, which differ from the corresponding compounds Ia1.001–Ia1.180 in that $R^{14}$ is n-propyl, $R^{15}$ is ethyl and $R^{16}$ is methyl:

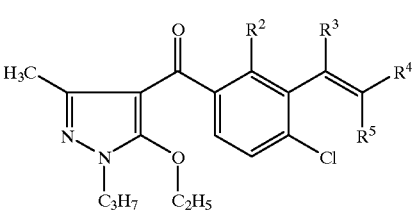

Ia358

Likewise, extraordinary preference is given to the compounds Ia359, in particular to the compounds Ia359.001–Ia359.180, which differ from the corresponding compounds Ia1.001–Ia1.180 in that $R^{14}$ is n-butyl, $R^{15}$ is ethyl and $R^{16}$ is methyl:

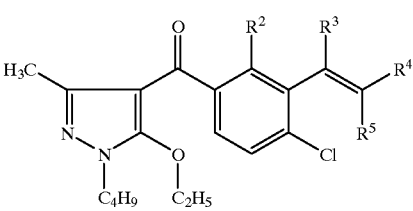

Ia359

Likewise, extraordinary preference is given to the compounds Ia360, in particular to the compounds Ia360.001–Ia360.180, which differ from the corresponding compounds Ia1.001–Ia1.180 in that $R^{14}$ is isobutyl, $R^{15}$ is ethyl and $R^{16}$ is methyl:

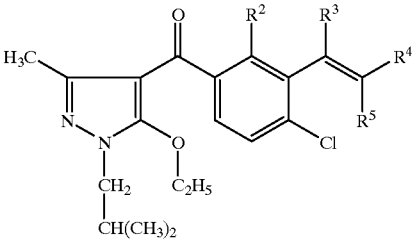

Ia360

Likewise, extraordinary preference is given to the compounds Ia361, in particular to the compounds Ia361.001–Ia361.180, which differ from the corresponding compounds Ia1.001–Ia1.180 in that $R^{14}$ is n-propyl and $R^{16}$ is methyl:

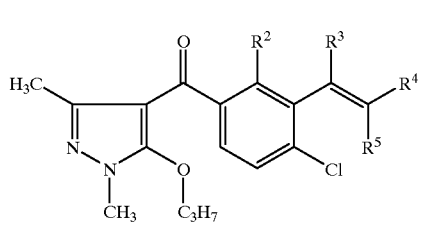
Ia361

Likewise, extraordinary preference is given to the compounds Ia362, in particular to the compounds Ia362.001–Ia362.180, which differ from the corresponding compounds Ia1.001–Ia1.180 in that $R^{14}$ is ethyl, $R^{15}$ is n-propyl and $R^{16}$ is methyl:

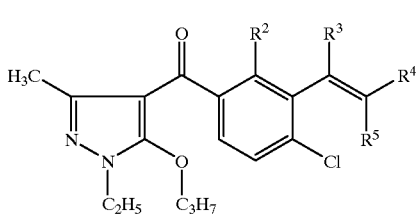
Ia362

Likewise, extraordinary preference is given to the compounds Ia363, in particular to the compounds Ia363.001–Ia363.180, which differ from the corresponding compounds Ia1.001–Ia1.180 in that $R^{14}$ and $R^{15}$ are each n-propyl and $R^{16}$ is methyl:

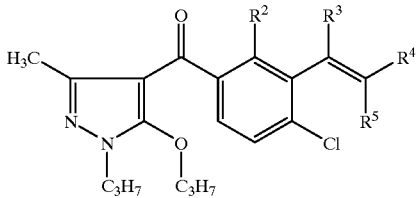
Ia363

Likewise, extraordinary preference is given to the compounds Ia364, in particular to the compounds Ia364.001–Ia364.180, which differ from the corresponding compounds Ia1.001–Ia1.180 in that $R^{14}$ is n-butyl, $R^{15}$ is n-propyl and $R^{16}$ is methyl:

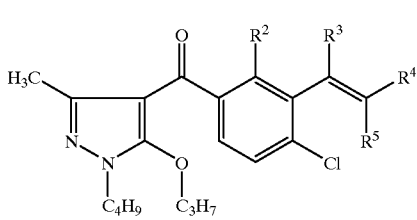
Ia364

Likewise, extraordinary preference is given to the compounds Ia365, in particular to the compounds Ia365.001–Ia365.180, which differ from the corresponding compounds Ia1.001–Ia1.180 in that $R^{14}$ is isobutyl, $R^{15}$ is n-propyl and $R^{16}$ is methyl:

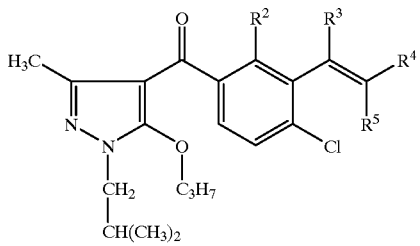
Ia365

Likewise, extraordinary preference is given to the compounds Ia366, in particular to the compounds Ia366.001–Ia366.180, which differ from the corresponding compounds Ia1.001–Ia1.180 in that $R^{15}$ is isopropyl and $R^{16}$ is methyl:

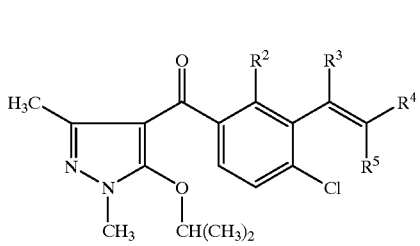
Ia366

Likewise, extraordinary preference is given to the compounds Ia367, in particular to the compounds Ia367.001–Ia367.180, which differ from the corresponding compounds Ia1.001–Ia1.180 in that $R^{14}$ is ethyl, $R^{15}$ is isopropyl and $R^{16}$ is methyl:

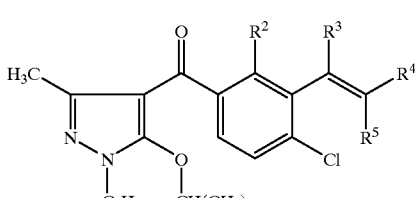
Ia367

Likewise, extraordinary preference is given to the compounds Ia368, in particular to the compounds Ia368.001–Ia368.180, which differ from the corresponding compounds Ia1.001–Ia1.180 in that $R^{14}$ is n-propyl, $R^{15}$ is isopropyl and $R^{16}$ is methyl:

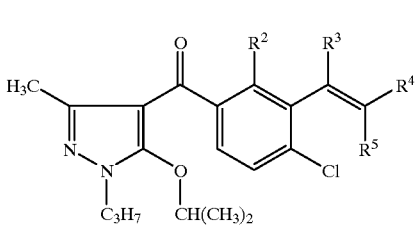
Ia368

Likewise, extraordinary preference is given to the compounds Ia369, in particular to the compounds Ia369.001–Ia369.180, which differ from the corresponding compounds Ia1.001–Ia1.180 in that $R^{14}$ is n-butyl, $R^{15}$ is isopropyl and $R^{16}$ is methyl:

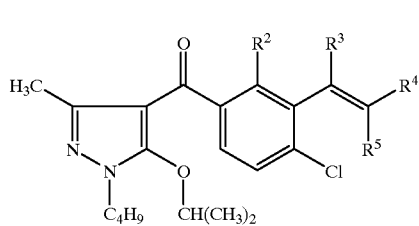
Ia369

Likewise, extraordinary preference is given to the compounds Ia370, in particular to the compounds Ia370.001–Ia370.180, which differ from the corresponding compounds Ia1.001–Ia1.180 in that $R^{14}$ is isobutyl, $R^{15}$ is isopropyl and $R^{16}$ is methyl:

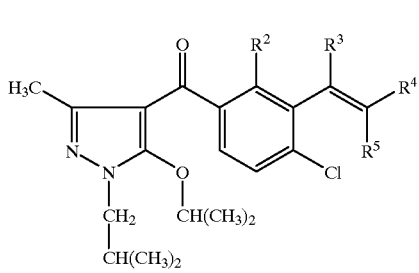
Ia370

Likewise, extraordinary preference is given to the compounds Ia371, in particular to the compounds Ia371.001–Ia371.180, which differ from the corresponding compounds Ia1.001–Ia1.180 in that $R^{15}$ is n-butyl and $R^{16}$ is methyl:

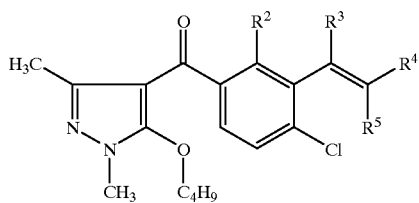
Ia371

Likewise, extraordinary preference is given to the compounds Ia372, in particular to the compounds Ia372.001–Ia372.180, which differ from the corresponding compounds Ia1.001–Ia1.180 in that $R^{14}$ is ethyl, $R^{15}$ is n-butyl and $R^{16}$ is methyl:

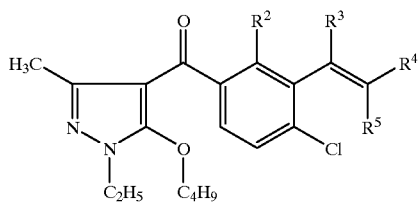
Ia372

Likewise, extraordinary preference is given to the compounds Ia373, in particular to the compounds Ia373.001–Ia373.180, which differ from the corresponding compounds Ia1.001–Ia1.180 in that $R^{14}$ is n-propyl, $R^{15}$ is n-butyl and $R^{16}$ is methyl:

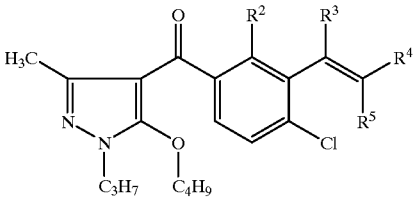
Ia373

Likewise, extraordinary preference is given to the compounds Ia374, in particular to the compounds Ia374.001–Ia374.180, which differ from the corresponding compounds Ia1.001–Ia1.180 in that $R^{14}$ and $R^{15}$ are each n-butyl and $R^{16}$ is methyl:

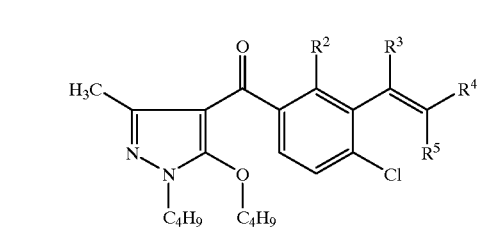
Ia374

Likewise, extraordinary preference is given to the compounds Ia375, in particular to the compounds Ia375.001–Ia375.180, which differ from the corresponding compounds Ia1.001–Ia1.180 in that $R^{14}$ is isobutyl, $R^{15}$ is n-butyl and $R^{16}$ is methyl:

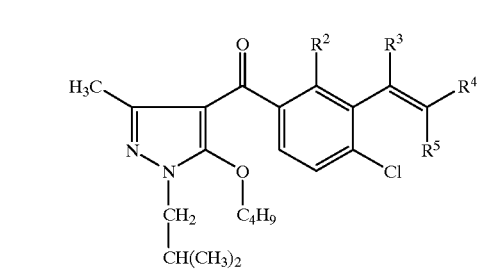
Ia375

Likewise, extraordinary preference is given to the compounds Ia376, in particular to the compounds Ia376.001–Ia376.180, which differ from the corresponding compounds Ia1.001–Ia1.180 in that $R^{15}$ is sec-butyl and $R^{16}$ is methyl:

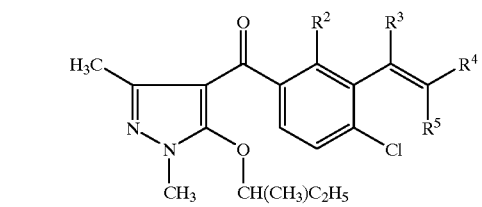
Ia376

Likewise, extraordinary preference is given to the compounds Ia377, in particular to the compounds Ia377.001–Ia377.180, which differ from the corresponding compounds Ia1.001–Ia1.180 in that $R^{14}$ is ethyl, $R^{15}$ is sec-butyl and $R^{16}$ is methyl:

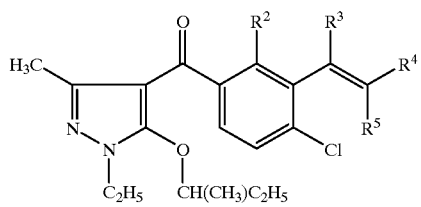
Ia377

Likewise, extraordinary preference is given to the compounds Ia378, in particular to the compounds Ia378.001–Ia378.180, which differ from the corresponding compounds Ia1.001–Ia1.180 in that $R^{14}$ is n-propyl, $R^{15}$ is sec-butyl and $R^{16}$ is methyl:

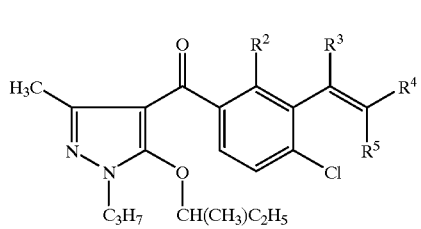
Ia378

Likewise, extraordinary preference is given to the compounds Ia379, in particular to the compounds Ia379.001–Ia379.180, which differ from the corresponding compounds Ia1.001–Ia1.180 in that $R^{14}$ is n-butyl, $R^{15}$ is sec-butyl and $R^{16}$ is methyl:

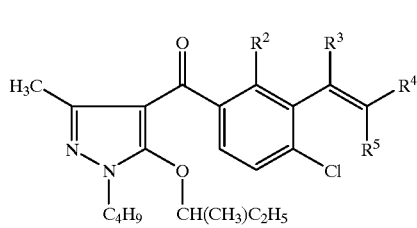
Ia379

Likewise, extraordinary preference is given to the compounds Ia380, in particular to the compounds Ia380.001–Ia380.180, which differ from the corresponding compounds Ia1.001–Ia1.180 in that $R^{14}$ is isobutyl, $R^{15}$ is sec-butyl and $R^{16}$ is methyl:

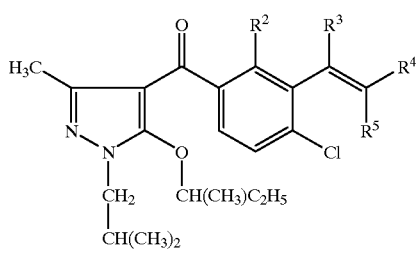
Ia380

Likewise, extraordinary preference is given to the compounds Ia381, in particular to the compounds Ia381.001–Ia381.180, which differ from the corresponding compounds Ia1.001–Ia1.180 in that $R^{15}$ is isobutyl and $R^{16}$ is methyl:

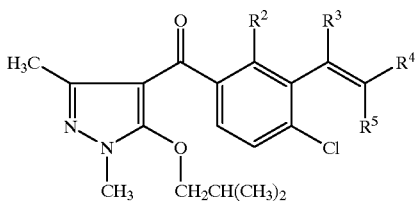
Ia381

Likewise, extraordinary preference is given to the compounds Ia382, in particular to the compounds Ia382.001–Ia382.180, which differ from the corresponding compounds Ia1.001–Ia1.180 in that $R^{14}$ is ethyl, $R^{15}$ is isobutyl and $R^{16}$ is methyl:

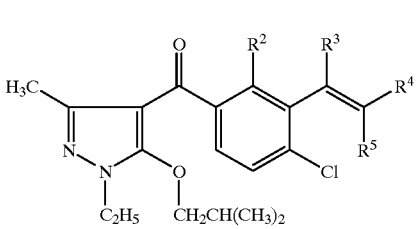
Ia382

Likewise, extraordinary preference is given to the compounds Ia383, in particular to the compounds Ia383.001–Ia383.180, which differ from the corresponding compounds Ia1.001–Ia1.180 in that $R^{14}$ is n-propyl, $R^{15}$ is isobutyl and $R^{16}$ is methyl:

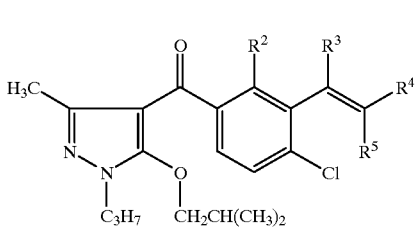
Ia383

Likewise, extraordinary preference is given to the compounds Ia384, in particular to the compounds Ia384.001–Ia384.180, which differ from the corresponding compounds Ia1.001–Ia1.180 in that $R^{14}$ is n-butyl, $R^{15}$ is isobutyl and $R^{16}$ is methyl:

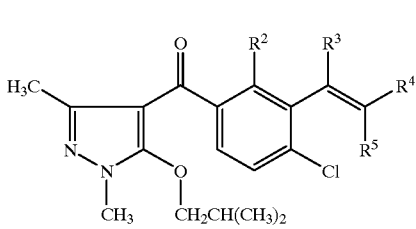
Ia384

Likewise, extraordinary preference is given to the compounds Ia385, in particular to the compounds Ia385.001–Ia385.180, which differ from the corresponding compounds Ia1.001–Ia1.180 in that $R^{14}$ and $R^{15}$ are each isobutyl and $R^{16}$ is methyl:

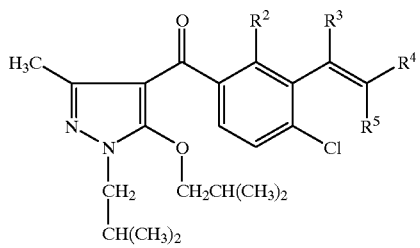

Ia385

Likewise, extraordinary preference is given to the compounds Ia386, in particular to the compounds Ia386.001–Ia386.180, which differ from the corresponding compounds Ia1.001–Ia1.180 in that $R^{15}$ is methylcarbonyl and $R^{16}$ is methyl:

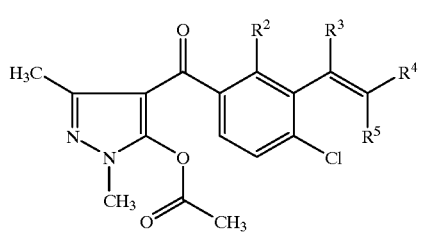

Ia386

Likewise, extraordinary preference is given to the compounds Ia387, in particular to the compounds Ia387.001–Ia387.180, which differ from the corresponding compounds Ia1.001–Ia1.180 in that $R^{14}$ is ethyl, $R^{15}$ is methylcarbonyl and $R^{16}$ is methyl:

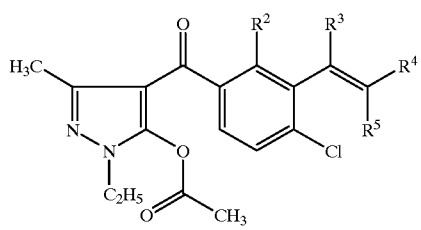

Ia387

Likewise, extraordinary preference is given to the compounds Ia388, in particular to the compounds Ia388.001–Ia388.180, which differ from the corresponding compounds Ia1.001–Ia1.180 in that $R^{14}$ is n-propyl, $R^{15}$ is methylcarbonyl and $R^{16}$ is methyl:

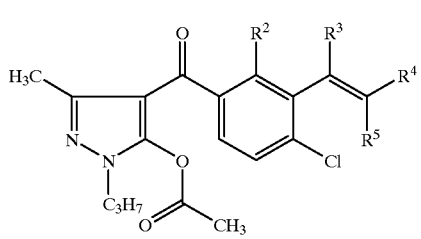

Ia388

Likewise, extraordinary preference is given to the compounds Ia389, in particular to the compounds Ia389.001–Ia389.180, which differ from the corresponding compounds Ia1.001–Ia1.180 in that $R^{14}$ is n-butyl, $R^{15}$ is methylcarbonyl and $R^{16}$ is methyl:

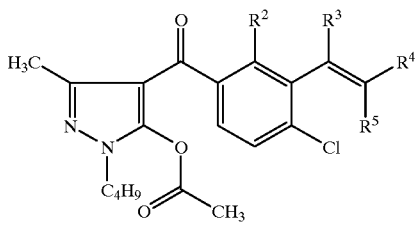

Ia389

Likewise, extraordinary preference is given to the compounds Ia390, in particular to the compounds Ia390.001–Ia390.180, which differ from the corresponding compounds Ia1.001–Ia1.180 in that $R^{14}$ is isobutyl, $R^{15}$ is methylcarbonyl and $R^{16}$ is methyl:

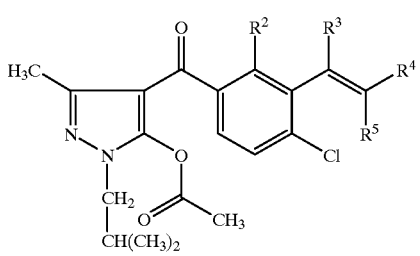

Ia390

Likewise, extraordinary preference is given to the compounds Ia391, in particular to the compounds Ia391.001–Ia391.180, which differ from the corresponding compounds Ia1.001–Ia1.180 in that $R^{14}$ is ethylcarbonyl and $R^{16}$ is methyl:

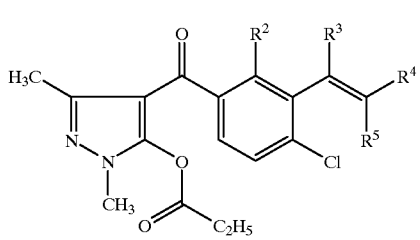

Ia391

Likewise, extraordinary preference is given to the compounds Ia392, in particular to the compounds Ia392.001–Ia392.180, which differ from the corresponding compounds Ia1.001–Ia1.180 in that $R^{14}$ is ethyl, $R^{15}$ is ethylcarbonyl and $R^{16}$ is methyl:

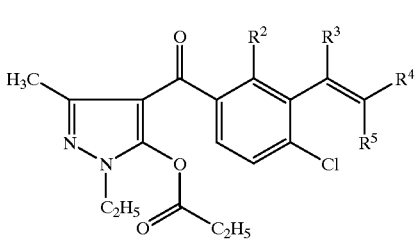

Ia392

Likewise, extraordinary preference is given to the compounds Ia393, in particular to the compounds Ia393.001–Ia393.180, which differ from the corresponding compounds Ia1.001–Ia1.180 in that $R^{14}$ is n-propyl, $R^{15}$ is ethyl and $R^{16}$ is methyl:

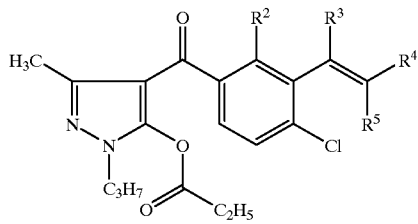
Ia393

Likewise, extraordinary preference is given to the compounds Ia394, in particular to the compounds Ia394.001–Ia394.180, which differ from the corresponding compounds Ia1.001–Ia1.180 in that $R^{14}$ is n-butyl, $R^{15}$ is ethylcarbonyl and $R^{16}$ is methyl:

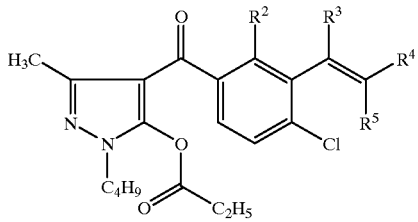
Ia394

Likewise, extraordinary preference is given to the compounds Ia395, in particular to the compounds Ia395.001–Ia395.180, which differ from the corresponding compounds Ia1.001–Ia1.180 in that $R^{14}$ is isobutyl, $R^{15}$ is ethylcarbonyl and $R^{16}$ is methyl:

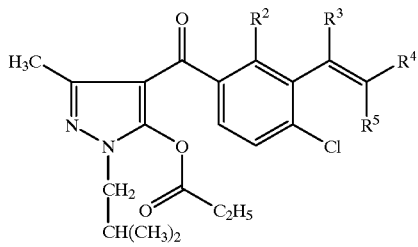
Ia395

Likewise, extraordinary preference is given to the compounds Ia396, in particular to the compounds Ia396.001–Ia396.180, which differ from the corresponding compounds Ia1.001–Ia1.180 in that $R^{15}$ is phenylsulfonyl and $R^{16}$ is methyl:

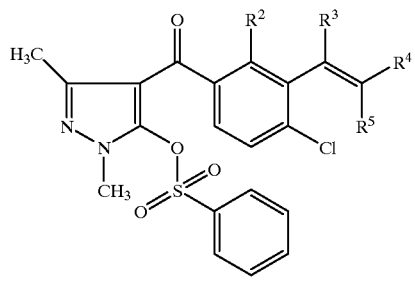
Ia396

Likewise, extraordinary preference is given to the compounds Ia397, in particular to the compounds Ia397.001–Ia397.180, which differ from the corresponding compounds Ia1.001–Ia1.180 in that $R^{14}$ is ethyl, $R^{15}$ is phenylsulfonyl and $R^{16}$ is methyl:

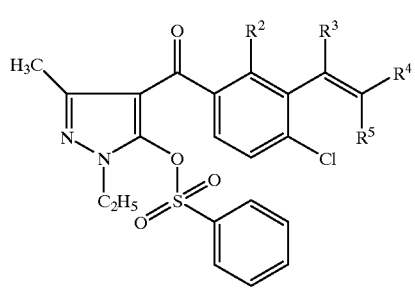
Ia397

Likewise, extraordinary preference is given to the compounds Ia398, in particular to the compounds Ia398.001–Ia398.180, which differ from the corresponding compounds Ia1.001–Ia1.180 in that $R^{14}$ is n-propyl, $R^{15}$ is phenylsulfonyl and $R^{16}$ is methyl:

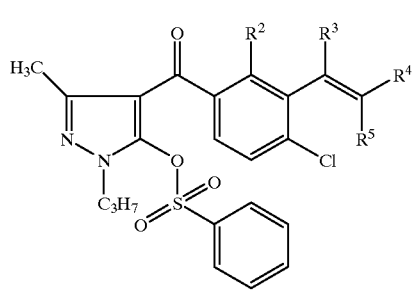
Ia398

Likewise, extraordinary preference is given to the compounds Ia399, in particular to the compounds Ia399.001–Ia399.180, which differ from the corresponding compounds Ia1.001–Ia1.180 in that $R^{14}$ is n-butyl, $R^{15}$ is phenylsulfonyl and $R^{16}$ is methyl:

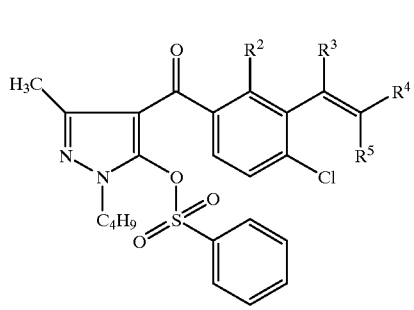

Ia399

Likewise, extraordinary preference is given to the compounds Ia400, in particular to the compounds Ia400.001–Ia400.180, which differ from the corresponding compounds Ia1.001–Ia1.180 in that $R^{14}$ is isobutyl, $R^{15}$ is phenylsulfonyl and $R^{16}$ is methyl:

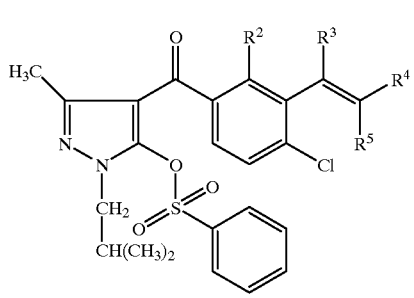

Ia400

Likewise, extraordinary preference is given to the compounds Ia401, in particular to the compounds Ia401.001–Ia401.180, which differ from the corresponding compounds Ia1.001–Ia1.180 in that $R^{15}$ is 4-methylphenylsulfonyl and $R^{16}$ is methyl:

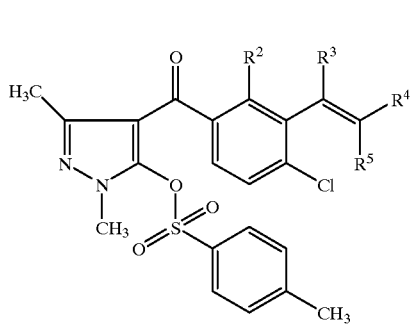

Ia401

Likewise, extraordinary preference is given to the compounds Ia402, in particular to the compounds Ia402.001–Ia402.180, which differ from the corresponding compounds Ia1.001–Ia1.180 in that $R^{14}$ is ethyl, $R^{15}$ is 4-methylphenylsulfonyl and $R^{16}$ is methyl:

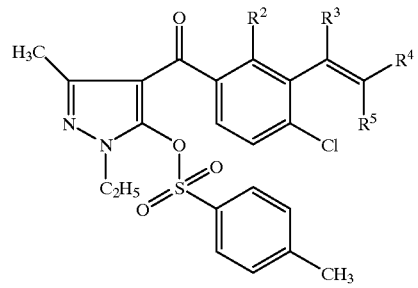

Ia402

Likewise, extraordinary preference is given to the compounds Ia403, in particular to the compounds Ia403.001–Ia403.180, which differ from the corresponding compounds Ia1.001–Ia1.180 in that $R^{14}$ is n-propyl, $R^{15}$ is 4-methylphenylsulfonyl and $R^{16}$ is methyl:

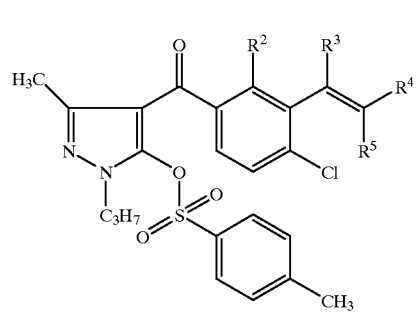

Ia403

Likewise, extraordinary preference is given to the compounds Ia404, in particular to the compounds Ia404.001–Ia404.180, which differ from the corresponding compounds Ia1.001–Ia1.180 in that $R^{14}$ is n-butyl, $R^{15}$ is 4-methylphenylsulfonyl and $R^{16}$ is methyl:

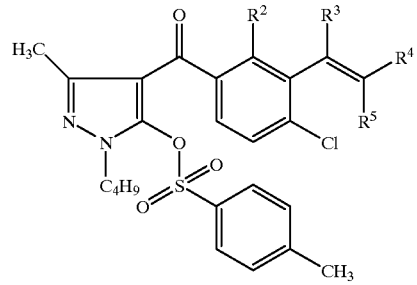

Ia404

Likewise, extraordinary preference is given to the compounds Ia405, in particular to the compounds Ia405.001–Ia405.180, which differ from the corresponding compounds Ia1.001–Ia1.180 in that $R^{14}$ is isobutyl, $R^{15}$ is 4-methylphenylsulfonyl and $R^{16}$ is methyl:

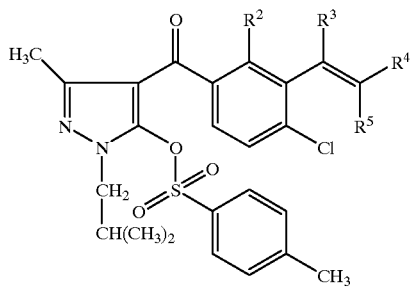

Ia405

Likewise, extraordinary preference is given to the compounds Ia406, in particular to the compounds Ia406.001–Ia406.180, which differ from the corresponding compounds Ia1.001–Ia1.180 in that $R^{15}$ is n-propylcarbonyl and $R^{16}$ is methyl:

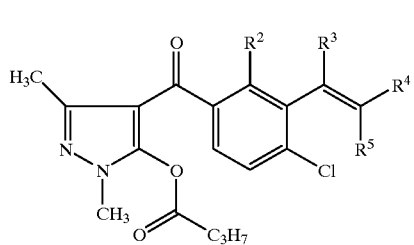

Ia406

Likewise, extraordinary preference is given to the compounds Ia407, in particular to the compounds Ia407.001–Ia407.180, which differ from the corresponding compounds Ia1.001–Ia1.180 in that $R^{14}$ is ethyl, $R^{15}$ is n-propylcarbonyl and $R^{16}$ is methyl:

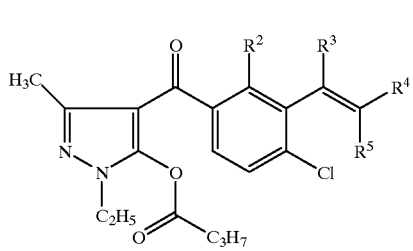

Ia407

Likewise, extraordinary preference is given to the compounds Ia408, in particular to the compounds Ia408.001–Ia408.180, which differ from the corresponding compounds Ia1.001–Ia1.180 in that $R^{14}$ is n-propyl, $R^{15}$ is n-propylcarbonyl and $R^{16}$ is methyl:

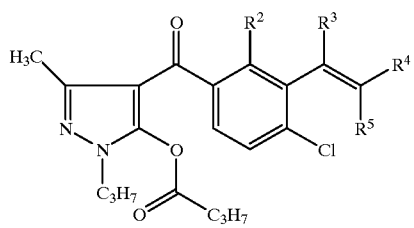

Ia408

Likewise, extraordinary preference is given to the compounds Ia409, in particular to the compounds Ia409.001–Ia409.180, which differ from the corresponding compounds Ia1.001–Ia1.180 in that $R^{14}$ is n-butyl, $R^{15}$ is n-propylcarbonyl and $R^{16}$ is methyl:

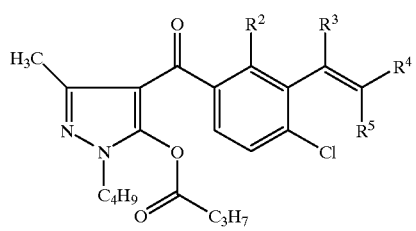

Ia409

Likewise, extraordinary preference is given to the compounds Ia410, in particular to the compounds Ia410.001–Ia410.180, which differ from the corresponding compounds Ia1.001–Ia1.180 in that $R^{14}$ is isobutyl, $R^{15}$ is n-propylcarbonyl and $R^{16}$ is methyl:

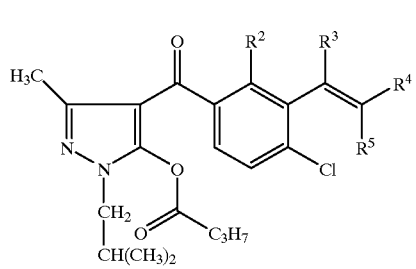

Ia410

Likewise, extraordinary preference is given to the compounds Ia410, in particular to the compounds Ia410.001–Ia410.180, which differ from the corresponding compounds Ia1.001–Ia1.180 in that $R^{15}$ is trifluoromethylcarbonyl and $R^{16}$ is methyl:

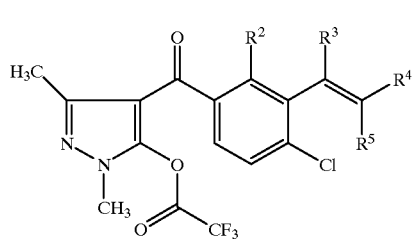

Ia411

Likewise, extraordinary preference is given to the compounds Ia412, in particular to the compounds Ia412.001–Ia412.180, which differ from the corresponding compounds Ia1.001–Ia1.180 in that $R^{14}$ is ethyl, $R^{15}$ is trifluoromethylcarbonyl and $R^{16}$ is methyl:

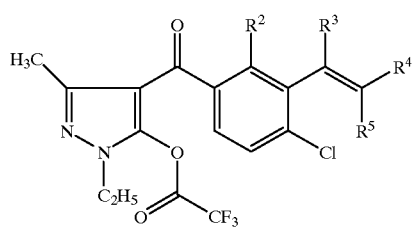

Ia412

Likewise, extraordinary preference is given to the compounds Ia413, in particular to the compounds Ia413.001–Ia413.180, which differ from the corresponding compounds Ia1.001–Ia1.180 in that $R^{14}$ is n-propyl, $R^{15}$ is trifluoromethylcarbonyl and $R^{16}$ is methyl:

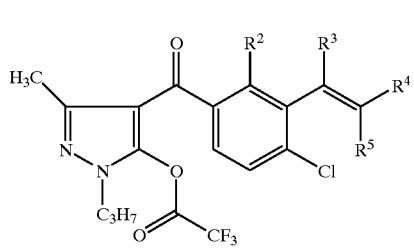

Likewise, extraordinary preference is given to the compounds Ia414, in particular to the compounds Ia414.001–Ia414.180, which differ from the corresponding compounds Ia1.001–Ia1.180 in that $R^{14}$ is n-butyl, $R^{15}$ is trifluoromethylcarbonyl and $R^{16}$ is methyl:

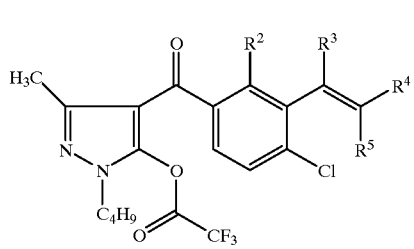

Likewise, extraordinary preference is given to the compounds Ia415, in particular to the compounds Ia415.001–Ia415.180, which differ from the corresponding compounds Ia1.001–Ia1.180 in that $R^{14}$ is isobutyl, $R^{15}$ is trifluoromethylcarbonyl and $R^{16}$ is methyl:

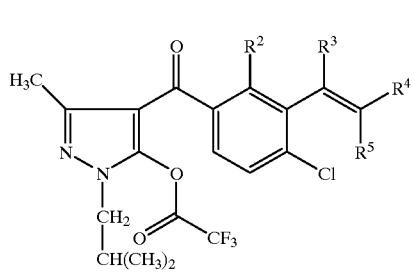

Likewise, extraordinary preference is given to the compounds Ia416, in particular to the compounds Ia416.001–Ia416.180, which differ from the corresponding compounds Ia1.001–Ia1.180 in that $R^{15}$ is methylsulfonyl and $R^{16}$ is methyl:

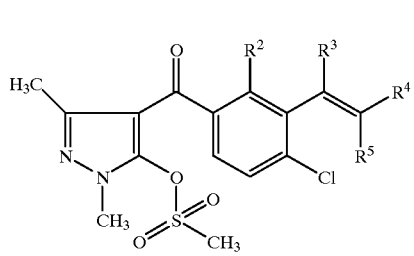

Likewise, extraordinary preference is given to the compounds Ia417, in particular to the compounds Ia417.001–Ia417.180, which differ from the corresponding compounds Ia1.001–Ia1.180 in that $R^{14}$ is ethyl, $R^{15}$ is methylsulfonyl and $R^{16}$ is methyl:

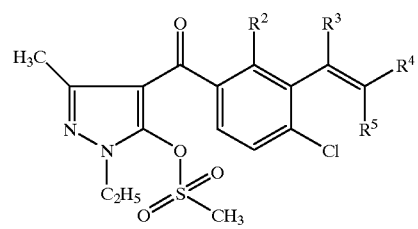

Likewise, extraordinary preference is given to the compounds Ia418, in particular to the compounds Ia418.001–Ia418.180, which differ from the corresponding compounds Ia1.001–Ia1.180 in that $R^{14}$ is n-propyl, $R^{15}$ is methylsulfonyl and $R^{16}$ is methyl:

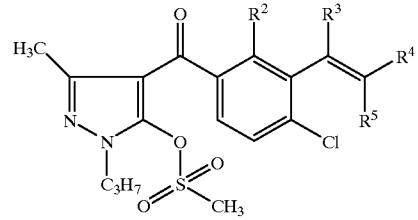

Likewise, extraordinary preference is given to the compounds Ia419, in particular to the compounds Ia419.001–Ia419.180, which differ from the corresponding compounds Ia1.001–Ia1.180 in that $R^{14}$ is n-butyl, $R^{15}$ is methylsulfonyl and $R^{16}$ is methyl:

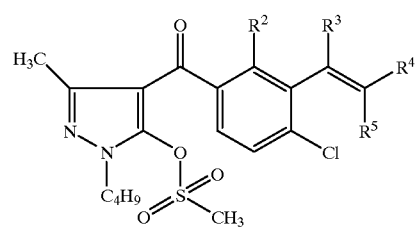

Likewise, extraordinary preference is given to the compounds Ia420, in particular to the compounds Ia420.001–Ia420.180, which differ from the corresponding compounds Ia1.001–Ia1.180 in that $R^{14}$ is isobutyl, $R^{15}$ is methylsulfonyl and $R^{16}$ is methyl:

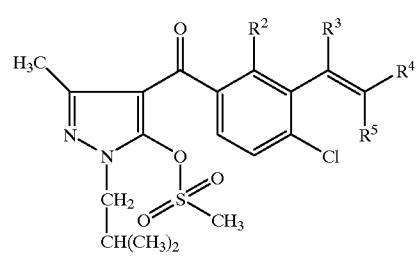

Likewise, extraordinary preference is given to the compounds Ia421, in particular to the compounds Ia421.001–Ia421.180, which differ from the corresponding compounds Ia1.001–Ia1.180 in that $R^{15}$ is ethylsulfonyl and $R^{16}$ is methyl:

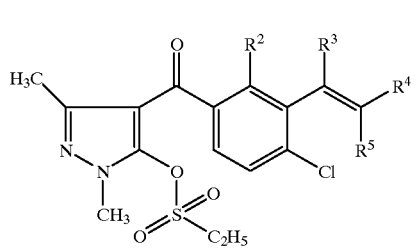

Ia421

Likewise, extraordinary preference is given to the compounds Ia422, in particular to the compounds Ia422.001–Ia422.180, which differ from the corresponding compounds Ia1.001–Ia1.180 in that $R^{14}$ is ethyl, $R^{15}$ is ethylsulfonyl and $R^{16}$ is methyl:

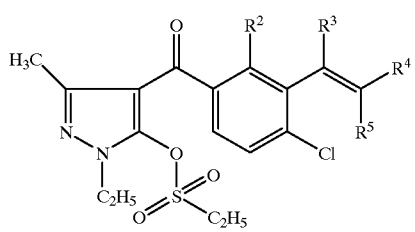

Ia422

Likewise, extraordinary preference is given to the compounds Ia423, in particular to the compounds Ia423.001–Ia423.180, which differ from the corresponding compounds Ia1.001–Ia1.180 in that $R^{14}$ is ethyl, $R^{15}$ is ethylsulfonyl and $R^{16}$ is methyl:

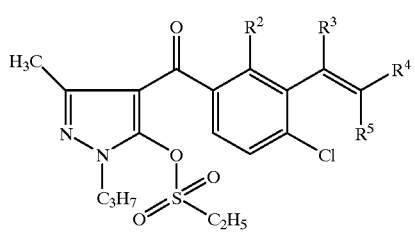

Ia423

Likewise, extraordinary preference is given to the compounds Ia424, in particular to the compounds Ia424.001–Ia424.180, which differ from the corresponding compounds Ia1.001–Ia1.180 in that $R^{14}$ is n-butyl, $R^{15}$ is ethylsulfonyl and $R^{16}$ is methyl:

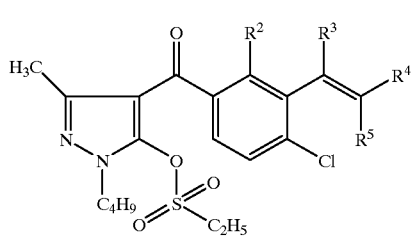

Ia424

Likewise, extraordinary preference is given to the compounds Ia425, in particular to the compounds Ia425.001–Ia425.180, which differ from the corresponding compounds Ia1.001–Ia1.180 in that $R^{14}$ is isobutyl, $R^{15}$ is ethylsulfonyl and $R^{16}$ is methyl:

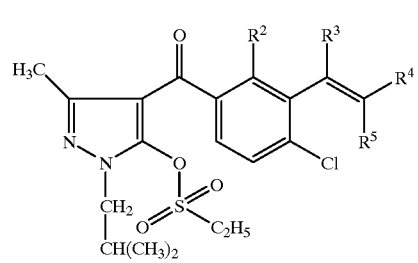

Ia425

Likewise, extraordinary preference is given to the compounds Ia426, in particular to the compounds Ia426.001–Ia426.180, which differ from the corresponding compounds Ia1.001–Ia1.180 in that $R^{15}$ is n-propylsulfonyl and $R^{16}$ is methyl:

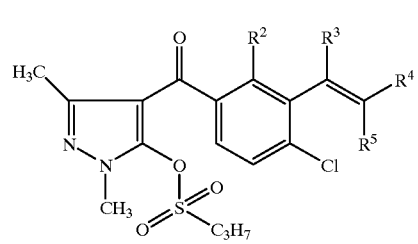

Ia426

Likewise, extraordinary preference is given to the compounds Ia427, in particular to the compounds Ia427.001–Ia427.180, which differ from the corresponding compounds Ia1.001–Ia1.180 in that $R^{14}$ is ethyl, $R^{15}$ is n-propylsulfonyl and $R^{16}$ is methyl:

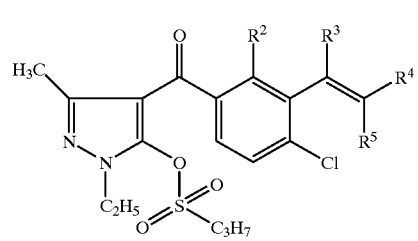

Ia427

Likewise, extraordinary preference is given to the compounds Ia428, in particular to the compounds Ia428.001–Ia428.180, which differ from the corresponding compounds Ia1.001–Ia1.180 in that $R^{14}$ is n-propyl, $R^{15}$ is n-propylsulfonyl and $R^{16}$ is methyl:

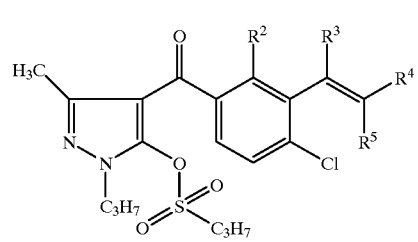

Ia428

Likewise, extraordinary preference is given to the compounds Ia429, in particular to the compounds Ia429.001–Ia429.180, which differ from the corresponding compounds Ia1.001–Ia1.180 in that $R^{14}$ is n-butyl, $R^{15}$ is n-propylsulfonyl and $R^{16}$ is methyl:

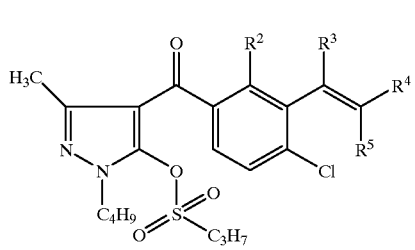

Likewise, extraordinary preference is given to the compounds Ia430, in particular to the compounds Ia430.001–Ia430.180, which differ from the corresponding compounds Ia1.001–Ia1.180 in that $R^{14}$ is isobutyl, $R^{15}$ is propylsulfonyl and $R^{16}$ is methyl:

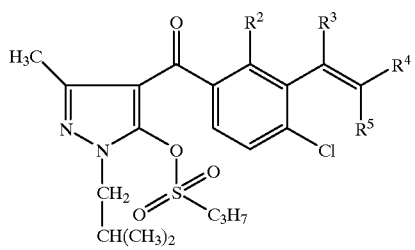

Likewise, extraordinary preference is given to the compounds Ia431, in particular to the compounds Ia431.001–Ia431.180, which differ from the corresponding compounds Ia1.001–Ia1.180 in that $R^{15}$ is isopropylsulfonyl and $R^{16}$ is methyl:

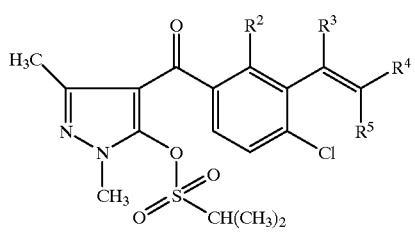

Likewise, extraordinary preference is given to the compounds Ia432, in particular to the compounds Ia432.001–Ia432.180, which differ from the corresponding compounds Ia1.001–Ia1.180 in that $R^{14}$ is ethyl, $R^{15}$ is isopropylsulfonyl and $R^{16}$ is methyl:

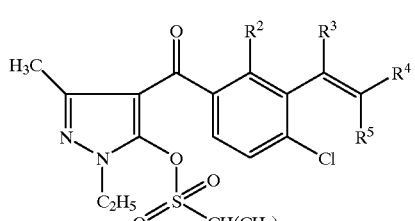

Likewise, extraordinary preference is given to the compounds Ia433, in particular to the compounds Ia433.001–Ia433.180, which differ from the corresponding compounds Ia1.001–Ia1.180 in that $R^{14}$ is n-propyl, $R^{15}$ is isopropylsulfonyl and $R^{16}$ is methyl:

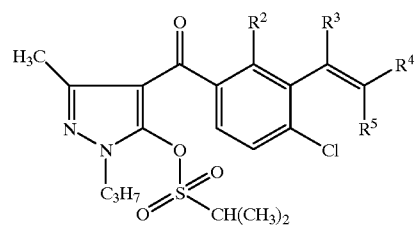

Likewise, extraordinary preference is given to the compounds Ia434, in particular to the compounds Ia434.001–Ia434.180, which differ from the corresponding compounds Ia1.001–Ia1.180 in that $R^{14}$ is n-butyl, $R^{15}$ is isopropylsulfonyl and $R^{16}$ is methyl:

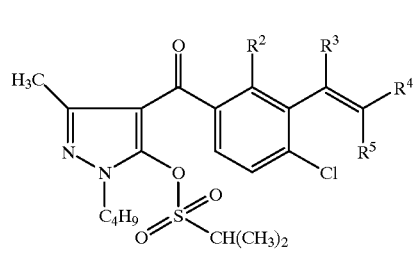

Likewise, extraordinary preference is given to the compounds Ia435, in particular to the compounds Ia435.001–Ia435.180, which differ from the corresponding compounds Ia1.001–Ia1.180 in that $R^{14}$ is isobutyl, $R^{15}$ is isopropylsulfonyl and $R^{16}$ is methyl:

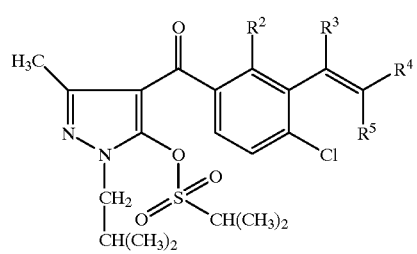

Likewise, extraordinary preference is given to the compounds Ia436, in particular to the compounds Ia436.001–Ia436.180, which differ from the corresponding compounds Ia1.001–Ia1.180 in that $R^{15}$ is n-butylsulfonyl and $R^{16}$ is methyl:

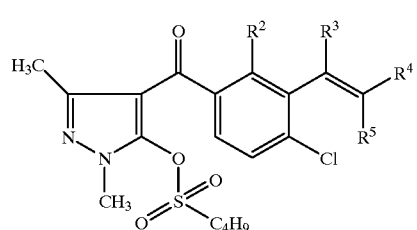

Likewise, extraordinary preference is given to the compounds Ia437, in particular to the compounds Ia437.001–Ia437.180, which differ from the corresponding compounds Ia1.001–Ia1.180 in that $R^{14}$ is ethyl, $R^{15}$ is n-butylsulfonyl and $R^{16}$ is methyl:

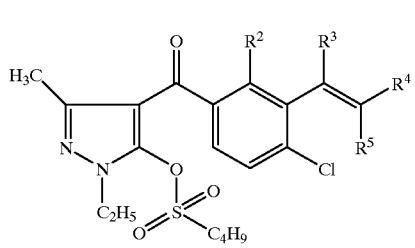

Ia437

Likewise, extraordinary preference is given to the compounds Ia438, in particular to the compounds Ia438.001–Ia438.180, which differ from the corresponding compounds Ia1.001–Ia1.180 in that $R^{14}$ is n-propyl, $R^{15}$ is n-butylsulfonyl and $R^{16}$ is methyl:

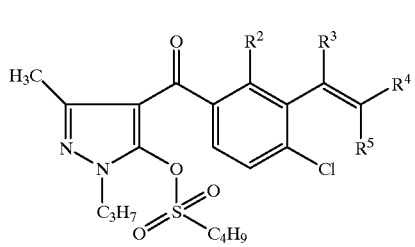

Ia438

Likewise, extraordinary preference is given to the compounds Ia439, in particular to the compounds Ia439.001–Ia439.180, which differ from the corresponding compounds Ia1.001–Ia1.180 in that $R^{14}$ is n-butyl, $R^{15}$ is n-butylsulfonyl and $R^{16}$ is methyl:

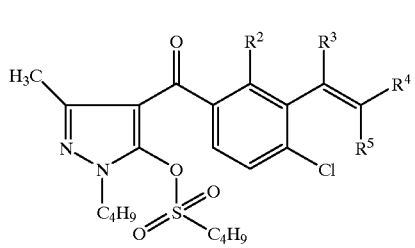

Ia439

Likewise, extraordinary preference is given to the compounds Ia440, in particular to the compounds Ia440.001–Ia440.180, which differ from the corresponding compounds Ia1.001–Ia1.180 in that $R^{14}$ is isobutyl, $R^{15}$ is n-butylsulfonyl and $R^{16}$ is methyl:

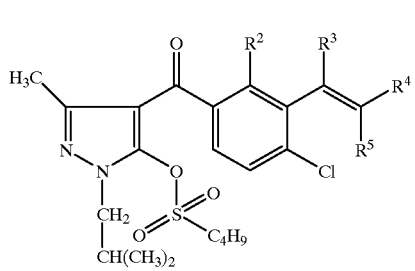

Ia440

Likewise, extraordinary preference is given to the compounds Ia441, in particular to the compounds Ia441.001–Ia441.180, which differ from the corresponding compounds Ia1.001–Ia1.180 in that $R^{15}$ is isobutylsulfonyl and $R^{16}$ is methyl:

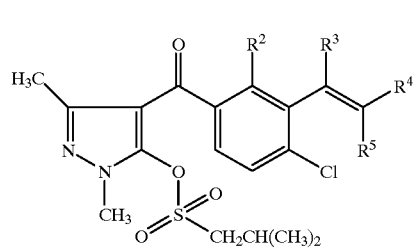

Ia441

Likewise, extraordinary preference is given to the compounds Ia442, in particular to the compounds Ia442.001–Ia442.180, which differ from the corresponding compounds Ia1.001–Ia1.180 in that $R^{14}$ is ethyl, $R^{15}$ is isobutylsulfonyl and $R^{16}$ is methyl:

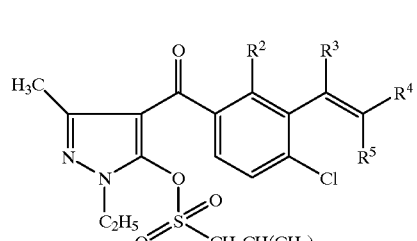

Ia442

Likewise, extraordinary preference is given to the compounds Ia443, in particular to the compounds Ia443.001–Ia443.180, which differ from the corresponding compounds Ia1.001–Ia1.180 in that $R^{14}$ is n-propyl, $R^{15}$ is isobutylsulfonyl and $R^{16}$ is methyl:

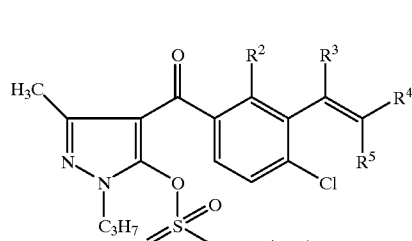

Ia443

Likewise, extraordinary preference is given to the compounds Ia444, in particular to the compounds Ia444.001–Ia444.180, which differ from the corresponding compounds Ia1.001–Ia1.180 in that $R^{14}$ is n-butyl, $R^{15}$ is isobutylsulfonyl and $R^{16}$ is methyl:

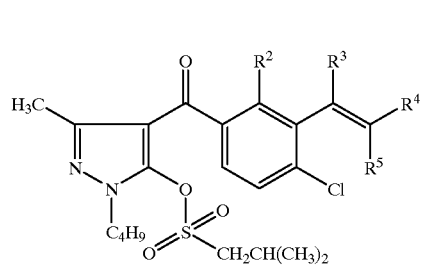

Ia444

Likewise, extraordinary preference is given to the compounds Ia445, in particular to the compounds Ia445.001–Ia445.180, which differ from the corresponding compounds Ia1.001–Ia1.180 in that $R^{14}$ is isobutyl, $R^{15}$ is isobutylsulfonyl and $R^{16}$ is methyl:

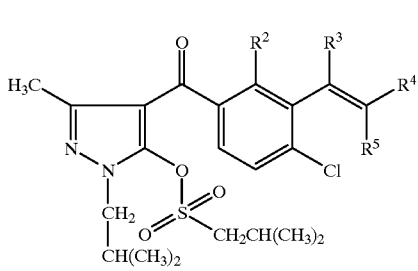

Ia445

Likewise, extraordinary preference is given to the compounds Ia446, in particular to the compounds Ia446.001–Ia446.180, which differ from the corresponding compounds Ia1.001–Ia1.180 in that $R^{15}$ is sec-butylsulfonyl and $R^{16}$ is methyl:

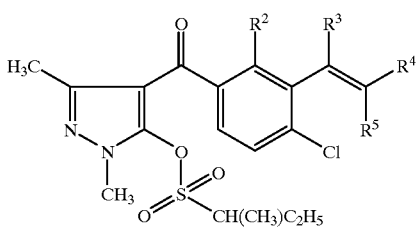

Ia446

Likewise, extraordinary preference is given to the compounds Ia447, in particular to the compounds Ia447.001–Ia447.180, which differ from the corresponding compounds Ia1.001–Ia1.180 in that $R^{14}$ is ethyl, $R^{15}$ is sec-butylsulfonyl and $R^{16}$ is methyl:

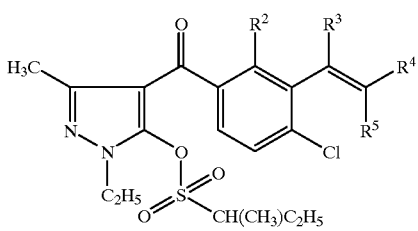

Ia447

Likewise, extraordinary preference is given to the compounds Ia448, in particular to the compounds Ia448.001–Ia448.180, which differ from the corresponding compounds Ia1.001–Ia1.180 in that $R^{14}$ is n-propyl, $R^{15}$ is sec-butylsulfonyl and $R^{16}$ is methyl:

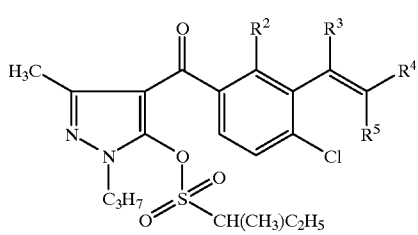

Ia448

Likewise, extraordinary preference is given to the compounds Ia449, in particular to the compounds Ia449.001–Ia449.180, which differ from the corresponding compounds Ia1.001–Ia1.180 in that $R^{14}$ is n-butyl, $R^{15}$ is sec-butylsulfonyl and $R^{16}$ is methyl:

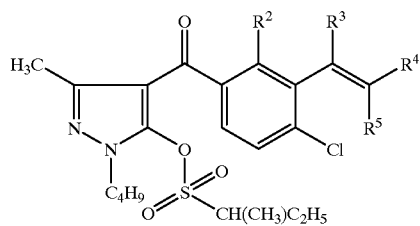

Ia449

Likewise, extraordinary preference is given to the compounds Ia450, in particular to the compounds Ia450.001–Ia450.180, which differ from the corresponding compounds Ia1.001–Ia1.180 in that $R^{14}$ is isobutyl, $R^{15}$ is sec-butylsulfonyl and $R^{16}$ is methyl:

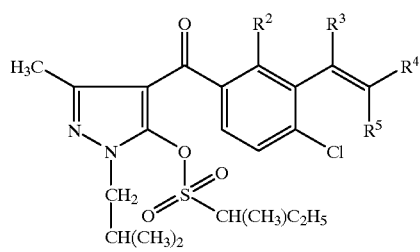

Ia450

Likewise, extraordinary preference is given to the compounds Ia451, in particular to the compounds Ia451.001–Ia451.180, which differ from the corresponding compounds Ia1.001–Ia1.180 in that $R^{15}$ is trifluoromethylsulfonyl and $R^{16}$ is methyl:

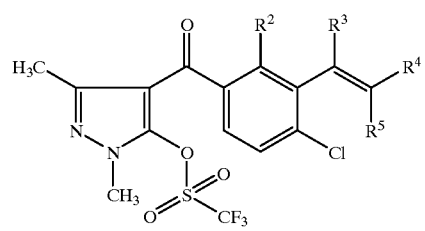

Ia451

Likewise, extraordinary preference is given to the compounds Ia452, in particular to the compounds Ia452.001–Ia452.180, which differ from the corresponding compounds Ia1.001–Ia1.180 in that $R^{14}$ is ethyl, $R^{15}$ is trifluoromethylsulfonyl and $R^{16}$ is methyl:

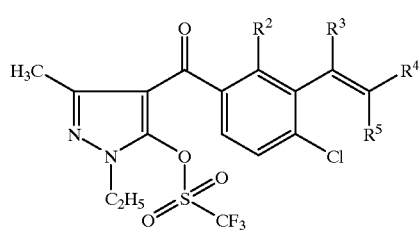

Ia452

Likewise, extraordinary preference is given to the compounds Ia453, in particular to the compounds Ia453.001–Ia453.180, which differ from the corresponding compounds Ia1.001–Ia1.180 in that $R^{14}$ is n-propyl, $R^{15}$ is trifluoromethylsulfonyl and $R^{16}$ is methyl:

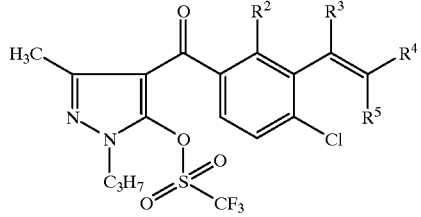

Ia453

Likewise, extraordinary preference is given to the compounds Ia454, in particular to the compounds Ia454.001–Ia454.180, which differ from the corresponding compounds Ia1.001–Ia1.180 in that $R^{14}$ is n-butyl, $R^{15}$ is trifluoromethylsulfonyl and $R^{16}$ is methyl:

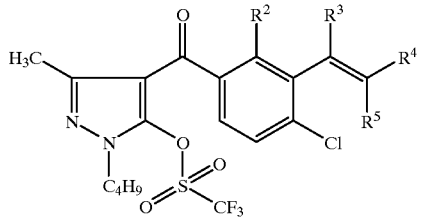

Ia454

Likewise, extraordinary preference is given to the compounds Ia455, in particular to the compounds Ia455.001–Ia455.180, which differ from the corresponding compounds Ia1.001–Ia1.180 in that $R^{14}$ is isobutyl, $R^{15}$ is trifluoromethylsulfonyl and $R^{16}$ is methyl:

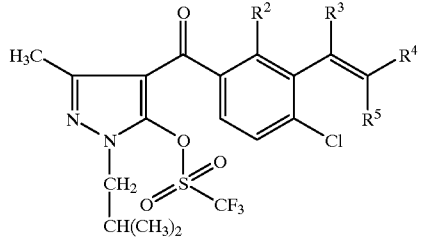

Ia455

Likewise, extraordinary preference is given to the compounds Ia456, in particular to the compounds Ia456.001–Ia456.180, which differ from the corresponding compounds Ia1.001–Ia1.180 in that $R^{15}$ is phenylcarbonylmethyl and $R^{16}$ is methyl:

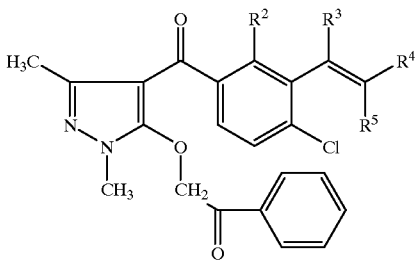

Ia456

Likewise, extraordinary preference is given to the compounds Ia457, in particular to the compounds Ia457.001–Ia457.180, which differ from the corresponding compounds Ia1.001–Ia1.180 in that $R^{14}$ is ethyl, $R^{15}$ is phenylcarbonylmethyl and $R^{16}$ is methyl:

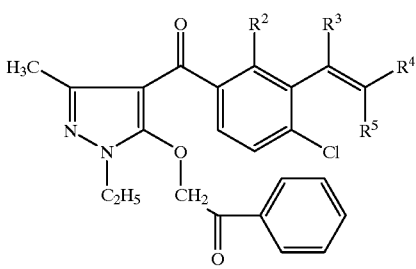

Ia457

Likewise, extraordinary preference is given to the compounds Ia458, in particular to the compounds Ia458.001–Ia458.180, which differ from the corresponding compounds Ia1.001–Ia1.180 in that $R^{14}$ is n-propyl, $R^{15}$ is phenylcarbonylmethyl and $R^{16}$ is methyl:

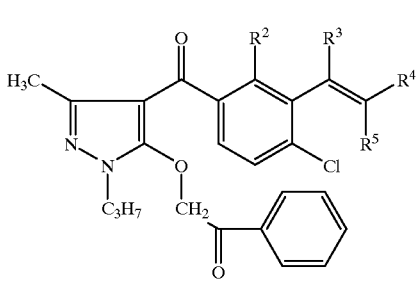

Ia458

Likewise, extraordinary preference is given to the compounds Ia459, in particular to the compounds Ia459.001–Ia459.180, which differ from the corresponding compounds Ia1.001–Ia1.180 in that $R^{14}$ is n-butyl, $R^{15}$ is phenylcarbonylmethyl and $R^{16}$ is methyl:

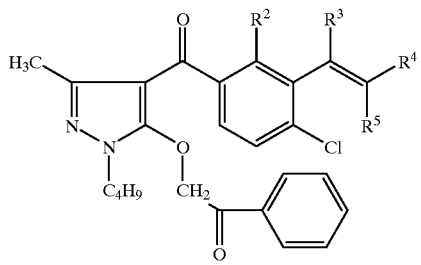

Ia459

Likewise, extraordinary preference is given to the compounds 15 Ia460, in particular to the compounds Ia460.001–Ia460.180, which differ from the corresponding compounds Ia1.001–Ia1.180 in that $R^{14}$ is isobutyl, $R^{15}$ is phenylcarbonylmethyl and $R^{16}$ is methyl:

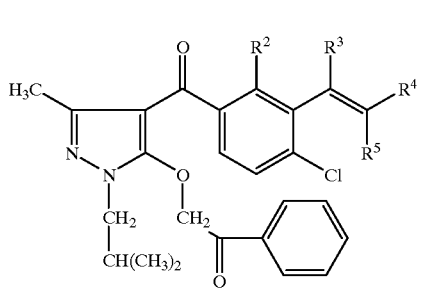

Ia460

Likewise, extraordinary preference is given to the compounds Ia461, in particular to the compounds Ia461.001–Ia461.180, which differ from the corresponding compounds Ia1.001–Ia1.180 in that $R^1$ is nitro and $R^{16}$ is methyl:

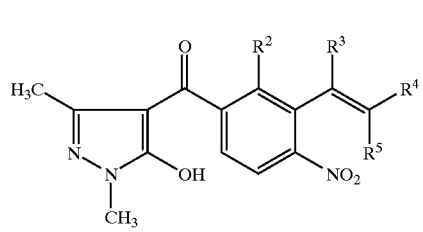

Ia461

Likewise, extraordinary preference is given to the compounds Ia462, in particular to the compounds Ia462.001–Ia462.180, which differ from the corresponding compounds Ia1.001–Ia1.180 in that $R^1$ is nitro, $R^{14}$ is ethyl and $R^{16}$ is methyl:

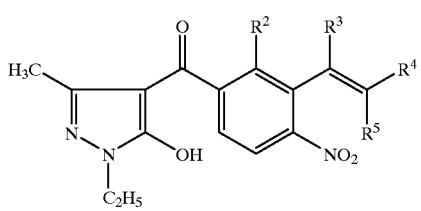

Ia462

Likewise, extraordinary preference is given to the compounds Ia463, in particular to the compounds Ia463.001–Ia463.180, which differ from the corresponding compounds Ia1.001–Ia1.180 in that $R^1$ is nitro, $R^{14}$ is n-propyl and $R^{16}$ is methyl:

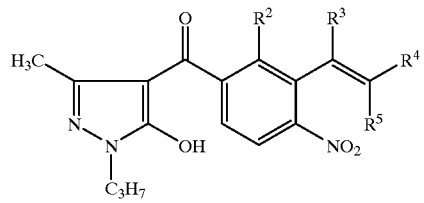

Ia463

Likewise, extraordinary preference is given to the compounds Ia463, in particular to the compounds Ia463.001–Ia463.180, which differ from the corresponding compounds Ia1.001–Ia1.180 in that $R^1$ is nitro, $R^{14}$ is n-propyl and $R^{16}$ is methyl:

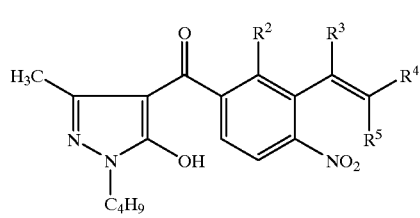

Ia464

Likewise, extraordinary preference is given to the compounds Ia464, in particular to the compounds Ia464.001–Ia464.180, which differ from the corresponding compounds Ia1.001–Ia1.180 in that $R^1$ is nitro, $R^{14}$ is n-butyl and $R^{16}$ is methyl:

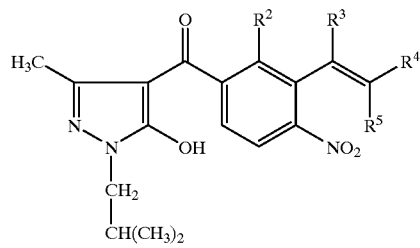

Ia465

Likewise, extraordinary preference is given to the compounds Ia466, in particular to the compounds Ia466.001–Ia466.180, which differ from the corresponding compounds Ia1.001–Ia1.180 in that $R^1$ is nitro and $R^{15}$ and $R^{16}$ are each methyl:

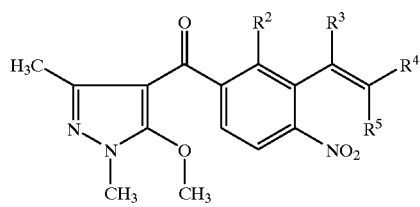

Ia466

Likewise, extraordinary preference is given to the compounds Ia467, in particular to the compounds Ia467.001–Ia467.180, which differ from the corresponding compounds Ia1.001–Ia1.180 in that $R^1$ is nitro, $R^{14}$ is ethyl, $R^{15}$ and $R^{16}$ are each methyl:

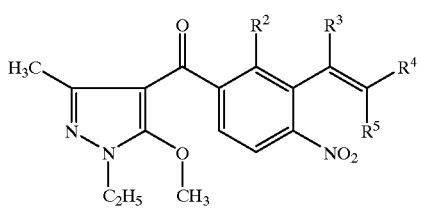
Ia467

Likewise, extraordinary preference is given to the compounds Ia468, in particular to the compounds Ia468.001–Ia468.180, which differ from the corresponding compounds Ia1.001–Ia1.180 in that $R^1$ is nitro, $R^{14}$ is n-propyl, $R^{15}$ and $R^{16}$ are each methyl:

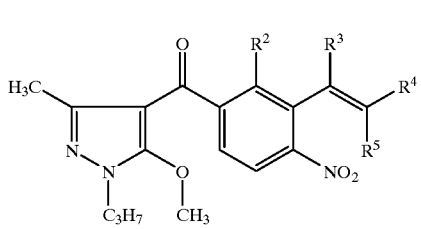
Ia468

Likewise, extraordinary preference is given to the compounds Ia469, in particular to the compounds Ia469.001–Ia469.180, which differ from the corresponding compounds Ia1.001–Ia1.180 in that $R^1$ is nitro, $R^{14}$ is n-butyl, $R^{15}$ and $R^{16}$ are each methyl:

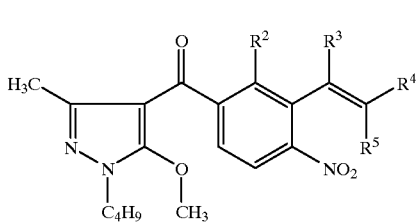
Ia469

Likewise, extraordinary preference is given to the compounds Ia470, in particular to the compounds Ia470.001–Ia470.180, which differ from the corresponding compounds Ia1.001–Ia1.180 in that $R^1$ is nitro, $R^{14}$ is isobutyl, $R^{15}$ and $R^{16}$ are each methyl:

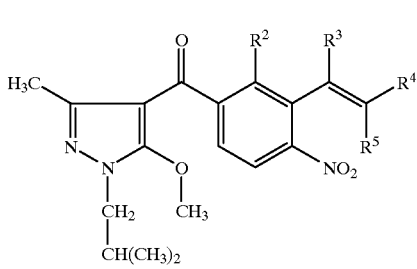
Ia470

Likewise, extraordinary preference is given to the compounds Ia471, in particular to the compounds Ia471.001–Ia471.180, which differ from the corresponding compounds Ia1.001–Ia1.180 in that $R^1$ is nitro, $R^{15}$ is ethyl and $R^{16}$ is methyl:

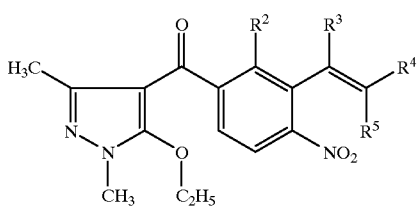
Ia471

Likewise, extraordinary preference is given to the compounds Ia472, in particular to the compounds Ia472.001–Ia472.180, which differ from the corresponding compounds Ia1.001–Ia1.180 in that $R^1$ is nitro, $R^{14}$ and $R^{15}$ are each ethyl and $R^{16}$ is methyl:

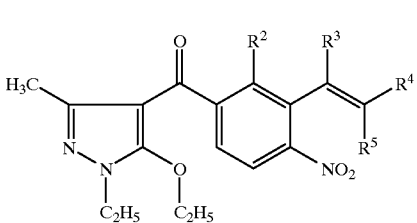
Ia472

Likewise, extraordinary preference is given to the compounds Ia473, in particular to the compounds Ia473.001–Ia473.180, which differ from the corresponding compounds Ia1.001–Ia1.180 in that $R^1$ is nitro, $R^{14}$ is n-propyl, $R^{15}$ is ethyl and $R^{16}$ is methyl:

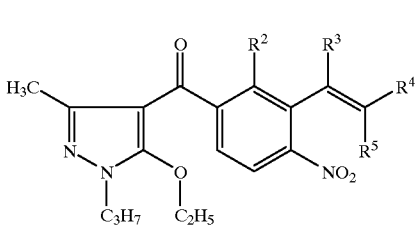
Ia473

Likewise, extraordinary preference is given to the compounds Ia474, in particular to the compounds Ia474.001–Ia474.180, which differ from the corresponding compounds Ia1.001–Ia1.180 in that $R^1$ is nitro, $R^{14}$ is n-butyl, $R^{15}$ is ethyl and $R^{16}$ is methyl:

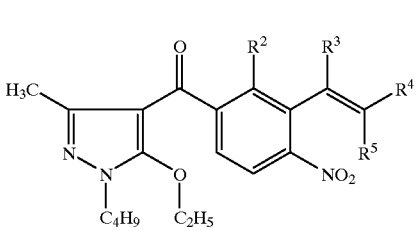
Ia474

Likewise, extraordinary preference is given to the compounds Ia475, in particular to the compounds Ia475.001–Ia475.180, which differ from the corresponding compounds Ia1.001–Ia1.180 in that $R^{14}$ is isobutyl, $R^{15}$ is ethyl and $R^{16}$ is methyl:

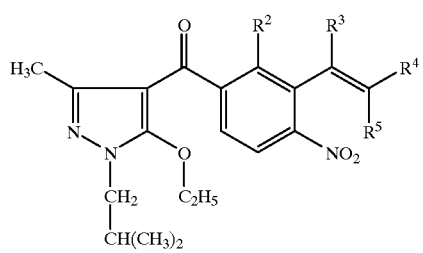
Ia475

Likewise, extraordinary preference is given to the compounds Ia476, in particular to the compounds Ia476.001–Ia476.180, which differ from the corresponding compounds Ia1.001–Ia1.180 in that $R^1$ is nitro, $R^{15}$ is n-propyl and $R^{16}$ is methyl:

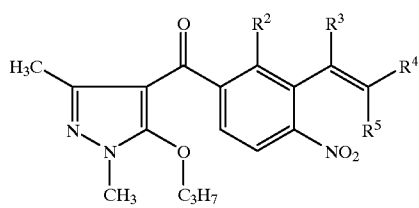
Ia476

Likewise, extraordinary preference is given to the compounds Ia477, in particular to the compounds Ia477.001–Ia477.180, which differ from the corresponding compounds Ia1.001–Ia1.180 in that $R^1$ is nitro, $R^{14}$ is ethyl, $R^{15}$ is n-propyl and $R^{16}$ is methyl:

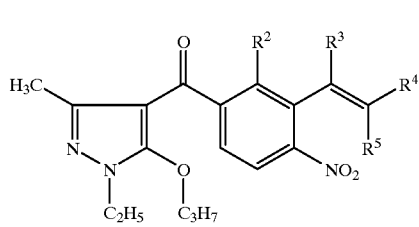
Ia477

Likewise, extraordinary preference is given to the compounds Ia478, in particular to the compounds Ia478.001–Ia478.180, which differ from the corresponding compounds Ia1.001–Ia1.180 in that $R^1$ is nitro, $R^{14}$ and $R^{15}$ are each n-propyl and $R^{16}$ is methyl:

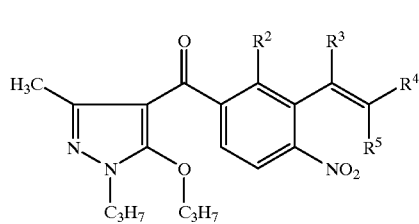
Ia478

Likewise, extraordinary preference is given to the compounds Ia479, in particular to the compounds Ia479.001–Ia479.180, which differ from the corresponding compounds Ia1.001–Ia1.180 in that $R^1$ is nitro, $R^{14}$ is n-butyl, $R^{15}$ is n-propyl and $R^{16}$ is methyl:

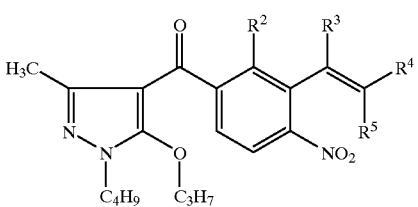
Ia479

Likewise, extraordinary preference is given to the compounds Ia480, in particular to the compounds Ia480.001–Ia480.180, which differ from the corresponding compounds Ia1.001–Ia1.180 in that $R^1$ is nitro, $R^{14}$ is isobutyl, $R^{15}$ is n-propyl and $R^{16}$ is methyl:

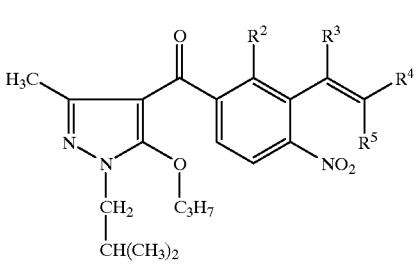
Ia480

Likewise, extraordinary preference is given to the compounds Ia481, in particular to the compounds Ia481.001–Ia481.180, which differ from the corresponding compounds Ia1.001–Ia1.180 in that $R^1$ is nitro, $R^{15}$ is isopropyl and $R^{16}$ is methyl:

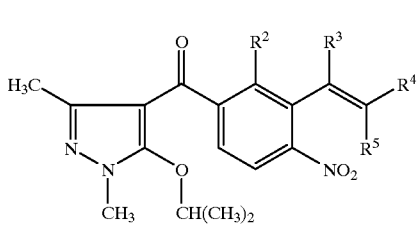
Ia481

Likewise, extraordinary preference is given to the compounds Ia482, in particular to the compounds Ia482.001–Ia482.180, which differ from the corresponding compounds Ia1.001–Ia1.180 in that $R^1$ is nitro, $R^{14}$ is ethyl, $R^{15}$ is isopropyl and $R^{16}$ is methyl:

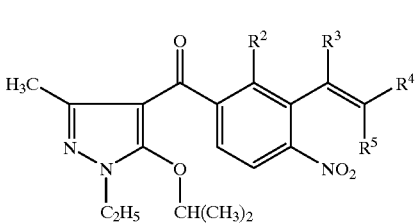
Ia482

Likewise, extraordinary preference is given to the compounds Ia483, in particular to the compounds Ia483.001–Ia483.180, which differ from the corresponding compounds Ia1.001–Ia1.180 in that $R^1$ is nitro, $R^{14}$ is n-propyl, $R^{15}$ is isopropyl and $R^{16}$ is methyl:

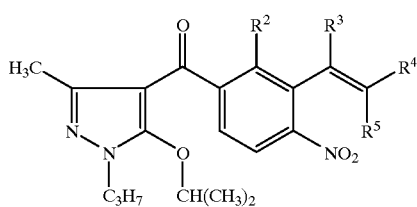
Ia483

Likewise, extraordinary preference is given to the compounds Ia484, in particular to the compounds Ia484.001–Ia484.180, which differ from the corresponding compounds Ia1.001–Ia1.180 in that $R^1$ is nitro, $R^{14}$ is n-butyl, $R^{15}$ is isopropyl and $R^{16}$ is methyl:

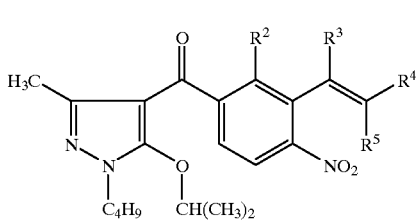
Ia484

Likewise, extraordinary preference is given to the compounds Ia485, in particular to the compounds Ia485.001–Ia485.180, which differ from the corresponding compounds Ia1.001–Ia1.180 in that $R^1$ is nitro, $R^{14}$ is isobutyl, $R^{15}$ is isopropyl and $R^{16}$ is methyl:

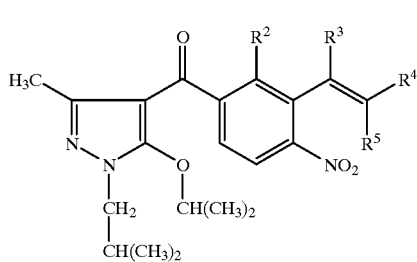
Ia485

Likewise, extraordinary preference is given to the compounds Ia486, in particular to the compounds Ia486.001–Ia486.180, which differ from the corresponding compounds Ia1.001–Ia1.180 in that $R^1$ is nitro, $R^{15}$ is n-butyl and $R^{16}$ is methyl:

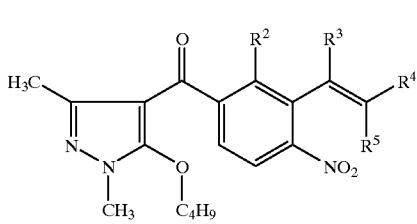
Ia486

Likewise, extraordinary preference is given to the compounds Ia487, in particular to the compounds Ia487.001–Ia487.180, which differ from the corresponding compounds Ia1.001–Ia1.180 in that $R^1$ is nitro, $R^{14}$ is ethyl, $R^{15}$ is n-butyl and $R^{16}$ is methyl:

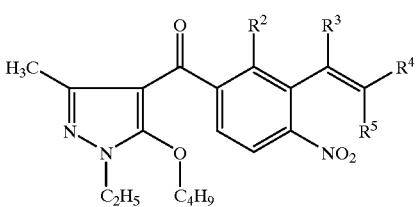
Ia487

Likewise, extraordinary preference is given to the compounds Ia488, in particular to the compounds Ia488.001–Ia488.180, which differ from the corresponding compounds Ia1.001–Ia1.180 in that $R^1$ is nitro, $R^{14}$ is n-propyl, $R^{15}$ is n-butyl and $R^{16}$ is methyl:

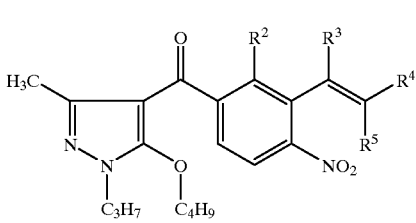
Ia488

Likewise, extraordinary preference is given to the compounds Ia489, in particular to the compounds Ia489.001–Ia489.180, which differ from the corresponding compounds Ia1.001–Ia1.180 in that $R^1$ is nitro, $R^{14}$ and $R^{15}$ are each n-butyl and $R^{16}$ is methyl:

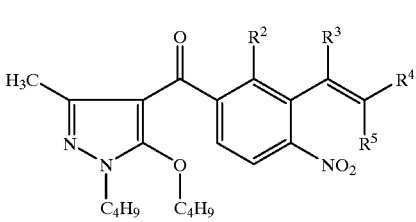
Ia489

Likewise, extraordinary preference is given to the compounds Ia490, in particular to the compounds Ia490.001–Ia490.180, which differ from the corresponding compounds Ia1.001–Ia1.180 in that $R^1$ is nitro, $R^{14}$ is isobutyl, $R^{15}$ is n-butyl and $R^{16}$ is methyl:

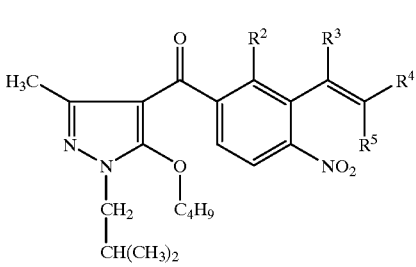
Ia490

Likewise, extraordinary preference is given to the compounds Ia491, in particular to the compounds Ia491.001–Ia491.180, which differ from the corresponding compounds Ia1.001–Ia1.180 in that $R^1$ is nitro, $Rl^5$ is sec-butyl and $R^{16}$ is methyl:

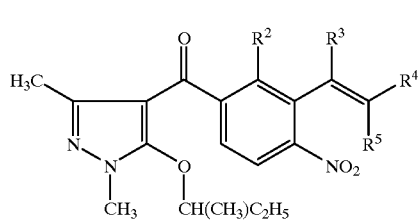
Ia491

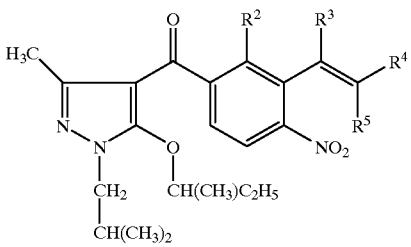
Ia495

Likewise, extraordinary preference is given to the compounds Ia492, in particular to the compounds Ia492.001–Ia492.180, which differ from the corresponding compounds Ia1.001–Ia1.180 in that $R^1$ is nitro, $R^{14}$ is ethyl, $R^{15}$ is sec-butyl and $R^{16}$ is methyl:

Likewise, extraordinary preference is given to the compounds Ia496, in particular to the compounds Ia496.001–Ia496.180, which differ from the corresponding compounds Ia1.001–Ia1.180 in that $R^1$ is nitro, $R^{15}$ is isobutyl and $R^{16}$ is methyl:

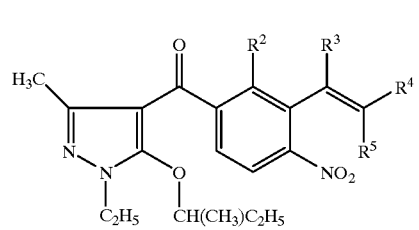
Ia492

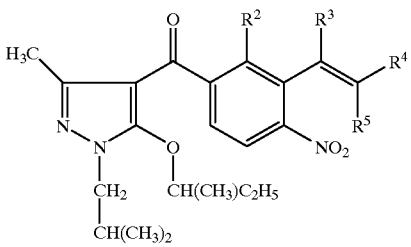
Ia496

Likewise, extraordinary preference is given to the compounds Ia493, in particular to the compounds Ia493.001–Ia493.180, which differ from the corresponding compounds Ia1.001–Ia1.180 in that $R^1$ is nitro, $R^{14}$ is n-propyl, $R^{15}$ is sec-butyl and $R^{16}$ is methyl:

Likewise, extraordinary preference is given to the compounds Ia497, in particular to the compounds Ia497.001–Ia497.180, which differ from the corresponding compounds Ia1.001–Ia1.180 in that $R^1$ is nitro, $R^{14}$ is ethyl, $R^{15}$ is isobutyl and $R^{16}$ is methyl:

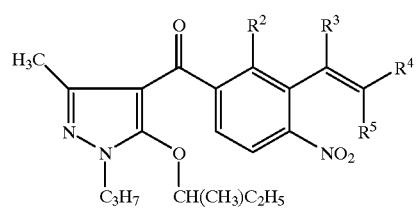
Ia493

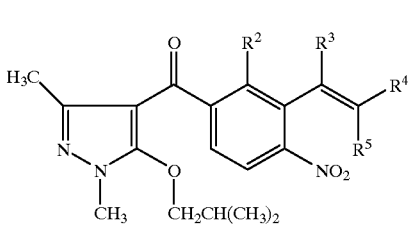
Ia497

Likewise, extraordinary preference is given to the compounds Ia494, in particular to the compounds Ia494.001–Ia494.180, which differ from the corresponding compounds Ia1.001–Ia1.180 in that $R^1$ is nitro, $R^{14}$ is n-butyl, $R^{15}$ is sec-butyl and $R^{16}$ is methyl:

Likewise, extraordinary preference is given to the compounds Ia498, in particular to the compounds Ia498.001–Ia498.180, which differ from the corresponding compounds Ia1.001–Ia1.180 in that $R^1$ is nitro, $R^{14}$ is n-propyl, $R^{15}$ is isobutyl and $R^{16}$ is methyl:

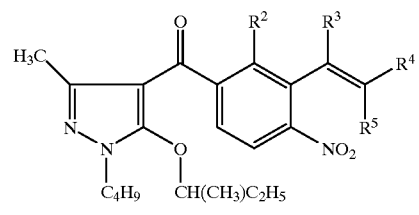
Ia494

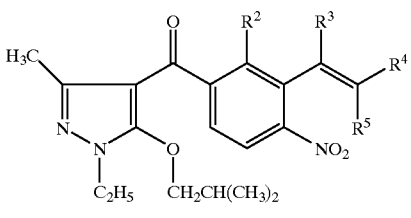
Ia498

Likewise, extraordinary preference is given to the compounds Ia495, in particular to the compounds Ia495.001–Ia495.180, which differ from the corresponding compounds Ia1.001–Ia1.180 in that $R^1$ is nitro, $R^{14}$ is isobutyl, $R^{15}$ is sec-butyl and $R^{16}$ is methyl:

Likewise, extraordinary preference is given to the compounds Ia499, in particular to the compounds Ia499.001–Ia499.180, which differ from the corresponding compounds Ia1.001–Ia1.180 in that $R^1$ is nitro, $R^{14}$ is n-butyl, $R^{15}$ is isobutyl and $R^{16}$ is methyl:

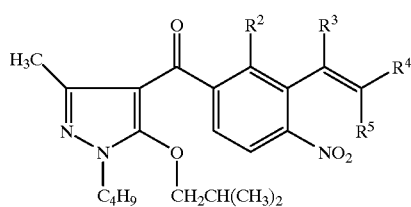

Ia499

Likewise, extraordinary preference is given to the compounds Ia500, in particular to the compounds Ia500.001–Ia500.180, which differ from the corresponding compounds Ia1.001–Ia1.180 in that $R^1$ is nitro, $R^{14}$ and $R^{15}$ are each isobutyl and $R^{16}$ is methyl:

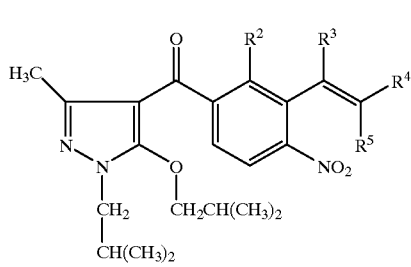

Ia500

Likewise, extraordinary preference is given to the compounds Ia501, in particular to the compounds Ia501.001–Ia501.180, which differ from the corresponding compounds Ia1.001–Ia1.180 in that $R^1$ is nitro, $R^{15}$ is methylcarbonyl and $R^{16}$ is methyl:

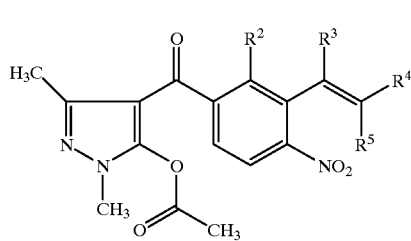

Ia501

Likewise, extraordinary preference is given to the compounds Ia502, in particular to the compounds Ia502.001–Ia502.180, which differ from the corresponding compounds Ia1.001–Ia1.180 in that $R^1$ is nitro, $R^{14}$ is ethyl, $R^{15}$ is methylcarbonyl and $R^{16}$ is methyl:

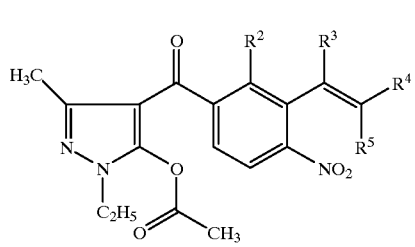

Ia502

Likewise, extraordinary preference is given to the compounds Ia503, in particular to the compounds Ia503.001–Ia503.180, which differ from the corresponding compounds Ia1.001–Ia1.180 in that $R^1$ is nitro, $R^{14}$ is n-propyl, $R^{15}$ is methylcarbonyl and $R^{16}$ is methyl:

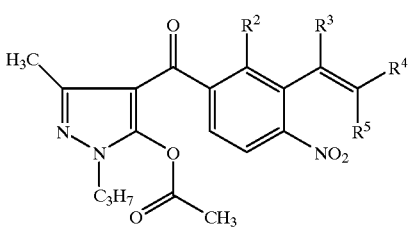

Ia503

Likewise, extraordinary preference is given to the compounds Ia504, in particular to the compounds Ia504.001–Ia504.180, which differ from the corresponding compounds Ia1.001–Ia1.180 in that $R^1$ is nitro, $R^{14}$ is n-butyl, $R^{15}$ is methylcarbonyl and $R^{16}$ is methyl:

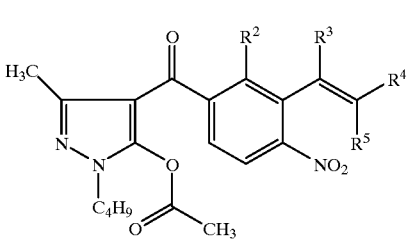

Ia504

Likewise, extraordinary preference is given to the compounds Ia505, in particular to the compounds Ia505.001–Ia505.180, which differ from the corresponding compounds Ia1.001–Ia1.180 in that $R^1$ is nitro, $R^{14}$ is isobutyl, $R^{15}$ is methylcarbonyl and $R^{16}$ is methyl:

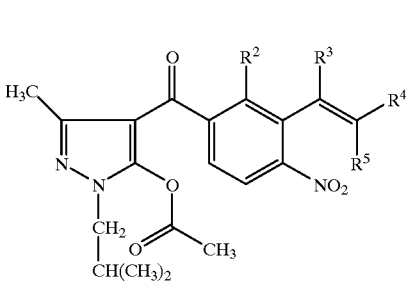

Ia505

Likewise, extraordinary preference is given to the compounds Ia506, in particular to the compounds Ia506.001–Ia506.180, which differ from the corresponding compounds Ia1.001–Ia1.180 in that $R^1$ is nitro, $R^{15}$ is ethylcarbonyl and $R^{16}$ is methyl:

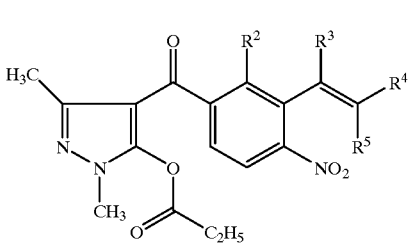

Ia506

Likewise, extraordinary preference is given to the compounds Ia507, in particular to the compounds Ia507.001–Ia507.180, which differ from the corresponding compounds Ia1.001–Ia1.180 in that $R^1$ is nitro, $R^{14}$ is ethyl, $R^{15}$ is ethylcarbonyl and $R^{16}$ is methyl:

Ia507

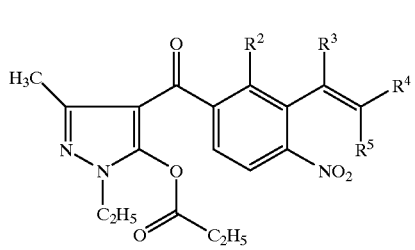

Likewise, extraordinary preference is given to the compounds Ia508, in particular to the compounds Ia508.001–Ia508.180, which differ from the corresponding compounds Ia1.001–Ia1.180 in that $R^1$ is nitro, $R^{14}$ is n-propyl, $R^{15}$ is ethylcarbonyl and $R^{16}$ is methyl:

Ia508

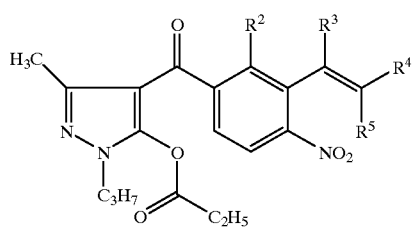

Likewise, extraordinary preference is given to the compounds Ia509, in particular to the compounds Ia509.001–Ia509.180, which differ from the corresponding compounds Ia1.001–Ia1.180 in that $R^1$ is nitro, $R^{14}$ is n-butyl, $R^{15}$ is ethylcarbonyl and $R^{16}$ is methyl:

Ia509

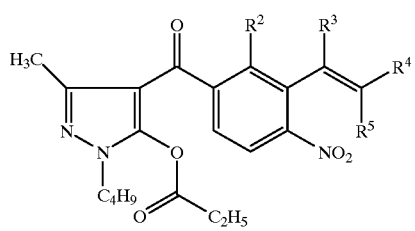

Likewise, extraordinary preference is given to the compounds Ia510, in particular to the compounds Ia510.001–Ia510.180, which differ from the corresponding compounds Ia1.001–Ia1.180 in that $R^1$ is nitro, $R^{14}$ is isobutyl, $R^{15}$ is ethylcarbonyl and $R^{16}$ is methyl:

Ia510

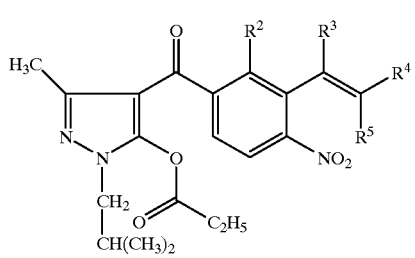

Likewise, extraordinary preference is given to the compounds Ia511, in particular to the compounds Ia511.001–Ia511.180, which differ from the corresponding compounds Ia1.001–Ia1.180 in that $R^1$ is nitro, $R^{15}$ is n-propylcarbonyl and $R^{16}$ is methyl:

Ia511

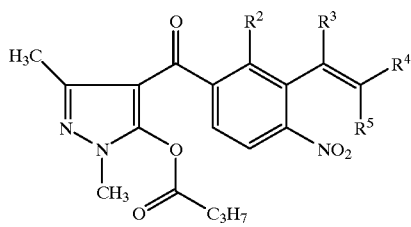

Likewise, extraordinary preference is given to the compounds Ia512, in particular to the compounds Ia512.001–Ia512.180, which differ from the corresponding compounds Ia1.001–Ia1.180 in that $R^1$ is nitro, $R^{14}$ is ethyl, $R^{15}$ is n-propylcarbonyl and $R^{16}$ is methyl:

Ia512

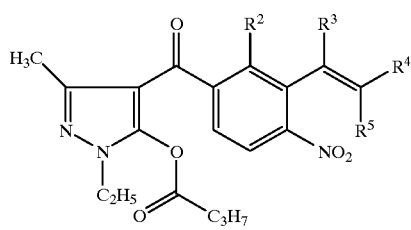

Likewise, extraordinary preference is given to the compounds Ia513, in particular to the compounds Ia513.001–Ia513.180, which differ from the corresponding compounds Ia1.001–Ia1.180 in that $R^1$ is nitro, $R^{14}$ is n-propyl, $R^{15}$ is n-propylcarbonyl and $R^{16}$ is methyl:

Ia513

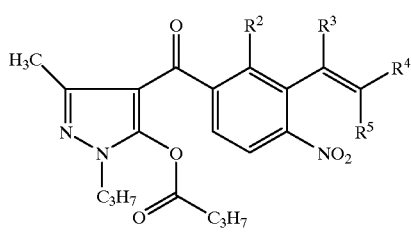

Likewise, extraordinary preference is given to the compounds Ia514, in particular to the compounds Ia514.001–Ia514.180, which differ from the corresponding compounds Ia1.001–Ia1.180 in that $R^1$ is nitro, $R^{14}$ is n-butyl, $R^{15}$ is n-propylcarbonyl and $R^{16}$ is methyl:

Ia514

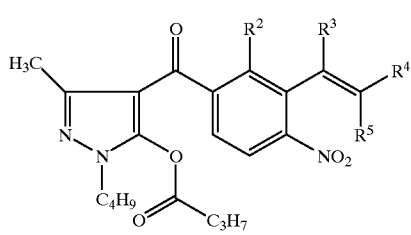

Likewise, extraordinary preference is given to the compounds Ia515, in particular to the compounds Ia515.001–Ia515.180, which differ from the corresponding compounds Ia1.001–Ia1.180 in that $R^1$ is nitro, $R^{14}$ is isobutyl, $R^{15}$ is n-propylcarbonyl and $R^{16}$ is methyl:

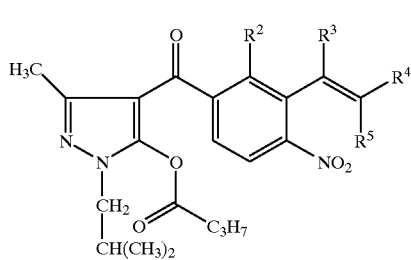

Ia515

Likewise, extraordinary preference is given to the compounds Ia516, in particular to the compounds Ia516.001–Ia516.180, which differ from the corresponding compounds Ia1.001–Ia1.180 in that $R^1$ is nitro, $R^{15}$ is trifluoromethylcarbonyl and $R^{16}$ is methyl:

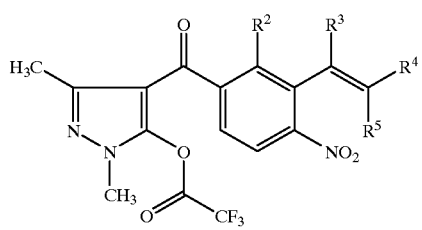

Ia516

Likewise, extraordinary preference is given to the compounds Ia517, in particular to the compounds Ia517.001–Ia517.180, which differ from the corresponding compounds Ia1.001–Ia1.180 in that $R^1$ is nitro, $R^{14}$ is ethyl, $R^{15}$ is trifluoromethylcarbonyl and $R^{16}$ is methyl:

Ia517

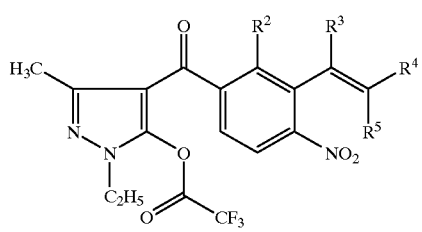

Likewise, extraordinary preference is given to the compounds Ia518, in particular to the compounds Ia518.001–Ia518.180, which differ from the corresponding compounds Ia1.001–Ia1.180 in that $R^1$ is nitro, $R^{14}$ is n-propyl, $R^{15}$ is trifluoromethylcarbonyl and $R^{16}$ is methyl:

Ia518

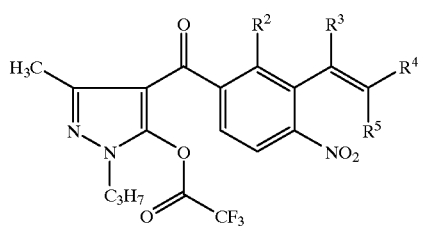

Likewise, extraordinary preference is given to the compounds Ia519, in particular to the compounds Ia519.001–Ia519.180, which differ from the corresponding compounds Ia1.001–Ia1.180 in that $R^1$ is nitro, $R^{14}$ is n-butyl, $R^{15}$ is trifluoromethylcarbonyl and $R^{16}$ is methyl:

Ia519

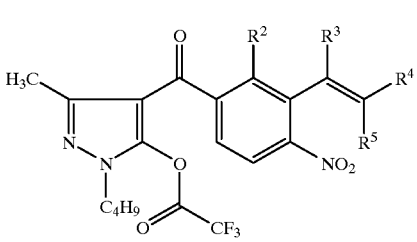

Likewise, extraordinary preference is given to the compounds Ia520, in particular to the compounds Ia520.001–Ia520.180, which differ from the corresponding compounds Ia1.001–Ia1.180 in that $R^1$ is nitro, $R^{14}$ is isobutyl, $R^{15}$ is trifluoromethylcarbonyl and $R^{16}$ is methyl:

Ia520

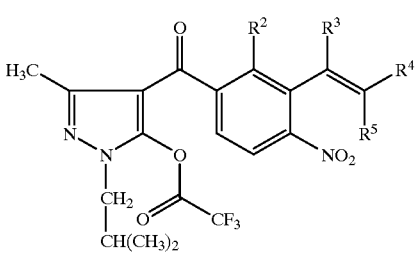

Likewise, extraordinary preference is given to the compounds Ia521, in particular to the compounds Ia521.001–Ia521.180, which differ from the corresponding compounds Ia1.001–Ia1.180 in that $R^1$ is nitro, $R^{15}$ is methylsulfonyl and $R^{16}$ is methyl:

Ia521

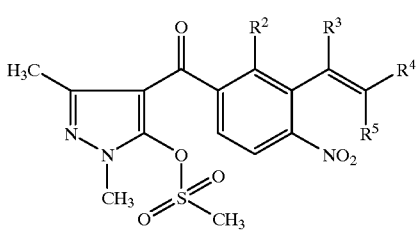

Likewise, extraordinary preference is given to the compounds Ia522, in particular to the compounds Ia522.001–Ia522.180, which differ from the corresponding compounds Ia1.001–Ia1.180 in that $R^1$ is nitro, $R^{14}$ is ethyl, $R^{15}$ is methylsulfonyl and $R^{16}$ is methyl:

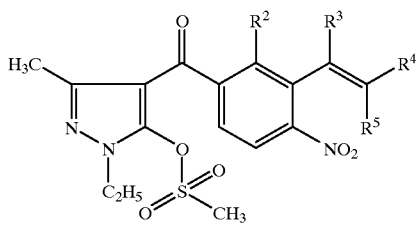

Ia522

Likewise, extraordinary preference is given to the compounds Ia523, in particular to the compounds Ia523.001–Ia523.180, which differ from the corresponding compounds Ia1.001–Ia1.180 in that $R^1$ is nitro, $R^{14}$ is n-propyl, $R^{15}$ is methylsulfonyl and $R^{16}$ is methyl:

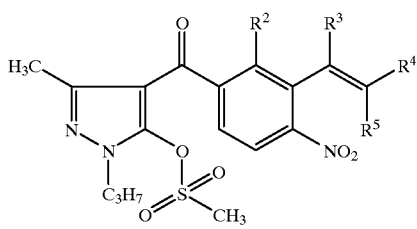

Ia523

Likewise, extraordinary preference is given to the compounds Ia524, in particular to the compounds Ia524.001–Ia524.180, which differ from the corresponding compounds Ia1.001–Ia1.180 in that $R^1$ is nitro, $R^{14}$ is n-butyl, $R^{15}$ is methylsulfonyl and $R^{16}$ is methyl:

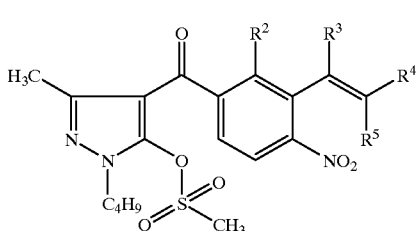

Ia524

Likewise, extraordinary preference is given to the compounds Ia525, in particular to the compounds Ia525.001–Ia525.180, which differ from the corresponding compounds Ia1.001–Ia1.180 in that $R^1$ is nitro, $R^{14}$ is isobutyl, $R^{15}$ is methylsulfonyl and $R^{16}$ is methyl:

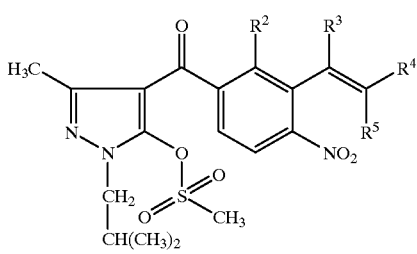

Ia525

Likewise, extraordinary preference is given to the compounds Ia526, in particular to the compounds Ia526.001–Ia526.180, which differ from the corresponding compounds Ia1.001–Ia1.180 in that $R^1$ is nitro, $R^{15}$ is ethylsulfonyl and $R^{16}$ is methyl:

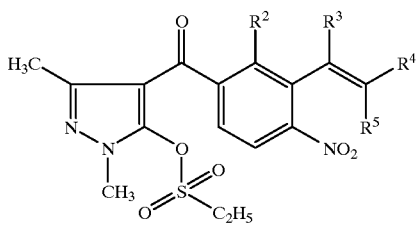

Ia526

Likewise, extraordinary preference is given to the compounds Ia527, in particular to the compounds Ia527.001–Ia527.180, which differ from the corresponding compounds Ia1.001–Ia1.180 in that $R^1$ is nitro, $R^{14}$ is ethyl, $R^{15}$ is ethylsulfonyl and $R^{16}$ is methyl:

Ia527

Likewise, extraordinary preference is given to the compounds Ia528, in particular to the compounds Ia528.001–Ia528.180, which differ from the corresponding compounds Ia1.001–Ia1.180 in that $R^1$ is nitro, $R^{14}$ is n-propyl, $R^{15}$ is ethylsulfonyl and $R^{16}$ is methyl:

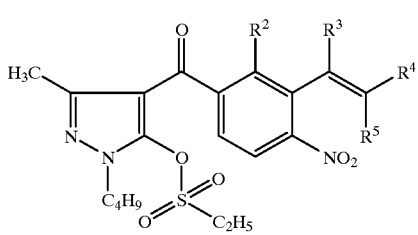

Ia528

Likewise, extraordinary preference is given to the compounds Ia529, in particular to the compounds Ia529.001–Ia529.180, which differ from the corresponding compounds Ia1.001–Ia1.180 in that $R^1$ is nitro, $R^{14}$ is n-butyl, $R^{15}$ is ethylsulfonyl and $R^{16}$ is methyl:

Ia529

Likewise, extraordinary preference is given to the compounds Ia530, in particular to the compounds Ia530.001–Ia530.180, which differ from the corresponding compounds Ia1.001–Ia1.180 in that $R^1$ is nitro, $R^{14}$ is isobutyl, $R^{15}$ is ethylsulfonyl and $R^{16}$ is methyl:

Ia530

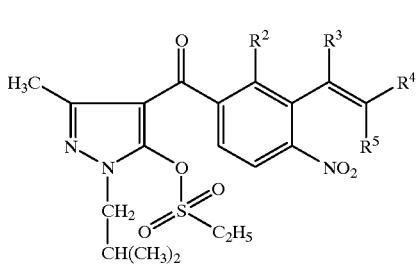

Likewise, extraordinary preference is given to the compounds Ia531, in particular to the compounds Ia531.001–Ia531.180, which differ from the corresponding compounds Ia1.001–Ia1.180 in that $R^1$ is nitro, $R^{15}$ is n-propylsulfonyl and $R^{16}$ is methyl:

Ia531

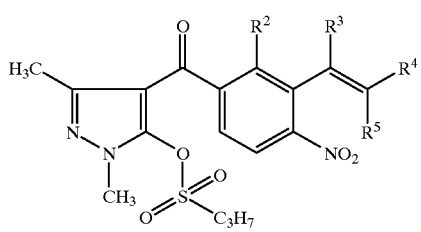

Likewise, extraordinary preference is given to the compounds Ia532, in particular to the compounds Ia532.001–Ia532.180, which differ from the corresponding compounds Ia1.001–Ia1.180 in that $R^1$ is nitro, $R^{14}$ is ethyl, $R^{15}$ is n-propylsulfonyl and $R^{16}$ is methyl:

Ia532

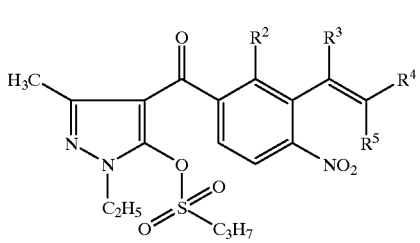

Likewise, extraordinary preference is given to the compounds Ia533, in particular to the compounds Ia533.001–Ia533.180, which differ from the corresponding compounds Ia1.001–Ia1.180 in that $R^1$ is nitro, $R^{14}$ is n-propyl, $R^{15}$ is n-propylsulfonyl and $R^{16}$ is methyl:

Ia533

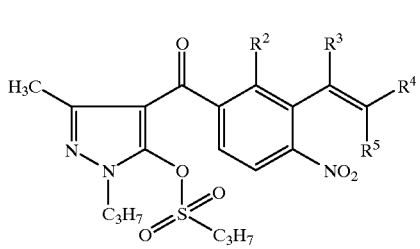

Likewise, extraordinary preference is given to the compounds Ia534, in particular to the compounds Ia534.001–Ia534.180, which differ from the corresponding compounds Ia1.001–Ia1.180 in that $R^1$ is nitro, $R^{14}$ is n-butyl, $R^{15}$ is n-propylsulfonyl and $R^{16}$ is methyl:

Ia534

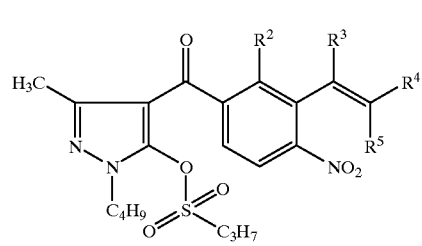

Likewise, extraordinary preference is given to the compounds Ia535, in particular to the compounds Ia535.001–Ia535.180, which differ from the corresponding compounds Ia1.001–Ia1.180 in that $R^1$ is nitro, $R^{14}$ is isobutyl, $R^{15}$ is n-propylsulfonyl and $R^{16}$ is methyl:

Ia535

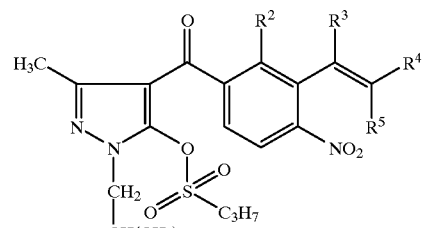

Likewise, extraordinary preference is given to the compounds Ia536, in particular to the compounds Ia536.001–Ia536.180, which differ from the corresponding compounds Ia1.001–Ia1.180 in that $R^1$ is nitro, $R^{15}$ is isopropylsulfonyl and $R^{16}$ is methyl:

Ia536

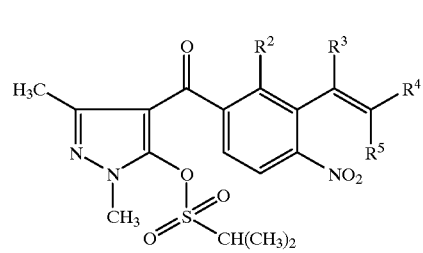

Likewise, extraordinary preference is given to the compounds Ia537, in particular to the compounds Ia537.001–Ia537.180, which differ from the corresponding compounds Ia1.001–Ia1.180 in that $R^1$ is nitro, $R^{14}$ is ethyl, $R^{15}$ is isopropylsulfonyl and $R^{16}$ is methyl:

Ia537

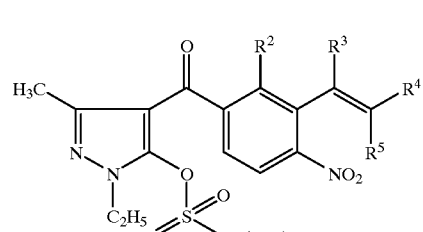

Likewise, extraordinary preference is given to the compounds Ia538, in particular to the compounds Ia538.001–Ia538.180, which differ from the corresponding compounds Ia1.001–Ia1.180 in that $R^1$ is nitro, $R^{14}$ is n-propyl, $R^{15}$ is isopropylsulfonyl and $R^{16}$ is methyl:

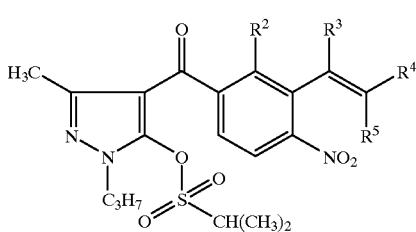

Ia538

Likewise, extraordinary preference is given to the compounds Ia539, in particular to the compounds Ia539.001–Ia539.180, which differ from the corresponding compounds Ia1.001–Ia1.180 in that $R^1$ is nitro, $R^{14}$ is n-butyl, $R^{15}$ is isopropylsulfonyl and $R^{16}$ is methyl:

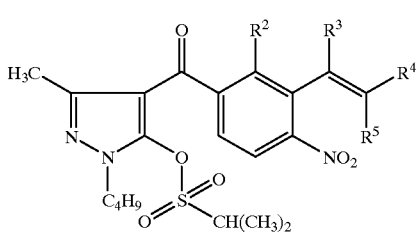

Ia539

Likewise, extraordinary preference is given to the compounds Ia540, in particular to the compounds Ia540.001–Ia540.180, which differ from the corresponding compounds Ia1.001–Ia1.180 in that $R^1$ is nitro, $R^{14}$ is isobutyl, $R^{15}$ is isopropylsulfonyl and $R^{16}$ is methyl:

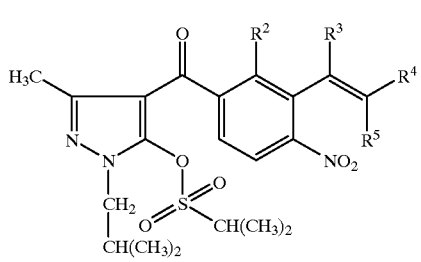

Ia540

Likewise, extraordinary preference is given to the compounds Ia541, in particular to the compounds Ia541.001–Ia541.180, which differ from the corresponding compounds Ia1.001–Ia1.180 in that $R^1$ is nitro, $R^{15}$ is n-butylsulfonyl and $R^{16}$ is methyl:

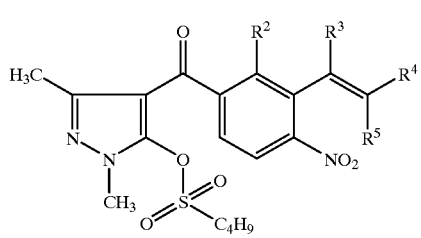

Ia541

Likewise, extraordinary preference is given to the compounds Ia542, in particular to the compounds Ia542.001–Ia542.180, which differ from the corresponding compounds Ia1.001–Ia1.180 in that $R^1$ is nitro, $R^{14}$ is ethyl, $R^{15}$ is n-butylsulfonyl and $R^{16}$ is methyl:

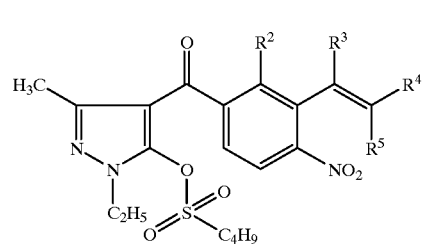

Ia542

Likewise, extraordinary preference is given to the compounds Ia543, in particular to the compounds Ia543.001–Ia543.180, which differ from the corresponding compounds Ia1.001–Ia1.180 in that $R^1$ is nitro, $R^{14}$ is n-propyl $R^{15}$ is n-butylsulfonyl and $R^{16}$ is methyl:

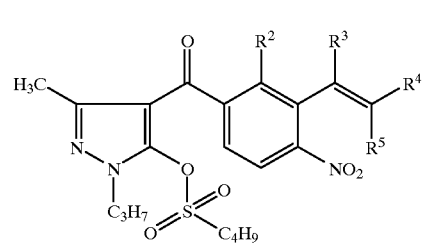

Ia543

Likewise, extraordinary preference is given to the compounds Ia544, in particular to the compounds Ia544.001–Ia544.180, which differ from the corresponding compounds Ia1.001–Ia1.180 in that $R^1$ is nitro, $R^{14}$ is n-butyl, $R^{15}$ is n-butylsulfonyl and $R^{16}$ is methyl:

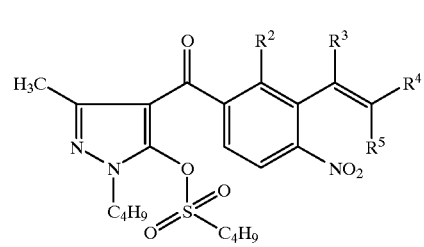

Ia544

Likewise, extraordinary preference is given to the compounds Ia545, in particular to the compounds Ia545.001–Ia545.180, which differ from the corresponding compounds Ia1.001–Ia1.180 in that $R^1$ is nitro, $R^{14}$ is isobutyl, $R^{15}$ is n-butylsulfonyl and $R^{16}$ is methyl:

Ia545

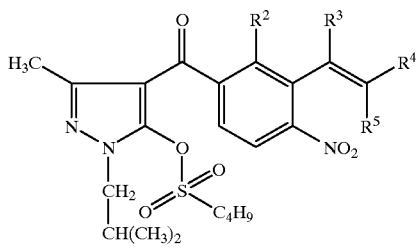

Likewise, extrodinary preference is given to the compounds Ia546, in particular to the compounds Ia546.001–Ia546.180, which differ from the corresponding compounds Ia1.001–Ia1.180 in that $R^1$ is nitro, $R^{15}$ is isobutylsulfonyl and $R^{16}$ is methyl:

Ia546

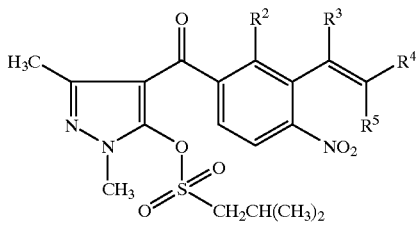

Likewise, extraordinary preference is given to the compounds Ia547, in particular to the compounds Ia547.001–Ia547.180, which differ from the corresponding compounds Ia1.001–Ia1.180 in that $R^1$ is nitro, $R^{14}$ is ethyl, $R^{15}$ is isobutylsulfonyl and $R^{16}$ is methyl:

Ia547

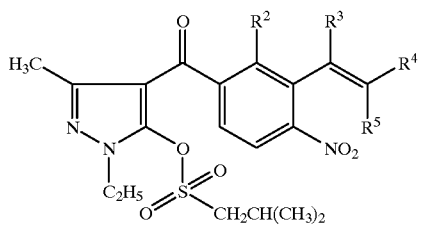

Likewise, extraordinary preference is given to the compounds Ia548, in particular to the compounds Ia548.001–Ia548.180, which differ from the corresponding compounds Ia1.001–Ia1.180 in that $R^1$ is nitro, $R^{14}$ is n-propyl, $R^{15}$ is isobutylsulfonyl and $R^{16}$ is methyl:

Ia548

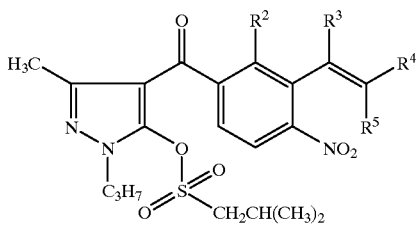

Likewise, extraordinary preference is given to the compounds Ia549, in particular to the compounds Ia549.001–Ia549.180, which differ from the corresponding compounds Ia1.001–Ia1.180 in that $R^1$ is nitro, $R^{14}$ is n-butyl, $R^{15}$ is isobutylsulfonyl and $R^{16}$ is methyl:

Ia549

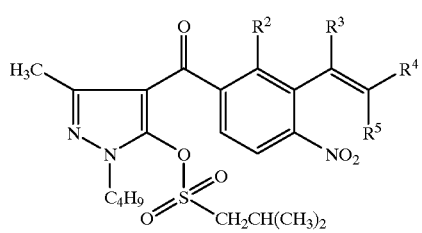

Likewise, extraordinary preference is given to the compounds Ia550, in particular to the compounds Ia550.001–Ia550.180, which differ from the corresponding compounds Ia1.001–Ia1.180 in that $R^1$ is nitro, $R^{14}$ is isobutyl, $R^{15}$ is isobutylsulfonyl and $R^{16}$ is methyl:

Ia550

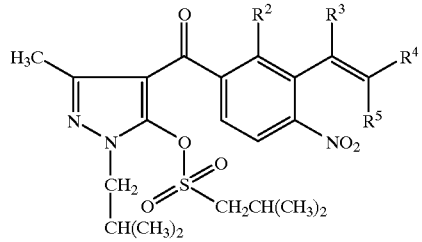

Likewise, extraordinary preference is given to the compounds Ia551, in particular to the compounds Ia551.001–Ia551.180, which differ from the corresponding compounds Ia1.001–Ia1.180 in that $R^1$ is nitro, $R^{15}$ is sec-butylsulfonyl and $R^{16}$ is methyl:

Ia551

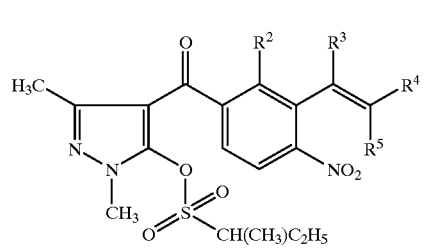

Likewise, extraordinary preference is given to the compounds Ia552, in particular to the compounds Ia552.001–Ia552.180, which differ from the corresponding compounds Ia1.001–Ia1.180 in that $R^1$ is nitro, $R^{14}$ is ethyl, $R^{15}$ is sec-butylsulfonyl and $R^{16}$ is methyl:

Ia552

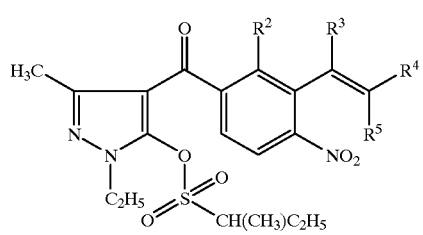

Likewise, extraordinary preference is given to the compounds Ia553, in particular to the compounds Ia553.001–Ia553.180, which differ from the corresponding compounds Ia1.001–Ia1.180 in that $R^1$ is nitro, $R^{14}$ is n-propyl, $R^{15}$ is sec-butylsulfonyl and $R^{16}$ is methyl:

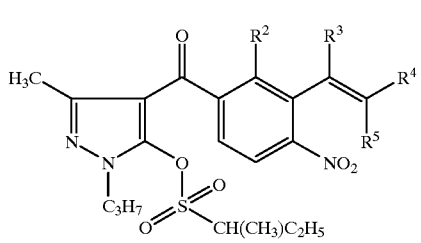

Ia553

Likewise, extraordinary preference is given to the compounds Ia554, in particular to the compounds Ia554.001–Ia554.180, which differ from the corresponding compounds Ia1.001–Ia1.180 in that $R^1$ is nitro, $R^{14}$ is n-butyl, $R^{15}$ is sec-butylsulfonyl and $R^{16}$ is methyl:

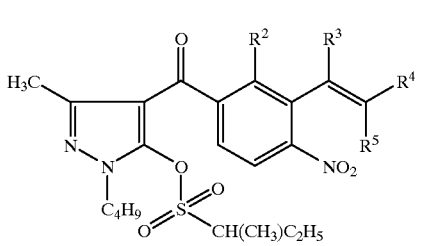

Ia554

Likewise, extraordinary preference is given to the compounds Ia555, in particular to the compounds Ia555.001–Ia555.180, which differ from the corresponding compounds Ia1.001–Ia1.180 in that $R^1$ is nitro, $R^{14}$ is isobutyl, $R^{15}$ is sec-butylsulfonyl and $R^{16}$ is methyl:

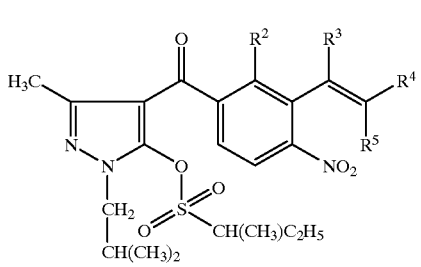

Ia555

Likewise, extraordinary preference is given to the compounds Ia556, in particular to the compounds Ia556.001–Ia556.180, which differ from the corresponding compounds Ia1.001–Ia1.180 in that $R^1$ is nitro, $R^{15}$ is trifluoromethylsulfonyl and $R^{16}$ is methyl:

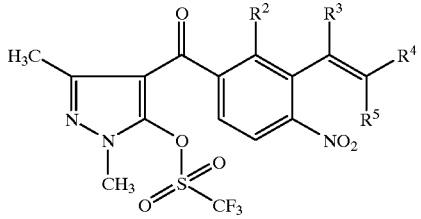

Ia556

Likewise, extraordinary preference is given to the compounds Ia557, in particular to the compounds Ia557.001–Ia557.180, which differ from the corresponding compounds Ia1.001–Ia1.180 in that $R^1$ is nitro, $R^{14}$ is ethyl, $R^{15}$ is trifluoromethylsulfonyl and $R^{16}$ is methyl:

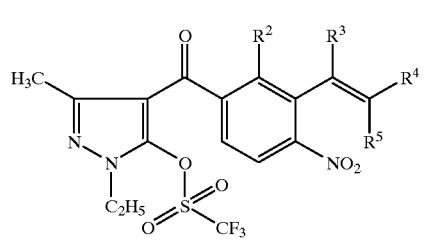

Ia557

Likewise, extraordinary preference is given to the compounds Ia558, in particular to the compounds Ia558.001–Ia558.180, which differ from the corresponding compounds Ia1.001–Ia1.180 in that $R^1$ is nitro, $R^{14}$ is n-propyl, $R^{15}$ is trifluoromethylsulfonyl and $R^{16}$ is methyl:

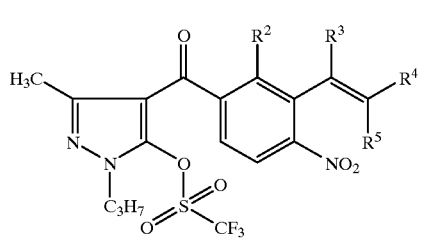

Ia558

Likewise, extraordinary preference is given to the compounds Ia559, in particular to the compounds Ia559.001–Ia559.180, which differ from the corresponding compounds Ia1.001–Ia1.180 in that $R^1$ is nitro, $R^{14}$ is n-butyl, $R^{15}$ is trifluoromethylsulfonyl and $R^{16}$ is methyl:

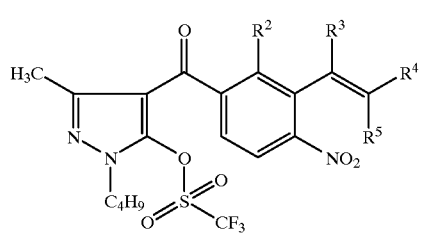

Ia559

Likewise, extraordinary preference is given to the compounds Ia560, in particular to the compounds Ia560.001–Ia560.180, which differ from the corresponding compounds Ia1.001–Ia1.180 in that $R^1$ is nitro, $R^{14}$ is isobutyl, $R^{15}$ is trifluoromethylsulfonyl and $R^{16}$ is methyl:

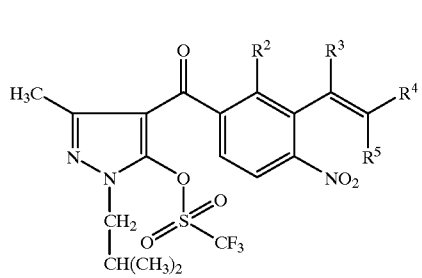

Ia560

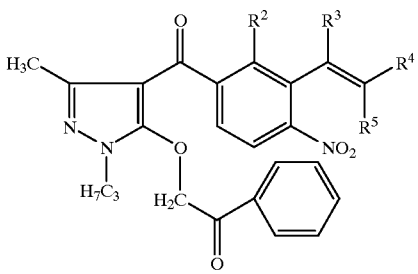

Ia563

Likewise, extraordinary preference is given to the compounds Ia561, in particular to the compounds Ia561.001–Ia561.180, which differ from the corresponding compounds Ia1.001–Ia1.180 in that $R^1$ is nitro, $R^{15}$ is phenylcarbonylmethyl and $R^{16}$ is methyl:

Likewise, extraordinary preference is given to the compounds Ia564, in particular to the compounds Ia564.001–Ia564.180, which differ from the corresponding compounds Ia1.001–Ia1.180 in that $R^1$ is nitro, $R^{14}$ is n-butyl, $R^{15}$ is phenylcarbonylmethyl and $R^{16}$ is methyl:

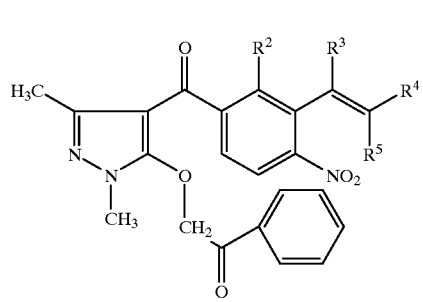

Ia561

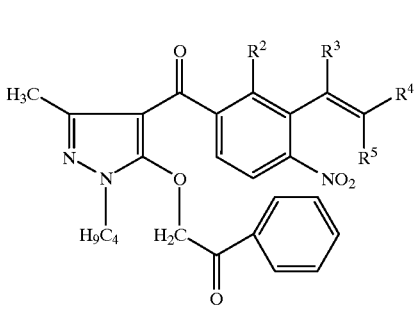

Ia564

Likewise, extraordinary preference is given to the compounds Ia562, in particular to the compounds Ia562.001–Ia562.180, which differ from the corresponding compounds Ia1.001–Ia1.180 in that $R^1$ is nitro, $R^{14}$ is ethyl, $R^{15}$ is phenylcarbonylmethyl and $R^{16}$ is methyl:

Likewise, extraordinary preference is given to the compounds Ia565, in particular to the compounds Ia565.001–Ia565.180, which differ from the corresponding compounds Ia1.001–Ia1.180 in that $R^1$ is nitro, $R^{14}$ is isobutyl, $R^{15}$ is phenylcarbonylmethyl and $R^{16}$ is methyl:

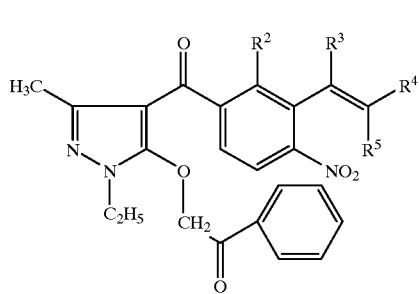

Ia562

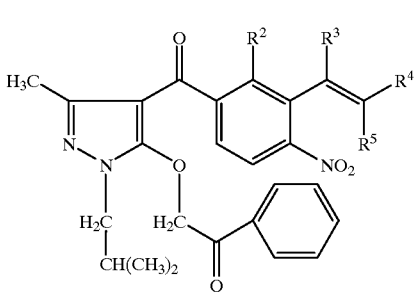

Ia565

Likewise, extraordinary preference is given to the compounds Ia563, in particular to the compounds Ia563.001–Ia563.180, which differ from the corresponding compounds Ia1.001–Ia1.180 in that $R^1$ is nitro, $R^{14}$ is n-propyl, $R^{15}$ is phenylcarbonylmethyl and $R^{16}$ is methyl:

Likewise, extraordinary preference is given to the compounds Ia566, in particular to the compounds Ia566.001–Ia566.180, which differ from the corresponding compounds Ia1.001–Ia1.180 in that $R^1$ is nitro, $R^{15}$ is phenylsulfonyl and $R^{16}$ is methyl:

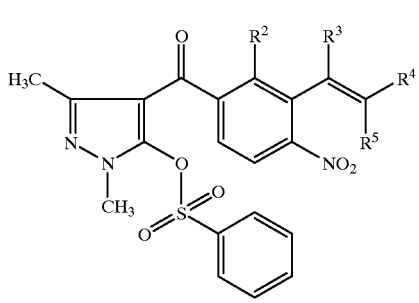

Ia566

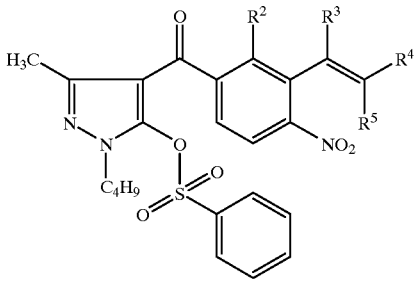

Ia569

Likewise, extraordinary preference is given to the compounds Ia567, in particular to the compounds Ia567.001–Ia567.180, which differ from the corresponding compounds Ia1.001–Ia1.180 in that $R^1$ is nitro, $R^{14}$ is ethyl, $R^{15}$ is phenylsulfonyl and $R^{16}$ is methyl:

Likewise, extraordinary preference is given to the compounds Ia570, in particular to the compounds Ia570.001–Ia570.180, which differ from the corresponding compounds Ia1.001–Ia1.180 in that $R^1$ is nitro, $R^{14}$ is isobutyl, $R^{15}$ is phenylsulfonyl and $R^{16}$ is methyl:

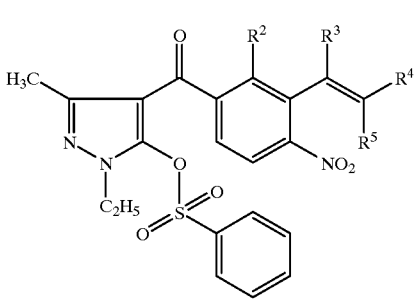

Ia567

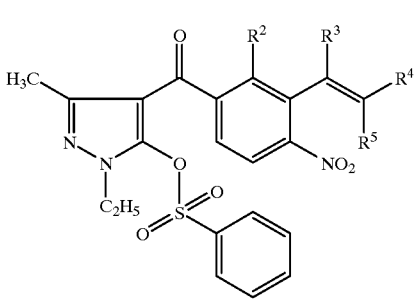

Ia570

Likewise, extraordinary preference is given to the compounds Ia568, in particular to the compounds Ia568.001–Ia568.180, which differ from the corresponding compounds Ia1.001–Ia1.180 in that $R^1$ is nitro, $R^{14}$ is ethyl, $R^{15}$ is phenylsulfonyl and $R^{16}$ is methyl:

Likewise, extraordinary preference is given to the compounds Ia571, in particular to the compounds Ia571.001–Ia571.180, which differ from the corresponding compounds Ia1.001–Ia1.180 in that $R^1$ is nitro, $R^{15}$ is 4-methylphenylsulfonyl and $R^{16}$ is methyl:

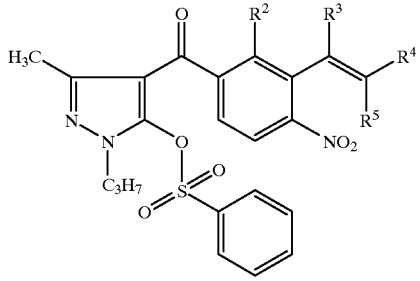

Ia568

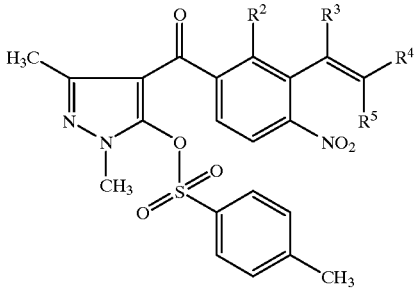

Ia571

Likewise, extraordinary preference is given to the compounds Ia569, in particular to the compounds Ia569.001–Ia569.180, which differ from the corresponding compounds Ia1.001–Ia1.180 in that $R^1$ is nitro, $R^{14}$ is n-butyl, $R^{15}$ is phenylsulfonyl and $R^{16}$ is methyl:

Likewise, extraordinary preference is given to the compounds Ia572, in particular to the compounds Ia572.001–Ia572.180, which differ from the corresponding compounds Ia1.001–Ia1.180 in that $R^1$ is nitro, $R^{14}$ is ethyl, $R^{15}$ is 4-methylphenylsulfonyl and $R^{16}$ is methyl:

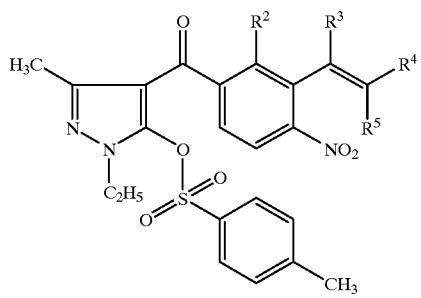

Ia572

Likewise, extraordinary preference is given to the compounds Ia573, in particular to the compounds Ia573.001–Ia573.180, which differ from the corresponding compounds Ia1.001–Ia1.180 in that $R^1$ is nitro, $R^{14}$ is n-propyl, $R^{15}$ is 4-methylphenylsulfonyl and $R^{16}$ is methyl:

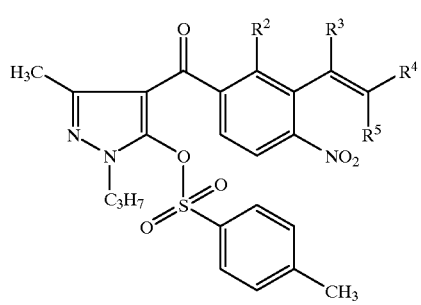

Ia573

Likewise, extraordinary preference is given to the compounds Ia574, in particular to the compounds Ia574.001–Ia574.180, which differ from the corresponding compounds Ia1.001–Ia1.180 in that $R^1$ is nitro, $R^{14}$ is n-butyl, $R^{15}$ is 4-mnethylphenylsulfonyl and $R^{16}$ is methyl:

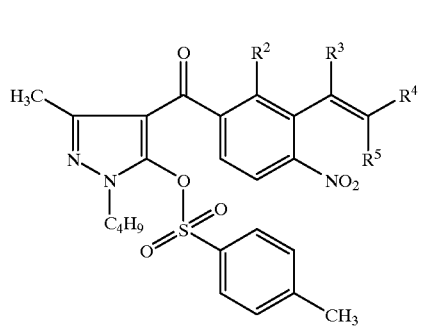

Ia574

Likewise, extraordinary preference is given to the compounds Ia575, in particular to the compounds Ia575.001–Ia575.180, which differ from the corresponding compounds Ia1.001–Ia1.180 in that $R^1$ is nitro, $R^{14}$ is isobutyl, $R^{15}$ is 4-methylphenylsulfonyl and $R^{16}$ is methyl:

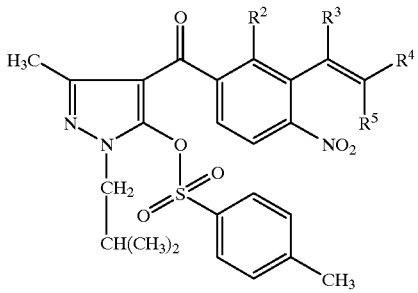

Ia575

Likewise, extraordinary preference is given to the compounds Ia576, in particular to the compounds Ia576.001–Ia576.180, which differ from the corresponding compounds Ia1.001–Ia1.180 in that $R^1$ is methylsulfonyl and $R^{16}$ is methyl:

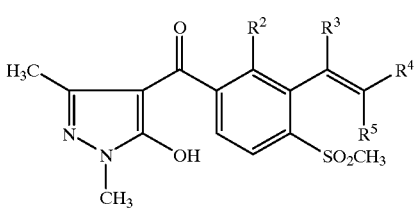

Ia576

Likewise, extraordinary preference is given to the compounds Ia577, in particular to the compounds Ia577.001–Ia577.180, which differ from the corresponding compounds Ia1.001–Ia1.180 in that $R^1$ is methylsulfonyl, $R^{14}$ is ethyl and $R^{15}$ is methyl:

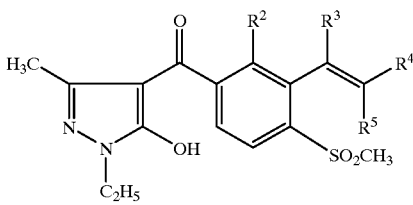

Ia577

Likewise, extraordinary preference is given to the compounds Ia578, in particular to the compounds Ia578.001–Ia578.180, which differ from the corresponding compounds Ia1.001–Ia1.180 in that $R^1$ is methylsulfonyl, $R^{14}$ is n-propyl and $R^{16}$ is methyl:

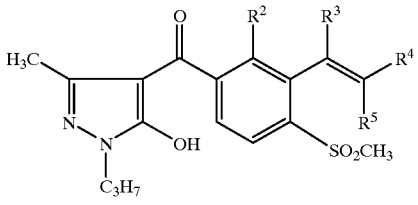

Ia578

Likewise, extraordinary preference is given to the compounds Ia579, in particular to the compounds Ia579.001–Ia579.180, which differ from the corresponding compounds Ia1.001–Ia1.180 in that R¹ is methylsulfonyl, R¹⁴ is n-butyl and R¹⁶ is methyl:

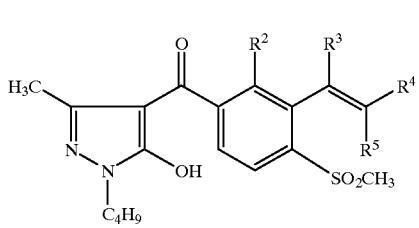
Ia579

Likewise, extraordinary preference is given to the compounds Ia580, in particular to the compounds Ia580.001–Ia580.180, which differ from the corresponding compounds Ia1.001–Ia1.180 in that R¹ is methylsulfonyl, R¹⁴ is isobutyl and R¹⁶ is methyl:

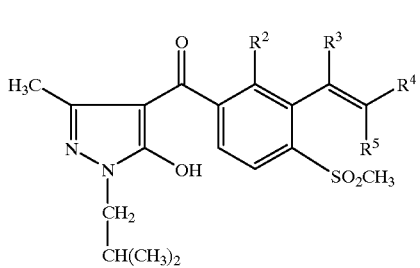
Ia580

Likewise, extraordinary preference is given to the compounds Ia581, in particular to the compounds Ia581.001–Ia581.180, which differ from the corresponding compounds Ia1.001–Ia1.180 in that R¹ is methylsulfonyl and R¹⁵ and R¹⁶ are each methyl:

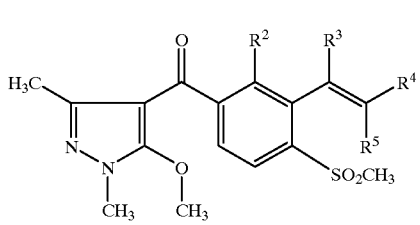
Ia581

Likewise, extraordinary preference is given to the compounds Ia582, in particular to the compounds Ia582.001–Ia582.180, which differ from the corresponding compounds Ia1.001–Ia1.180 in that R¹ is methylsulfonyl, R¹⁴ is ethyl and R¹⁵ and R¹⁶ are each methyl:

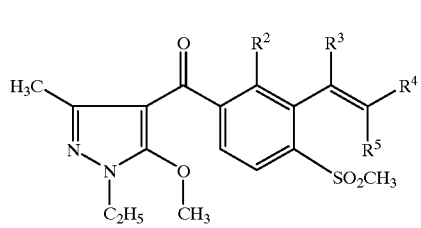
Ia582

Likewise, extraordinary preference is given to the compounds Ia583, in particular to the compounds Ia583.001–Ia583.180, which differ from the corresponding compounds Ia1.001–Ia1.180 in that R¹ is methylsulfonyl, R¹⁴ is n-propyl and R¹⁵ and R¹⁶ are each methyl:

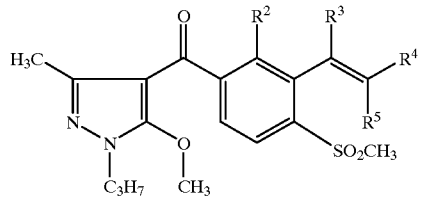
Ia583

Likewise, extraordinary preference is given to the compounds Ia584, in particular to the compounds Ia584.001–Ia584.180, which differ from the corresponding compounds Ia1.001–Ia1.180 in that R¹ is methylsulfonyl, R¹⁴ is n-butyl and R¹⁵ and R¹⁶ are each methyl:

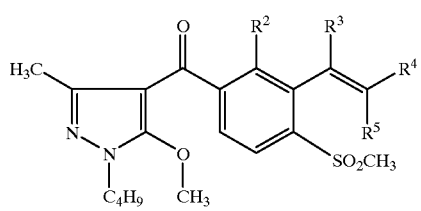
Ia584

Likewise, extraordinary preference is given to the compounds Ia585, in particular to the compounds Ia585.001–Ia585.180, which differ from the corresponding compounds Ia1.001–Ia1.180 in that R¹ is methylsulfonyl, R¹⁴ is isobutyl and R¹⁵ and R¹⁶ are each methyl:

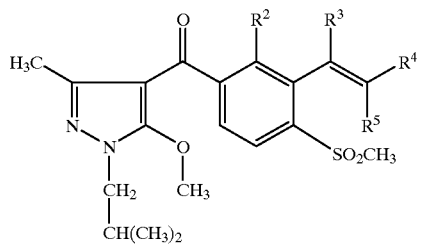
Ia585

Likewise, extraordinary preference is given to the compounds Ia586, in particular to the compounds Ia586.001–Ia586.180, which differ from the corresponding compounds Ia1.001–Ia1.180 in that R¹ is methylsulfonyl, R¹⁵ is ethyl and R¹⁶ is methyl:

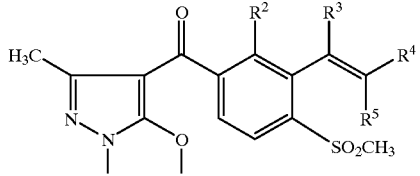
Ia586

Likewise, extraordinary preference is given to the compounds Ia587, in particular to the compounds Ia587.001–Ia587.180, which differ from the corresponding compounds Ia1.001–Ia1.180 in that R¹ is methylsulfonyl, R¹⁴ and R¹⁵ are each ethyl and R¹⁶ is methyl:

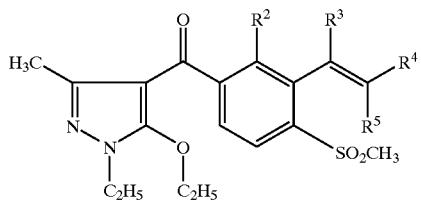

Ia587

Likewise, extraordinary preference is given to the compounds Ia588, in particular to the compounds Ia588.001–Ia588.180, which differ from the corresponding compounds Ia1.001–Ia1.180 in that $R^1$ is methylsulfonyl, $R^{14}$ is n-propyl, $R^{15}$ is ethyl and $R^{16}$ is methyl:

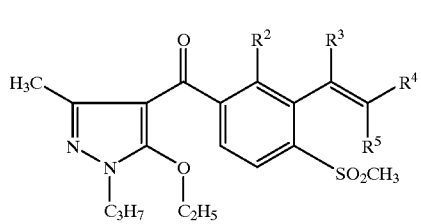

Ia588

Likewise, extraordinary preference is given to the compounds Ia589, in particular to the compounds Ia589.001–Ia589.180, which differ from the corresponding compounds Ia1.001–Ia1.180 in that $R^1$ is methylsulfonyl, $R^{14}$ is n-butyl, $R^{15}$ is ethyl and $R^{16}$ is methyl:

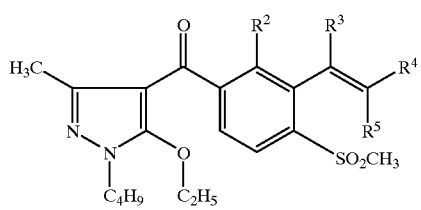

Ia589

Likewise, extraordinary preference is given to the compounds Ia590, in particular to the compounds Ia590.001–Ia590.180, which differ from the corresponding compounds Ia1.001–Ia1.180 in that $R^1$ is methylsulfonyl, $R^{14}$ is isobutyl, $R^{15}$ is ethyl and $R^{16}$ is methyl:

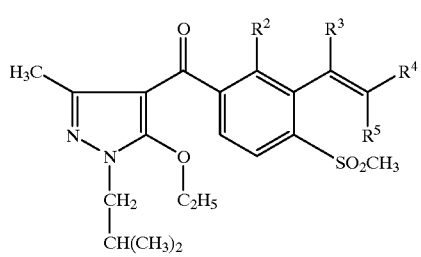

Ia590

Likewise, extraordinary preference is given to the compounds Ia591, in particular to the compounds Ia591.001–Ia591.180, which differ from the corresponding compounds Ia1.001–Ia1.180 in that $R^1$ is methylsulfonyl, $R^{15}$ is n-propyl and $R^{16}$ is methyl:

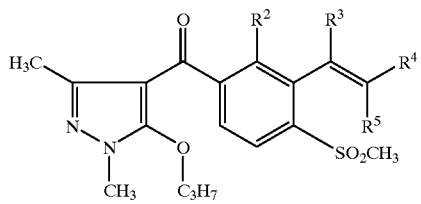

Ia591

Likewise, extraordinary preference is given to the compounds Ia592, in particular to the compounds Ia592.001–Ia592.180, which differ from the corresponding compounds Ia1.001–Ia1.180 in that $R^1$ is methylsulfonyl, $R^{14}$ is ethyl, $R^{15}$ is n-propyl and $R^{16}$ is methyl:

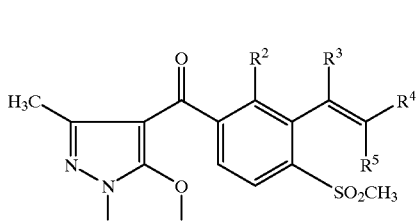

Ia592

Likewise, extraordinary preference is given to the compounds Ia593, in particular to the compounds Ia593.001–Ia593.180, which differ from the corresponding compounds Ia1.001–Ia1.180 in that $R^1$ is methylsulfonyl, $R^{14}$ and $R^{15}$ are each n-propyl and $R^{16}$ is methyl:

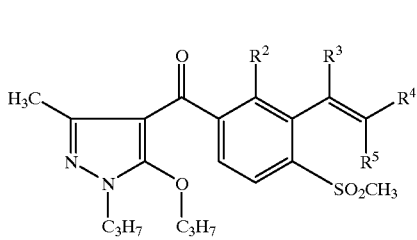

Ia593

Likewise, extraordinary preference is given to the compounds Ia594, in particular to the compounds Ia594.001–Ia594.180, which differ from the corresponding compounds Ia1.001–Ia1.180 in that $R^1$ is methylsulfonyl, $R^{14}$ is n-butyl, $R^{15}$ is n-propyl and $R^{16}$ is methyl:

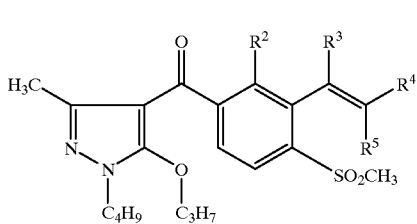

Ia594

Likewise, extraordinary preference is given to the compounds Ia595, in particular to the compounds Ia595.001–Ia595.180, which differ from the corresponding compounds Ia1.001–Ia1.180 in that $R^1$ is methylsulfonyl, $R^{14}$ is isobutyl, $R^{15}$ is n-propyl and $R^{16}$ is methyl:

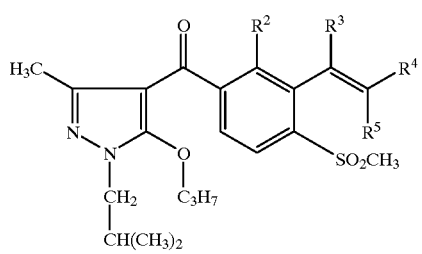
Ia595

Likewise, extraordinary preference is given to the compounds Ia596, in particular to the compounds Ia596.001–Ia596.180, which differ from the corresponding compounds Ia1.001–Ia1.180 in that $R^1$ is methylsulfonyl, $R^{15}$ is isopropyl and $R^{16}$ is methyl:

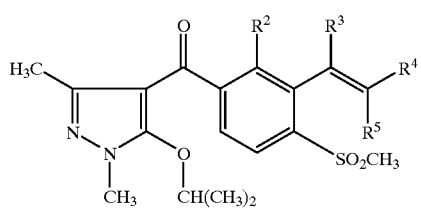
Ia596

Likewise, extraordinary preference is given to the compounds Ia597, in particular to the compounds Ia597.001–Ia597.180, which differ from the corresponding compounds Ia1.001–Ia1.180 in that $R^1$ is methylsulfonyl, $R^{14}$ is ethyl, $R^{15}$ is isopropyl and $R^{16}$ is methyl:

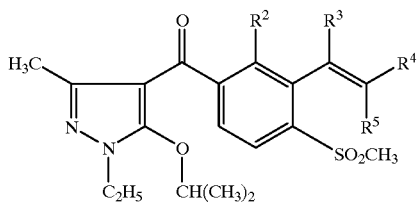
Ia597

Likewise, extraordinary preference is given to the compounds Ia598, in particular to the compounds Ia598.001–Ia598.180, which differ from the corresponding compounds Ia1.001–Ia1.180 in that $R^1$ is methylsulfonyl, $R^{14}$ is n-propyl, $R^{15}$ is isopropyl and $R^{16}$ is methyl:

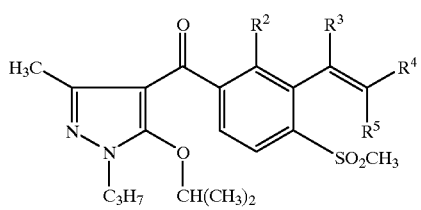
Ia598

Likewise, extraordinary preference is given to the compounds Ia599, in particular to the compounds Ia599.001–Ia599.180, which differ from the corresponding compounds Ia1.001–Ia1.180 in that $R^1$ is methylsulfonyl, $R^{14}$ is n-butyl, $R^{15}$ is isopropyl and $R^{16}$ is methyl:

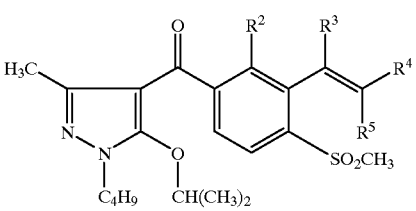
Ia599

Likewise, extraordinary preference is given to the compounds Ia600, in particular to the compounds Ia600.001–Ia600.180, which differ from the corresponding compounds Ia1.001–Ia1.180 in that $R^1$ is methylsulfonyl, $R^{14}$ is isobutyl, $R^{15}$ is isopropyl and $R^{16}$ is methyl:

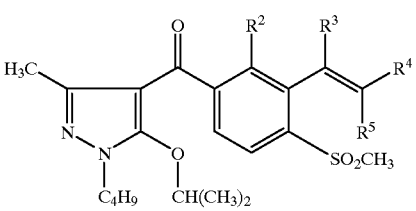
Ia600

Likewise, extraordinary preference is given to the compounds Ia601, in particular to the compounds Ia601.001–Ia601.180, which differ from the corresponding compounds Ia1.001–Ia1.180 in that $R^1$ is methylsulfonyl, $R^{15}$ is n-butyl and $R^{16}$ is methyl:

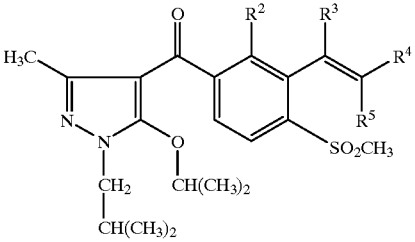
Ia601

Likewise, extraordinary preference is given to the compounds Ia602, in particular to the compounds Ia602.001–Ia602.180, which differ from the corresponding compounds Ia1.001–Ia1.180 in that $R^1$ is methylsulfonyl, $R^{14}$ is ethyl, $R^{15}$ is n-butyl and $R^{16}$ is methyl.

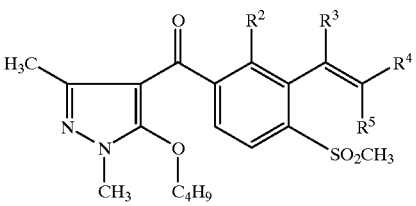
Ia602

Likewise, extraordinary preference is given to the compounds Ia603, in particular to the compounds Ia603.001–Ia603.180, which differ from the corresponding compounds Ia1.001–Ia1.180 in that $R^{14}$ is n-propyl, $R^{15}$ is n-butyl and $R^{16}$ is methyl:

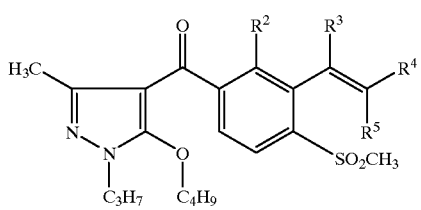
Ia603

Likewise, extraordinary preference is given to the compounds Ia604, in particular to the compounds Ia604.001–Ia604.180, which differ from the corresponding compounds Ia1.001–Ia1.180 in that $R^1$ is methylsulfonyl, $R^{14}$ and $R^{15}$ are each n-butyl and $R^{16}$ is methyl:

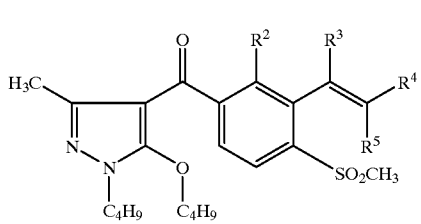
Ia604

Likewise, extraordinary preference is given to the compounds Ia605, in particular to the compounds Ia605.001–Ia605.180, which differ from the corresponding compounds Ia1.001–Ia1.180 in that $R^1$ is methylsulfonyl, $R^{14}$ is isobutyl, $R^{15}$ is n-butyl and $R^{16}$ is methyl:

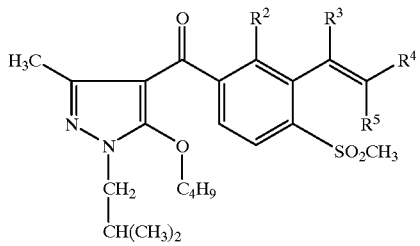
Ia605

Likewise, extraordinary preference is given to the compounds Ia606, in particular to the compounds Ia606.001–Ia606.180, which differ from the corresponding compounds Ia1.001–Ia1.180 in that $R^1$ is methylsulfonyl, $R^{15}$ is sec-butyl and $R^{16}$ is methyl:

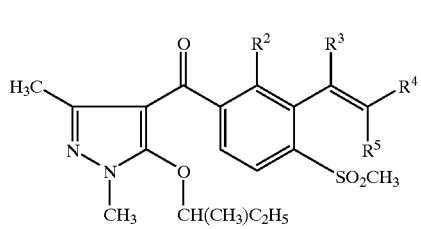
Ia606

Likewise, extraordinary preference is given to the compounds Ia607, in particular to the compounds Ia607.001–Ia607.180, which differ from the corresponding compounds Ia1.001–Ia1.180 in that $R^1$ is methylsulfonyl, $R^{14}$ is ethyl, $R^{15}$ is sec-butyl and $R^{16}$ is methyl:

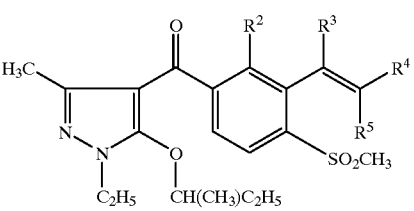
Ia607

Likewise, extraordinary preference is given to the compounds Ia608, in particular to the compounds Ia608.001–Ia608.180, which differ from the corresponding compounds Ia1.001–Ia1.180 in that $R^1$ is methylsulfonyl, $R^{14}$ is n-propyl, $R^{15}$ is sec-butyl and $R^{16}$ is methyl:

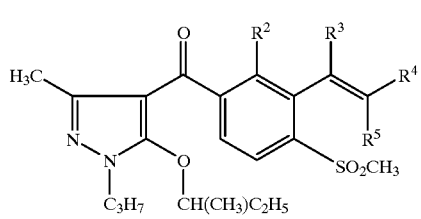
Ia608

Likewise, extraordinary preference is given to the compounds Ia609, in particular to the compounds Ia609.001–Ia609.180, which differ from the corresponding compounds Ia1.001–Ia1.180 in that $R^1$ is methylsulfonyl, $R^{14}$ is n-butyl, $R^{15}$ is sec-butyl and $R^{16}$ is methyl:

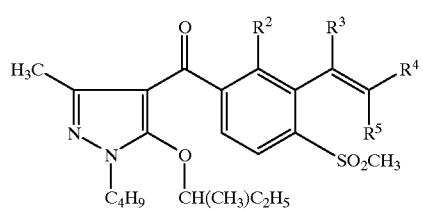
Ia609

Likewise, extraordinary preference is given to the compounds Ia610, in particular to the compounds Ia610.001–Ia610.180, which differ from the corresponding compounds Ia1.001–Ia1.180 in that $R^1$ is methylsulfonyl, $R^{14}$ is isobutyl, $R^{15}$ is sec-butyl and $R^{16}$ is methyl:

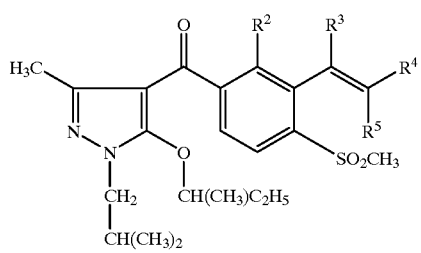
Ia610

Likewise, extraordinary preference is given to the compounds Ia611, in particular to the compounds Ia611.001–Ia611.180, which differ from the corresponding compounds Ia1.001–Ia1.180 in that $R^{15}$ is isobutyl and $R^{16}$ is methyl:

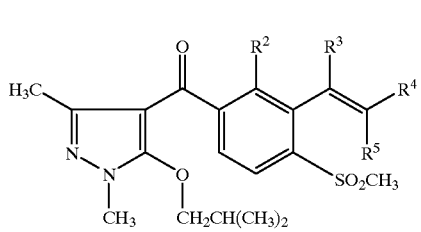

Ia611

Likewise, extraordinary preference is given to the compounds Ia612, in particular to the compounds Ia612.001–Ia612.180, which differ from the corresponding compounds Ia1.001–Ia1.180 in that $R^1$ is methylsulfonyl, $R^{14}$ is ethyl, $R^{15}$ is isobutyl and $R^{16}$ is methyl:

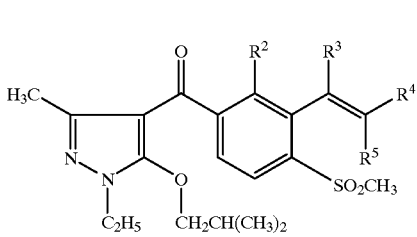

Ia612

Likewise, extraordinary preference is given to the compounds Ia613, in particular to the compounds Ia613.001–Ia613.180, which differ from the corresponding compounds Ia1.001–Ia1.180 in that $R^1$ is methylsulfonyl, $R^{14}$ is n-propyl, $R^{15}$ is isobutyl and $R^{16}$ is methyl:

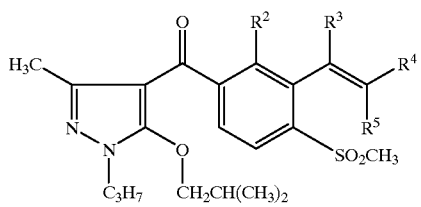

Ia613

Likewise, extraordinary preference is given to the compounds Ia614, in particular to the compounds Ia614.001–Ia614.180, which differ from the corresponding compounds Ia1.001–Ia1.180 in that $R^1$ is methylsulfonyl, $R^{14}$ is n-butyl, $R^{15}$ is isobutyl and $R^{16}$ is methyl:

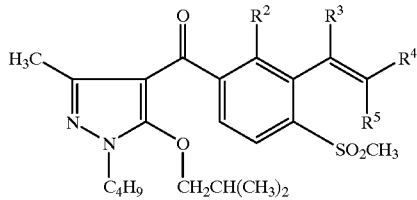

Ia614

Likewise, extraordinary preference is given to the compounds Ia615, in particular to the compounds Ia615.001–Ia615.180, which differ from the corresponding compounds Ia1.001–Ia1.180 in that $R^1$ is methylsulfonyl, $R^{14}$ and $R^{15}$ are each isobutyl and $R^{16}$ is methyl:

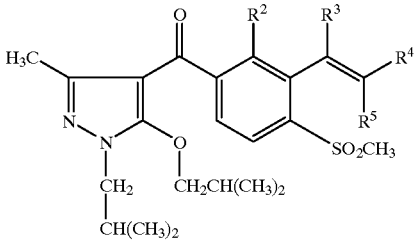

Ia615

Likewise, extraordinary preference is given to the compounds Ia616, in particular to the compounds Ia616.001–Ia616.180, which differ from the corresponding compounds Ia1.001–Ia1.180 in that $R^1$ is methylsulfonyl, $R^{15}$ is methylcarbonyl and $R^{16}$ is methyl:

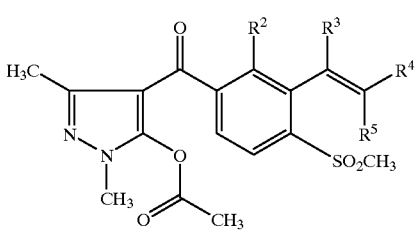

Ia616

Likewise, extraordinary preference is given to the compounds Ia617, in particular to the compounds Ia617.001–Ia617.180, which differ from the corresponding compounds Ia1.001–Ia1.180 in that $R^1$ is methylsulfonyl, $R^{14}$ is ethyl, $R^{15}$ is methylcarbonyl and $R^{16}$ is methyl:

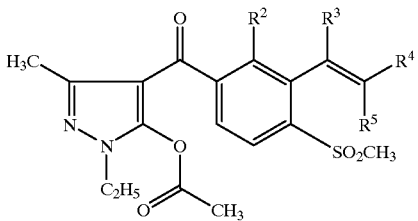

Ia617

Likewise, extraordinary preference is given to the compounds Ia618, in particular to the compounds Ia618.001–Ia618.180, which differ from the corresponding compounds Ia1.001–Ia1.180 in that $R^1$ is methylsulfonyl, $R^{14}$ is n-propyl, $R^{15}$ is methylcarbonyl and $R^{16}$ is methyl:

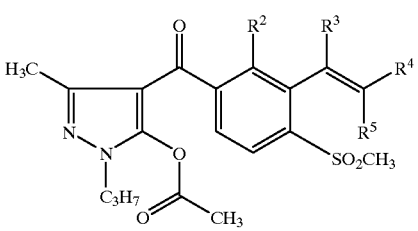

Ia618

Likewise, extraordinary preference is given to the compounds Ia619, in particular to the compounds Ia619.001–Ia619.180, which differ from the corresponding compounds Ia1.001–Ia1.180 in that $R^1$ is methylsulfonyl, $R^{14}$ is n-butyl, $R^{15}$ is methylcarbonyl and $R^{16}$ is methyl:

Ia619

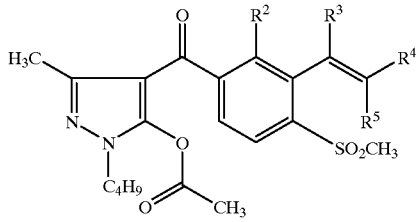

Likewise, extraordinary preference is given to the compounds Ia620, in particular to the compounds Ia620.001–Ia620.180, which differ from the corresponding compounds Ia1.001–Ia1.180 in that $R^1$ is methylsulfonyl, $R^{14}$ is isobutyl, $R^{15}$ is methylcarbonyl and $R^{16}$ is methyl:

Ia620

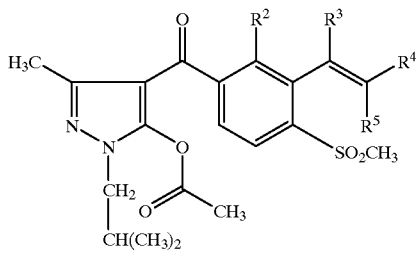

Likewise, extraordinary preference is given to the compounds Ia621, in particular to the compounds Ia621.001–Ia621.180, which differ from the corresponding compounds Ia1.001–Ia1.180 in that $R^1$ is methylsulfonyl, $R^{15}$ is ethylcarbonyl and $R^{16}$ is methyl:

Ia621

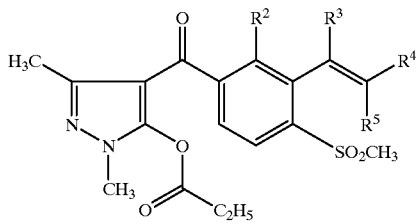

Likewise, extraordinary preference is given to the compounds Ia622, in particular to the compounds Ia622.001–Ia622.180, which differ from the corresponding compounds Ia1.001–Ia1.180 in that $R^1$ is methylsulfonyl, $R^{14}$ is ethyl, $R^{15}$ is ethylcarbonyl and $R^{16}$ is methyl:

Ia622

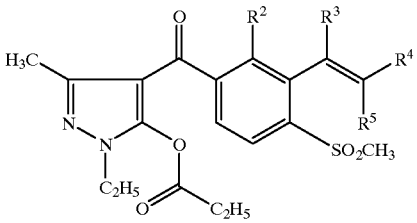

Likewise, extraordinary preference is given to the compounds Ia623, in particular to the compounds Ia623.001–Ia623.180, which differ from the corresponding compounds Ia1.001–Ia1.180 in that $R^1$ is methylsulfonyl, $R^{14}$ is n-propyl, $R^{15}$ is ethylcarbonyl and $R^{16}$ is methyl:

Ia623

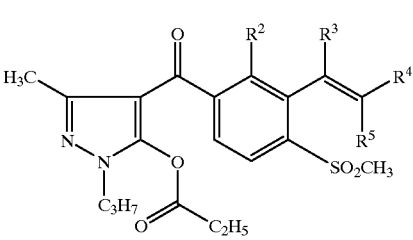

Likewise, extraordinary preference is given to the compounds Ia624, in particular to the compounds Ia624.001–Ia624.180, which differ from the corresponding compounds Ia1.001–Ia1.180 in that $R^1$ is methylsulfonyl, $R^{14}$ is n-butyl, $R^{15}$ is ethylcarbonyl and $R^{16}$ is methyl:

Ia624

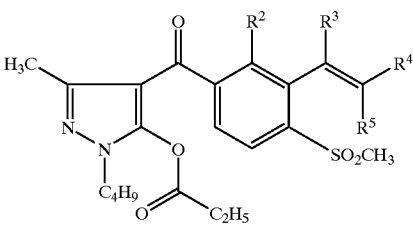

Likewise, extraordinary preference is given to the compounds Ia625, in particular to the compounds Ia625.001–Ia625.180, which differ from the corresponding compounds Ia1.001–Ia1.180 in that $R^1$ is methylsulfonyl, $R^{14}$ is isobutyl, $R^{15}$ is ethylcarbonyl and $R^{16}$ is methyl:

Ia625

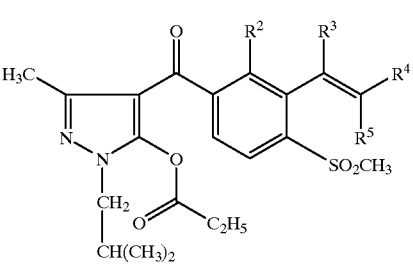

Likewise, extraordinary preference is given to the compounds Ia626, in particular to the compounds Ia626.001–Ia626.180, which differ from the corresponding compounds Ia1.001–Ia1.180 in that $R^1$ is methylsulfonyl, $R^{15}$ is n-propylcarbonyl and $R^{16}$ is methyl:

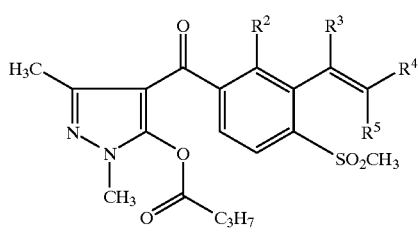

Ia626

Likewise, extraordinary preference is given to the compounds Ia627, in particular to the compounds Ia627.001–Ia627.180, which differ from the corresponding compounds Ia1.001–Ia1.180 in that $R^1$ is methylsulfonyl, $R^{14}$ is ethyl, $R^{15}$ is n-propylcarbonyl and $R^{16}$ is methyl:

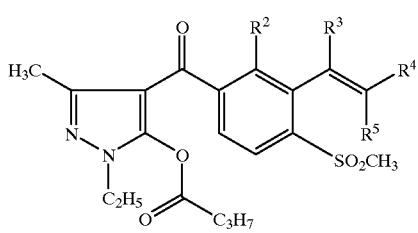

Ia627

Likewise, extraordinary preference is given to the compounds Ia628, in particular to the compounds Ia628.001–Ia628.180, which differ from the corresponding compounds Ia1.001–Ia1.180 in that $R^1$ is methylsulfonyl, $R^{14}$ is n-propyl, $R^{15}$ is n-propylcarbonyl and $R^{16}$ is methyl:

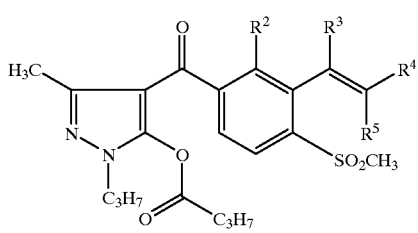

Ia628

Likewise, extraordinary preference is given to the compounds Ia629, in particular to the compounds Ia629.001–Ia629.180, which differ from the corresponding compounds Ia1.001–Ia1.180 in that $R^1$ is methylsulfonyl, $R^{14}$ is n-butyl, $R^{15}$ is n-propylcarbonyl and $R^{16}$ is methyl:

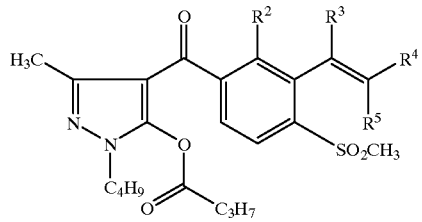

Ia629

Likewise, extraordinary preference is given to the compounds Ia630, in particular to the compounds Ia630.001–Ia630.180, which differ from the corresponding compounds Ia1.001–Ia1.180 in that $R^1$ is methylsulfonyl, $R^{14}$ is isobutyl, $R^{15}$ is n-propylcarbonyl and $R^{16}$ is methyl:

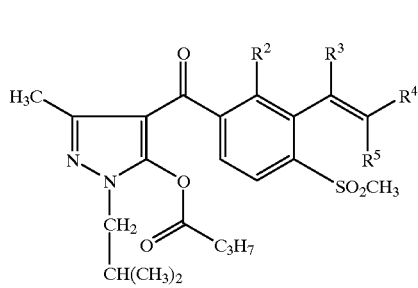

Ia630

Likewise, extraordinary preference is given to the compounds Ia631, in particular to the compounds Ia631.001–Ia631.180, which differ from the corresponding compounds Ia1.001–Ia1.180 in that $R^1$ is methylsulfonyl, $R^{15}$ is trifluoromethylcarbonyl and $R^{16}$ is methyl:

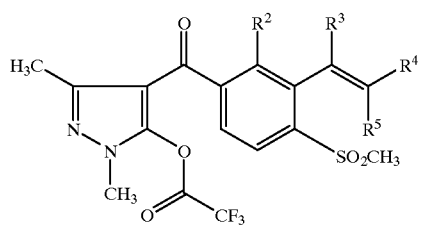

Ia631

Likewise, extraordinary preference is given to the compounds Ia632, in particular to the compounds Ia632.001–Ia632.180, which differ from the corresponding compounds Ia1.001–Ia1.180 in that $R^1$ is methylsulfonyl, $R^{14}$ is ethyl, $R^{15}$ is trifluoromethylcarbonyl and $R^{16}$ is methyl:

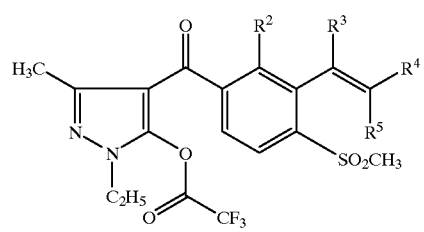

Ia632

Likewise, extraordinary preference is given to the compounds Ia633, in particular to the compounds Ia633.001–Ia633.180, which differ from the corresponding compounds Ia1.001–Ia1.180 in that $R^1$ is methylsulfonyl, $R^{14}$ is n-propyl, $R^{15}$ is trifluoromethylcarbonyl and $R^{16}$ is methyl:

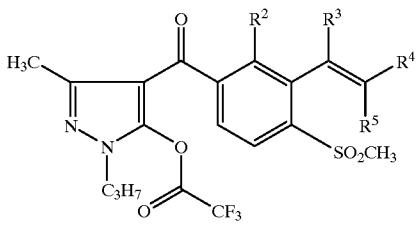

Ia633

Likewise, extraordinary preference is given to the compounds Ia634, in particular to the compounds Ia634.001–Ia634.180, which differ from the corresponding compounds Ia1.001–Ia1.180 in that $R^1$ is methylsulfonyl, $R^{14}$ is n-butyl, $R^{15}$ is trifluoromethylcarbonyl and $R^{16}$ is methyl:

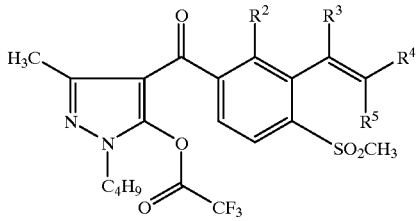

Ia634

Likewise, extraordinary preference is given to the compounds Ia635, in particular to the compounds Ia635.001–Ia635.180, which differ from the corresponding compounds Ia1.001–Ia1.180 in that $R^1$ is methylsulfonyl, $R^{14}$ is isobutyl, $R^{15}$ is trifluoromethylcarbonyl and $R^{16}$ is methyl:

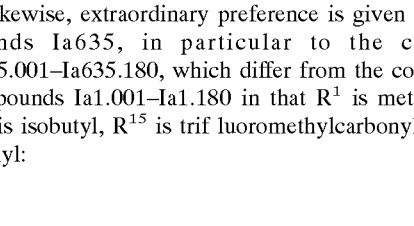

Ia635

Likewise, extraordinary preference is given to the compounds Ia636, in particular to the compounds Ia636.001–Ia636.180, which differ from the corresponding compounds Ia1.001–Ia1.180 in that $R^1$ and $R^{15}$ are each methylsulfonyl and $R^{16}$ is methyl:

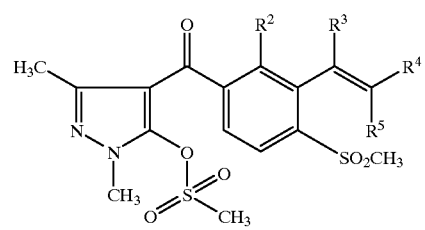

Ia636

Likewise, extraordinary preference is given to the compounds Ia637, in particular to the compounds Ia637.001–Ia637.180, which differ from the corresponding compounds Ia1.001–Ia1.180 in that $R^1$ and $R^{15}$ are each methylsulfonyl, $R^{14}$ is ethyl and $R^{16}$ is methyl:

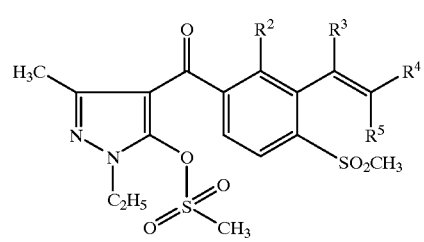

Ia637

Likewise, extraordinary preference is given to the compounds Ia638, in particular to the compounds Ia638.001–Ia638.180, which differ from the corresponding compounds Ia1.001–Ia1.180 in that $R^1$ and $R^{15}$ are each methylsulfonyl, $R^{14}$ is n-propyl and $R^{16}$ is methyl:

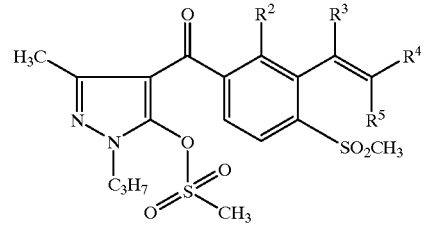

Ia638

Likewise, extraordinary preference is given to the compounds Ia639, in particular to the compounds Ia639.001–Ia639.180, which differ from the corresponding compounds Ia1.001–Ia1.180 in that $R^1$ and $R^{15}$ are each methylsulfonyl, $R^{14}$ is n-butyl and $R^{16}$ is methyl:

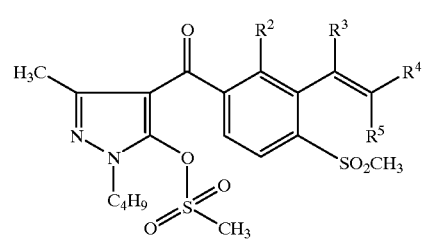

Ia639

Likewise, extraordinary preference is given to the compounds Ia640, in particular to the compounds Ia640.001–Ia640.180, which differ from the corresponding compounds Ia1.001–Ia1.180 in that $R^1$ and $R^{15}$ are each methylsulfonyl, $R^{14}$ is isobutyl and $R^{16}$ is methyl:

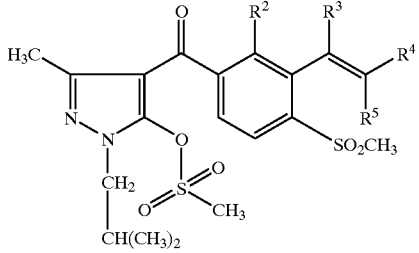

Ia640

Likewise, extraordinary preference is given to the compounds Ia641, in particular to the compounds Ia641.001–Ia641.180, which differ from the corresponding compounds Ia1.001–Ia1.180 in that $R^1$ is methylsulfonyl, $R^{15}$ is ethylsulfonyl and $R^{16}$ is methyl:

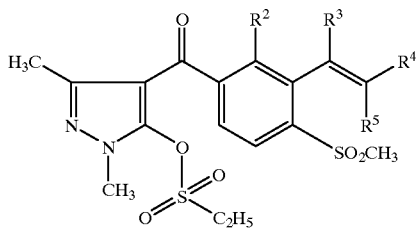

Ia641

Likewise, extraordinary preference is given to the compounds Ia642, in particular to the compounds Ia642.001–Ia642.180, which differ from the corresponding compounds Ia1.001–Ia1.180 in that $R^1$ is methylsulfonyl, $R^{14}$ is ethyl, $R^{15}$ is ethylsulfonyl and $R^{16}$ is methyl:

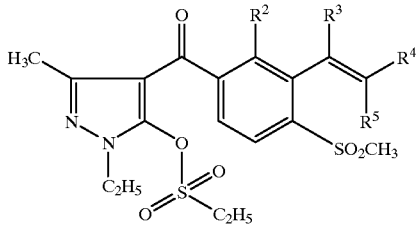

Ia642

Likewise, extraordinary preference is given to the compounds Ia643, in particular to the compounds Ia643.001–Ia643.180, which differ from the corresponding compounds Ia1.001–Ia1.180 in that $R^1$ is methylsulfonyl, $R^{14}$ is n-propyl, $R^{15}$ is ethylsulfonyl and $R^{16}$ is methyl:

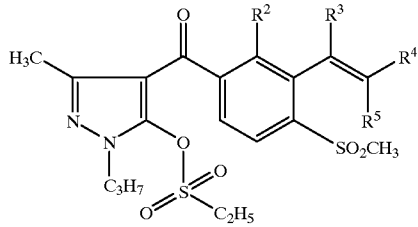

Ia643

Likewise, extraordinary preference is given to the compounds Ia644, in particular to the compounds Ia644.001–Ia644.180, which differ from the corresponding compounds Ia1.001–Ia1.180 in that $R^1$ is methylsulfonyl, $R^{14}$ is n-butyl, $R^{15}$ is ethylsulfonyl and $R^{16}$ is methyl:

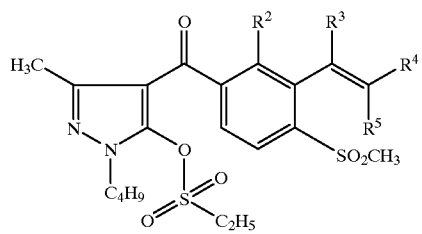

Ia644

Likewise, extraordinary preference is given to the compounds Ia645, in particular to the compounds Ia645.001–Ia645.180, which differ from the corresponding compounds Ia1.001–Ia1.180 in that $R^1$ and $R^{15}$ are each methylsulfonyl, $R^{14}$ is isobutyl, $R^{15}$ is ethylsulfonyl and $R^{16}$ is methyl:

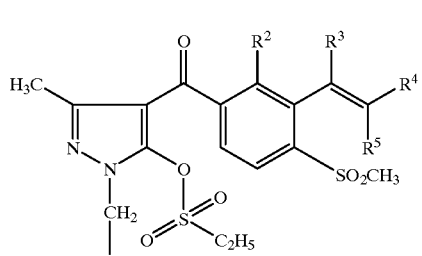

Ia645

Likewise, extraordinary preference is given to the compounds Ia646, in particular to the compounds Ia646.001–Ia646.180, which differ from the corresponding compounds Ia1.001–Ia1.180 in that $R^1$ is methylsulfonyl, $R^{15}$ is n-propylsulfonyl and $R^{16}$ is methyl:

Ia646

Likewise, extraordinary preference is given to the compounds Ia647, in particular to the compounds Ia647.001–Ia647.180, which differ from the corresponding compounds Ia1.001–Ia1.180 in that $R^1$ is methylsulfonyl, $R^{14}$ is ethyl, $R^{15}$ is n-propylsulfonyl and $R^{16}$ is methyl:

Ia647

Likewise, extraordinary preference is given to the compounds Ia648, in particular to the compounds Ia648.001–Ia648.180, which differ from the corresponding compounds Ia1.001–Ia1.180 in that $R^1$ is methylsulfonyl, $R^{14}$ is n-propyl, $R^{15}$ is n-propylsulfonyl and $R^{16}$ is methyl:

Ia648

Likewise, extraordinary preference is given to the compounds Ia649, in particular to the compounds Ia649.001–Ia649.180, which differ from the corresponding compounds Ia1.001–Ia1.180 in that $R^1$ is methylsulfonyl, $R^{14}$ is n-butyl, $R^{15}$ is n-propylsulfonyl and $R^{16}$ is methyl:

Ia649

Likewise, extraordinary preference is given to the compounds Ia650, in particular to the compounds Ia650.001–Ia650.180, which differ from the corresponding compounds Ia1.001–Ia1.180 in that $R^1$ and $R^{15}$ are each methylsulfonyl, $R^{14}$ is isobutyl, $R^{15}$ is n-propylsulfonyl and $R^{16}$ is methyl:

Ia650

Likewise, extraordinary preference is given to the compounds Ia651, in particular to the compounds Ia651.001–Ia651.180, which differ from the corresponding compounds Ia1.001–Ia1.180 in that $R^1$ is methylsulfonyl, $R^{15}$ is isopropylsulfonyl and $R^{16}$ is methyl:

Ia651

Likewise, extraordinary preference is given to the compounds Ia652, in particular to the compounds Ia652.001–Ia652.180, which differ from the corresponding compounds Ia1.001–Ia1.180 in that $R^1$ is methylsulfonyl, $R^{14}$ is ethyl, $R^{15}$ is isopropylsulfonyl and $R^{16}$ is methyl:

Ia652

Likewise, extraordinary preference is given to the compounds Ia653, in particular to the compounds Ia653.001–Ia653.180, which differ from the corresponding compounds Ia1.001–Ia1.180 in that $R^1$ is methylsulfonyl, $R^{14}$ is n-propyl, $R^{15}$ is isopropylsulfonyl and $R^{16}$ is methyl:

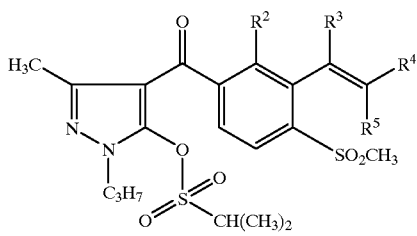

Ia653

Likewise, extraordinary preference is given to the compounds Ia654, in particular to the compounds Ia654.001–Ia654.180, which differ from the corresponding compounds Ia1.001–Ia1.180 in that $R^1$ is methylsulfonyl, $R^{14}$ is n-butyl, $R^{15}$ is isopropylsulfonyl and $R^{16}$ is methyl:

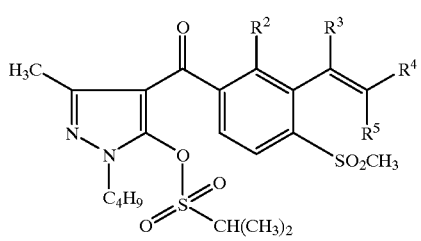

Ia654

Likewise, extraordinary preference is given to the compounds Ia655, in particular to the compounds Ia655.001–Ia655.180, which differ from the corresponding compounds Ia1.001–Ia1.180 in that $R^1$ is methylsulfonyl, $R^{14}$ is isobutyl, $R^{15}$ is isopropylsulfonyl and $R^{16}$ is methyl:

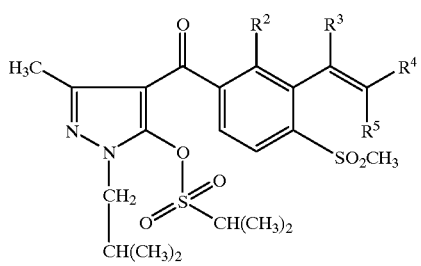

Ia655

Likewise, extraordinary preference is given to the compounds Ia656, in particular to the compounds Ia656.001–Ia656.180, which differ from the corresponding compounds Ia1.001–Ia1.180 in that $R^1$ is methylsulfonyl, $R^{15}$ is n-butylsulfonyl and $R^{16}$ is methyl:

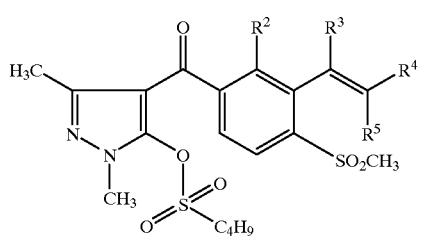

Ia656

Likewise, extraordinary preference is given to the compounds Ia657, in particular to the compounds Ia657.001–Ia657.180, which differ from the corresponding compounds Ia1.001–Ia1.180 in that $R^1$ is methylsulfonyl, $R^{14}$ is ethyl, $R^{15}$ is n-butylsulfonyl and $R^{16}$ is methyl:

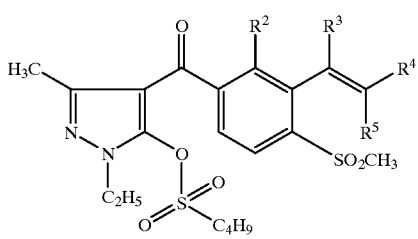

Ia657

Likewise, extraordinary preference is given to the compounds Ia658, in particular to the compounds Ia658.001–Ia658.180, which differ from the corresponding compounds Ia1.001–Ia1.180 in that $R^1$ is methylsulfonyl, $R^{14}$ is n-propyl, $R^{15}$ is n-butylsulfonyl and $R^{16}$ is methyl:

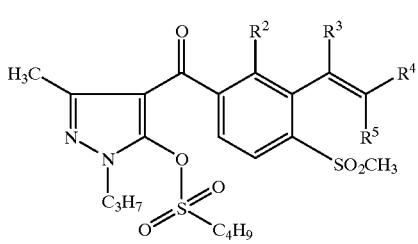

Ia658

Likewise, extraordinary preference is given to the compounds Ia659, in particular to the compounds Ia659.001–Ia659.180, which differ from the corresponding compounds Ia1.001–Ia1.180 in that $R^1$ is methylsulfonyl, $R^{14}$ is n-butyl, $R^{15}$ is n-butylsulfonyl and $R^{16}$ is methyl:

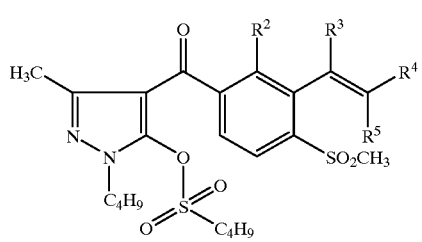

Ia659

Likewise, extraordinary preference is given to the compounds Ia660, in particular to the compounds Ia660.001–Ia660.180, which differ from the corresponding compounds Ia1.001–Ia1.180 in that $R^1$ and $R^{15}$ are each methylsulfonyl, $R^{14}$ is isobutyl, $R^{15}$ is n-butylsulfonyl and $R^{16}$ is methyl:

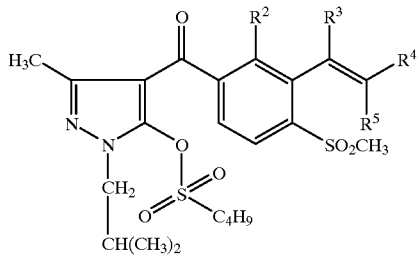

Ia660

Likewise, extraordinary preference is given to the compounds Ia661, in particular to the compounds Ia661.001–Ia661.180, which differ from the corresponding compounds Ia1.001–Ia1.180 in that $R^1$ is methylsulfonyl, $R^{15}$ is isobutylsulfonyl and $R^{16}$ is methyl:

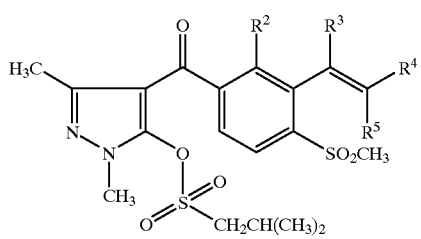

Ia661

Likewise, extraordinary preference is given to the compounds Ia662, in particular to the compounds Ia662.001–Ia662.180, which differ from the corresponding compounds Ia1.001–Ia1.180 in that $R^1$ is methylsulfonyl, $R^{14}$ is ethyl, $R^{15}$ is isobutylsulfonyl and $R^{16}$ is methyl:

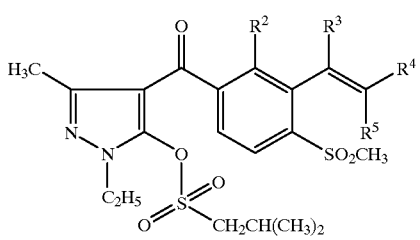

Ia662

Likewise, extraordinary preference is given to the compounds Ia663, in particular to the compounds Ia663.001–Ia663.180, which differ from the corresponding compounds Ia1.001–Ia1.180 in that $R^1$ is methylsulfonyl, $R^{14}$ is n-propyl, $R^{15}$ is isobutylsulfonyl and $R^{16}$ is methyl:

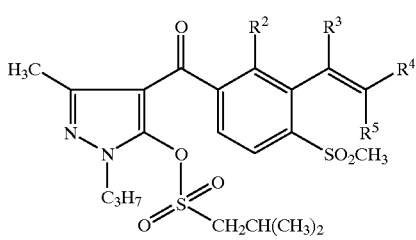

Ia663

Likewise, extraordinary preference is given to the compounds Ia664, in particular to the compounds Ia664.001–Ia664.180, which differ from the corresponding compounds Ia1.001–Ia1.180 in that $R^1$ is methylsulfonyl, $R^{14}$ is n-butyl, $R^{15}$ is isobutylsulfonyl and $R^{16}$ is methyl:

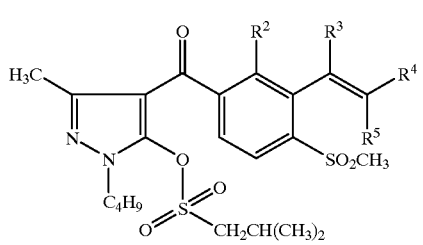

Ia664

Likewise, extraordinary preference is given to the compounds Ia665, in particular to the compounds Ia665.001–Ia665.180, which differ from the corresponding compounds Ia1.001–Ia1.180 in that $R^1$ is methylsulfonyl, $R^{14}$ is isobutyl, $R^{15}$ is isobutylsulfonyl and $R^{16}$ is methyl:

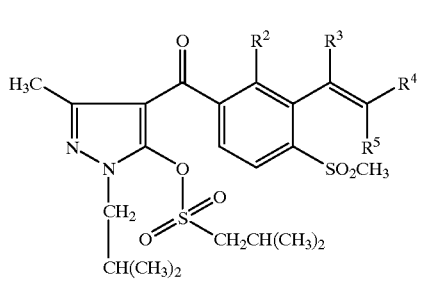

Ia665

Likewise, extraordinary preference is given to the compounds Ia666, in particular to the compounds Ia666.001–Ia666.180, which differ from the corresponding compounds Ia1.001–Ia1.180 in that $R^1$ is methylsulfonyl, $R^{15}$ is sec-butylsulfonyl and $R^{16}$ is methyl:

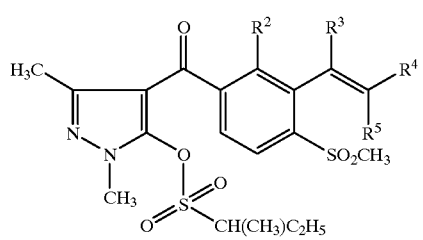

Ia666

Likewise, extraordinary preference is given to the compounds Ia667, in particular to the compounds Ia667.001–Ia667.180, which differ from the corresponding compounds Ia1.001–Ia1.180 in that $R^1$ is methylsulfonyl, $R^{14}$ is ethyl, $R^{15}$ is sec-butylsulfonyl and $R^{16}$ is methyl:

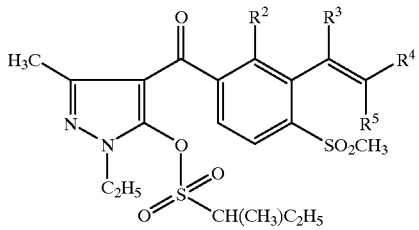
Ia667

Likewise, extraordinary preference is given to the compounds Ia668, in particular to the compounds Ia668.001–Ia668.180, which differ from the corresponding compounds Ia1.001–Ia1.180 in that $R^1$ is methylsulfonyl, $R^{14}$ is n-propyl, $R^{15}$ is sec-butylsulfonyl and $R^{16}$ is methyl:

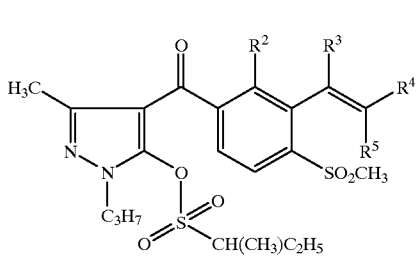
Ia668

Likewise, extraordinary preference is given to the compounds Ia669, in particular to the compounds Ia669.001–Ia669.180, which differ from the corresponding compounds Ia1.001–Ia1.180 in that $R^1$ is methylsulfonyl, $R^{14}$ is n-butyl, $R^{15}$ is sec-butylsulfonyl and $R^{16}$ is methyl:

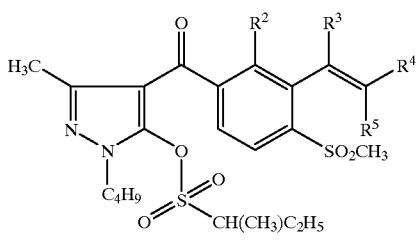
Ia669

Likewise, extraordinary preference is given to the compounds Ia670, in particular to the compounds Ia670.001–Ia670.180, which differ from the corresponding compounds Ia1.001–Ia1.180 in that $R^1$ is methylsulfonyl, $R^{14}$ is isobutyl, $R^{15}$ is sec-butylsulfonyl and $R^{16}$ is methyl:

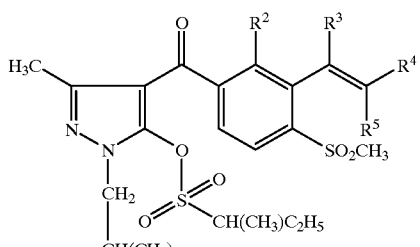
Ia670

Likewise, extraordinary preference is given to the compounds Ia671, in particular to the compounds Ia671.001–Ia671.180, which differ from the corresponding compounds Ia1.001–Ia1.180 in that $R^1$ is methylsulfonyl, $R^{15}$ is trifluoromethylsulfonyl and $R^{16}$ is methyl:

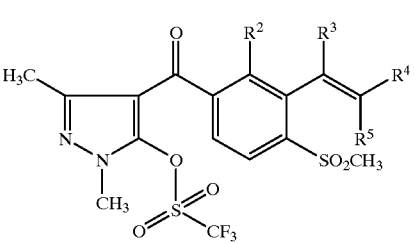
Ia671

Likewise, extraordinary preference is given to the compounds Ia672, in particular to the compounds Ia672.001–Ia672.180, which differ from the corresponding compounds Ia1.001–Ia1.180 in that $R^1$ is methylsulfonyl, $R^{14}$ is ethyl, $R^{15}$ is trifluoromethylsulfonyl and $R^{16}$ is methyl:

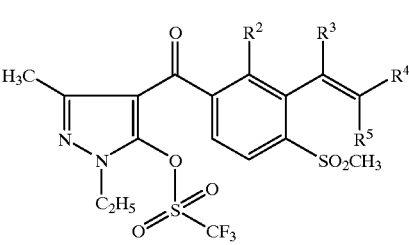
Ia672

Likewise, extraordinary preference is given to the compounds Ia673, in particular to the compounds Ia673.001–Ia673.180, which differ from the corresponding compounds Ia1.001–Ia1.180 in that $R^1$ is methylsulfonyl, $R^{14}$ is n-propyl, $R^{15}$ is trifluoromethylsulfonyl and $R^{16}$ is methyl:

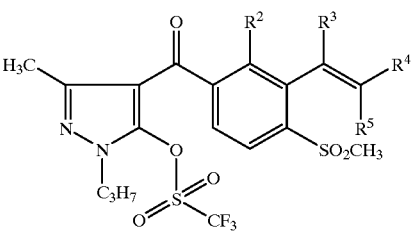
Ia673

Likewise, extraordinary preference is given to the compounds Ia674, in particular to the compounds Ia674.001–Ia674.180, which differ from the corresponding compounds Ia1.001–Ia1.180 in that $R^1$ is methylsulfonyl, $R^{14}$ is n-butyl, $R^{15}$ is trifluoromethylsulfonyl and $R^{16}$ is methyl:

Ia674

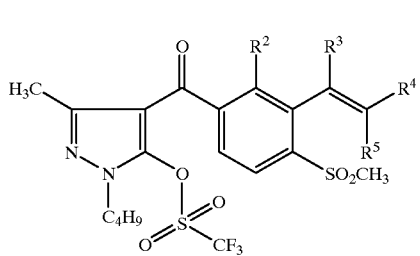

Likewise, extraordinary preference is given to the compounds Ia675, in particular to the compounds Ia675.001–Ia675.180, which differ from the corresponding compounds Ia1.001–Ia1.180 in that $R^1$ is methylsulfonyl, $R^{14}$ is isobutyl, $R^{15}$ is trifluoromethylsulfonyl and $R^{16}$ is methyl:

Ia675

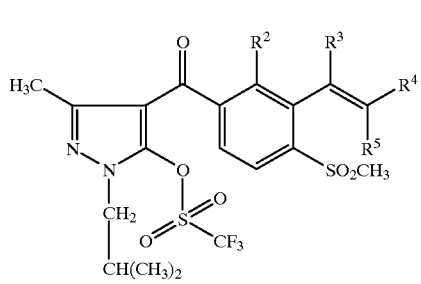

Likewise, extraordinary preference is given to the compounds Ia676, in particular to the compounds Ia676.001–Ia676.180, which differ from the corresponding compounds Ia1.001–Ia1.180 in that $R^1$ is methylsulfonyl, $R^{14}$ is methyl, $RI^5$ is phenylcarbonylmethyl and $R^{16}$ is methyl:

Ia676

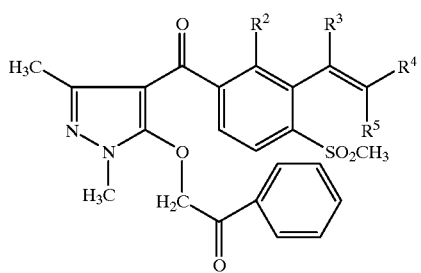

Likewise, extraordinary preference is given to the compounds Ia677, in particular to the compounds Ia677.001–Ia677.180, which differ from the corresponding compounds Ia1.001–Ia1.180 in that $R^1$ is methylsulfonyl, $R^{14}$ is ethyl, $R^{15}$ is phenylcarbonylmethyl and $R^{16}$ is methyl:

Ia677

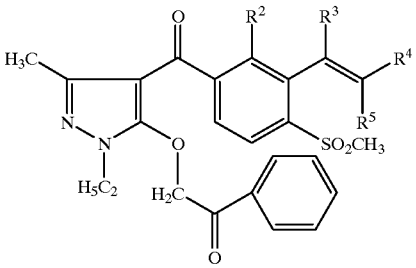

Likewise, extraordinary preference is given to the compounds Ia678, in particular to the compounds Ia678.001–Ia678.180, which differ from the corresponding compounds Ia1.001–Ia1.180 in that $R^1$ is methylsulfonyl, $R^{14}$ is n-propyl, $R^{15}$ is phenylcarbonylmethyl and It16 is methyl:

Ia678

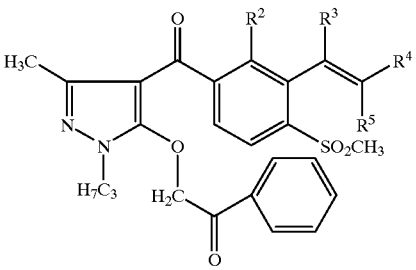

Likewise, extraordinary preference is given to the compounds Ia679, in particular to the compounds Ia679.001–Ia679.180, which differ from the corresponding compounds Ia1.001–Ia1.180 in that $R^1$ is methylsulfonyl, $R^{14}$ is n-butyl, $R^{15}$ is phenylcarbonylmethyl and $R^{16}$ is methyl:

Ia679

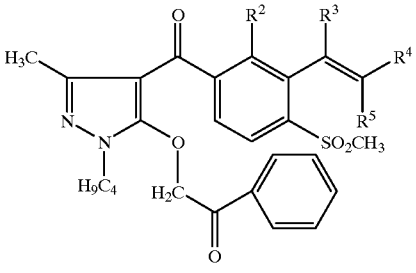

Likewise, extraordinary preference is given to the compounds Ia680, in particular to the compounds Ia680.001–Ia680.180, which differ from the corresponding compounds Ia1.001–Ia1.180 in that $R^1$ is methylsulfonyl, $R^{14}$ is isobutyl, $R^{15}$ is phenylcarbonylmethyl and $R^{16}$ is methyl:

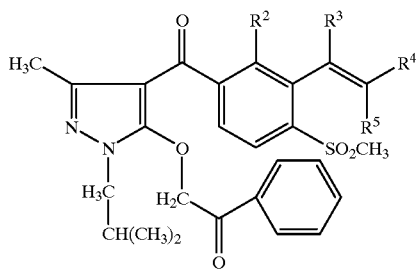

Ia680

Likewise, extraordinary preference is given to the compounds Ia681, in particular to the compounds Ia681.001–Ia681.180, which differ from the corresponding compounds Ia1.001–Ia1.180 in that $R^1$ is methylsulfonyl, $R^{15}$ is phenylsulfonyl and $R^{16}$ is methyl:

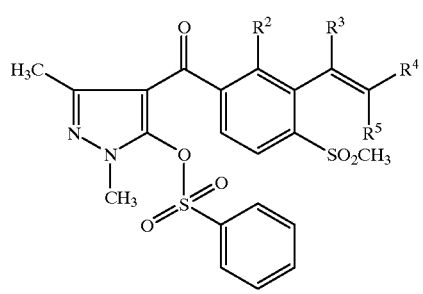

Ia681

Likewise, extraordinary preference is given to the compounds Ia682, in particular to the compounds Ia682.001–Ia682.180, which differ from the corresponding compounds Ia1.001–Ia1.180 in that $R^1$ is methylsulfonyl, $R^{14}$ is n-propyl, $R^{15}$ is phenylsulfonyl and $R^{16}$ is methyl:

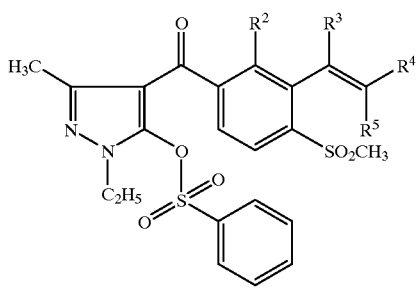

Ia682

Likewise, extraordinary preference is given to the compounds Ia683, in particular to the compounds Ia683.001–Ia683.180, which differ from the corresponding compounds Ia1.001–Ia1.180 in that $R^1$ is methylsulfonyl, $R^{14}$ is ethyl, $R^{15}$ is phenylsulfonyl and $R^{16}$ is methyl:

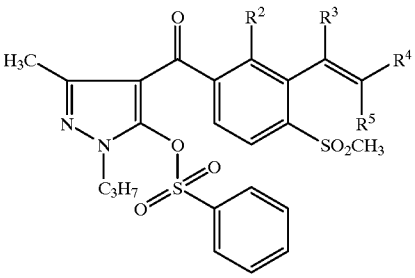

Ia683

Likewise, extraordinary preference is given to the compounds Ia684, in particular to the compounds Ia684.001–Ia684.180, which differ from the corresponding compounds Ia1.001–Ia1.180 in that $R^1$ is methylsulfonyl, $R^{14}$ is n-butyl, $R^{15}$ is phenylsulfonyl and $R^{16}$ is methyl:

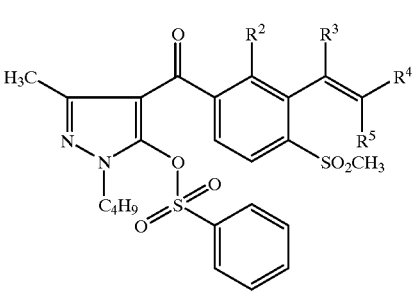

Ia684

Likewise, extraordinary preference is given to the compounds Ia685, in particular to the compounds Ia685.001–Ia685.180, which differ from the corresponding compounds Ia1.001–Ia1.180 in that $R^1$ is methylsulfonyl, $R^{14}$ is isobutyl, $R^{15}$ is phenylsulfonyl and $R^{16}$ is methyl:

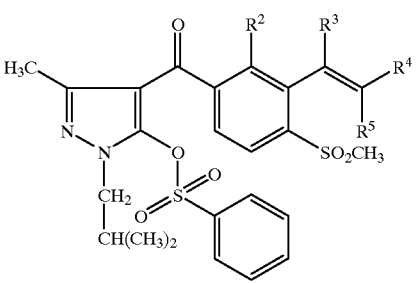

Ia685

Likewise, extraordinary preference is given to the compounds Ia686, in particular to the compounds Ia686.001–Ia686.180, which differ from the corresponding compounds Ia1.001–Ia1.180 in that $R^1$ is methylsulfonyl, $R^{15}$ is 4-methylphenyl sulfonyl and $R^{16}$ is methyl:

Likewise, extraordinary preference is given to the compounds Ia687, in particular to the compounds Ia687.001–Ia687.180, which differ from the corresponding compounds Ia1.001–Ia1.180 in that $R^1$ is methylsulfonyl, $R^{14}$ is ethyl, $R^{15}$ is 4-methylphenylsulfonyl and $R^{16}$ is methyl:

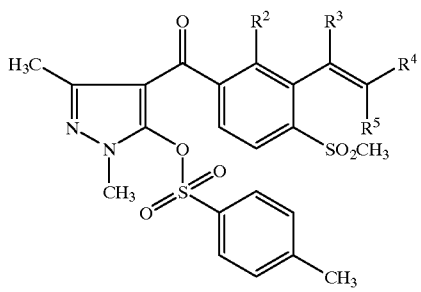

Ia686

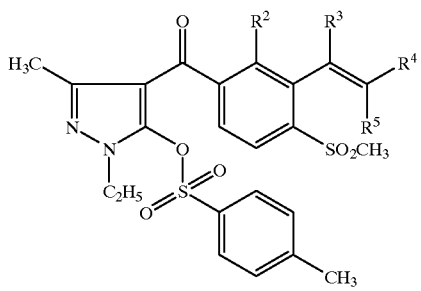

Ia687

Likewise, extraordinary preference is given to the compounds Ia688, in particular to the compounds Ia688.001–Ia688.180, which differ from the corresponding compounds Ia1.001–Ia1.180 in that $R^1$ is methylsulfonyl, $R^{14}$ is n-propyl, $R^{15}$ is 4-methylphenylsulfonyl and $R^{16}$ is methyl:

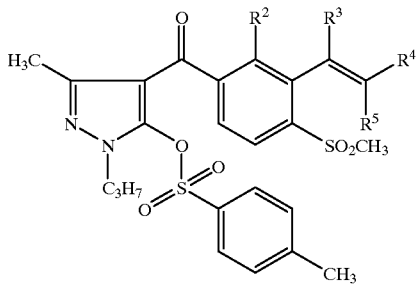

Ia688

Likewise, extraordinary preference is given to the compounds Ia689, in particular to the compounds Ia689.001–Ia689.180, which differ from the corresponding compounds Ia1.001–Ia1.180 in that $R^1$ is methylsulfonyl, $R^{14}$ is n-butyl, $R^{15}$ is 4-methylphenylsulfonyl and $R^{16}$ is methyl:

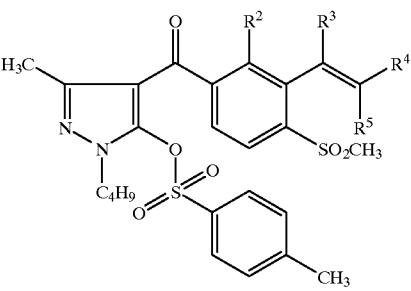

Ia689

Likewise, extraordinary preference is given to the compounds Ia690, in particular to the compounds Ia690.001–Ia690.180, which differ from the corresponding compounds Ia1.001–Ia1.180 in that $R^1$ is methylsulfonyl, $R^{14}$ is isobutyl, $R^{15}$ is 4-methylphenylsulfonyl and $R^{16}$ is methyl:

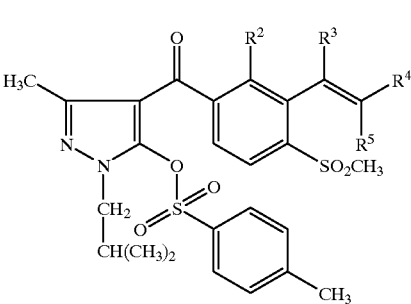

Ia690

Likewise, extraordinary preference is given to the compounds of the formula I, where
- $R^1$ is halogen such as chlorine or bromine, $C_1$–$C_6$-alkylsulfonyl such as methylsulfonyl or ethylsulfonyl; particularly preferably chlorine or methylsulfonyl;
- $R^2$ is halogen such as chlorine or bromine; particularly preferably chlorine;
- $R^3$ is hydrogen
- $R^4$ is hydrogen, cyano, $C_1$–$C_6$-alkyl such as methyl, ethyl, isopropyl, pentyl, $C_1$–$C_4$-hydroxyalkyl, formyl, $C_1$–$C_6$-alkylcarbonyl such as methylcarbonyl or ethylcarbonyl, hydroxycarbonyl, $C_1$–$C_6$-alkoxycarbonyl such as methoxycarbonyl or ethoxycarbonyl, —$C(R^{12})$=$NR^{13}$; heterocyclyl, heterocyclyl-$C_1$–$C_4$-alkyl, phenyl, hetaryl, it being possible for the last four radicals to be substituted in turn by one to three halogen atoms and/or to carry one to three radicals from the following group: nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl, $C_1$–$C_4$-alkoxycarbonyl, in particular $C_1$–$C_4$-alkyl;
particularly preferably hydrogen, cyano, methyl, isopropyl, pentyl, formyl, methylcarbonyl, hydroxycarbonyl, ethoxycarbonyl, —$C(R^{12})$=$NR^{13}$, 2-methyl-1,3-dioxolan-4-yl, 2,2-dimethyl-1,3-dioxolan-4-yl, 1,3-dioxan-2-yl, 1,3-dioxan-2-ylmethyl, phenyl, 2-furyl, 3-furyl, 2-thienyl, 3-thienyl;
- $R^5$ is hydrogen, halogen such as chlorine or bromine, $C_1$–$C_6$-alkyl such as methyl or ethyl; particularly preferably hydrogen, chlorine or methyl;
- $R^{12}$ is hydrogen, $C_1$–$C_6$-alkyl such as methyl or ethyl, $C_1$–$C_6$-alkoxycarbonyl such as methoxycarbonyl or ethoxycarbonyl;

particularly preferably hydrogen, methyl or ethoxycarbonyl;

$R^{13}$ is $C_1$–$C_6$-alkoxy such as methoxy or ethoxy, or phenyl-$C_1$–$C_4$-alkoxy, where the last radical may be partially or fully halogenated and/or may carry one to three radicals from the following group:

nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylcarbonyl, $C_1$–$C_4$-alkoxycarbonyl;

$R^{14}$ is $C_1$–$C_6$-alkyl;

particularly preferably methyl or ethyl;

$R^{15}$ is hydrogen, $C_1$–$C_6$-alkylsulfonyl such as methylsulfonyl or ethylsulfonyl, phenyl-$C_1$–$C_4$-alkyl, where the phenyl of the last substituent may be partially or fully halogenated and/or carries one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy;

particularly preferably hydrogen, methylsulfonyl or benzyl;

$R^{16}$ is hydrogen or $C_1$–$C_6$-alkyl such as methyl;

particularly preferably hydrogen.

The 4-(3-alkenylbenzoyl)pyrazoles of the formula I can be obtained by various routes, for example by the following processes:

Process A:

Reaction of pyrazoles of the formula II where $R^{15}$=H with an activated carboxylic acid IIIα or a carboxylic acid IIIβ, which is preferably activated in situ, to give the acylation product IV, followed by a rearrangement reaction.

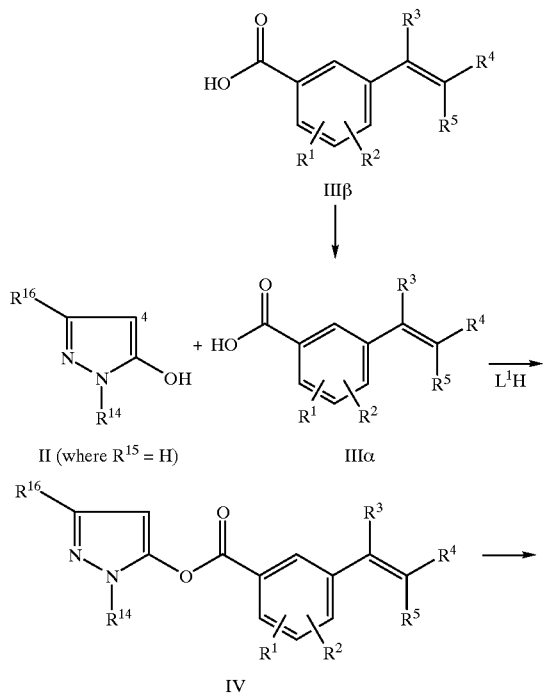

-continued

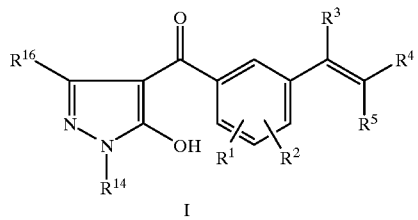

$L^1$ is a nucleophilically displaceable leaving group such as halogen, eg. bromine, chlorine, hetaryl, eg. imidazolyl, pyridyl, carboxylate, eg. acetate, trifluoroacetate, etc.

The activated carboxylic acid can be employed directly, as in the case of the carboxylic acid halides, or prepared in situ, eg. with dicyclohexylcarbodiimide, triphenylphosphine/ azodicarboxylic ester, 2-pyridine disulfide/ triphenylphosphine, carbonyldiimidazole, etc.

If appropriate, it may be advantageous to carry out the acylation reaction in the presence of a base. The starting materials and the auxiliary base are advantageously employed in equimolar amounts. Under certain conditions, a slight excess of the auxiliary base, for example 1.2 to 1.5 mole equivalents, based on II, may be advantageous.

Suitable auxiliary bases are tertiary alkylamines, pyridine or alkali metal carbonates. Examples of solvents which can be used are chlorinated hydrocarbons such as methylene chloride and 1,2-dichloroethane, aromatic hydrocarbons such as toluene and xylene, chlorobenzene, ethers such as diethyl ether, methyl tert-butyl ether, tetrahydrofuran and dioxane, polar aprotic solvents such as acetonitrile, dimethylformamide and dimethyl sulfoxide, or esters such as ethyl acetate, or mixtures of these.

If carboxylic acid halides are employed as activated carboxylic acid component, it may be advantageous to cool the reaction mixture to 0–10° C. when adding this reactant. The mixture is subsequently stirred at 20–100° C., preferably at 25–50° C., until the reaction has gone to completion. Work-up is carried out in the customary manner, for example by pouring the reaction mixture into water and extracting the product of value. Solvents which are especially suitable for this purpose are methylene chloride, diethyl ether and ethyl acetate. The organic phase is dried, the solvent is removed and the crude enol ester of the formula IV is purified, preferably by chromatography. Alternatively, it is possible to employ the crude enol ester of the formula IV for the rearrangement reaction without any further purification.

The rearrangement of the enol esters of the formula IV to give the compounds of the formula I is advantageously carried out at from 20 to 40° C. in a solvent and in the presence of an auxiliary base and, if appropriate, by using a cyano compound as catalyst.

Examples of solvents which can be used are acetonitrile, methylene chloride, 1,2-dichloroethane, dioxane, ethyl acetate, toluene, or mixtures of these. Preferred solvents are acetonitrile and dioxane.

Suitable bases are tertiary amines such as triethylamine and pyridine or alkali metal carbonates such as sodium carbonate and potassium carbonate, which are preferably employed in equimolar amounts or up to a four-fold excess, based on the ester. Preference is given to using triethylamine or alkali metal carbonates.

Suitable cyano compounds are inorganic cyanides such as sodium cyanide and potassium cyanide, and organic cyano compounds such as acetone cyanohydrin and trimethylsilyl cyanide. They are employed in an amount of 1 to 50 mol percent, based on the ester. Preference is given to using acetone cyano hydrin or trimethylsilyl cyanide, for example in an amount of 5 to 15, preferably 10, mol percent, based on the ester.

Particular preference is given to using alkali metal carbonates such as potassium carbonate in acetonitrile or dioxane.

Work-up can be carried out in a manner known per se. For example, the reaction mixture is acidifed with dilute mineral acid, such as 5% strength hydrochloric or sulfuric acid, and extracted with an organic solvent, eg. methylene chloride or ethyl acetate. The organic extract can be extracted with 5–10% strength alkali metal carbonate solution, eg. sodium carbonate or potassium carbonate solution. The aqueous phase is acidified and the resulting precipitate is filtered off with suction and/or extracted with methylene chloride or ethyl acetate, dried and concentrated. (Examples of the synthesis of esters from hydroxypyrazoles and of the rearrangement of the esters are mentioned, for example, in EP-A 282 944 or U.S. Pat. No. 4,643,757).

Process B:

Reaction of 4-(3-alkenylbenzoyl)pyrazoles of the formula I where $R^{15}$=H with a compound of the formula V (where $R^{15} \neq H$):

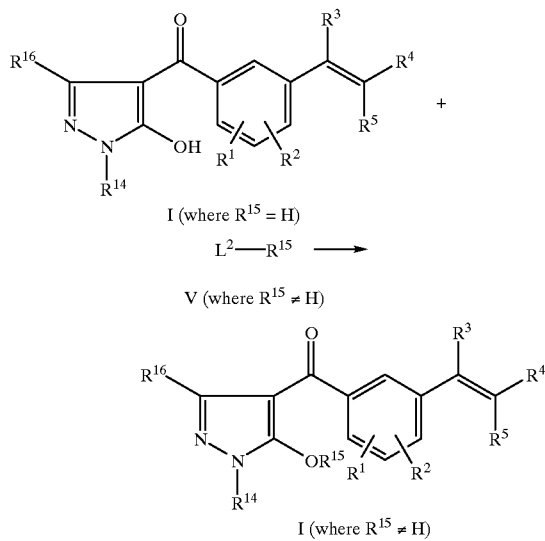

$L^2$ is a nucleophilically displaceable leaving group such as halogen, eg. bromine or chlorine, hetaryl, eg. imidazolyl or pyridyl, carboxylate, eg. acetate or trifluoroacetate, sulfonate, eg. mesylate or triflate, etc.

The compounds of the formula V can be employed directly, for example in the case of the alkyl halides, carboxylic acid halides, sulfonyl halides, carboxylic anhydrides and sulfonic anhydrides, or prepared in situ, for example activated carboxylic acids (by means of carboxylic acid and dicyclohexylcarbodiimide, carbonyldiimidazole, etc.).

In general, the starting materials are employed in an equimolar ratio. However, it may also be advantageous to employ one or other component in an excess.

Where appropriate, it may be advantageous to carry out the reaction in the presence of a base. The starting materials and the auxiliary base are advantageously employed in equimolar amounts. Under certain circumstances, an excess of the auxiliary base, for example 1.5 to 3 mole equivalents, based on II, may be advantageous.

Suitable auxiliary bases are tertiary alkylamines such as triethylamine, pyridine, alkali metal carbonates, eg. sodium carbonate and potassium carbonate, and alkali metal hydrides, eg. sodium hydride. Preference is given to using triethylamine, pyridine or potassium carbonate.

Examples of suitable solvents are chlorinated hydrocarbons such as methylene chloride and 1,2-dichloroethane, aromatic hydrocarbons, eg. toluene, xylene and chlorobenzene, ethers such as diethyl ether, methyl tertbutyl ether, tetrahydrofuran and dioxane, polar aprotic solvents such as acetonitrile, dimethylformamide and dimethyl sulfoxide, or esters such as ethyl acetate, or mixtures of these.

The reaction temperature is generally in the range of from 0° C. to the boiling point of the reaction mixture.

Work-up can be carried out in a manner known per se to give the product.

Those pyrazoles of the formula II (where $R^{15}$=H) used as starting materials which are not already known can be obtained in a conventional manner (for example EP-A 240 001, J. Prakt. Chem. 315 (1973) 383).

Those activated carboxylic acids IIIα which are not prepared in situ can be obtained in a conventional manner. Carboxylic acid halides of the formula IIIα (where L=halogen), for example, can be synthesized analogously to methods known from the literature (cf. L. G. Fieser, M. Fieser "Reagents for Organic Synthesis", Vol. I, pp. 767–769 (1967)) by reaction of benzoic acids of the formula IIIβ with halogenating agents such as thionyl chloride, thionyl bromide, phosgene, diphosgene, triphosgene, oxalyl chloride, oxalyl bromide.

Those 3-alkenylbenzoic acids of the formula IIIβ which are not known from the literature can be obtained analogously to methods known from the literature, for example by hydrolyzing the corresponding 3-alkenylbenzoic esters of the formula IIIB (where M=$C_1$–$C_6$-alkoxy).

The 3-alkenylbenzoic esters (where M=$C_1$–$C_6$-alkoxy) of the formula IIIγ can be obtained by various routes, for example by the following processes:

A)

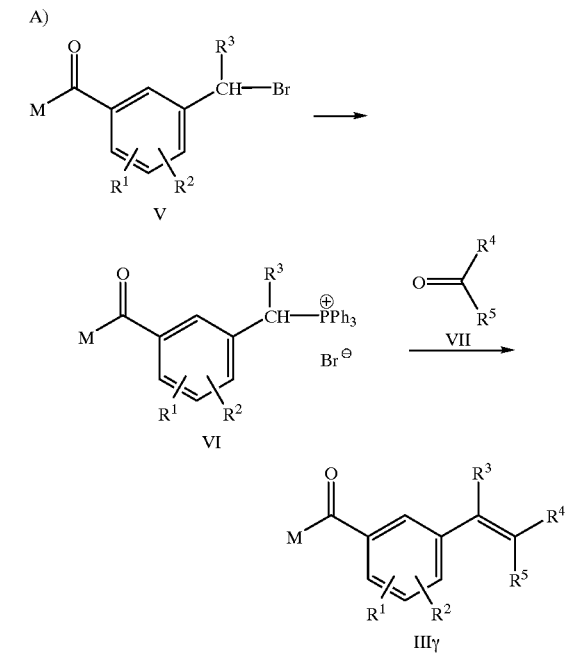

The compounds of the general formula IIIγ can be obtained in a manner known per se (J. March, "Advanced Organic Chemistry", 3rd edition, p. 864 ff., Wiley- Interscience Publication, 1985) by Wittig reaction of phosphonium salts of formula VI with aldehydes or ketones (VII).

The phosphonium salts of the formula VI are accessible in a manner known per se (J. March, "Advanced Organic Chemistry", 3rd edition, p. 377 ff., Wiley-Interscience Publication, 1985) from the bromine compounds of the formula V.

B)

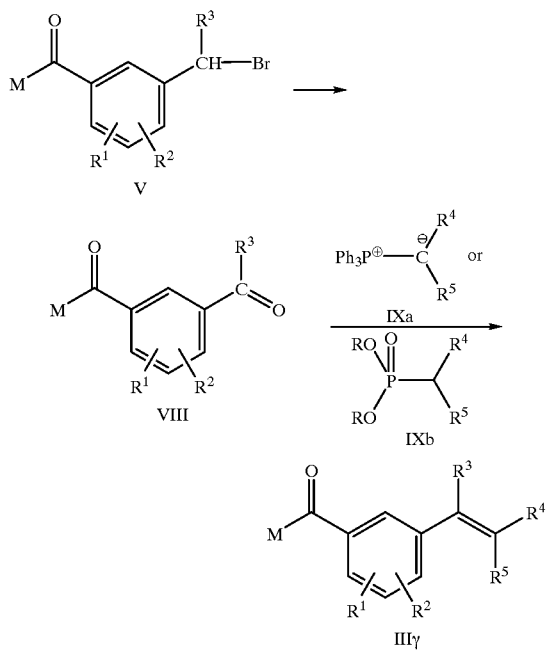

It is also possible to obtain the compounds of the general formula IIIγ by Wittig reaction or Horner-Emmons reaction of aldehydes or ketones of the formula VIII with phosphonium salts IXa (see A) or phosphonates IXb (J. March, "Advanced Organic Chemistry", 3rd edition, p. 867 ff., Wiley-Interscience Publication, 1985).

The compounds of the formula VIII are accessible in a manner known per se (J. March, "Advanced Organic Chemistry", 3rd edition, p. 1105 ff., Wiley-Interscience Publication, 1985) by oxidation of bromine compounds of the formula V.

C)

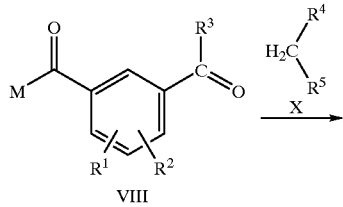

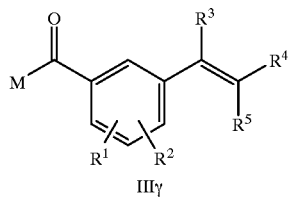

The compounds of the general formula IIIγ can also be obtained, again in a manner known per se (J. March, "Advanced Organic Chemistry", 3rd edition, p. 849 ff., Wiley-Interscience Publications, 1985) by aldol condensation and related reactions of aldehydes or ketones of the formula VIII.

PREPARATION EXAMPLES

4-{2',4'-Dichloro-3'-[2''-(3'''-furyl)ethen-1''-yl]benzoyl}-2-ethyl-3-hydroxypyrazole (compound 2.1)

A solution of 3.0 g (10 mmol) of 2,4-dichloro-3-[2''-(3''-furyl)ethen-1'-yl]benzoyl chloride in 30 ml of acetonitrile was admixed with 1.2 g (10 mmol) of 2-ethyl-3-hydroxypyrazole and 1.5 ml (10 mmol) of triethylamine. The reaction mixture was stirred at room temperature for 12 hours, taken up in water and extracted three times with ethyl acetate. The extracts were dried, the solvent was removed under reduced pressure and the residue was chromatographed over silica gel (cyclohexane/ethyl acetate=8/2 to 4/6). The resulting ester was dissolved in 100 ml of dioxane, admixed with 1.2 g (9 mmol) of finely powdered potassium carbonate and heated under reflux for 10 hours. After cooling, the precipitate that had formed was separated off, washed with dioxane and stirred into water. The pH was subsequently adjusted to 1–2 using 10% strength hydrochloric acid, the mixture was stirred at room temperature for 30 minutes and the precipitate was separated off. After drying, 1.4 g (37% of theory) of a white solid of mp. 115–120° C. remained.

$^1$H NMR(DMSO/δ in ppm): 7.75 (1H); 7.60 (1H); 7.50 (1H); 7.25 (2H); 7.00 (1H); 6.85 (1H); 6.80 (1H); 3.90 (2H); 1.30 (3H).

In Table 2 below, further 4-(3-alkenylbenzoyl)pyrazoles of the formula I which were prepared in a similar manner are listed in addition to those described above:

TABLE 2

Ia (where $R^{16}$ = H)

| No. | $R^1$ | $R^2$ | $R^3$ | $R^4$ | $R^5$ | $R^{14}$ | $R^{15}$ | Physical data mp. [° C.]; $^1$H NMR [ppm] |
|---|---|---|---|---|---|---|---|---|
| 2.1 | Cl | Cl | H | 3-furyl | H | $C_2H_5$ | H | 115–120 |
| 2.2 | Cl | Cl | H | 2-thienyl | H | $C_2H_5$ | H | 105–107 |
| 2.3 | Cl | Cl | H | 2-furyl | H | $C_2H_5$ | H | 65–83 |
| 2.4 | Cl | Cl | H | phenyl | H | $C_2H_5$ | H | 132–147 |
| 2.5 | Cl | Cl | H | 3-thienyl | H | $C_2H_5$ | H | 125–132 |
| 2.6 | Cl | Cl | H | $CH_3$ | H | $C_2H_5$ | H | 8.20(1H); 7.35–7.15(3H); 6.35–6.00(2H); 4.05(2H); 2.00–1.50(3H); 1.35(3H) |
| 2.7 | Cl | Cl | H | $CO_2C_2H_5$ | $OC_2H_5$ | $C_2H_5$ | H | 76–82 |
| 2.8 | Cl | Cl | H | 1,3-dioxan-2-yl-methyl | H | $C_2H_5$ | H | |
| 2.9 | Cl | Cl | H | 2-methyl-1,3-dioxolan-4-yl | H | $C_2H_5$ | H | |
| 2.10 | Cl | Cl | H | 1,3-dioxan-2-yl | H | $C_2H_5$ | H | oil |
| 2.11 | Cl | Cl | H | $CO_2C_2H_5$ | Cl | $C_2H_5$ | H | |
| 2.12 | Cl | Cl | H | CN | H | $C_2H_5$ | H | oil |
| 2.13 | Cl | Cl | H | $COCH_3$ | H | $C_2H_5$ | H | oil |
| 2.14 | Cl | Cl | H | $C(CO_2CH_3)=NOCH_3$ | H | $C_2H_5$ | H | 9.50(1H); 8.00(1H); 7.80(1H); 7.65(1H); 7.40(1H); 7.15(1H); 4.20(3H); 4.05(2H); 3.95(3H); 1.40(3H) |
| 2.15 | Cl | Cl | H | $C(CH_3)=NOCH_3$ | H | $C_2H_5$ | H | 96–108 |
| 2.16 | Cl | Cl | H | $C(H)=NOCH_3$ | H | $C_2H_5$ | H | 64–66 |
| 2.17 | $SO_2CH_3$ | Cl | H | phenyl | H | $C_2H_5$ | H | |
| 2.18 | Cl | Cl | H | H | H | $C_2H_5$ | H | 91–94 |
| 2.19 | Cl | Cl | H | $CH_3$ | H | $CH_3$ | H | 121–127 |
| 2.20 | $SO_2CH_3$ | Cl | H | $CH_3$ | H | $CH_3$ | H | 174–180 |
| 2.21 | Cl | Cl | H | $CH(CH_3)_2$ | H | $C_2H_5$ | H | 78–95 |
| 2.22 | Cl | Cl | H | $CH_3$ | $CH_3$ | $C_2H_5$ | H | resin |
| 2.23 | Cl | Cl | H | $COOC_2H_5$ | H | $C_2H_5$ | H | oil |
| 2.24 | Cl | Cl | H | $C(CH_3)=NOCH_2$-phenyl | H | $C_2H_5$ | H | oil |
| 2.25 | Cl | Cl | H | 2,2-dimethyl-1,3-dioxolan-4-yl | H | $C_2H_5$ | H | 53–60 |
| 2.26 | $SO_2CH_3$ | Cl | H | H | H | $CH_3$ | H | oil |
| 2.27 | $SO_2CH_3$ | Cl | H | $CH_3$ | H | $C_2H_5$ | H | 144–145 |
| 2.28 | $SO_2CH_3$ | Cl | H | H | $CH_3$ | $C_2H_5$ | H | 61–62 |
| 2.29 | Cl | Cl | H | $(CH_2)_4CH_3$ | H | $CH_3$ | H | 125–126 |
| 2.30 | Cl | Cl | H | $C(CH_3)=NO-CH(CH_3)-$(4-Cl-phenyl) | H | $CH_3$ | H | oil |
| 2.31 | $SO_2CH_3$ | Cl | H | $CH_3$ | H | $CH_3$ | H | 150–158 |
| 2.32 | Cl | Cl | H | $CH_2CH_3OH$ | H | $CH_3$ | H | |
| 2.33 | $SO_2CH_3$ | Cl | H | 1,3-dioxan-2-yl | H | $CH_3$ | H | |
| 2.34 | $SO_2CH_3$ | Cl | H | $COCH_3$ | H | $CH_3$ | H | |
| 2.35 | $SO_2CH_3$ | Cl | H | CN | H | $CH_3$ | H | |
| 2.36 | $SO_2CH_3$ | Cl | H | $COOC_2H_5$ | H | $CH_3$ | H | 155–156 |
| 2.37 | $SO_2CH_3$ | Cl | H | $C(CH_3)=NOCH_3$ | H | $CH_3$ | H | 85–100 |
| 2.38 | $SO_2CH_3$ | Cl | H | $C(H)=NOCH_3$ | H | $CH_3$ | H | |
| 2.39 | Cl | Cl | H | CHO | H | $CH_3$ | H | 146–154 |
| 2.40 | Cl | Cl | H | $C(H)=NOC_2H_5$ | H | $CH_3$ | H | oil |
| 2.41 | $SO_2CH_3$ | Cl | H | $CH_3$ | H | $C_2H_5$ | $CH_2$phenyl | oil |
| 2.42 | $SO_2CH_3$ | Cl | H | $CH_3$ | H | $C_2H_5$ | $SO_2CH_3$ | oil |
| 2.43 | Cl | Cl | H | $(CH_2)_4CH_3$ | H | $CH_3$ | $CH_2$phenyl | oil |
| 2.44 | Cl | Cl | H | $(CH_2)_4CH_3$ | H | $CH_3$ | $SO_2CH_3$ | oil |
| 2.45 | Cl | Cl | H | CHO | H | $C_2H_5$ | H | resin |
| 2.46 | $SO_2CH_3$ | Cl | H | $COOC_2H_5$ | H | $C_2H_5$ | H | 71–72 |
| 2.47 | $SO_2CH_3$ | Cl | H | COOH | H | $C_2H_5$ | H | 178–180 |

The syntheses of some starting materials are given below:

2-Chloro-4-methylsulfonyl-3-(2'-phenylethen-1'-yl)-benzoic acid (compound 3.02)

Step a) Methyl 2-chloro-4-methylsulfonyl-3-(2'-phenylethen-1'-yl)-benzoate (compound 3.01)

A solution of 52.0 g (120 mmol) of benzyltriphenylphosphonium bromide in 400 ml of tetrahydrofuran was admixed with 10.1 g (90 mmol) of potassium tert-butoxide. The mixture was stirred at room temperature for 30 minutes, 16.6 g (60 mmol) of methyl 2-chloro-3-formyl-4-methylsulfonylbenzoate in 100 ml of tetrahydrofuran were then added dropwise and the mixture was stirred at room temperature for a further 3 hours. The reaction mixture was subsequently stirred into 500 ml of water and extracted with methyl t-butyl ether. The solvent was removed under reduced pressure, the residue was digested with diethyl ether and the precipitated triphenylphosphine oxide was filtered off with suction. The residue was purified by chromatography over silica gel (cyclohexane/ethyl acetate=95/5 to 1/1). 10.9 g (52% of theory) of a slightly yellow oil which slowly solidified were obtained.

$^1$H NMR (CDCl$_3$/δ in ppm): 8.15 (1H); 7.70 (1H); 7.60–7.30 (7H); 7.0 (1H); 4.0 (3H); 3.10 (3H).

Step b) 2-Chloro-4-methylsulfonyl-3-(2'-phenylethen-1'-yl)-benzoic acid 10.0 g (28 mmol) of methyl 2-chloro-4-methylsulfonyl-3-(2'-phenylethen-1'-yl)benzoate were dissolved in 200 ml of tetrahydrofuran/methanol (1/1) and admixed with 35.2 g of 10% strength aqueous sodium hydroxide solution. The mixture was then stirred at room temperature for 12 hours and the solvent was subsequently removed under reduced pressure. The residue was admixed with 400 ml of water and washed with ethyl acetate. The pH was then adjusted to 1 using 10% strength hydrochloric acid, and the resulting precipitate was filtered off with suction. After drying, 9.4 g (97% of theory) of a white powder of mp.: 232–233° C. remained.

$^1$H NMR (CDCl$_3$/δ in ppm): 8.20 (1H); 7.90 (1H); 7.55 (2H); 7.40 (4H); 7.00 (1H); 3.10 (3H).

Methyl 2,4-dichloro-3-[2'-(2"-furyl)ethen-1'-yl] benzoate (compound 3.05)

Step a) 2,4-Dichloro-3-methylacetophenone

At 100° C., 235.0 g (3.0 mol) of acetyl chloride were added dropwise with stirring over a period of 2 hours to a solution of 502.0 g (3.12 mol) of 2,6-dichlorotoluene and 408.0 g (3.06 mol) of aluminum trichloride. The reaction mixture was stirred at 100–105° C. for 2 hours, cooled and poured into 3 l of ice and 1 l of water. The resulting solid precipitate was filtered off with suction and washed with water until neutral. Drying at 40° C. afforded 500.0 g of crude 2,4-dichloro-3-methylacetophenone which was subsequently distilled at high vacuum.

(bp.: 121–128° C. (4 mbar)).

Step b) 2,4-Dichloro-3-methylbenzoic acid

At 0–10° C., a solution of 520.0 g (13 mol) of sodium hydroxide in 2600 ml of water was admixed dropwise first with 655.2 g (4.1 mol) of bromine and then with 203.0 g (1.0 mol) of 2,4-dichloro-3-methylacetophenone in 1300 ml of 1,4-dioxan. The mixture was stirred for 12 hours, the organic phase was separated off and the aqueous phase was admixed with 30% strength aqueous sodium pyrosulfite solution and adjusted to pH 1 with hydrochloric acid. The resulting precipitate was filtered off with suction, washed with water and dried under reduced pressure at 60° C. 197.0 g of 2,4-dichloro-3-methylbenzoic acid were obtained.

(mp.: 173–175° C.).

Step c) Methyl 2,4-dichloro-3-methylbenzoate 60 ml of conc. sulfuric acid were added dropwise to a solution of 424.0 g (2 mol) of 2,4-dichloro-3-methylbenzoic acid and 1500 ml of methanol. The reaction mixture was refluxed for 5 hours, cooled, concentrated under reduced pressure and subsequently taken up in 1000 ml of methylene chloride. The organic phase was washed with water, then with 5% strength sodium bicarbonate solution and then once more with water, dried and concentrated under reduced pressure. 401.0 g of methyl 2,4-dichloro-3-methylbenzoate were obtained.

(bp: 103–107° C. (1–1.5 mbar)).

Step d) Methyl 3-bromomethyl-2,4-dichlorobenzoate 1.0 g of azobisisobutyronitrile was added to a solution of 84.0 g (0.38 mol) of methyl 2,4-dichloro-3-methylbenzoate and 67.6 g (0.38 mol) of N-bromosuccinimide in 380 ml of carbon tetrachloride. The reaction mixture was refluxed for 3.5 hours and then cooled, and the precipitate which had formed was filtered off with suction. The filtrate was concentrated under reduced pressure and the resulting residue was triturated with methyl t-butyl ether. 108.0 g of methyl 3-bromomethyl-2,4-dichlorobenzoate were obtained.

(mp.: 51–54° C.).

Step e) (2,6-Dichloro-3-methoxycarbonyl)benzyl-triphenyl-phosphonium bromide 80.65 g (262 mmol) of methyl 3-bromomethyl-2,4-dichlorobenzoate were dissolved in 800 ml of toluene and admixed with 68.7 g (262 mmol) of triphenylphosphine. The mixture was refluxed with stirring for 9 hours and cooled, and the precipitate which had formed was filtered off with suction. After drying, 129.0 g (89% of theory) of a light-beige powder remained.

(mp.: 238–239° C.).

Step f) Methyl 2,4-dichloro-3-[2'-(2"-furyl)ethen-1'-yl] benzoate 28.0 g (50 mmol) of (2,6-dichloro-3-methoxy-carbonyl)-benzyltriphenylphosphonium bromide were suspended in 200 ml of tetrahydrofuran and admixed with 5.6 g (50 mmol) of potassium t-butoxide at 0° C. The mixture was then cooled to −20° C. and a solution of 6.2 g (65 mmol) of furfural in 50 ml of tetrahydrofuran was added dropwise. The mixture was warmed to room temperature and stirred for a further 12 hours. The reaction mixture was stirred into 200 ml of water and extracted with methyl tert-butyl ether. The solvent was removed under reduced pressure, the residue was digested with diethyl ether and the precipitated triphenylphosphine oxide was separated off. The residue was purified by silica gel chromatography (cyclohexane/ethyl acetate=98/2 to 90/10). 8.2 g (55% of theory) of a yellow oil were obtained.

$^1$H NMR (CDCl$_3$/δ in ppm): 7.55 (1H); 7.50 (1H); 7.40 (1H); 7.05 (1H); 6.95 (1H); 6.45 (2H); 3.95 (3H).

Methyl 2,4-dichloro-3-(3'-methoxycarbonyl-3'-5 methoxyimino-prop-1'-en-1'-yl)benzoate (compound 3.13)

1.9 g (75 mmol) of sodium hydride were added to 17.9 g (75 mmol) of (2-methoxycarbonyl-2-methoxyiminoethyl) dimethyl-phosphonate in 150 ml of tetrahydrofuran, and the mixture was stirred at room temperature for 2 hours. 11.7 g (50 mmol) of methyl 2,4-dichloro-3-formylbenzoate in 50 ml of tetrahydrofuran were subsequently added dropwise and the mixture was stirred at room temperature for a further 12 hours. The reaction mixture was taken up in water and extracted with methyl t-butyl ether and the extract was dried and the solvent was removed under reduced pressure. The residue was digested with diethyl ether and the precipitate was separated off. After drying, 11.3 g (65% of theory) of a white powder remained.

(mp.: 96–97° C.).

In Table 3 below, further 3-alkenylbenzoic acid derivatives of the formula IIIa which were prepared or are preparable in a similar manner are listed in addition to the compounds described above.

TABLE 3

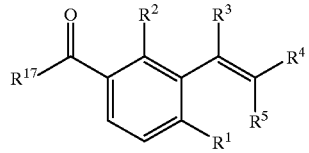

IIIa ($\equiv$ III where $R^1$ is attached in position 4 and $R^2$ is attached in position 2 and $R^{17} = L^1$, OH or M)

| No. | $R^1$ | $R^2$ | $R^3$ | $R^4$ | $R^5$ | $R^{17}$ | mp. [° C.] |
|---|---|---|---|---|---|---|---|
| 3.1 | $SO_2CH_3$ | Cl | H | phenyl | H | $OCH_3$ | 97–99 |
| 3.2 | $SO_2CH_3$ | Cl | H | phenyl | H | OH | 232–233 |
| 3.3 | Cl | Cl | H | phenyl | H | $OCH_3$ | oil |
| 3.4 | Cl | Cl | H | phenyl | H | OH | 161–166 |
| 3.5 | Cl | Cl | H | 2-furyl | H | $OCH_3$ | oil |
| 3.6 | Cl | Cl | H | 2-furyl | H | OH | 171–172 |
| 3.7 | Cl | Cl | H | $COCH_3$ | H | $OCH_3$ | 38–39 |
| 3.8 | Cl | Cl | H | $COCH_3$ | H | OH | |
| 3.9 | Cl | Cl | H | 2-thienyl | H | $OCH_3$ | oil |
| 3.10 | Cl | Cl | H | 2-thienyl | H | OH | 134–143 |
| 3.11 | Cl | Cl | H | 3-furyl | H | $OCH_3$ | 62–64 |
| 3.12 | Cl | Cl | H | 3-furyl | H | OH | 167–168 |
| 3.13 | Cl | Cl | H | $C(=NOCH_3)CO_2-CH_3$ | H | $OCH_3$ | 96–97 |
| 3.14 | Cl | Cl | H | $C(=NOCH_3)CO_2-CH_3$ | H | OH | 161 |
| 3.15 | Cl | Cl | H | 3-thienyl | H | $OCH_3$ | oil |
| 3.16 | Cl | Cl | H | 3-thienyl | H | OH | |
| 3.17 | Cl | Cl | H | 3-isopropyl-isoxazol-5-yl | H | $OCH_3$ | oil |
| 3.18 | Cl | Cl | H | 3-isopropyl-isoxazol-5-yl | H | OH | |
| 3.19 | Cl | Cl | H | CN | H | $OCH_3$ | 50–53 |
| 3.20 | Cl | Cl | H | CN | H | OH | |
| 3.21 | Cl | Cl | H | $OCH_3$ | H | $OCH_3$ | 38–40 |
| 3.22 | Cl | Cl | H | $OCH_3$ | H | OH | |
| 3.23 | Cl | Cl | Cl | $CO_2CH_3$ | H | $OCH_3$ | oil |
| 3.24 | Cl | Cl | Cl | $CO_2CH_3$ | H | OH | |
| 3.25 | Cl | Cl | H | 1,3-dioxan-2-yl | H | $OCH_3$ | 51–52 |
| 3.26 | Cl | Cl | H | 1,3-dioxan-2-yl | H | OH | 93–102 |
| 3.27 | Cl | Cl | H | (1,3-dioxan-2-yl)methyl | H | $OCH_3$ | oil |
| 3.28 | Cl | Cl | H | (1,3-dioxan-2-yl)methyl | H | OH | |
| 3.29 | Cl | Cl | $OC_2H_5$ | $CO_2C_2H_5$ | H | $OCH_3$ | oil |
| 3.30 | Cl | Cl | $OC_2H_5$ | $CO_2C_2H_5$ | H | OH | |
| 3.31 | Cl | Cl | H | 2-methyl-1,3-dioxolan-4-yl | H | $OCH_3$ | oil |
| 3.32 | Cl | Cl | H | 2-methyl-1,3-dioxolan-4-yl | H | OH | |
| 3.33 | Cl | Cl | H | CHO | H | $OCH_3$ | 66–68 |
| 3.34 | Cl | Cl | H | CHO | H | OH | |
| 3.35 | Cl | Cl | H | $CH_2-CHO$ | H | $OCH_3$ | oil |
| 3.36 | Cl | Cl | H | $CH_2-CHO$ | H | OH | |

The 4-(3-alkenylbenzoyl)pyrazoles of the formula I and their agriculturally useful salts are suitable as herbicides, both in the form of stereoisomer mixtures and in the form of the pure stereoisomers. The herbicidal compositions comprising compounds of the formula I effect very good control of vegetation on non-crop areas, especially at high rates of application. In crops such as wheat, rice, maize, soybeans and cotton they act against broad-leaved weeds and grass weeds without damaging the crop plants substantially. This effect is observed especially at low rates of application.

Depending on the application method in question, the 4-(3-alkenylbenzoyl)pyrazoles of the formula I, or compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica,*

*Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.*

Moreover, the compounds of the formula I can also be used in crops which tolerate the action of herbicides due to breeding including genetic engineering methods.

The compounds of the formula I, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended purposes; in any case, they should guarantee the finest possible distribution of the active ingredients according to the invention.

The herbicidal compositions comprise a herbicidally effective amount of at least one compound of the formula I or of an agriculturally useful salt of I and auxiliaries conventionally used for the formulation of crop protection products.

Essentially the following are suitable inert auxiliaries: mineral oil fractions of medium to high boiling point such as kerosene and diesel oil, furthermore coal tar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol, cyclohexanol, ketones such as cyclohexanone or strongly polar solvents, eg. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the 4-(3-alkenylbenzoyl)pyrazoles, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants (adjuvants) are the alkali metal, alkaline earth metal and ammonium salts of aromatic sulfonic acids, eg. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or concomitantly grinding the active substances with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the compounds of the formula I in the ready-to-use products can be varied within wide ranges. In general, the formulations comprise approximately from 0.001 to 98% by weight, preferably 0.01 to 95% by weight, of at least one active ingredient. The active ingredients a re employed in a purity of from 90% to 100%, preferably 95% to 100% (according to NMR spectrum.

The compounds I according to the invention can be formulated for example as follows:

I. parts by weight of the compound No. 2.1 are dissolved in a mixture composed of 80 parts by weight of alkylated benzene, 10 parts by weight of the adduct of 8 to 10 mol of ethylene oxide and 1 mol of oleic acid N-monoethanolamide, parts by weight of calcium dodecylbenzenesulfonate and 5 parts by weight of the adduct of 40 mol of ethylene oxide and 1 mol of castor oil. Pouring the solution in to 100,000 parts by weight of water and finely distributing it therein gives an aqueous dispersion which comprises 0.02% by weight of the active ingredient.

II. 20 parts by weight of the compound No. 2.2 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 2.3 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 2.4 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 2.5 are mixed with 97 parts by weight of finely divided kaolin. This gives a dust which comprises 3% by weight of the active ingredient.

VI. 20 parts by weight of the active ingredient No. 2.1 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 2.2 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 2.4 is dissolved in a mixture composed of 80 parts by weight of cyclohexanone and 20 parts by weight of Wettol® EM 31 (nonionic emulsifier based on ethoxylated castor oil). This gives a stable emulsion concentrate.

The active ingredients of the formula I, or the herbicidal compositions, can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

To widen the spectrum of action and to achieve synergistic effects, the compounds of the formula I can be mixed and applied jointly with a large number of representatives of other groups of herbicidal or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(aroyl/hetaroyl)-1,3-cyclohexandiones, hetaryl aryl ketones, benzylisoxazolidinones, meta-$CF_3$-phenylderivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds of the formula I, alone or in combination with other herbicides, in the form of a mixture with additional other crop protection agents, for example with agents for controlling pests, phytopathogenic fungi or bacteria. Also of interest is the miscibility with mineral salt solutions which are employed for treating nutritional and trace element deficiencies. Non-phytotoxic oils and oil concentrates can also be added.

Depending on the intended purpose, the season, the target plants and the growth stage, the rates of application of active ingredient are 0.001 to 3.0, preferably 0.01 to 1.0, kg/ha active substance (a.s.)

USE EXAMPLES

The herbicidal action of the 4-(3-alkenylbenzoyl) pyrazoles of the formula I was demonstrated by greenhouse experiments:

The culture containers used were plastic pots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active ingredients.

For the post-emergence treatment, the test plants were first grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 0.5 and 0.25 kg/ha a.s.

Depending on the species, the plants were kept at from 10–25° C. and 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific name | Common name |
| --- | --- |
| Chenopodium album | lambsquarters (goosefoot) |
| Sinapis alba | white mustard |
| Solanum nigrum | black nightshade |
| Triticum aestivum | summer wheat |

At rates of application of 0.5 and 0.25 kg/ha a.s., compound 2.4 was very efficient post-emergence against the abovementioned weeds and did not damage summer wheat crops.

We claim:

1. 4-(3-Alkenylbenzoyl)pyrazoles of the formula I

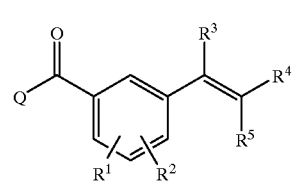

where:
$R^1$ and $R^2$ are each hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$, —$OCOR^7$, —$OSO_2R^7$, —SH, —$S(O)_nR^8$, —$SO_2OR^6$, —$SO_2NR^6R^9$, —$NR^9SO_2R^7$ or —$NR^9COR^7$;

$R^3$ is hydrogen, halogen, $C_1$–$C_6$-alkyl, $C_1$–$C_6$-haloalkyl, $C_1$–$C_6$-alkoxy, $C_2$–$C_6$-alkenyl or $C_2$–$C_6$-alkynyl;

$R^4$ and $R^5$ are each hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{10}$, —$CO_2R^{11}$, —$COSR^{10}$, —$CONR^{10}R^{11}$, —$C(R^{12})$=$NR^{13}$, —$PO(OR^{10})(OR^{11})$, $C_1$–$C_4$-alkyl which carries a radical from the following group: hydroxyl, —COR$^{10}$, —CO$_2$R$^{10}$, —COSR$^{10}$, —CONR$^{10}$R$^{11}$ or —C(R$^{12}$)=NR$^{13}$; heterocyclyl, heterocyclyl-C$_1$–C$_4$-alkyl (where the heterocyclyl radical of the two last-mentioned radicals is three- to seven-membered, saturated or partially unsaturated, mono- or polycyclic and contains one to three heteroatoms selected from the group consisting of oxygen, nitrogen and sulfur), phenyl, phenyl-C$_1$–C$_4$-alkyl, hetaryl or hetaryl-C$_1$–C$_4$-alkyl (where the hetaryl radical of the two last-mentioned radicals is aromatic, mono- or polycyclic and may, in addition to carbon ring members, additionally contain one to 4 nitrogen atoms or one to three nitrogen atoms and one oxygen or one sulfur atom or one oxygen or one sulfur atom), it being possible for the last six radicals to be substituted;

or

R$^4$ and R$^5$ together form a C$_2$–C$_6$-alkanediyl chain which may be mono- to tetrasubstituted by C$_1$–C$_4$-alkyl and/or interrupted by oxygen or sulfur or by nitrogen with or without substitution by C$_1$–C$_4$-alkyl;

n is 0, 1 or 2;

R$^6$ is hydrogen, C$_1$–C$_6$-alkyl, C$_1$–C$_6$-haloalkyl, C$_1$–C$_6$-alkoxy-C$_2$–C$_6$-alkyl, C$_3$–C$_6$-alkenyl or C$_3$–C$_6$-alkynyl;

R$^7$ is C$_1$–C$_6$-alkyl or C$_1$–C$_6$-haloalkyl;

R$^8$ is C$_1$–C$_6$-alkyl, C$_1$–C$_6$-haloalkyl, C$_1$–C$_6$-alkoxy-C$_2$–C$_6$-alkyl, C$_3$–C$_6$-alkenyl or C$_3$–C$_6$-alkynyl;

R$^9$ is hydrogen or C$_1$–C$_6$-alkyl;

R$^{10}$ is hydrogen, C$_1$–C$_6$-alkyl, C$_3$–C$_6$-cycloalkyl, C$_1$–C$_6$-haloalkyl, C$_3$–C$_6$-alkenyl, C$_3$–C$_6$-alkynyl, phenyl or benzyl, it being possible for the last two radicals to be partially or fully halogenated and/or to carry one to three radicals from the following group:
nitro, cyano, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylcarbonyl or C$_1$–C$_4$-alkoxycarbonyl;

R$^{11}$ is hydrogen, C$_1$–C$_6$-alkyl, C$_3$–C$_6$-alkenyl or C$_3$–C$_6$-alkynyl;

or

R$^{10}$ and R$^{11}$ together form a C$_2$–C$_6$-alkanediyl chain which may be mono- to tetrasubstituted by C$_1$–C$_4$-alkyl and/or interrupted by oxygen or sulfur or by nitrogen with or without substitution by C$_1$–C$_4$-alkyl;

R$^{12}$ is hydrogen, C$_1$–C$_6$-alkyl, C$_1$–C$_6$-haloalkyl, C$_1$–C$_6$-alkoxy, C$_1$–C$_6$-alkoxycarbonyl, C$_3$–C$_6$-cycloalkyl, C$_2$–C$_6$-alkenyl, C$_2$–C$_6$-alkynyl, phenyl or benzyl, it being possible for the last two radicals to be partially or fully halogenated and/or to carry one to three radicals of the following group:
nitro, cyano, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylcarbonyl or C$_1$–C$_4$-alkoxycarbonyl;

R$^{13}$ is C$_1$–C$_6$-alkyl, C$_1$–C$_6$-haloalkyl, C$_3$–C$_6$-cycloalkyl, C$_3$–C$_6$-alkenyl, C$_3$–C$_6$-alkynyl, C$_1$–C$_6$-alkoxy, C$_1$–C$_6$-haloalkoxy, C$_3$–C$_6$-cycloalkoxy, C$_3$–C$_6$-alkenyloxy, C$_3$–C$_6$-alkynyloxy, phenyl, benzyl or phenyl-C$_1$–C$_4$-alkoxy, it being possible for the last three radicals to be partially or fully halogenated and/or to carry one to three radicals from the following group:
nitro, cyano, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylcarbonyl or C$_1$–C$_4$-alkoxycarbonyl;

Q is a pyrazole of the formula II

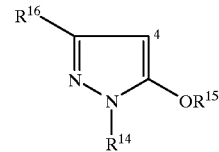

II which is linked in position 4 and where

R$^{14}$ is C$_1$–C$_6$-alkyl, C$_1$–C$_6$-haloalkyl, phenyl or phenyl which is partially or fully halogenated and/or carries one to three of the following radicals:
nitro, cyano, C$_1$–C$_4$-alkyl, C$_1$–C$_4$-haloalkyl, C$_1$–C$_4$-alkoxy, C$_1$–C$_4$-haloalkoxy;

R$^{15}$ is hydrogen, C$_1$–C$_6$-alkyl, C$_1$–C$_6$-haloalkyl, C$_1$–C$_6$-alkylcarbonyl, C$_1$–C$_6$-haloalkylcarbonyl, C$_1$–C$_6$-alkoxycarbonyl, C$_1$–C$_6$-alkylsulfonyl, C$_1$–C$_6$-haloalkylsulfonyl, phenyl-C$_1$–C$_4$-alkyl, phenylcarbonyl, phenylcarbonylmethyl, phenoxycarbonyl or phenylsulfonyl, the last five substituents being unsubstituted or the phenyl ring in question being partially or fully halogenated and/or carrying one to three of the following radicals:
nitro, cyano, C$_1$–C$_4$-alkyl, C$_1$–C$_4$-haloalkyl, C$_1$–C$_4$-alkoxy, C$_1$–C$_4$-haloalkoxy;

R$^{16}$ is hydrogen, C$_1$–C$_6$-alkyl or C$_1$–C$_6$-haloalkyl;

and agriculturally useful salts thereof.

2. 2-(3-Alkenylbenzoyl)pyrazoles of formula I as claimed in claim 1 where

R$^4$ and R$^5$ are each hydrogen, nitro, halogen, cyano, thiocyanato, C$_1$–C$_6$-alkyl, C$_1$–C$_6$-haloalkyl, C$_3$–C$_6$-cycloalkyl, C$_2$–C$_6$-alkenyl, C$_4$–C$_6$-cycloalkenyl, C$_2$–C$_6$-alkynyl, C$_1$–C$_6$-alkylthio, C$_1$–C$_6$-haloalkoxy, —COR$^{10}$, —CO$_2$R$^{10}$, —COSR$^{10}$, —CONR$^{10}$R$^{11}$, —C(R$^{12}$)=NR$^{13}$, —PO(OR$^{10}$)(OR$^{11}$), C$_1$–C$_4$-alkyl which carries a radical from the following group: —COR$^{10}$, —CO$_2$R$^{10}$, —COSR$^{10}$, —CONR$^{10}$R$^{11}$ or —C(R$^{12}$)=NR$^{13}$; heterocyclyl, heterocyclyl-C$_1$–C$_4$-alkyl (where the heterocyclyl radical of the two last-mentioned radicals is three- to seven-membered, saturated or partially unsaturated, mono- or polycyclic and contains one to three heteroatoms selected from the group consisting of oxygen, nitrogen and sulfur), phenyl, phenyl-C$_1$–C$_4$-alkyl, hetaryl or hetaryl-C$_1$–C$_4$-alkyl (where the hetaryl radical of the two last-mentioned radicals is aromatic, mono- or polycyclic and may, in addition to carbon ring members, additionally contain one to 4 nitrogen atoms or one to three nitrogen atoms and one oxygen or one sulfur atom or one oxygen or one sulfur atom), it being possible for the last six radicals to be substituted;

or

R$^4$ and R$^5$ together form a C$_2$–C$_6$-alkanediyl chain which may be mono- to tetrasubstituted by C$_1$–C$_4$-alkyl and/or interrupted by oxygen or sulfur or by nitrogen with or without substitution by C$_1$–C$_4$-alkyl, R$^{13}$ is C$_1$–C$_6$-alkyl, C$_1$–C$_6$-haloalkyl, C$_3$–C$_6$-cycloalkyl, C$_3$–C$_6$-alkenyl, C$_3$–C$_6$-alkynyl, C$_1$–C$_6$-alkoxy, C$_1$–C$_6$-haloalkoxy, C$_3$–C$_6$-cycloalkoxy, C$_3$–C$_6$-alkenyloxy, C$_3$–C$_6$-alkynyloxy, phenyl, benzyl or benzyloxy, it being possible for the last three radicals to be partially or fully halogenated and/or to carry one to three radicals from the following group:
nitro, cyano, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylcarbonyl or C$_1$–C$_4$-alkoxycarbonyl;

$R^{15}$ is hydrogen, $C_1$–$C_6$-alkyl, $C_1$–$C_6$-haloalkyl, $C_1$–$C_6$-alkylcarbonyl, $C_1$–$C_6$-haloalkylcarbonyl, $C_1$–$C_6$-alkoxycarbonyl, $C_1$–$C_6$-alkylsulfonyl, $C_1$–$C_6$-haloalkylsulfonyl, phenylcarbonyl, phenylcarbonylmethyl, phenoxycarbonyl or phenylsulfonyl, the last four substituents being unsubstituted or the phenyl ring in question being partially or fully halogenated and/or carrying one to three of the following radicals:

nitro, cyano, $C_1$–$C_4$-alkyl, $C_1$–$C_4$-haloalkyl, $C_1$–$C_4$-alkoxy, $C_1$–$C_4$-haloalkoxy.

3. 4-(3-Alkenylbenzoyl)pyrazoles of the formula I as claimed in claim 1 or 2 where $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^6$ or —$S(O)_n R^8$;

$R^2$ is hydrogen or a radical as mentioned above under $R^1$.

4. 4-(3-Alkenylbenzoyl)pyrazoles of the formula I as claimed in claim 1 where $R^4$ is hydrogen, nitro, halogen, cyano, thiocyanato, $C_1$–$C_6$-alkyl, $C_1$–$C_6$-haloalkyl, $C_3$–$C_6$-cycloalkyl, $C_2$–$C_6$-alkenyl, $C_4$–$C_6$-cycloalkenyl, $C_2$–$C_6$-alkynyl, $C_1$–$C_6$-alkylthio, $C_1$–$C_6$-haloalkoxy, —$COR^{10}$, —$CO_2R^{10}$, —$COSR^{10}$, —$CONR^{10}R^{11}$, —$C(R^{12})$=$NR^{13}$, —$PO(OR^{10})(OR^{11})$, $C_1$–$C_4$-alkyl which carries a radical from the following group:
—$COR^{10}$, —$CO_2R^{10}$, —$COSR^{10}$, —$CONR^{10}R^{11}$ or —$C(R^{12})$=$NR^{13}$; heterocyclyl, heterocyclyl-$C_1$–$C_4$-alkyl (where the heterocyclyl radical of the two last-mentioned radicals is three- to seven-membered, saturated or partially unsaturated, mono- or polycyclic and contains one to three heteroatoms selected from the group consisting of oxygen, nitrogen and sulfur), phenyl, phenyl-$C_1$–$C_4$-alkyl, hetaryl or hetaryl-$C_1$–$C_4$-alkyl (where the hetaryl radical of the two last-mentioned radicals is aromatic, mono- or polycyclic and may, in addition to carbon ring members, additionally contain one to 4 nitrogen atoms or one to three nitrogen atoms and one oxygen or one sulfur atom or one oxygen or one sulfur atom), it being possible for the last six radicals to be substituted;

$R^5$ is hydrogen, halogen, cyano, thiocyanato, $C_1$–$C_6$-alkyl, $C_1$–$C_6$-haloalkyl, —$COR^{10}$, —$CO_2R^{10}$, —$COSR^{10}$, —$CONR^{10}R^{11}$ or —$PO(OR^{10})(OR^{11})$;

or $R^4$ and $R^5$ together form a $C_2$–$C_6$-alkanediyl chain which may be mono- to tetrasubstituted by $C_1$–$C_4$-alkyl and/or interrupted by oxygen or sulfur or by nitrogen with or without substitution by $C_1$–$C_4$-alkyl.

5. 4-(3-Alkenylbenzoyl)pyrazoles of the formula Ia

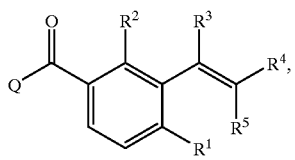

Ia where the variables $R^1$ to $R^5$ and Q are each as defined under claim 1.

6. A process for preparing 4-(3-alkenylbenzoyl)pyrazoles of the formula I as claimed claim 1, which comprises acylating a pyrazole of the formula II (where $R^{15}$=H), where the variables $R^{14}$ and $R^{16}$ are each as defined

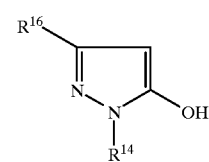

II with an activated carboxylic acid IIIα or with a carboxylic acid IIIβ,

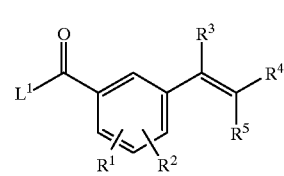

IIIα

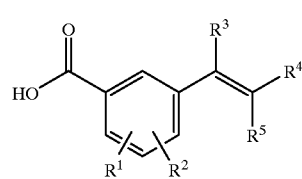

IIIβ where the variables $R^1$ to $R^5$ are each as defined under claim 1 and $L^1$ is a nucleophilically displaceable leaving group, subjecting the acylation product to a rearrangement reaction, if appropriate in the presence of a catalyst, to give the compounds I (where $R^{15}$=H) and, if desired, to prepare 4-(3-alkenylbenzoyl)pyrazoles of the formula I where $R^{15}$≠H reacting the product with a compound of the formula V,

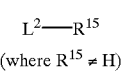

V (where $R^{15}$ ≠ H)

where $R^{15}$ is as defined under claim 1 with the exception of hydrogen and $L^2$ is a nucleophilically displaceable leaving group.

7. A composition comprising a herbicidally effective amount of at least one 4-(3-alkenylbenzoyl)pyrazole of the formula I or of an agriculturally useful salt of I as claimed in claim 1 and auxiliaries conventionally used for formulation of crop protection products.

8. A process for preparing the composition of claim 7, which comprises mixing a herbicidally effective amount of at least one 4-(3-alkenylbenzoyl)pyrazole of the formula I or of an agriculturally useful salt of I as claimed in auxiliaries conventionally used in the formulation of crop protection products.

9. A method of controlling undesirable vegetation, which comprises allowing a herbicidally effective amount of at least one 4-(3-alkenylbenzoyl)pyrazole of the formula I or of an agriculturally useful salt of I as claimed in claim 1 to act on plants, their habitat and/or on seeds.

* * * * *

UNITED STATES PATENT AND TRADEMARK OFFICE
CERTIFICATE OF CORRECTION

PATENT NO.: 6,143,696

DATED: November 7, 2000

INVENTOR(S): BAUMANN et al.

It is certified that error appears in the above-identified patent and that said Letters Patent is hereby corrected as shown below:

Col. 220, claim 1, line 66, "-$CO_2R^{11}$," should be -- -$CO_2R^{10}$,--.

Col. 223, claim 3, line 14, delete "or 2".

Col. 223, claim 6, line 67, "claimed claim 1" should be --claimed in claim 1--.

Col. 224, claim 6, line 2, after "defined" insert --in claim 1--.

Col. 224, claim 8, line 58, "as claimed in" should be --with--.

Signed and Sealed this

Eighth Day of May, 2001

NICHOLAS P. GODICI

*Attest:*

*Attesting Officer*   *Acting Director of the United States Patent and Trademark Office*